United States Patent
Goldberg et al.

(10) Patent No.: US 9,861,618 B2
(45) Date of Patent: Jan. 9, 2018

(54) THIAZOLES AS MODULATORS OF RORγT

(71) Applicant: Janssen Pharmaceutica NV, Beerse (BE)

(72) Inventors: Steven Goldberg, Carlsbad, CA (US); Christoph Steeneck, Heidelberg (DE); Christian Gege, Ehingen (DE); Olaf Kinzel, Heidelberg (DE); Gerald Kleymann, Bad Salzuflen (DE); Thomas Hoffmann, Speyer (DE)

(73) Assignee: Janssen Pharmaceutica NV, Beerse (BE)

( * ) Notice: Subject to any disclaimer, the term of this patent is extended or adjusted under 35 U.S.C. 154(b) by 0 days.

(21) Appl. No.: 14/927,501

(22) Filed: Oct. 30, 2015

(65) Prior Publication Data
US 2016/0120850 A1 May 5, 2016

Related U.S. Application Data

(60) Provisional application No. 62/072,614, filed on Oct. 30, 2014.

(51) Int. Cl.
| | | |
|---|---|---|
| *A61K 31/426* | (2006.01) | |
| *C07D 417/04* | (2006.01) | |
| *A61K 31/427* | (2006.01) | |
| *A61K 45/06* | (2006.01) | |
| *C07D 417/14* | (2006.01) | |
| *A61K 31/5377* | (2006.01) | |
| *A61K 31/4725* | (2006.01) | |
| *A61K 31/454* | (2006.01) | |
| *A61K 31/433* | (2006.01) | |
| *C07D 277/30* | (2006.01) | |
| *A61K 31/506* | (2006.01) | |

(52) U.S. Cl.
CPC .......... *A61K 31/426* (2013.01); *A61K 31/427* (2013.01); *A61K 31/433* (2013.01); *A61K 31/454* (2013.01); *A61K 31/4725* (2013.01); *A61K 31/506* (2013.01); *A61K 31/5377* (2013.01); *A61K 45/06* (2013.01); *C07D 277/30* (2013.01); *C07D 417/04* (2013.01); *C07D 417/14* (2013.01)

(58) Field of Classification Search
CPC ... C07D 417/04; C07D 417/14; C07D 277/30
See application file for complete search history.

(56) References Cited

U.S. PATENT DOCUMENTS

| | | | |
|---|---|---|---|
| 5,342,835 A | 8/1994 | Pepin et al. | |
| 7,138,403 B2 * | 11/2006 | Love | C07D 277/28 514/266.2 |
| 2015/0038350 A1 | 2/2015 | Nishinaga et al. | |
| 2015/0072890 A1 | 3/2015 | James | |

FOREIGN PATENT DOCUMENTS

| | | |
|---|---|---|
| EP | 360701 A1 | 3/1990 |
| EP | 2738170 | 6/2014 |
| WO | WO 9603392 A1 | 2/1996 |
| WO | WO 02083111 A2 | 10/2002 |
| WO | WO 03015776 A1 | 2/2003 |
| WO | WO 2006124687 A1 | 11/2006 |
| WO | WO 2007087427 A2 | 8/2007 |
| WO | WO 2008064317 A1 | 5/2008 |
| WO | WO 2008064318 A2 | 5/2008 |
| WO | WO 2009011850 | 1/2009 |
| WO | WO 2010006713 | 1/2010 |
| WO | WO 2011053948 A1 | 5/2011 |
| WO | WO 2011112263 A1 | 9/2011 |
| WO | WO 2011112264 A1 | 9/2011 |

(Continued)

OTHER PUBLICATIONS

PCT/US2015/058193, Written Opinion dated Jan. 26, 2016.

(Continued)

*Primary Examiner* — Rebecca L Anderson
(74) *Attorney, Agent, or Firm* — Yuriy P. Stercho

(57) ABSTRACT

The present invention comprises compounds of Formula I

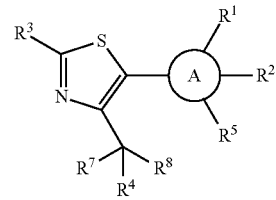

Formula I wherein:
$R^1$, $R^2$, $R^3$, $R^4$, $R^5$, $R^7$, $R^8$, and

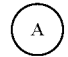

are defined in the specification.

The invention also comprises a method of treating or ameliorating a syndrome, disorder or disease, wherein the syndrome, disorder or disease is rheumatoid arthritis or psoriasis. The invention also comprises a method of modulating RORγt activity in a mammal by administration of a therapeutically effective amount of at least one compound of Formula I.

8 Claims, No Drawings

(56) References Cited

FOREIGN PATENT DOCUMENTS

| | | |
|---|---|---|
| WO | WO 2011115892 A1 | 9/2011 |
| WO | WO 2012027965 | 3/2012 |
| WO | WO 2012074547 A2 | 6/2012 |
| WO | WO 2012129491 | 9/2012 |
| WO | WO 2012158784 A2 | 11/2012 |
| WO | WO 2013036912 A2 | 3/2013 |
| WO | WO 2013079223 A | 6/2013 |
| WO | WO 2013092939 A1 | 6/2013 |
| WO | WO 2013178362 A1 | 12/2013 |
| WO | WO 2015035278 A1 | 3/2015 |
| WO | WO 2015042212 A1 | 3/2015 |
| WO | WO 2015082533 A1 | 6/2015 |
| WO | WO 2015103507 A1 | 7/2015 |
| WO | WO 2015103508 A1 | 7/2015 |
| WO | WO 2015103509 A1 | 7/2015 |
| WO | WO 2015103510 A1 | 7/2015 |
| WO | WO 2015145371 A1 | 10/2015 |

OTHER PUBLICATIONS

PCT/US2015/058198, Written Opinion dated Jan. 21, 2016.
PCT/US2015/058200, Written Opinion dated Jan. 27, 2016.
Liegault, et al., "Establishment of Broadly Applicable reaction condisions for the Palladium-Catalyzed Direct Arylation of Heteroatom-Containing Aromatic Compounds", The Journal of Organic Chemistry, (2009), vol. 74, No. 5, 6, pp. 1826-1834.
Kumar N, "The Benzenesulfoamide T0901317 [N-(2,2,2-Trifluoroethyl)-N-[4-[2,2,2-trifluoro-1-hydroxy-1-(trifluoromethyl)ethyl]phenyl]-benzenesulfonamide] Is a Novel Retinoic Acid Receptor-Related Orphan Receptor-α/γ Inverse Agonist", Molecular Pharmacology (2010), 77(2), 228-236.
Chang M, "Pharmacologic Repression of Retinoic Acid Receptor—Related Orphan Nuclear Receptor γ Is Therapeutic in the Collagen-Induced Arthritis Experimental Model", Arthritis & Rheumatology (2014), 66(3), 579-588.
Yao, et al, "Preparation Method of N-butyl-5-phenylthiazole-4-Formamide Derivative Via Coupling Reaction Under Catalysis of Copper Catalyst", Database accession No. 2014:924023, 2014.
Zhang, et al., "Decarboxylative Cross-Coupling of Azoyl Carboxylic Acids with Aryl Halides", Organic Letters, (2010) vol. 12, No. 21, pp. 4745-47457.
PCT/US2015/058193, International Search Report, Dated Jan. 26, 2016.
PCT/US2015/058198, International Search Report, Dated Jan. 21, 2016.
PCT/US2015/058200, International Search Report, Dated Jan. 27, 2016.
U.S. Appl. No. 14/927,499, Office Action Dated Feb. 24, 2016.
U.S. Appl. No. 14/927,499.
U.S. Appl. No. 14/927,502.
Fauber et al., J. Med. Chem. 2014, 57, 5871-5892.
Yang et al., Trends in Pharmacological Sciences, Oct. 2014, vol. 35, No. 10, 493-500.
Steven Goldberg et al., U.S. Appl. No. 15/497,565.
Barczyk, A., W. Pierzchala, et al. (2003). "Interleukin-17 in sputum correlates with airway hyperresponsiveness to methacholine." Respir Med 97(6): 726-33.
Beurel, E., Harrington, L. E., Jope, R. S. (2013) "Inflammatory T helper 17 cells promote depression-like behavior in mice." Biol Psychiatry 73(7): 622-30.
Bowes, J. and A. Barton "The genetics of psoriatic arthritis: lessons from genome-wide association studies." Discov Med 10(52): 177-83 (2010).
Chang, M. R. et al. (2015) "Antiobesity Effect of a Small Molecule Repressor of RORγ." Mol Pharmacol. 88(1): 48-56.
Chen, Y., et al. (2011). "Emerging tendency towards autoimmune process in major depressive patients: A novel insight from Th17 cells." Psychiatry Research 188(2): 224-230.
Cua, D. J., J. Sherlock, et al. (2003). "Interleukin-23 rather than interleukin-12 is the critical cytokine for autoimmune inflammation of the brain." Nature 421(6924): 744-8.
Dong, C. (2006). "Diversification of T-helper-cell lineages: finding the family root of IL-17-producing cells." Nat Rev Immunol 6(4): 329-33.
Fujino, S., A. Andoh, et al. (2003). "Increased expression of interleukin 17 in inflammatory bowel disease." Gut 52(1): 65-70.
Garber K. (2011). "Psoriasis: from bed to bench and back" Nat Biotech 29, 563-566.
Gazouli, M., I. Pachoula, et al. "NOD2/CARD15, ATG16L1 and IL23R gene polymorphisms and childhood-onset of Crohn's disease." World J Gastroenterol 16(14): 1753-8 (2010).
Hueber, W., Patel, D.D., Dryja, T., Wright, A.M., Koroleva, I., Bruin, G., Antoni, C., Draelos, Z., Gold, M.H., Durez, P., Tak, P.P., Gomez-Reino, J.J., Foster, C.S., Kim, R.Y., Samson, C.M., Falk, N.S., Chu, D.S., Callanan, D., Nguyen, Q.D., Rose, K., Haider, A., Di Padova, F. (2010) Effects of AIN457, a fully human antibody to interleukin-17A, on psoriasis, rheumatoid arthritis, and uveitis. Sci Transl Med 2, 5272.
Ivanov, II, B. S. McKenzie, et al. (2006). "The orphan nuclear receptor RORgammat directs the differentiation program of proinflammatory IL-17+ T helper cells." Cell 126(6): 1121-33.
Kochi, Y., Y. Okada, et al. (2010) "A regulatory variant in CCR6 is associated with rheumatoid arthritis susceptibility." Nat Genet 42(6): 515-9.
Kolls, J. K. and A. Linden (2004). "Interleukin-17 family members and inflammation." Immunity 21(4): 467-76.
Korn, T., E. Bettelli, et al. (2009). "IL-17 and Th17 Cells." Annu Rev Immunol 27: 485-517.
Krueger, J. G., S. Fretzin, et al. "IL-17A is essential for cell activation and inflammatory gene circuits in subjects with psoriasis." J Allergy Clin Immunol 130(1): 145-154 e9 (2012).
Langrish, C. L., Y. Chen, et al. (2005). "IL-23 drives a pathogenic T cell population that induces autoimmune inflammation." J Exp Med 201(2): 233-40.
Leonardi, C., R. Matheson, et al. "Anti-interleukin-17 monoclonal antibody ixekizumab in chronic plaque psoriasis." N Engl J Med 366(13): 1190-9 (2012).
Lock, C., G. Hermans, et al. (2002). "Gene-microarray analysis of multiple sclerosis lesions yields new targets validated in autoimmune encephalomyelitis." Nat Med 8(5): 500-8.
Matulis, D., Kranz, J. K., Salemme, F. R., and Todd, M. J. (2005) Thermodynamic stability of carbonic anhydrase: measurements of binding affinity and stoichiometry using ThermoFluor. *Biochemistry* 44, 5258-66.
McKenzie, B. S., R. A. Kastelein, et al. (2006). "Understanding the IL-23-IL-17 immune pathway." Trends Immunol 27(1): 17-23.
Meissburger, B. et al. (2011) "Adipogenesis and insulin sensitivity in obesity are regulated by retinoid-related orphan receptor gamma." EMBO Mol Med. 3(11): 637-651.
Nunez, C., B. Dema, et al. (2008). "IL23R: a susceptibility locus for celiac disease and multiple sclerosis?" Genes Immun 9(4): 289-93.
Pantoliano, M. W., Petrella, E. C., Kwasnoski, J. D., Lobanov, V. S., Myslik, J., Graf, E., Carver, T., Asel, E., Springer, B. A., Lane, P., and Salemme, F. R. (2001) High-density miniaturized thermal shift assays as a general strategy for drug discovery. *J Biomol Screen 6*, 429-40.
Papp, K. A., "Brodalumab, an anti-interleukin-17-receptor antibody for psoriasis." N Engl J Med 2012 366(13): 1181-9.
Stamp, L. K., M. J. James, et al. (2004). "Interleukin-17: the missing link between T-cell accumulation and effector cell actions in rheumatoid arthritis" Immunol Cell Biol 82(1): 1-9.
Tonel, G., C. Conrad, et al. "Cutting edge: A critical functional role for IL-23 in psoriasis." J Immunol 185(10): 5688-91 (2010).
Yen, D., J. Cheung, et al. (2006). "IL-23 is essential for T cell-mediated colitis and promotes inflammation via IL-17 and IL-6." J Clin Invest 116(5): 1310-6.

* cited by examiner

THIAZOLES AS MODULATORS OF RORγT

CROSS-REFERENCE TO RELATED APPLICATIONS

This application claims priority from U.S. Application No. 62/072,614, filed on Oct. 30, 2014, which is incorporated herein by reference.

FIELD OF THE INVENTION

The invention is directed to substituted thiazole compounds, which are modulators of the nuclear receptor RORγt, pharmaceutical compositions, and methods for use thereof. More particularly, the RORγt modulators are useful for preventing, treating or ameliorating an RORγt mediated inflammatory syndrome, disorder or disease.

BACKGROUND OF THE INVENTION

Retinoic acid-related nuclear receptor gamma t (RORγt) is a nuclear receptor, exclusively expressed in cells of the immune system, and a key transcription factor driving Th17 cell differentiation. Th17 cells are a subset of $CD4^+$ T cells, expressing CCR6 on their surface to mediate their migration to sites of inflammation, and dependent on IL-23 stimulation, through the IL-23 receptor, for their maintenance and expansion. Th17 cells produce several proinflammatory cytokines including IL-17A, IL-17F, IL-21, and IL-22 (Korn, T., E. Bettelli, et al. (2009). "IL-17 and Th17 Cells." Annu Rev Immunol 27: 485-517), which stimulate tissue cells to produce a panel of inflammatory chemokines, cytokines and metalloproteases, and promote recruitment of granulocytes (Kolls, J. K. and A. Linden (2004). "Interleukin-17 family members and inflammation." Immunity 21(4): 467-76; Stamp, L. K., M. J. James, et al. (2004). "Interleukin-17: the missing link between T-cell accumulation and effector cell actions in rheumatoid arthritis" Immunol Cell Biol 82(1): 1-9). Th17 cells have been shown to be the major pathogenic population in several models of autoimmune inflammation, including collagen-induced arthritis (CIA) and experimental autoimmune encephalomyelitis (EAE) (Dong, C. (2006). "Diversification of T-helper-cell lineages: finding the family root of IL-17-producing cells." Nat Rev Immunol 6(4): 329-33; McKenzie, B. S., R. A. Kastelein, et al. (2006). "Understanding the IL-23-IL-17 immune pathway." Trends Immunol 27(1): 17-23). RORγt-deficient mice are healthy and reproduce normally, but have shown impaired Th17 cell differentiation in vitro, a significantly reduced Th17 cell population in vivo, and decreased susceptibility to EAE (Ivanov, II, B. S. McKenzie, et al. (2006). "The orphan nuclear receptor RORgammat directs the differentiation program of proinflammatory IL-17+ T helper cells." Cell 126(6): 1121-33). Mice deficient for IL-23, a cytokine required for Th17 cell survival, fail to produce Th17 cells and are resistant to EAE, CIA, and inflammatory bowel disease (IBD) (Cua, D. J., J. Sherlock, et al. (2003). "Interleukin-23 rather than interleukin-12 is the critical cytokine for autoimmune inflammation of the brain." Nature 421(6924): 744-8; Langrish, C. L., Y. Chen, et al. (2005). "IL-23 drives a pathogenic T cell population that induces autoimmune inflammation." J Exp Med 201(2): 233-40; Yen, D., J. Cheung, et al. (2006). "IL-23 is essential for T cell-mediated colitis and promotes inflammation via IL-17 and IL-6." J Clin Invest 116(5): 1310-6). Consistent with these findings, an anti-IL23-specific monoclonal antibody blocks development of psoriasis-like inflammation in a murine disease model (Tonel, G., C. Conrad, et al. "Cutting edge: A critical functional role for IL-23 in psoriasis." J Immunol 185(10): 5688-91).

In humans, a number of observations support the role of the IL-23/Th17 pathway in the pathogenesis of inflammatory diseases. IL-17, the key cytokine produced by Th17 cells, is expressed at elevated levels in a variety of allergic and autoimmune diseases (Barczyk, A., W. Pierzchala, et al. (2003). "Interleukin-17 in sputum correlates with airway hyperresponsiveness to methacholine." Respir Med 97(6): 726-33; Fujino, S., A. Andoh, et al. (2003). "Increased expression of interleukin 17 in inflammatory bowel disease." Gut 52(1): 65-70; Lock, C., G. Hermans, et al. (2002). "Gene-microarray analysis of multiple sclerosis lesions yields new targets validated in autoimmune encephalomyelitis." Nat Med 8(5): 500-8; Krueger, J. G., S. Fretzin, et al. "IL-17A is essential for cell activation and inflammatory gene circuits in subjects with psoriasis." J Allergy Clin Immunol 130(1): 145-154 e9). Furthermore, human genetic studies have shown association of polymorphisms in the genes for Th17 cell-surface receptors, IL-23R and CCR6, with susceptibility to IBD, multiple sclerosis (MS), rheumatoid arthritis (RA) and psoriasis (Gazouli, M., I. Pachoula, et al. "NOD2/CARD15, ATG16L1 and IL23R gene polymorphisms and childhood-onset of Crohn's disease." World J Gastroenterol 16(14): 1753-8, Nunez, C., B. Dema, et al. (2008). "IL23R: a susceptibility locus for celiac disease and multiple sclerosis?" Genes Immun 9(4): 289-93; Bowes, J. and A. Barton "The genetics of psoriatic arthritis: lessons from genome-wide association studies." Discov Med 10(52): 177-83; Kochi, Y., Y. Okada, et al. "A regulatory variant in CCR6 is associated with rheumatoid arthritis susceptibility." Nat Genet 42(6): 515-9).

Ustekinumab (Stelara®), an anti-p40 monoclonal antibody blocking both IL-12 and IL-23, is approved for the treatment of adult patients (18 years or older), with moderate to severe plaque psoriasis, who are candidates for phototherapy or systemic therapy. Currently, monoclonal antibodies specifically targeting only IL-23, to more selectively inhibit the Th17 subset, are also in clinical development for psoriasis (Garber K. (2011). "Psoriasis: from bed to bench and back" Nat Biotech 29, 563-566), further implicating the important role of the IL-23- and RORγt-driven Th17 pathway in this disease. Results from recent phase II clinical studies strongly support this hypothesis, as anti-IL-17 receptor and anti-IL-17 therapeutic antibodies both demonstrated high levels of efficacy in patients with chronic psoriasis (Papp, K. A., "Brodalumab, an anti-interleukin-17-receptor antibody for psoriasis." N Engl J Med 2012 366(13): 1181-9; Leonardi, C., R. Matheson, et al. "Anti-interleukin-17 monoclonal antibody ixekizumab in chronic plaque psoriasis." N Engl J Med 366(13): 1190-9). Anti-IL-17 antibodies have also demonstrated clinically relevant responses in early trials in RA and uveitis (Hueber, W., Patel, D. D., Dryja, T., Wright, A. M., Koroleva, I., Bruin, G., Antoni, C., Draelos, Z., Gold, M. H., Durez, P., Tak, P. P., Gomez-Reino, J. J., Foster, C. S., Kim, R. Y., Samson, C. M., Falk, N. S., Chu, D. S., Callanan, D., Nguyen, Q. D., Rose, K., Haider, A., Di Padova, F. (2010) Effects of AIN457, a fully human antibody to interleukin-17A, on psoriasis, rheumatoid arthritis, and uveitis. Sci Transl Med 2, 5272).

All the above evidence supports inhibition of the Th17 pathway by modulating RORγt activity as an effective strategy for the treatment of immune-mediated inflammatory diseases.

SUMMARY OF THE INVENTION

The present invention comprises compounds of Formula I:

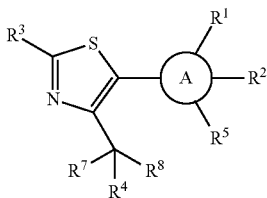

Formula I wherein

is phenyl, pyridyl, pyrimidyl, pyrazinyl, or pyridazyl;

$R^1$ is H, Cl, OCF$_3$, C$_{(1-4)}$alkyl, —CN, F, OC$_{(1-4)}$alkyl, OCHF$_2$, Br, I, or cyclopropyl; wherein said C$_{(1-4)}$alkyl is optionally substituted with up to six fluorine atoms;

$R^2$ is H, F, Cl, —CN, OC$_{(1-4)}$alkyl, OCHF$_2$, OCF$_3$, cyclopropyl, or C$_{(1-4)}$alkyl; wherein said C$_{(1-4)}$alkyl is optionally substituted with up to five fluorine atoms, and said cyclopropyl is optionally substituted with OH, CH$_3$, CF$_3$, —CN, and up to five fluorine atoms; or $R^1$ and $R^2$ may be taken together with their attached ring A to form a fused ring system selected from the group consisting of naphthalenyl, isoquinolinyl, tetrahydronaphthalenyl, quinolinyl, 2,3-dihydro-1H-indenyl, chromanyl, isochromanyl, and naphthyridinyl; wherein said naphthalenyl, isoquinolinyl, tetrahydronaphthalenyl, quinolinyl, 2,3-dihydro-1H-indenyl, chromanyl, isochromanyl, and naphthyridinyl are optionally substituted up to three times with F, C$_{(1-3)}$alkyl, or OC$_{(1-3)}$alkyl; wherein each substituent is selected independently; wherein said OC$_{(1-3)}$alkyl and C$_{(1-3)}$ alkyl is optionally substituted with up to five fluorine atoms; provided that $R^2$ may not be H if $R^1$ is H;

$R^3$ is oxadiazolyl, thiazolyl, thiadiazolyl, isoxadiazolyl, isoxazolyl, phenyl, oxazolyl, triazolyl, tetrazolyl, 1,2,4-oxadiazol-5(4H)-on-3-yl, pyridyl, pyrimidyl, pyridazyl, pyrazyl, imidazolyl, pyrrolyl, or furanyl; wherein said oxadiazolyl, thiazolyl, thiadiazolyl, isoxadiazolyl, isoxazolyl, phenyl, oxazolyl, triazolyl, pyridyl, pyrimidyl, pyridazyl, pyrazyl, imidazolyl, pyrrolyl, or furanyl is optionally substituted with $R^6$, and further optionally substituted with one substituent selected from the group consisting of F, CH$_3$, and CF$_3$;

$R^6$ is

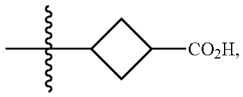 [SMILES: *C1CC(C(=O)O)C1]

C$_{(1-6)}$alkyl, C(O)NH$_2$, —CN, C$_{(3-6)}$cycloalkyl, NH$_2$, NH(C$_{(1-6)}$alkyl), N(C$_{(1-6)}$alkyl)$_2$, NHCO(C$_{(1-6)}$alkyl), N(C$_{(1-6)}$alkyl)CO(C$_{(1-6)}$alkyl), NHSO$_2$(C$_{(1-6)}$alkyl), N(C$_{(1-6)}$alkyl)SO$_2$(C$_{(1-6)}$alkyl), O(C$_{(1-6)}$alkyl), C(O)NH$_2$, CONH(C$_{(1-6)}$alkyl), CON(C$_{(1-6)}$alkyl)$_2$, SO$_2$NH$_2$, SO$_2$NH(C$_{(1-6)}$alkyl), SO$_2$NH(COC$_{(1-6)}$alkyl), or SO$_2$N(C$_{(1-6)}$alkyl)$_2$; wherein said C$_{(1-6)}$alkyl or C$_{(3-6)}$cycloalkyl is optionally independently substituted with up to six fluorine atoms, CO$_2$H, OH, —CN, C(O)NH$_2$, NH$_2$, OCH$_3$, OCHF$_2$, OCF$_3$, —(CX$_2$)$_m$—, or N(CH$_3$)$_2$;

wherein m is 2, 3, 4, or 5;

X is H, or F; wherein each occurrence of X in a single molecule is independently defined;

$R^4$ is H, C$_{(3-8)}$cycloalkyl, C$_{(3-8)}$alkyl, OC$_{(1-8)}$alkyl, phenyl, pyridyl, CH$_2$SO$_2$C$_{(1-3)}$alkyl, NA$^1$A$^2$, CH$_2$O—C$_{(3-8)}$alkyl, O—C$_{(3-8)}$cycloalkyl, tetrahydrofuranyl, tetrahydropyranyl, thiadiazolyl, oxadiazolyl, isoxadiazolyl, oxazolyl, isoxazolyl, triazolyl, tetrazolyl, pyrimidyl, pyridazyl, pyrazyl, imidazolyl, pyrrolyl, or furanyl, wherein said C$_{(3-8)}$alkyl and O—C$_{(3-8)}$alkyl are optionally substituted with 1 to 4 substituents independently selected from F, Cl, OH, OCH$_3$, OCHF$_2$, OCF$_3$, and —CN; and said C$_{(3-8)}$cycloalkyl, O—C$_{(3-8)}$cycloalkyl, tetrahydrofuranyl, tetrahydropyranyl, phenyl, thiadiazolyl, oxadiazolyl, isoxadiazolyl, oxazolyl, isoxazolyl, triazolyl, tetrazolyl, pyridyl, pyrimidyl, pyridazyl, pyrazyl, imidazolyl, pyrrolyl, and furanyl are optionally substituted with 1 to 4 substituents independently selected from the group consisting of F, Cl, CH$_3$, CHF$_2$, CF$_3$, OH, OCH$_3$, OCHF$_2$, OCF$_3$, and —CN;

$A^1$ is H, or C$_{(1-4)}$alkyl; wherein said C$_{(1-4)}$alkyl is optionally substituted with up to six fluorine atoms, Cl, —CN, OCH$_3$, OCHF$_2$, or OCF$_3$;

$A^2$ is C$_{(1-6)}$alkyl, C$_{(0-2)}$alkyl-C$_{(3-6)}$cycloalkyl,

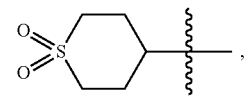

CH$_2$—C$_6$H$_4$—C(O)NH$_2$, —C$_6$H$_4$—F, or CH$_2$—CCH; wherein said C$_{(1-6)}$alkyl, and said C$_{(0-2)}$alkyl-C$_{(3-6)}$cycloalkyl are optionally substituted with up to six fluorine atoms, Cl, —CN, OCH$_3$, OCHF$_2$, or OCF$_3$;

or $A^1$ and $A^2$ may be taken together with their attached nitrogen to form a ring selected from the group consisting of:

thiomorpholinyl, piperidinyl, pyrrolidinyl, piperazinyl, morpholinyl, azetidinyl, and aziridinyl; wherein said piperidinyl, pyrrolidinyl, piperazinyl, morpholinyl, azetidinyl, and aziridinyl are optionally substituted with CF$_3$, CHF$_2$, CH$_2$F, CH$_2$CH$_2$F, C$_{(1-2)}$alkyl, C$_{(3-6)}$cycloalkyl, —CN, OH, CH$_2$OH, F, Cl, OCH$_3$, OCHF$_2$, OCF$_3$, —(CX$_2$)$_n$O(CX$_2$)$_n$—, or —(CX$_2$)$_n$— and up to three additional substituents selected from the group consisting of CH$_3$, and F;

wherein n is independently 0, 1, 2, 3, or 4;

X is H, or F; wherein each occurrence of X in a single molecule is independently defined;

$R^5$ is SO$_2$NA$^3$A$^4$, CONA$^3$A$^4$, NA$^3$A$^4$, or C$_{(1-6)}$alkyl; wherein said C$_{(1-6)}$alkyl is optionally substituted with OH, Cl, —CN, OCH$_3$, OCHF$_2$, OCF$_3$, NA$^3$A$^4$, or cyclopropyl, and up to six fluorine atoms;

$A^3$ is H, or C$_{(1-4)}$alkyl; wherein said C$_{(1-4)}$alkyl is optionally substituted with OH, Cl, —CN, OCH$_3$, OCHF$_2$, or OCF$_3$; and up to six fluorine atoms;

$A^4$ is C$_{(1-6)}$alkyl, C$_{(3-6)}$cycloalkyl, or C$_{(3-6)}$heterocycloalkyl; wherein said C$_{(1-6)}$alkyl is optionally substituted with cyclopropyl, morpholinyl, OH, OCH$_3$, C(O)NH$_2$, Cl, —CN, OCHF$_2$, OCF$_3$ and additionally substituted with up to three fluorine atoms; and wherein said C$_{(3-6)}$cycloalkyl, and C$_{(3-6)}$heterocycloalkyl are optionally substituted with CF₃, CH₃, —CN, C(O)NH₂, and up to three fluorine atoms;

or A³ and A⁴ can be taken together with their attached nitrogen to form a ring selected from the group consisting of azetidinyl, piperidinyl, morpholinyl, piperazinyl, pyrrolidinyl, and aziridinyl wherein said azetidinyl, piperidinyl, morpholinyl, piperazinyl pyrrolidinyl, and aziridinyl are optionally substituted with up to four groups selected from the group consisting of CF₃, OH, CH₃, CH₂F, and CHF₂; and further optionally substituted with up to six fluorine atoms;

R⁷ is H, F, OH, OCH₃, CH₃, CHF₂, CH₂F, or CF₃;

R⁸ is H, or F; or if R⁴ is H, then R⁷ and R⁸ may be taken together to form a C₍₃₋₆₎cycloalkyl ring; and pharmaceutically acceptable salts thereof.

DETAILED DESCRIPTION OF THE INVENTION

The present invention comprises compounds of Formula I:

Formula I

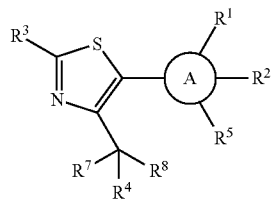

wherein

is phenyl, pyridyl, pyrimidyl, pyrazinyl, or pyridazyl;

R¹ is H, Cl, OCF₃, C₍₁₋₄₎alkyl (including C₍₁₋₃₎alkyl), —CN, F, OC₍₁₋₄₎alkyl (including C₍₁₋₃₎alkyl), OCHF₂, Br, I, or cyclopropyl; wherein said C₍₁₋₄₎alkyl is optionally substituted with up to six fluorine atoms;

R² is H, F, Cl, —CN, OC₍₁₋₄₎alkyl, OCHF₂, OCF₃, cyclopropyl, or C₍₁₋₄₎alkyl; wherein said C₍₁₋₄₎alkyl is optionally substituted with up to five fluorine atoms, and said cyclopropyl is optionally substituted with OH, CH₃, CF₃, —CN, and up to five fluorine atoms; or R¹ and R² may be taken together with their attached ring A to form a fused ring system selected from the group consisting of naphthalenyl, isoquinolinyl, tetrahydronaphthalenyl, quinolinyl, 2,3-dihydro-1H-indenyl, chromanyl, isochromanyl, and naphthyridinyl; wherein said naphthalenyl, isoquinolinyl, tetrahydronaphthalenyl, quinolinyl, 2,3-dihydro-1H-indenyl, chromanyl, isochromanyl, and naphthyridinyl are optionally substituted up to three times with F, C₍₁₋₃₎alkyl, or OC₍₁₋₃₎alkyl; wherein each substituent is selected independently; wherein said OC₍₁₋₃₎alkyl and C₍₁₋₃₎ alkyl is optionally substituted with up to five fluorine atoms; provided that R² may not be H if R¹ is H;

R³ is oxadiazolyl, thiazolyl, thiadiazolyl, isoxadiazolyl, isoxazolyl, phenyl, oxazolyl, triazolyl, tetrazolyl, 1,2,4-oxadiazol-5(4H)-on-3-yl, pyridyl, pyrimidyl, pyridazyl, pyrazyl, imidazolyl, pyrrolyl, or furanyl; wherein said oxadiazolyl, thiazolyl, thiadiazolyl, isoxadiazolyl, isoxazolyl, phenyl, oxazolyl, triazolyl, pyridyl, pyrimidyl, pyridazyl, pyrazyl, imidazolyl, pyrrolyl, or furanyl is optionally substituted with R⁶, and further optionally substituted with one substituent selected from the group consisting of F, CH₃, and CF₃;

R⁶ is

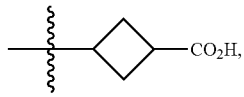 [SMILES: *C1CC(C(=O)O)C1]

C₍₁₋₆₎alkyl, C(O)NH₂, —CN, C₍₃₋₆₎cycloalkyl, NH₂, NH(C₍₁₋₆₎alkyl), N(C₍₁₋₆₎alkyl)₂, NHCO(C₍₁₋₆₎alkyl), N(C₍₁₋₆₎alkyl)CO(C₍₁₋₆₎alkyl), NHSO₂(C₍₁₋₆₎alkyl), N(C₍₁₋₆₎alkyl)SO₂(C₍₁₋₆₎alkyl), O(C₍₁₋₆₎alkyl), C(O)NH₂, CONH(C₍₁₋₆₎alkyl), CON(C₍₁₋₆₎alkyl)₂, SO₂NH₂, SO₂NH(C₍₁₋₆₎alkyl), SO₂NH(COC₍₁₋₆₎alkyl), or SO₂N(C₍₁₋₆₎alkyl)₂; wherein said C₍₁₋₆₎alkyl or C₍₃₋₆₎cycloalkyl is optionally independently substituted with up to six fluorine atoms, CO₂H, OH, —CN, C(O)NH₂, NH₂, OCH₃, OCHF₂, OCF₃, —(CX₂)ₘ—, or N(CH₃)₂;

wherein m is 2, 3, 4, or 5;

X is H, or F; wherein each occurrence of X in a single molecule is independently defined;

R⁴ is H, C₍₃₋₈₎cycloalkyl, C₍₃₋₈₎alkyl, OC₍₁₋₈₎alkyl, phenyl, pyridyl, CH₂SO₂C₍₁₋₃₎alkyl, NA¹A², CH₂O—C₍₃₋₈₎alkyl, O—C₍₃₋₈₎cycloalkyl, tetrahydrofuranyl, tetrahydropyranyl, thiadiazolyl, oxadiazolyl, isoxadiazolyl, oxazolyl, isoxazolyl, triazolyl, tetrazolyl, pyrimidyl, pyridazyl, pyrazyl, imidazolyl, pyrrolyl, or furanyl, wherein said C₍₃₋₈₎alkyl and O—C₍₃₋₈₎alkyl are optionally substituted with 1 to 4 substituents independently selected from F, Cl, OH, OCH₃, OCHF₂, OCF₃, and —CN; and said C₍₃₋₈₎cycloalkyl, O—C₍₃₋₈₎cycloalkyl, tetrahydrofuranyl, tetrahydropyranyl, phenyl, thiadiazolyl, oxadiazolyl, isoxadiazolyl, oxazolyl, isoxazolyl, triazolyl, tetrazolyl, pyridyl, pyrimidyl, pyridazyl, pyrazyl, imidazolyl, pyrrolyl, and furanyl are optionally substituted with 1 to 4 substituents independently selected from the group consisting of F, Cl, CH₃, CHF₂, CF₃, OH, OCH₃, OCHF₂, OCF₃, and —CN;

A¹ is H, or C₍₁₋₄₎alkyl; wherein said C₍₁₋₄₎alkyl is optionally substituted with up to six fluorine atoms, Cl, —CN, OCH₃, OCHF₂, or OCF₃;

A² is C₍₁₋₆₎alkyl, C₍₀₋₂₎alkyl-C₍₃₋₆₎cycloalkyl,

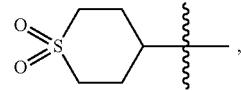

CH₂—C₆H₄—C(O)NH₂, —C₆H₄—F, or CH₂—CCH; wherein said C₍₁₋₆₎alkyl, and said C₍₀₋₂₎alkyl-C₍₃₋₆₎cycloalkyl are optionally substituted with up to six fluorine atoms, Cl, —CN, OCH₃, OCHF₂, or OCF₃;

or A¹ and A² may be taken together with their attached nitrogen to form a ring selected from the group consisting of:

thiomorpholinyl, piperidinyl, pyrrolidinyl, piperazinyl, morpholinyl, azetidinyl, and aziridinyl; wherein said piperidinyl, pyrrolidinyl, piperazinyl, morpholinyl, azetidinyl, and aziridinyl are optionally substituted with CF₃, CHF₂, CH₂F, CH₂CH₂F, C₍₁₋₂₎alkyl, C₍₃₋₆₎cycloalkyl, —CN, OH, CH₂OH, F, Cl, OCH₃, OCHF₂, $OCF_3$, $-(CX_2)_nO(CX_2)_n-$, or $-(CX_2)_n-$ and up to three additional substituents selected from the group consisting of $CH_3$, and F (including

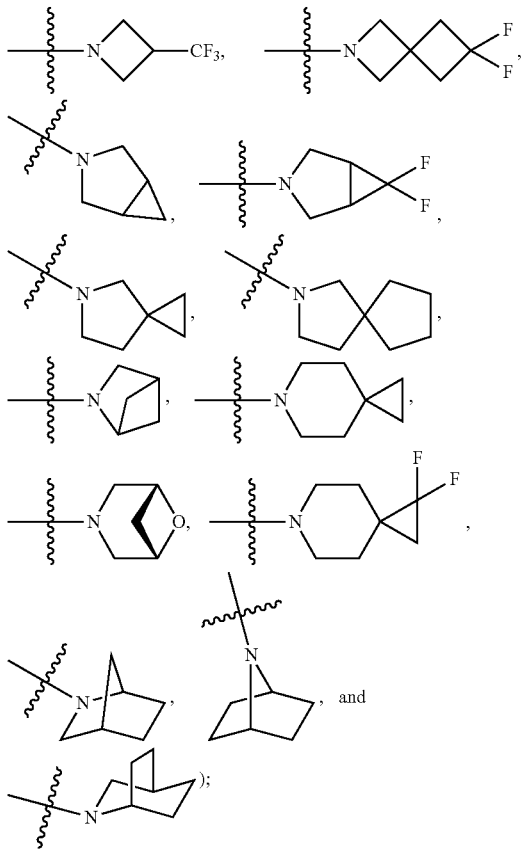

wherein n is independently 0, 1, 2, 3, or 4;
X is H, or F; wherein each occurrence of X in a single molecule is independently defined;
$R^5$ is $SO_2NA^3A^4$, $CONA^3A^4$ (including  ), $NA^3A^4$, or $C_{(1-6)}$alkyl; wherein said $C_{(1-6)}$alkyl is optionally substituted with OH, Cl, —CN, $OCH_3$, $OCHF_2$, $OCF_3$, $NA^3A^4$, or cyclopropyl, and up to six fluorine atoms;
$A^3$ is H, or $C_{(1-4)}$alkyl; wherein said $C_{(1-4)}$alkyl is optionally substituted with OH, Cl, —CN, $OCH_3$, $OCHF_2$, or $OCF_3$; and up to six fluorine atoms;
$A^4$ is $C_{(1-6)}$alkyl, $C_{(3-6)}$cycloalkyl, or $C_{(3-6)}$heterocycloalkyl; wherein said $C_{(1-6)}$alkyl is optionally substituted with cyclopropyl, morpholinyl, OH, $OCH_3$, $C(O)NH_2$, Cl, —CN, $OCHF_2$, $OCF_3$ and additionally substituted with up to three fluorine atoms; and wherein said $C_{(3-6)}$cycloalkyl, and $C_{(3-6)}$heterocycloalkyl are optionally substituted with $CF_3$, $CH_3$, —CN, $C(O)NH_2$, and up to three fluorine atoms;
or $A^3$ and $A^4$ can be taken together with their attached nitrogen to form a ring selected from the group consisting of azetidinyl, piperidinyl, morpholinyl, piperazinyl, pyrrolidinyl, and aziridinyl wherein said azetidinyl, piperidinyl, morpholinyl, piperazinyl pyrrolidinyl, and aziridinyl are optionally substituted with up to four groups selected from the group consisting of $CF_3$, OH, $CH_3$, $CH_2F$, and $CHF_2$; and further optionally substituted with up to six fluorine atoms;
$R^7$ is H, F, OH, $OCH_3$, $CH_3$, $CHF_2$, $CH_2F$, or $CF_3$;
$R^8$ is H, or F; or if $R^4$ is H, then $R^7$ and $R^8$ may be taken together to form a $C_{(3-6)}$cycloalkyl ring; and pharmaceutically acceptable salts thereof.

In another embodiment of the invention:

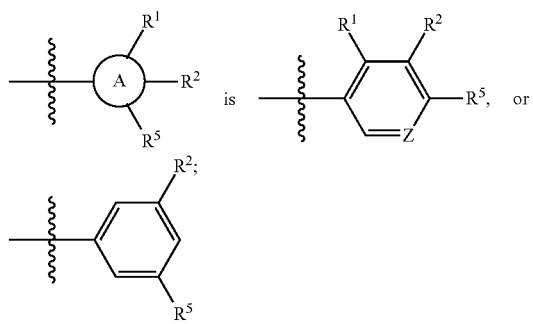

Z is N, or CH;
$R^1$ is H, Cl, $OCF_3$, $C_{(1-3)}$alkyl, —CN, F, $OC_{(1-3)}$alkyl, $OCHF_2$, Br, I, or cyclopropyl; wherein said $C_{(1-3)}$alkyl is optionally substituted with up to five fluorine atoms;
$R^2$ is H, F, Cl, —CN, $OCH_3$, $OCHF_2$, $OCF_3$, cyclopropyl, or $C_{(1-4)}$alkyl; wherein said $C_{(1-4)}$alkyl is optionally substituted with up to five fluorine atoms (including $CF_3$, and $CHF_2$), and said cyclopropyl is optionally substituted with OH, $CH_3$, $CF_3$, —CN, and up to five fluorine atoms; or $R^1$ and $R^2$ may be taken together with their attached ring A to form a fused ring system selected from the group consisting of naphthalenyl, isoquinolinyl, tetrahydronaphthalenyl, and quinolinyl, wherein said naphthalenyl, isoquinolinyl, tetrahydronaphthalenyl, and quinolinyl are optionally substituted with F, $CHF_2$, $CH_2F$, $CF_3$, or $CH_3$; provided that $R^2$ may not be H if $R^1$ is H;
$R^3$ is oxadiazolyl, thiazolyl, thiadiazolyl, isoxadiazolyl, isoxazolyl, phenyl, oxazolyl, triazolyl, tetrazolyl, 1,2,4-oxadiazol-5(4H)-on-3-yl, pyridyl, pyrimidyl, pyridazyl, pyrazyl, imidazolyl, or pyrrolyl; wherein said oxadiazolyl, thiazolyl, thiadiazolyl, isoxadiazolyl, isoxazolyl, phenyl, oxazolyl, triazolyl, pyridyl, pyrimidyl, pyridazyl, pyrazyl, imidazolyl, or pyrrolyl is optionally substituted with $R^6$;
$R^6$ is

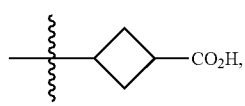 [SMILES: *C1CC(C(=O)O)C1]

$C_{(1-4)}$alkyl (including $C_{(1-2)}$alkyl), $C(O)NH_2$, or —CN; wherein said $C_{(1-4)}$alkyl is optionally substituted with up to six fluorine atoms, $CO_2H$, OH, or —CN (including $CH_2C(CH_3)_2CO_2H$, $CH_2C(CH_3)_2CN$, and $C_{(1-6)}$alkyl$C(CH_3)_2$OH);
$R^4$ is $C_{(3-6)}$cycloalkyl, isopropyl, $C(CH_3)_2OCH_3$, $OC_{(1-4)}$alkyl, fluorophenyl, difluorophenyl, pyridyl, $CH_2SO_2CH_3$, or NA¹A², wherein said $C_{(3-6)}$cycloalkyl is optionally substituted with $OCH_3$, two fluoro groups or two methyl groups;

A¹ is H, or $C_{(1-3)}$alkyl; wherein said $C_{(1-3)}$alkyl is optionally substituted with up to five fluorine atoms, Cl, —CN, $OCH_3$, $OCHF_2$, or $OCF_3$;

A² is $C_{(1-4)}$alkyl, $C_{(0-2)}$alkyl-$C_{(3-6)}$cycloalkyl, $CH_2$—$C_6H_4$—$C(O)NH_2$, —$C_6H_4$—F, or $CH_2$—CCH; wherein said $C_{(1-4)}$alkyl, and said $C_{(0-2)}$alkyl-$C_{(3-6)}$cycloalkyl are optionally substituted with up to three fluorine atoms, Cl, —CN, $OCH_3$, $OCHF_2$, or $OCF_3$ (including $CH_2CH_2$—CN);

or A¹ and A² may be taken together with their attached nitrogen to form a ring selected from the group consisting of:

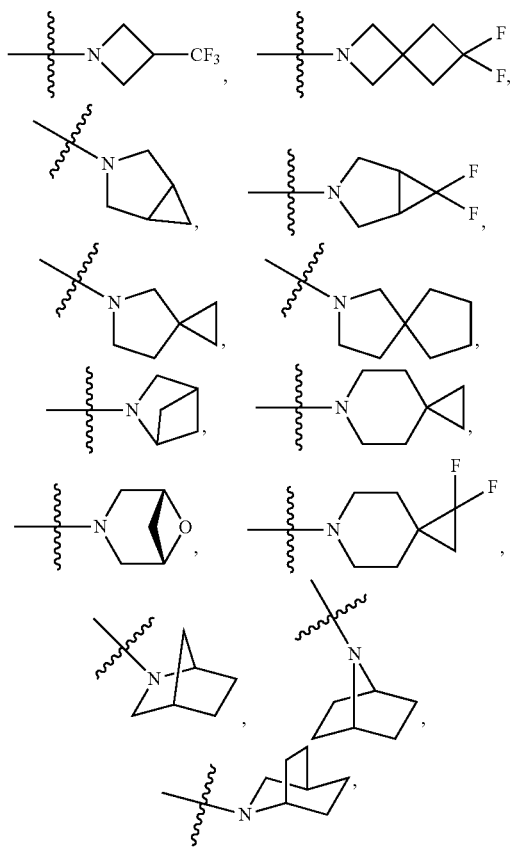

thiomorpholinyl, piperidinyl, pyrrolidinyl, piperazinyl, and morpholinyl; wherein said piperidinyl, pyrrolidinyl, piperazinyl, and morpholinyl are optionally substituted with $CF_3$, $CH_2F$, $CH_2CH_2F$, $C_{(1-2)}$alkyl, —CN, OH, $CH_2OH$, F, Cl, $OCH_3$, $OCHF_2$, or $OCF_3$, and up to three additional substituents selected from the group consisting of $CH_3$, and F;

R⁵ is $SO_2NA_3A_4$, $C_{(1-6)}$alkyl,

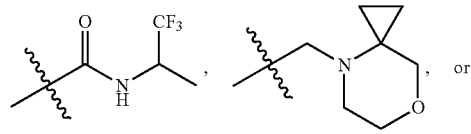

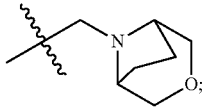

wherein said $C_{(1-6)}$alkyl is optionally substituted with OH, Cl, —CN, $OCH_3$, $OCHF_2$, $OCF_3$, or $NA^3A^4$; and up to six fluorine atoms;

A³ is H, or $C_{(1-4)}$alkyl; wherein said $C_{(1-4)}$alkyl is optionally substituted with OH, Cl, —CN, $OCH_3$, $OCHF_2$, or $OCF_3$; and up to six fluorine atoms;

A₄ is $C_{(1-6)}$alkyl, $C_{(3-6)}$cycloalkyl (including cyclopropyl, and cyclobutyl), oxetanyl, or tetrahydrofuranyl; wherein said $C_{(1-6)}$alkyl is optionally substituted with cyclopropyl, morpholinyl, OH, $OCH_3$, or $C(O)NH_2$, and additionally substituted with up to three fluorine atoms; and wherein said $C_{(3-6)}$cycloalkyl, oxetanyl, and tetrahydrofuranyl are optionally substituted with $CF_3$, $CH_3$, —CN, or $C(O)NH_2$;

or A³ and A⁴ can be taken together with their attached nitrogen to form a ring selected from the group consisting of azetidinyl, piperidinyl, morpholinyl, piperazinyl, and pyrrolidinyl wherein said azetidinyl, piperidinyl, morpholinyl, and piperazinyl are optionally substituted with up to four groups selected from the group consisting of $CF_3$, OH, and $CH_3$; and further optionally substituted with up to six fluorine atoms;

R⁷ is H, F, OH, or $OCH_3$;

R⁸ is H;

and pharmaceutically acceptable salts thereof.

In another embodiment of the invention:

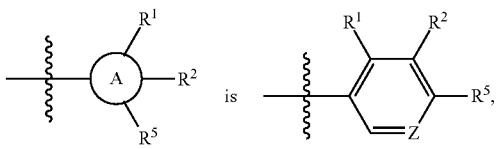

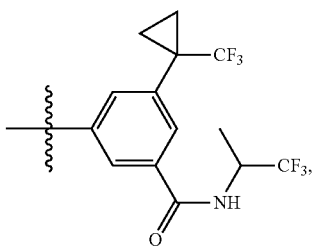

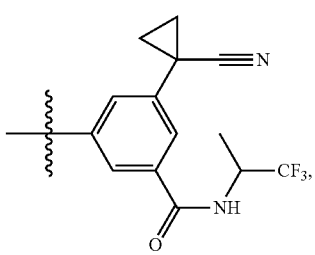

-continued

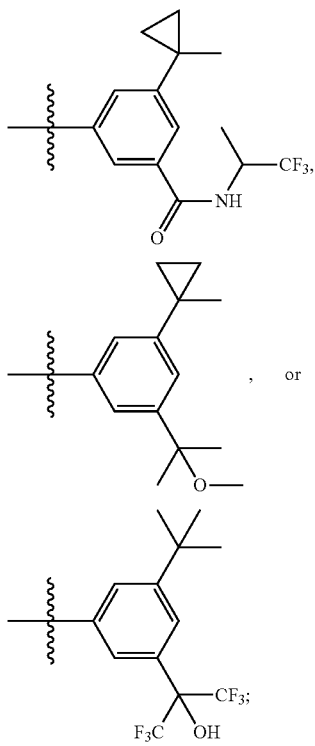

Z is N, or CH;

R¹ is H, Cl, OCF₃, C₍₁₋₃₎alkyl, —CN, F, OC₍₁₋₃₎alkyl, OCHF₂, or cyclopropyl, wherein said C₍₁₋₂₎alkyl is optionally substituted with up to five fluorine atoms (including CHF₂, and CF₃);

R² is CHF₂, CF₃, H, F, Cl, —CN,

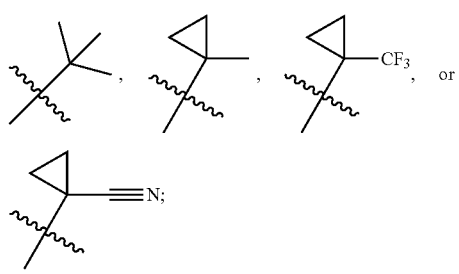

or R¹ and R² may be taken together with their attached ring A to form a fused ring system selected from the group consisting of naphthalenyl, isoquinolinyl, tetrahydronaphthalenyl, and quinolinyl, wherein said naphthalenyl, isoquinolinyl, tetrahydronaphthalenyl, and quinolinyl are optionally substituted with F, CHF₂, CH₂F, CF₃, or CH₃; provided that R² may not be H if R¹ is H;

R³ is oxadiazolyl, thiazolyl, thiadiazolyl, isoxadiazolyl, isoxazolyl, phenyl, oxazolyl, triazolyl, tetrazolyl, 1,2,4-oxadiazol-5(4H)-on-3-yl, pyridyl, pyrimidyl, pyridazyl, or pyrazyl; wherein said oxadiazolyl, thiazolyl, thiadiazolyl, isoxadiazolyl, isoxazolyl, phenyl, oxazolyl, triazolyl, pyridyl, pyrimidyl, pyridazyl, or pyrazyl is optionally substituted with R⁶;

R⁶ is

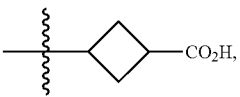 [SMILES: *C1CC(C(=O)O)C1]

C₍₁₋₂₎alkyl (including CH₃), CH₂C(CH₃)₂CO₂H, C₍₀₋₁₎alkylC(CH₃)₂OH, CH₂C(CH₃)₂CN, C(O)NH₂, or —CN; wherein said C₍₁₋₂₎alkyl is optionally substituted with up to five fluorine atoms;

R⁴ is C₍₃₋₆₎cycloalkyl, isopropyl, C(CH₃)₂OCH₃, OC₍₁₋₄₎alkyl (including OC(CH₃)₃ and OCH(CH₃)₂), fluorophenyl, difluorophenyl, pyridyl, CH₂SO₂CH₃, or NA¹A², wherein said C₍₃₋₆₎cycloalkyl is optionally substituted with OCH₃, two fluoro groups or two methyl groups;

A¹ is H, or C₍₁₋₃₎alkyl; wherein said C₍₁₋₃₎alkyl is optionally substituted with up to five fluorine atoms (including CH₂CH₂F);

A² is C₍₁₋₄₎alkyl (including C₍₂₋₄₎alkyl), C₍₀₋₂₎alkyl-C₍₃₋₆₎cycloalkyl (including CH₂-cyclopentyl, CH₂-cyclopropyl, CH₂CH₂-cyclopropyl, C₍₃₋₄₎cycloalkyl, and

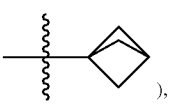

CH₂—C₆H₄—C(O)NH₂, —C₆H₄—F, CH₂—CCH, or CH₂CH₂—CN; wherein said C₍₁₋₄₎alkyl, and said C₍₀₋₂₎alkyl-C₍₃₋₆₎cycloalkyl are optionally substituted with up to three fluorine atoms;

or A¹ and A² may be taken together with their attached nitrogen to form a ring selected from the group consisting of:

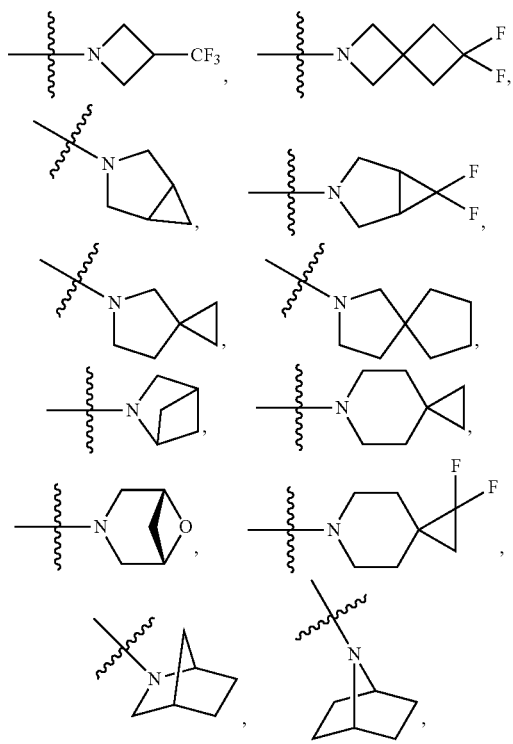

-continued

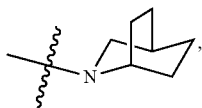

thiomorpholinyl, piperidinyl, pyrrolidinyl, piperazinyl, and morpholinyl; wherein said piperidinyl, pyrrolidinyl, piperazinyl, and morpholinyl are optionally substituted with $CF_3$, $CH_2F$, $CH_2CH_2F$, $C_{(1-2)}$alkyl, —CN, OH, $CH_2OH$, or F, and up to three additional substituents selected from the group consisting of $CH_3$, and F;

$R^5$ is $SO_2NA_3A_4$, $C_{(1-6)}$alkyl,

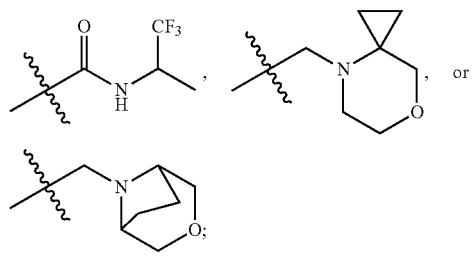

wherein said $C_{(1-6)}$alkyl is optionally substituted with OH, $OCH_3$, or $NA^3A^4$; and up to six fluorine atoms (including $C(CF_3)_2OH$);

$A^3$ is H, or $C_{(1-4)}$alkyl (including $CH_3CH_2$, and $C(CH_3)_3$);

$A_4$ is $C_{(1-6)}$alkyl, cyclopropyl, cyclobutyl, oxetanyl, or tetrahydrofuranyl; wherein said $C_{(1-6)}$alkyl is optionally substituted with cyclopropyl, morpholinyl, OH, $OCH_3$, or $C(O)NH_2$, and additionally substituted with up to three fluorine atoms (including $C(CH_3)_2CH_2OCH_3$, $C(CH_3)_2CH_2OH$, $C(CH_3)_2CH_2$-morpholinyl, $C(CH_3)_2CH_2CH_2OH$, $C(CH_3)_2CH_2C(O)NH_2$, and $CH_2C(CH_3)_2OH$); and wherein said cyclopropyl cyclobutyl, oxetanyl, and tetrahydrofuranyl are optionally substituted with $CF_3$, $CH_3$, —CN, or $C(O)NH_2$;

or $A^3$ and $A^4$ can be taken together with their attached nitrogen to form a ring selected from the group consisting of azetidinyl, piperidinyl, morpholinyl, piperazinyl, and pyrrolidinyl wherein said azetidinyl, piperidinyl, morpholinyl, and piperazinyl are optionally substituted with up to two groups selected from the group consisting of $CF_3$, OH, and $CH_3$; and further optionally substituted with up to three fluorine atoms;

$R^7$ is H, F, OH, or $OCH_3$;

$R^8$ is H;

and pharmaceutically acceptable salts thereof.

In another embodiment of the invention:

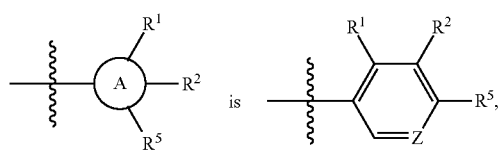

-continued

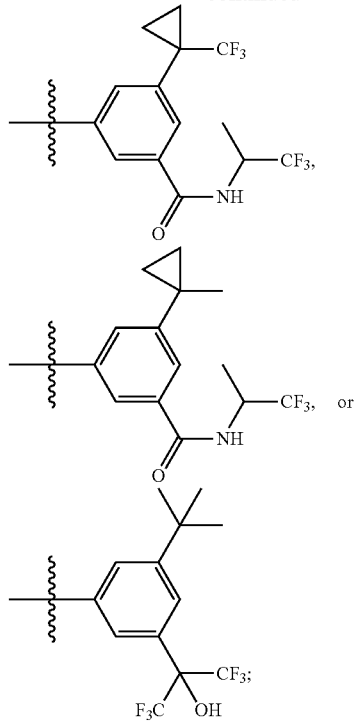

Z is N, or CH;

$R^1$ is H, Cl, $OCF_3$, $CF_3$, $CHF_2$, $C_{(1-3)}$alkyl (including $CH_2CH_3$), —CN, F, $OC_{(1-3)}$alkyl (including $OCH_3$), or $OCHF_2$;

$R^2$ is $CHF_2$, $CF_3$, H, F, Cl,

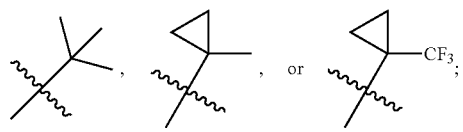

or $R^1$ and $R^2$ may be taken together with their attached ring A to form a fused ring system selected from the group consisting of naphthalenyl, isoquinolinyl, and tetrahydronaphthalenyl; provided that $R^2$ may not be H if $R^1$ is H;

$R^3$ is oxadiazolyl, thiazolyl, thiadiazolyl, isoxadiazolyl, isoxazolyl, phenyl, oxazolyl, triazolyl, tetrazolyl, 1,2,4-oxadiazol-5(4H)-on-3-yl, pyridyl, or pyrimidyl, wherein said oxadiazolyl, thiazolyl, thiadiazolyl, isoxadiazolyl, isoxazolyl, phenyl, oxazolyl, triazolyl, pyridyl or pyrimidyl is optionally substituted with $R^6$;

$R^6$ is

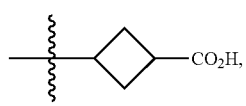 [SMILES: *C1CC(C(=O)O)C1]

$CH_3$, $CH_2C(CH_3)_2CO_2H$, $C_{(1-6)}$alkyl$C(CH_3)_2OH$ (including $C(CH_3)_2OH$), $CH_2C(CH_3)_2CN$, or $C(O)NH_2$;

$R^4$ is $C_{(3-6)}$cycloalkyl (including $C_{(4-6)}$cycloalkyl), isopropyl, $C(CH_3)_2OCH_3$, $OCH(CH_3)_2$, $OC(CH_3)_3$, fluorophenyl, difluorophenyl, or $NA^1A^2$, wherein said $C_{(3-6)}$cycloalkyl is optionally substituted with $OCH_3$, two fluoro groups or two methyl groups;

$A^1$ is H, $C_{(1-3)}$alkyl (including $CH_2CH_3$), or $CH_2CH_2F$;
$A^2$ is $C_{(2-4)}$alkyl (including $CH_2CH_3$), $CH_2$-cyclopentyl, $CH_2CH_2$-cyclopropyl, $C_{(3-4)}$cycloalkyl,

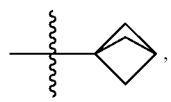 [SMILES: *C12CC(C1)C2]

$CH_2$—$C_6H_4$—$C(O)NH_2$, —$C_6H_4$—F, $CH_2$—CCH, or $CH_2CH_2$—CN; wherein said $C_{(3-4)}$cycloalkyl is optionally substituted with one fluorine atom and said $C_{(2-4)}$alkyl is optionally substituted with up to three fluorine atoms (including $CH_2CF_3$);
or $A^1$ and $A^2$ may be taken together with their attached nitrogen to form a ring selected from the group consisting of:

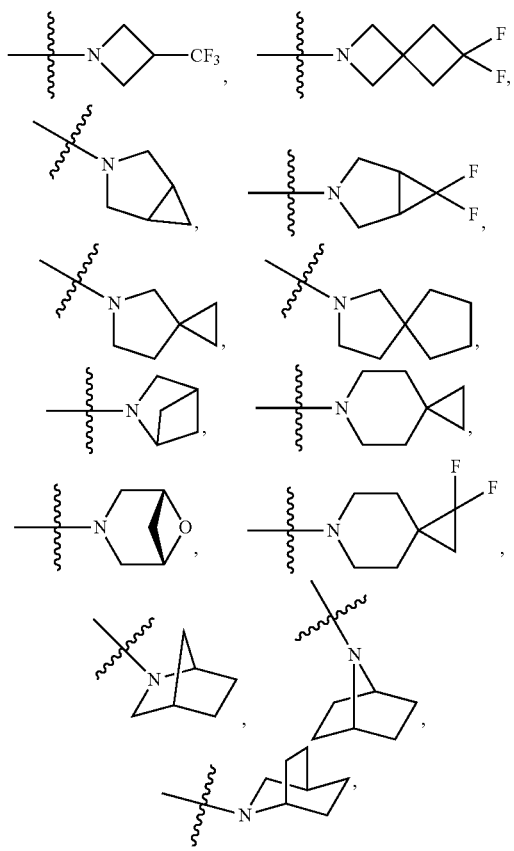

thiomorpholinyl, piperidinyl, pyrrolidinyl, and morpholinyl; wherein said piperidinyl, and pyrrolidinyl are optionally substituted with $CF_3$, $CH_2F$, $CH_2CH_2F$, $C_{(1-2)}$alkyl (including $CH_3$), —CN, OH, or $CH_2OH$, and up to three additional substituents selected from the group consisting of $CH_3$, and F (including difluoropiperidinyl, fluoropiperidinyl);
$R^5$ is $SO_2NA_3A_4$, $C(CF_3)_2OH$,

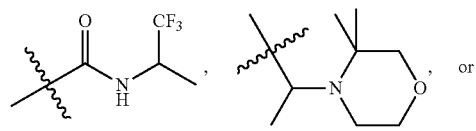

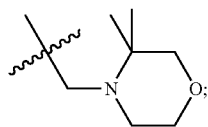

$A^3$ is H, $CH_3CH_2$, or $C(CH_3)_3$;
$A^4$ is $C_{(1-6)}$alkyl (including $C(CH_3)_3$),

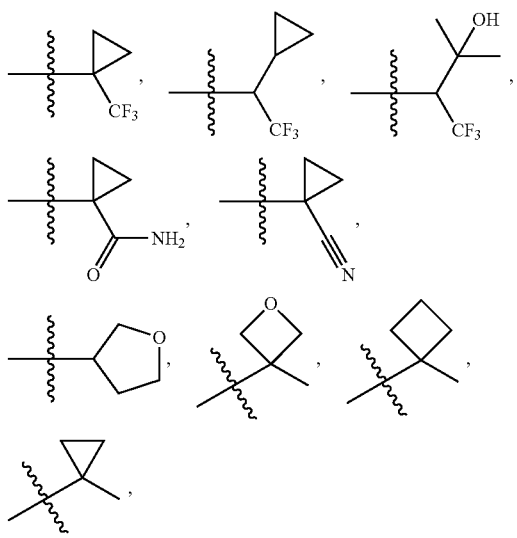

$C(CH_3)_2CH_2OCH_3$, $C(CH_3)_2CH_2OH$, $C(CH_3)_2CH_2$-morpholinyl, $C(CH_3)_2CH_2CH_2OH$, $C(CH_3)_2CH_2C(O)NH_2$, or $CH_2C(CH_3)_2OH$; wherein said $C_{(1-6)}$alkyl is optionally substituted with up to three fluorine atoms;
or $A^3$ and $A^4$ can be taken together with their attached nitrogen to form a ring selected from the group consisting of

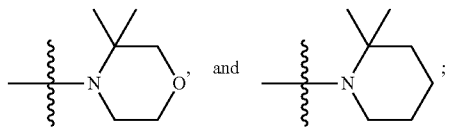

$R^7$ is H;
$R^8$ is H;
and pharmaceutically acceptable salts thereof.
In another embodiment of the invention:

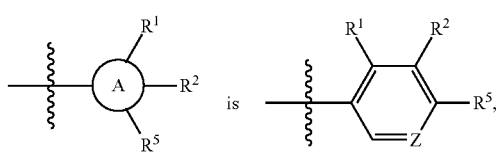

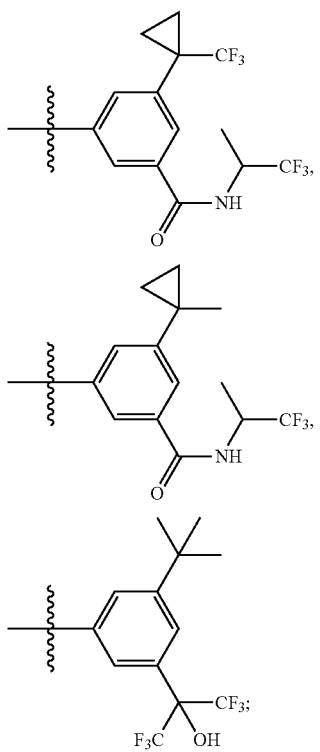

Z is N, or CH;

R¹ is H, Cl, OCF₃, CF₃, CHF₂, or F;

R² is CHF₂, CF₃, H, F, Cl,

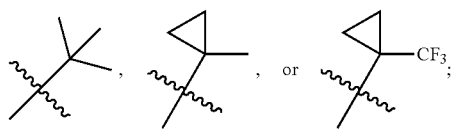

or R¹ and R² may be taken together with their attached ring A to form a fused ring system selected from the group consisting of naphthalenyl, and isoquinolinyl; provided that R² may not be H if R¹ is H;

R³ is

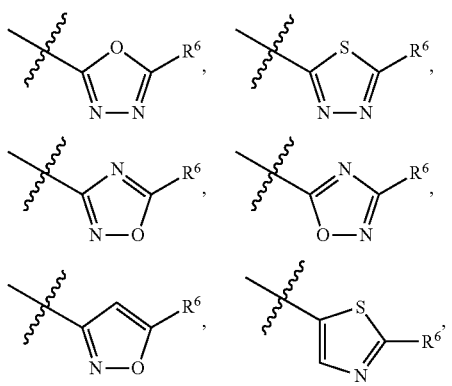

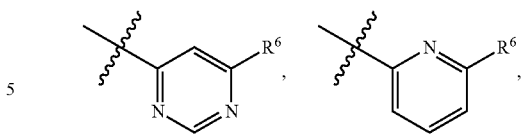

or phenyl, wherein said phenyl is optionally substituted with R⁶;

R⁶ is

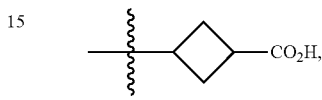

CH₃, CH₂C(CH₃)₂CO₂H, or C(CH₃)₂OH;

R⁴ is C₍₄₋₆₎cycloalkyl, isopropyl, C(CH₃)₂OCH₃, OCH(CH₃)₂, difluoropiperidinyl, fluoropiperidinyl, fluorophenyl, or NA¹A², wherein said C₍₄₋₆₎cycloalkyl is optionally substituted with OCH₃, two fluoro groups or two methyl groups; and wherein A¹ and A² are taken together with their attached nitrogen to form a pyrrolidinyl ring, wherein said pyrrolidinyl ring is optionally substituted with CH₃, CH₂F, and up to three additional substituents selected from the group consisting of CH₃, and F;

R⁵ is SO₂NA³A₄, C(CF₃)₂OH,

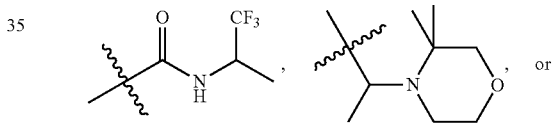

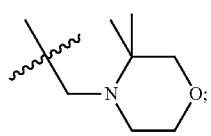

A³ is H;

A⁴ is

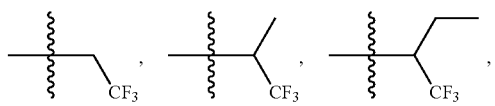

or C(CH₃)₃;

R⁷ is H;

R⁸ is H;

and pharmaceutically acceptable salts thereof.

Another embodiment of the invention is a compound selected from the group consisting of:
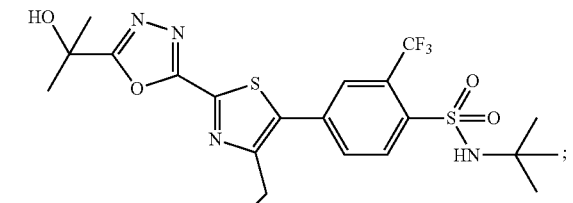
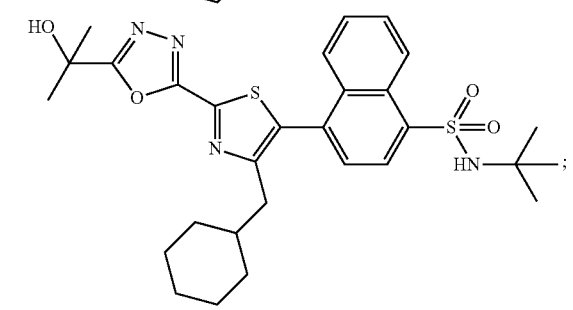
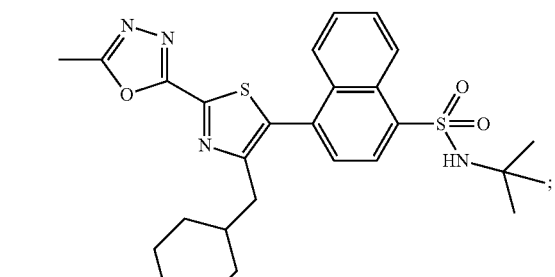
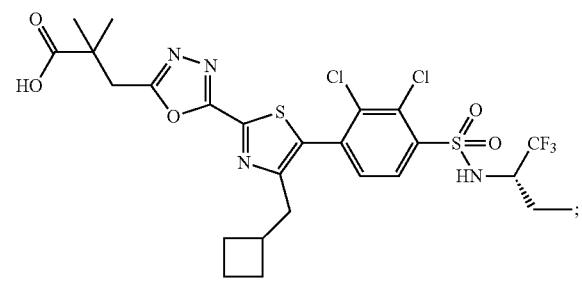
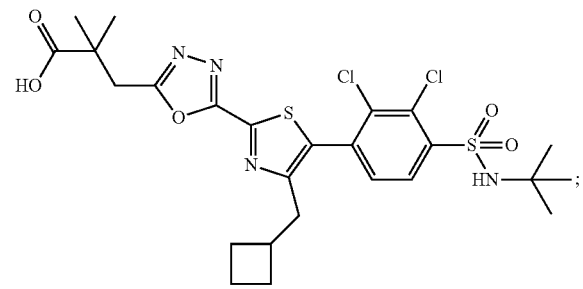
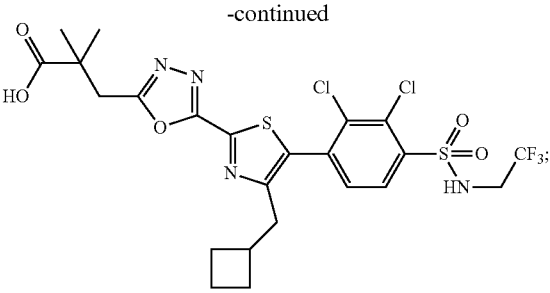
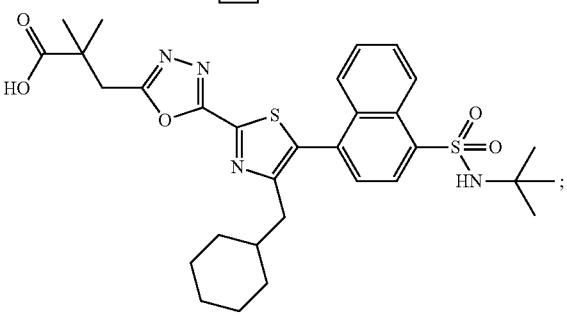
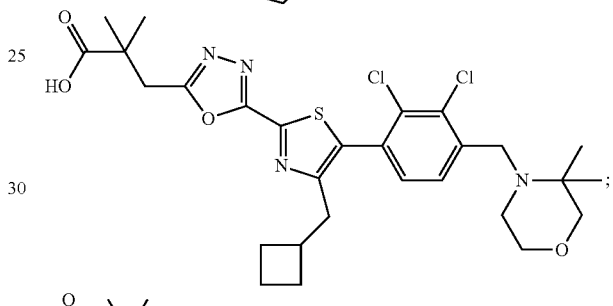
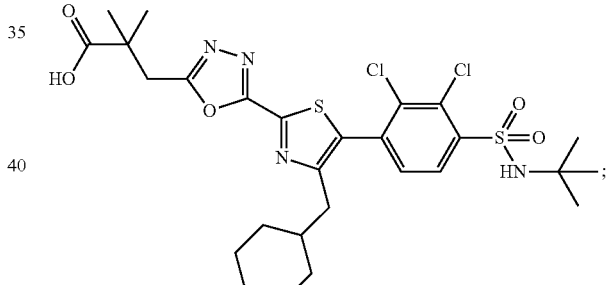
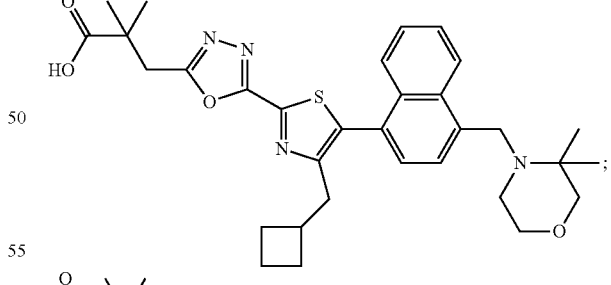
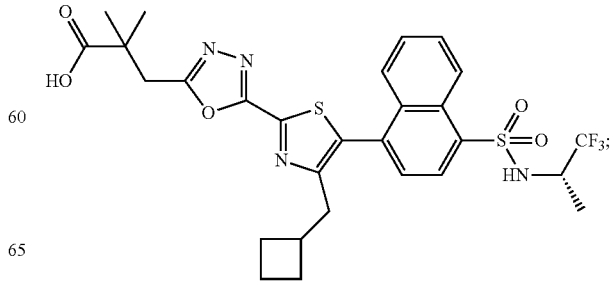

-continued
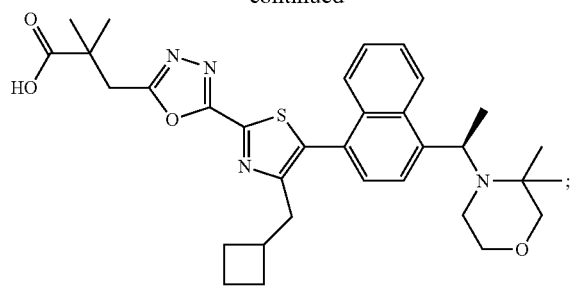
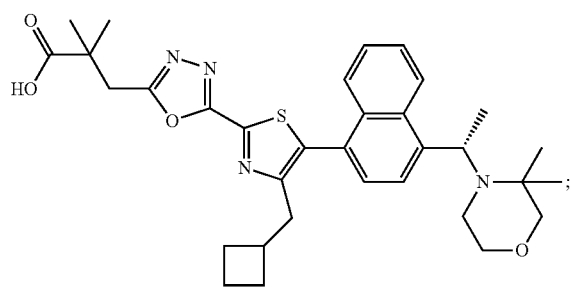
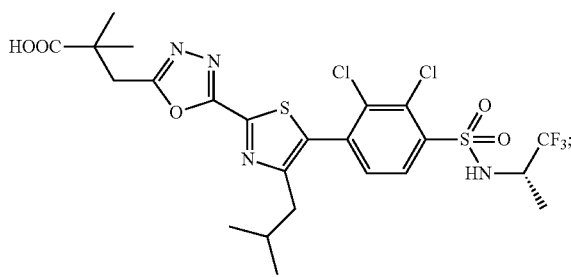
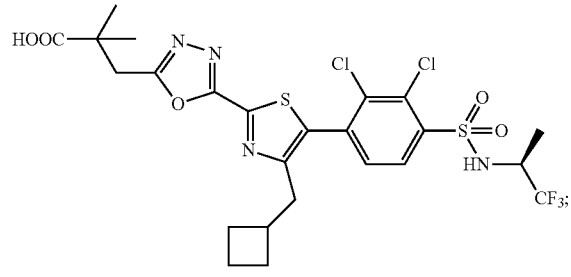
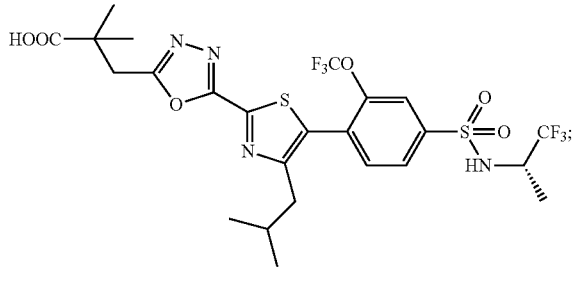
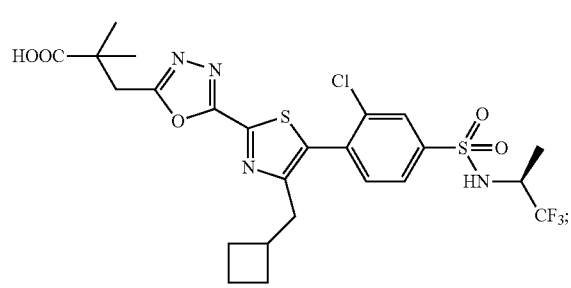
-continued
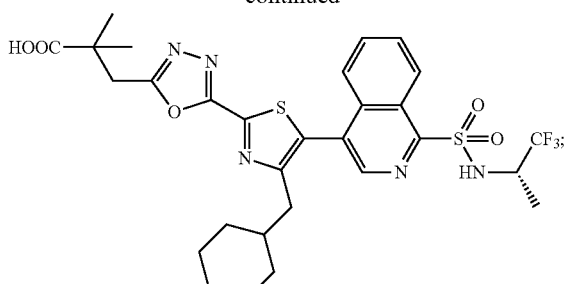
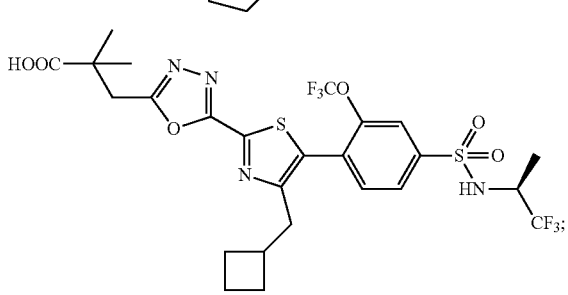
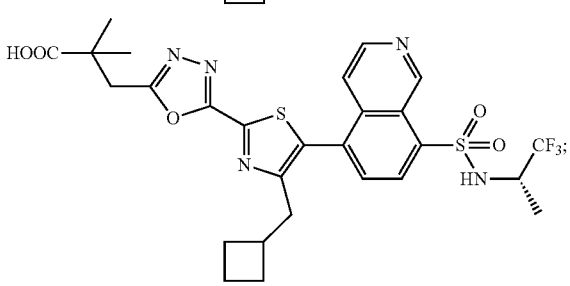
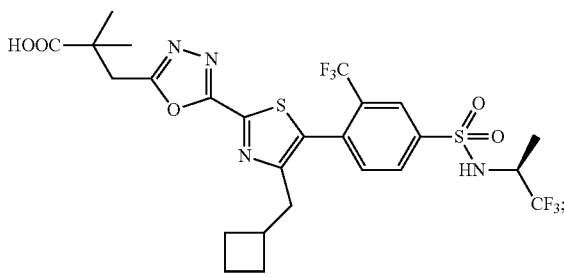
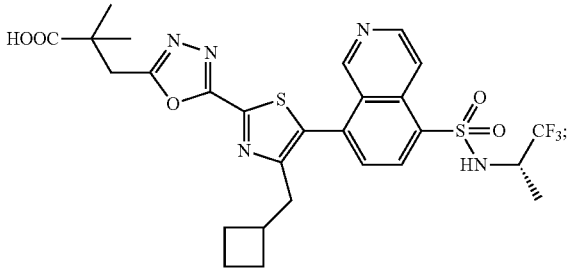
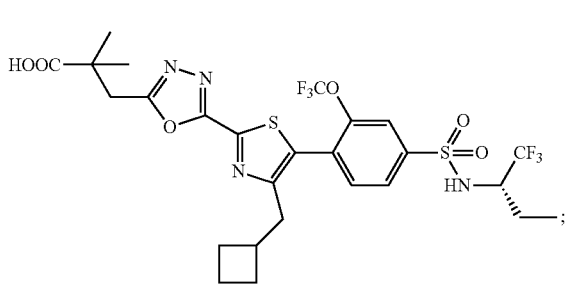

23
-continued
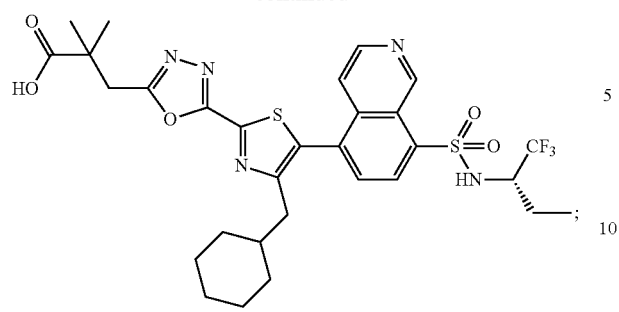
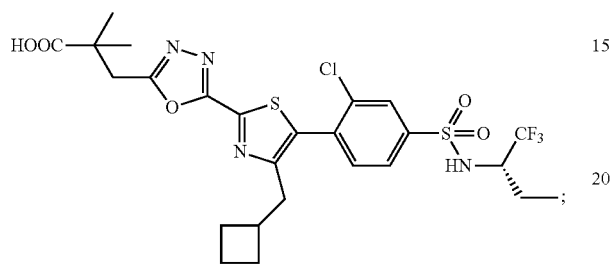
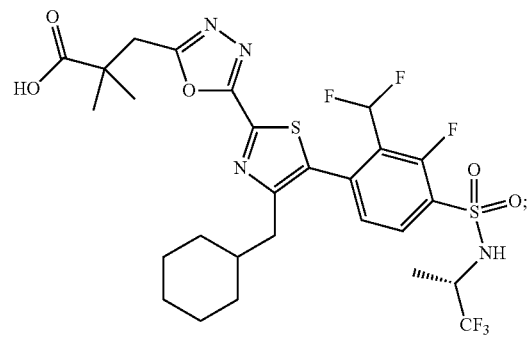
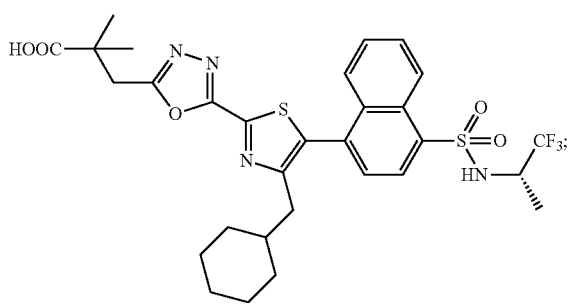
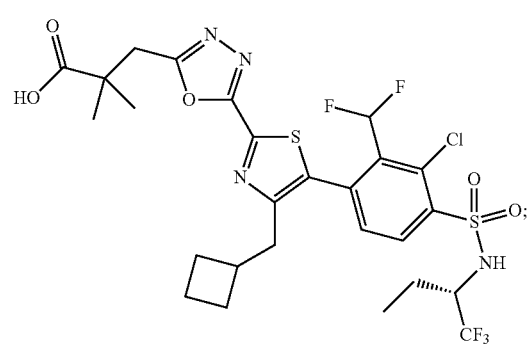
24
-continued
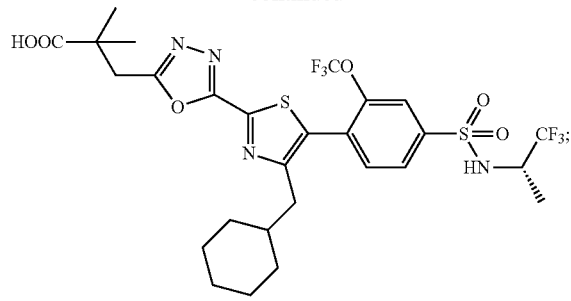
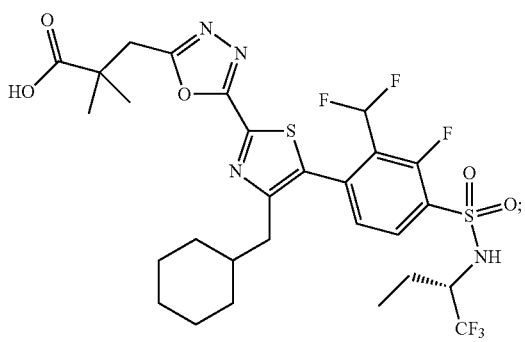
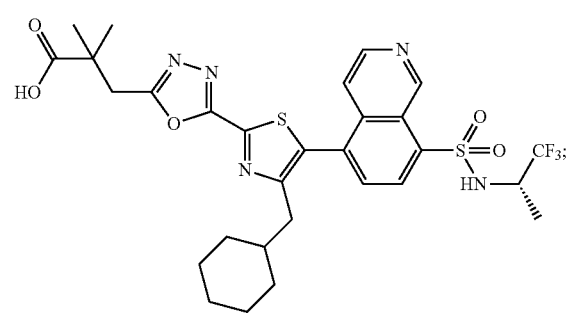
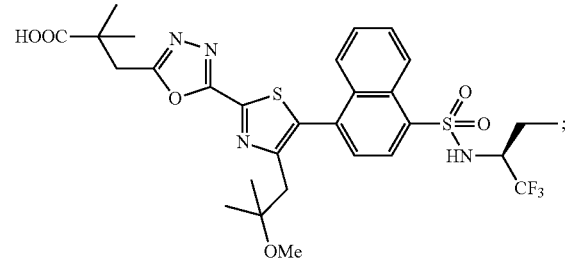
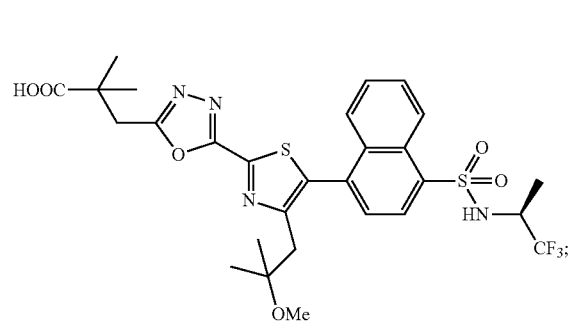

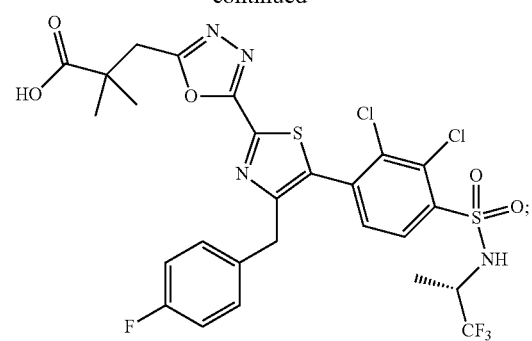
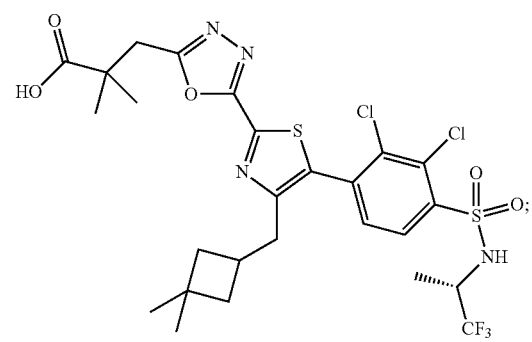
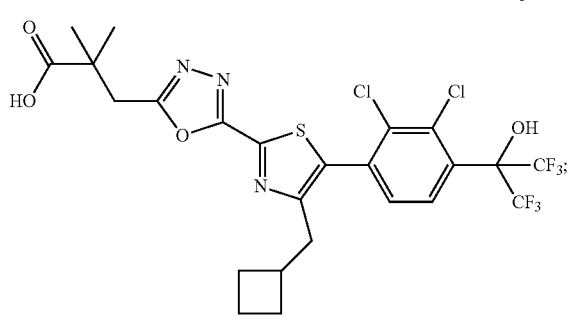
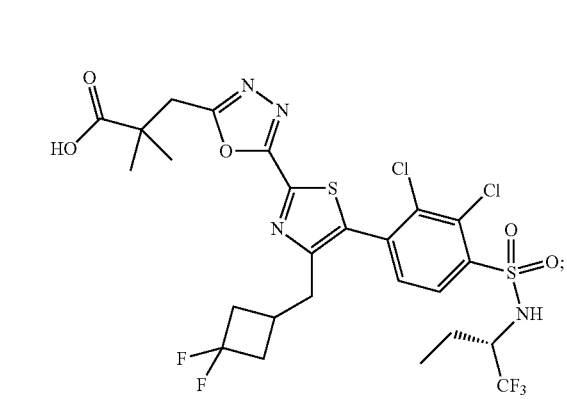
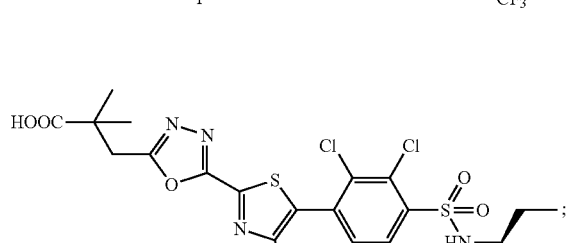
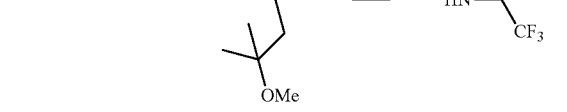
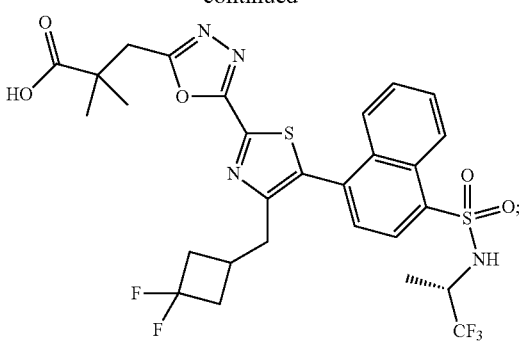
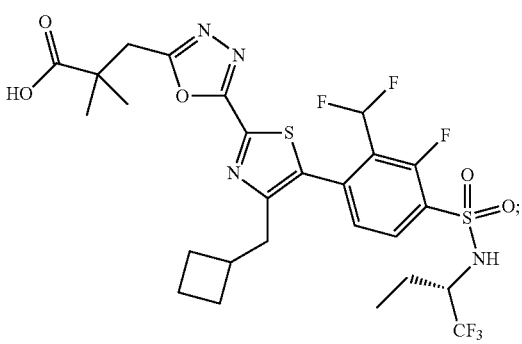
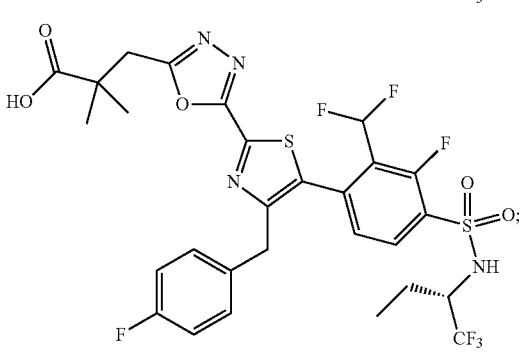
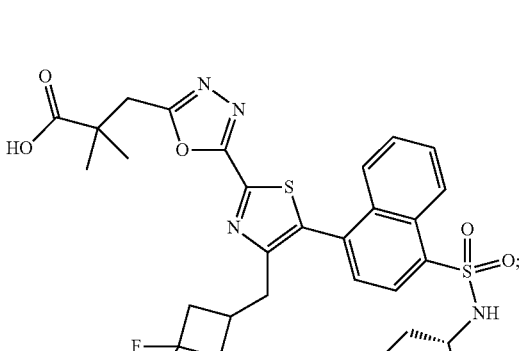
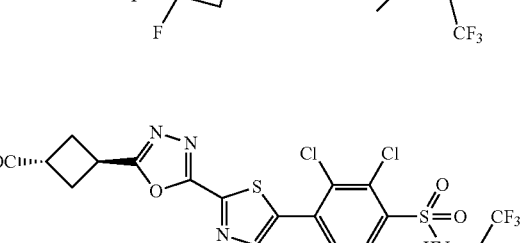
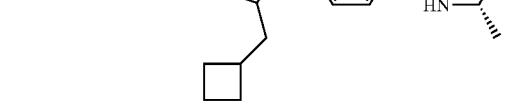

27
-continued
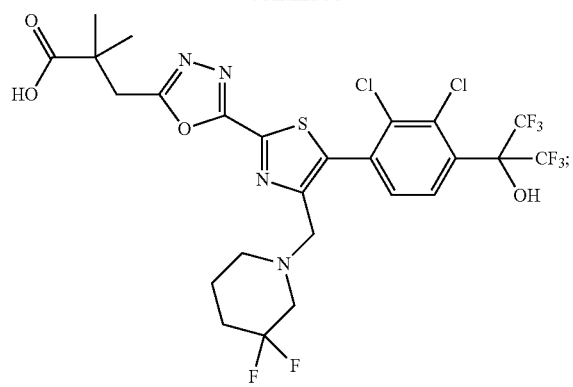
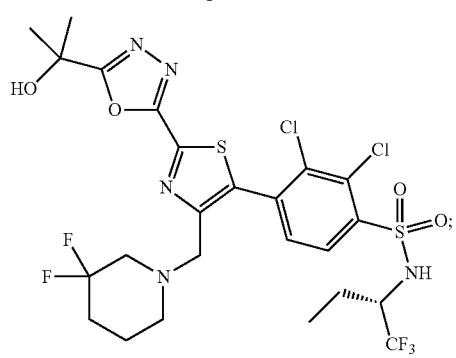
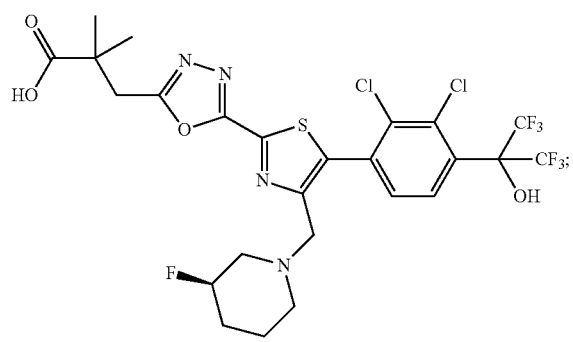
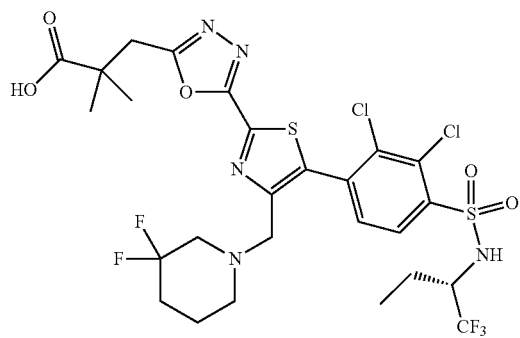
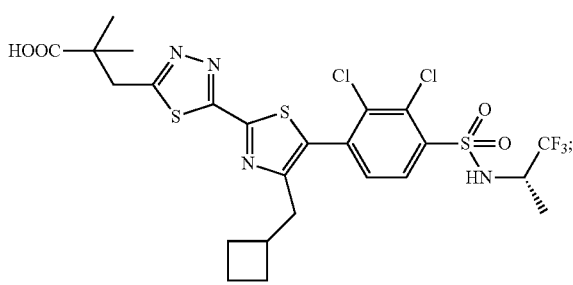
28
-continued
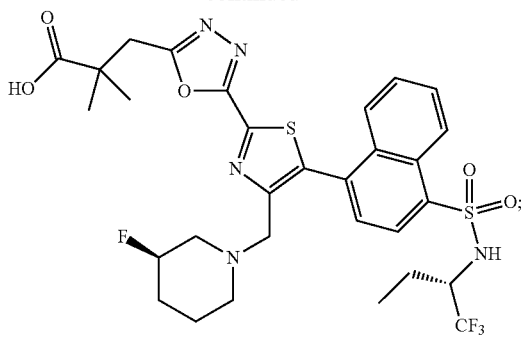
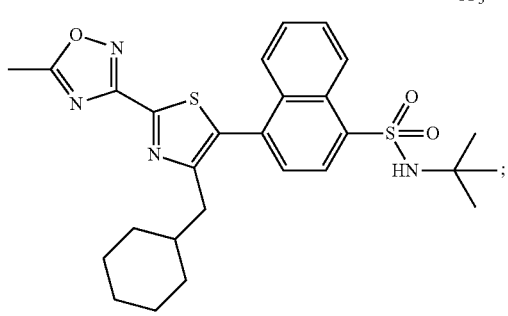
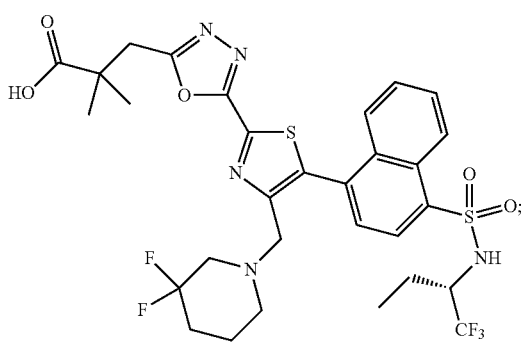
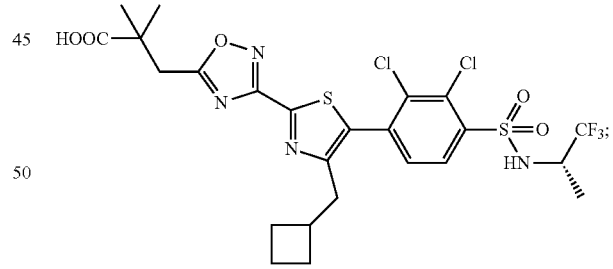
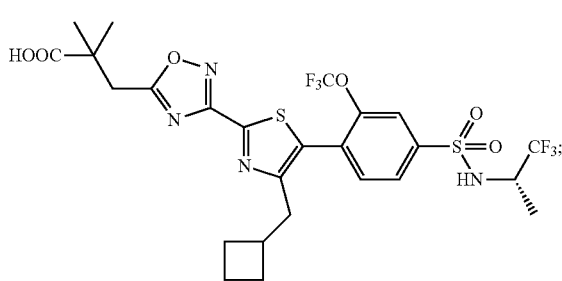

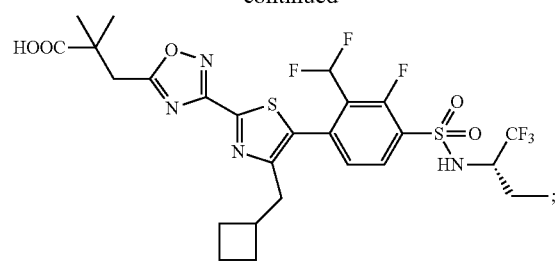
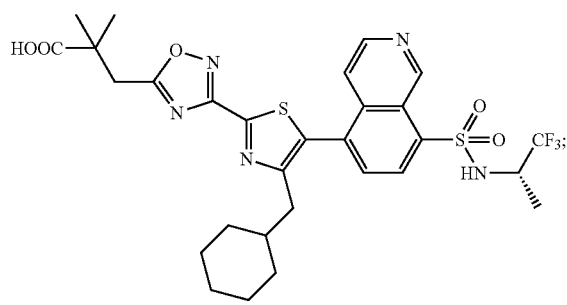
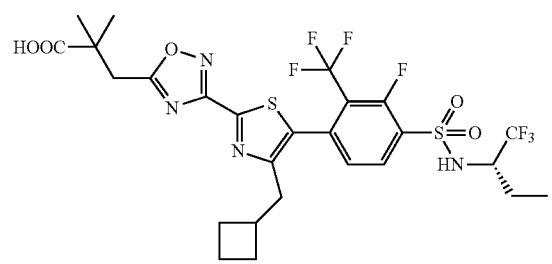
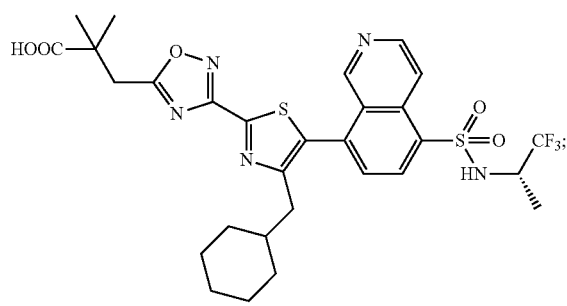
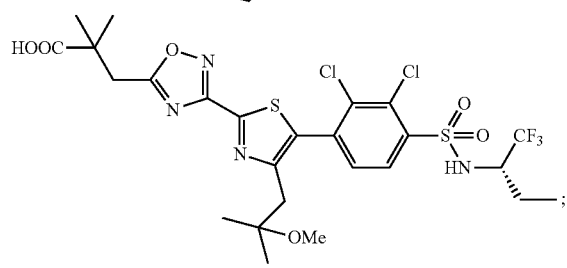
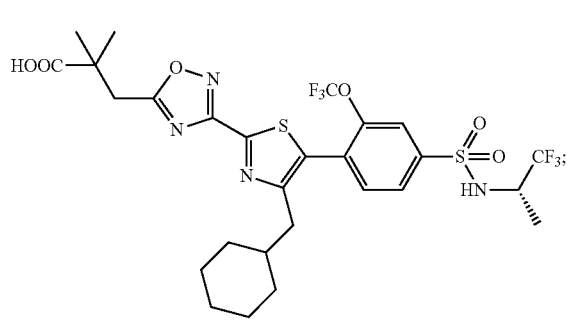
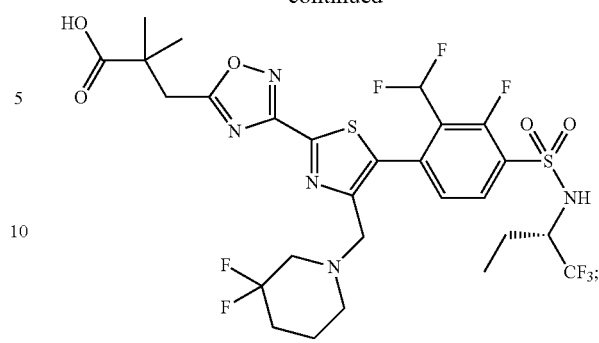
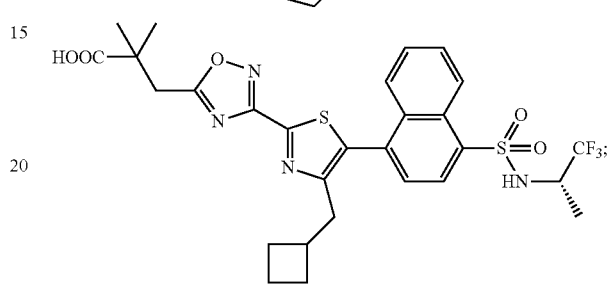
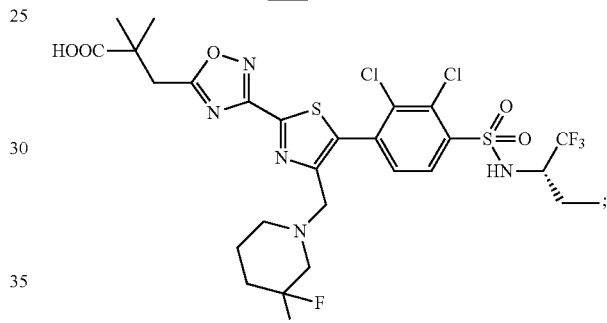
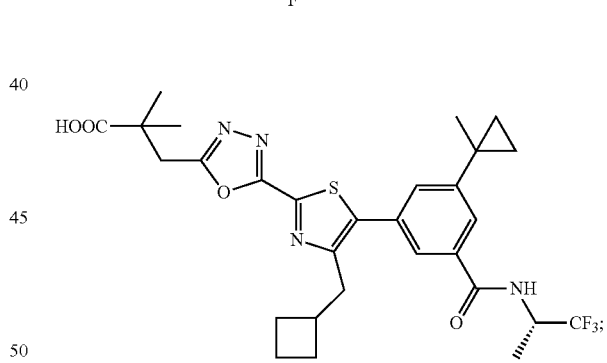
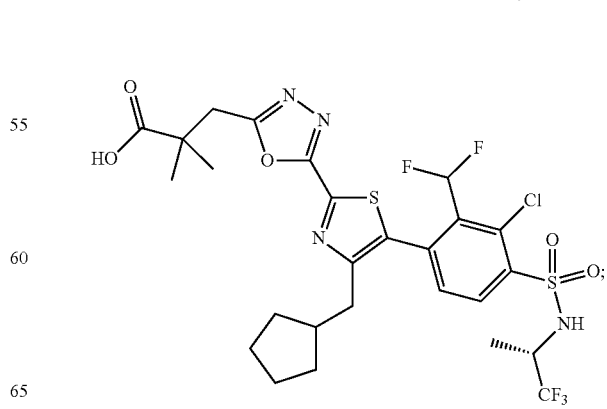

-continued
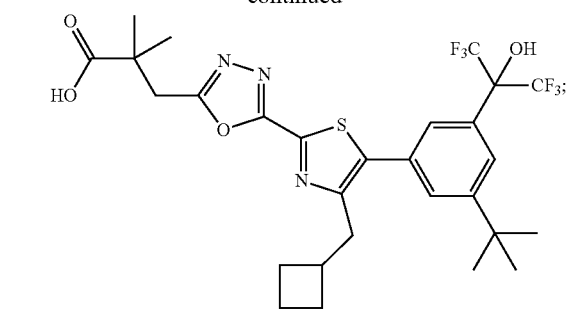
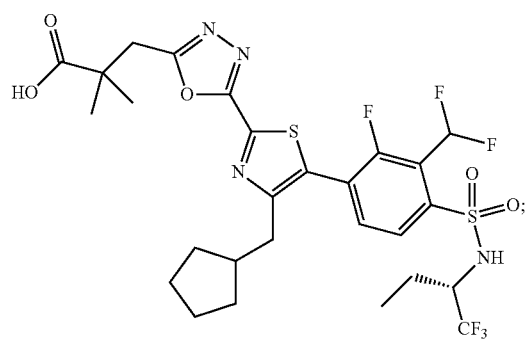
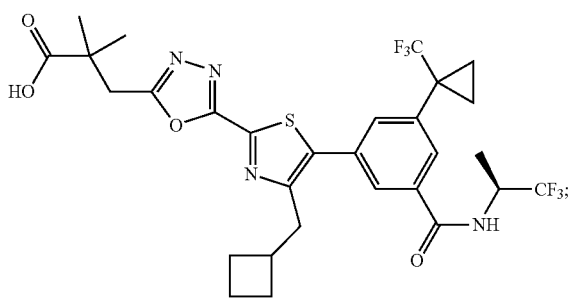
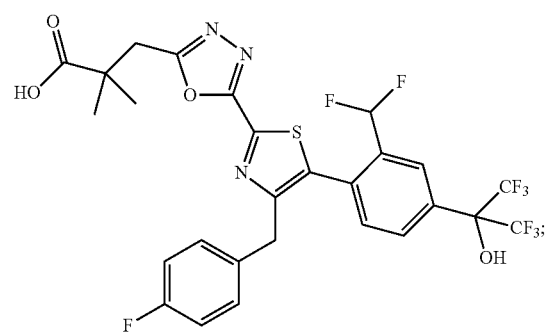
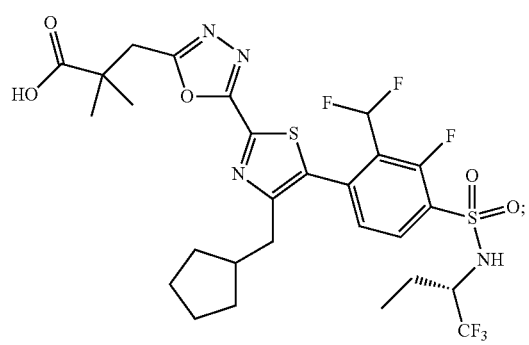
-continued
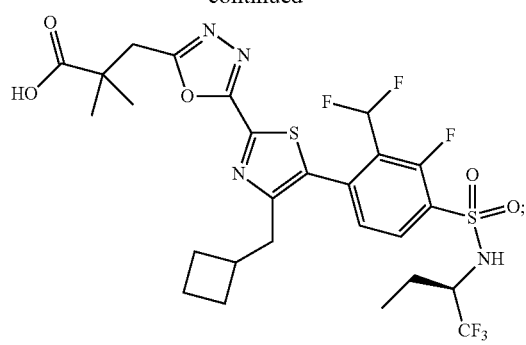
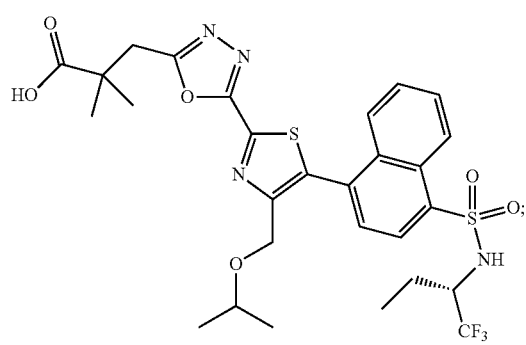
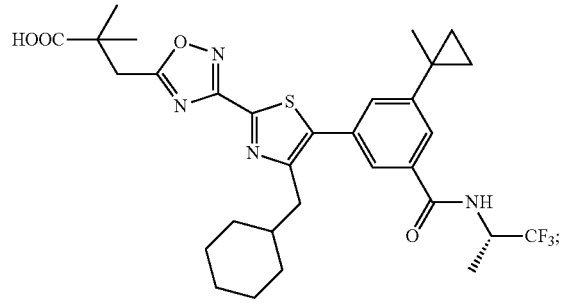
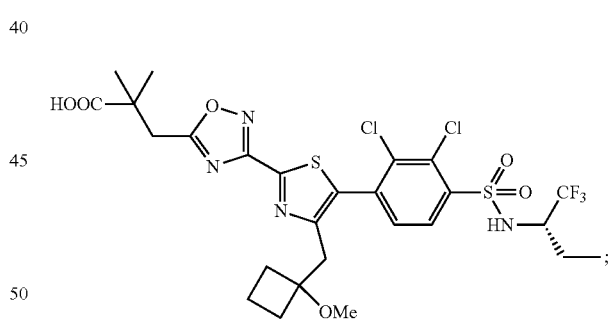
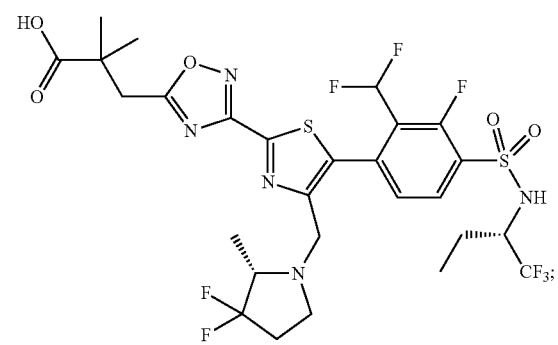

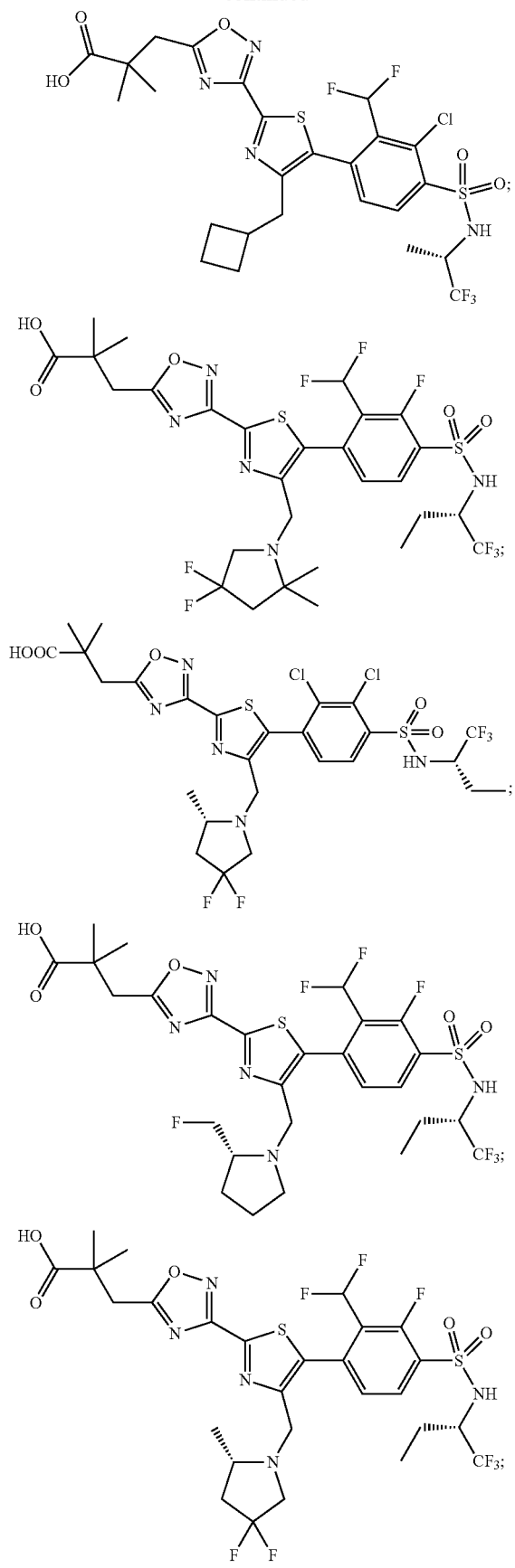
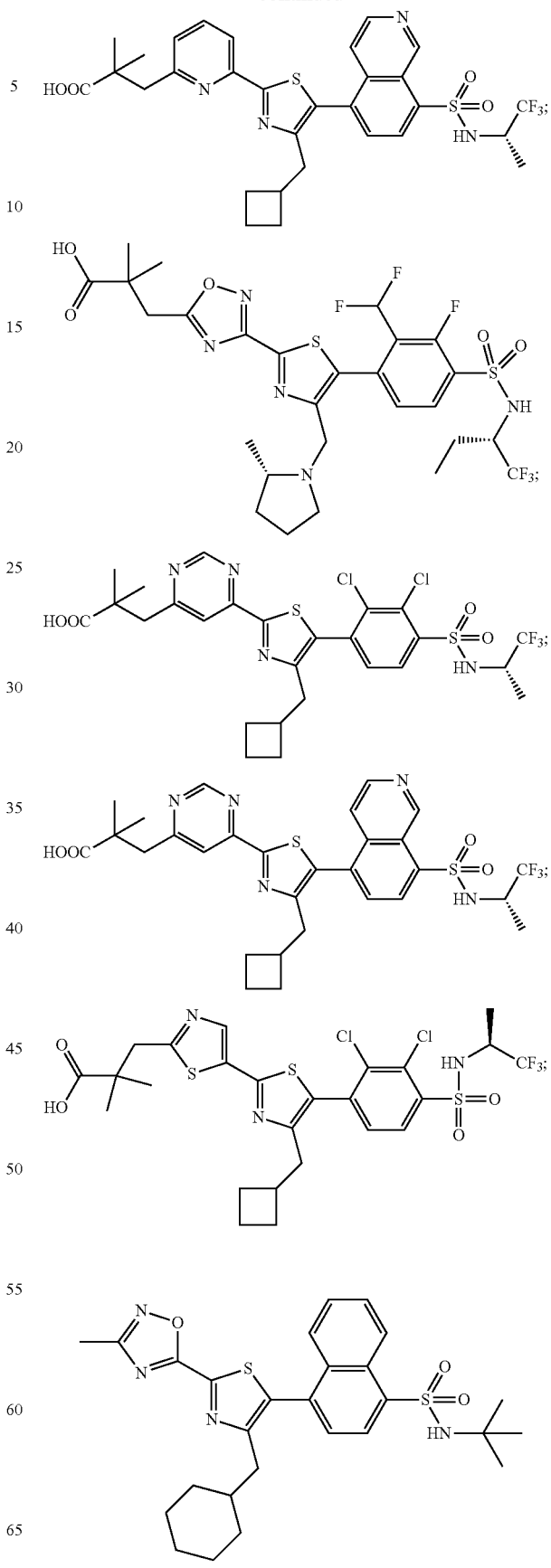

-continued

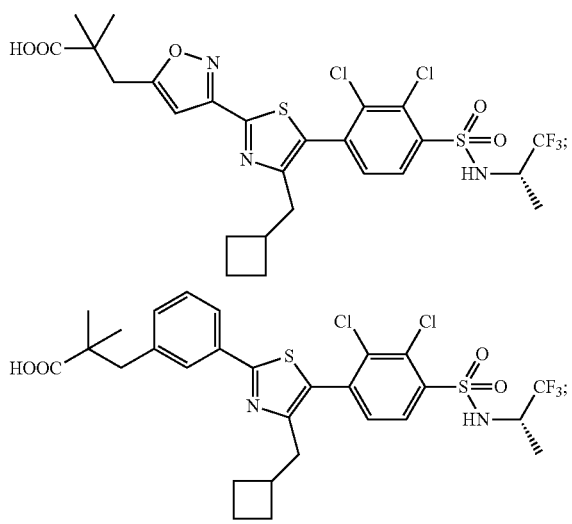

and pharmaceutically acceptable salts thereof.

Another embodiment of the invention is a compound selected from the group consisting of:

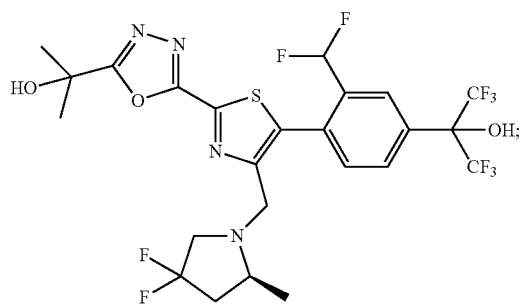

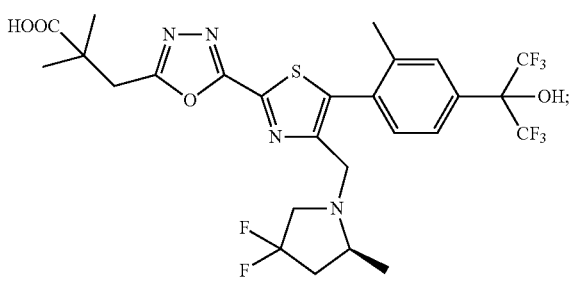

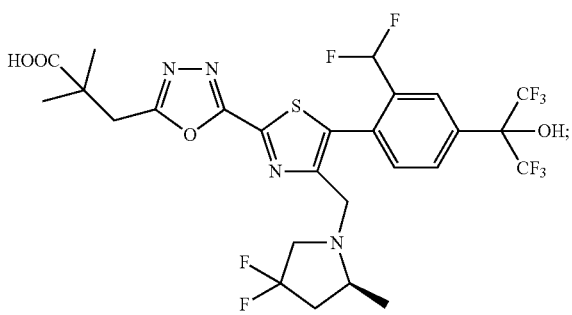

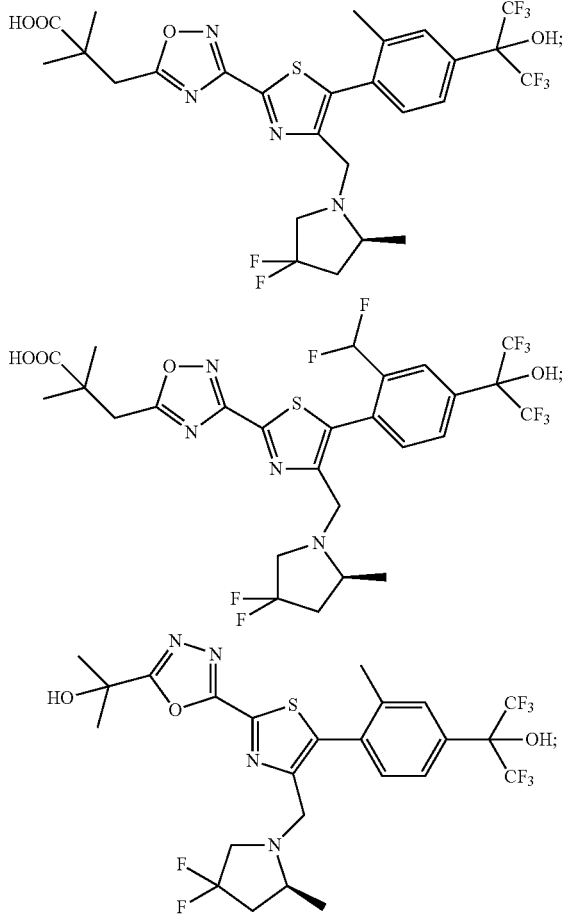

and pharmaceutically acceptable salts thereof.

Another embodiment of the invention comprises a compound of Formula I and a pharmaceutically acceptable carrier.

The present invention also provides a method for preventing, treating or ameliorating an RORγt mediated inflammatory syndrome, disorder or disease comprising administering to a subject in need thereof an effective amount of a compound of Formula I or a form, composition or medicament thereof.

The present invention provides a method of preventing, treating or ameliorating a syndrome, disorder or disease, wherein said syndrome, disorder or disease is selected from the group consisting of: ophthalmic disorders, uveitis, atherosclerosis, rheumatoid arthritis, psoriasis, psoriatic arthritis, atopic dermatitis, multiple sclerosis, Crohn's Disease, ulcerative colitis, ankylosing spondylitis, nephritis, organ allograft rejection, fibroid lung, cystic fibrosis, renal insufficiency, diabetes and diabetic complications, diabetic nephropathy, diabetic retinopathy, diabetic retinitis, diabetic microangiopathy, tuberculosis, chronic obstructive pulmonary disease, sarcoidosis, invasive staphylococcia, inflammation after cataract surgery, allergic rhinitis, allergic conjunctivitis, chronic urticaria, systemic lupus erythematosus, asthma, allergic asthma, steroid resistant asthma, neutrophilic asthma, periodontal diseases, periodontitis, gingivitis, gum disease, diastolic cardiomyopathies, cardiac infarction, myocarditis, chronic heart failure, angiostenosis, restenosis, reperfusion disorders, glomerulonephritis, solid tumors and cancers, chronic lymphocytic leukemia, chronic myelocytic leukemia, multiple myeloma, malignant myeloma, Hodgkin's disease, and carcinomas of the bladder, breast, cervix, colon, lung, prostate, or stomach comprising administering to a subject in need thereof an effective amount of a compound of Formula I or a form, composition or medicament thereof.

The present invention provides a method of treating or ameliorating a syndrome, disorder or disease, wherein said syndrome, disorder or disease is selected from the group consisting of: rheumatoid arthritis, psoriasis, chronic obstructive pulmonary disorder, psoriatic arthritis, ankylosing spondylitis, Crohn's disease, and ulcerative colitis.

The present invention provides a method of treating or ameliorating a syndrome, disorder or disease, wherein said syndrome, disorder or disease is selected from the group consisting of: rheumatoid arthritis, psoriasis, chronic obstructive pulmonary disorder, psoriatic arthritis, ankylosing spondylitis, Crohn's disease, and ulcerative colitis comprising administering to a subject in need thereof an effective amount of a compound of Formula I or a form, composition or medicament thereof.

The present invention provides a method of treating or ameliorating a syndrome, disorder or disease, wherein said syndrome, disorder or disease is selected from the group consisting of: inflammatory bowel diseases, rheumatoid arthritis, psoriasis, chronic obstructive pulmonary disorder, psoriatic arthritis, ankylosing spondylitis, neutrophilic asthma, steroid resistant asthma, multiple sclerosis, and systemic lupus erythematosus comprising administering to a subject in need thereof an effective amount of a compound of Formula I or a form, composition or medicament thereof.

The present invention provides a method of treating or ameliorating a syndrome, disorder or disease, wherein said syndrome, disorder or disease is selected from the group consisting of: rheumatoid arthritis, and psoriasis comprising administering to a subject in need thereof an effective amount of a compound of Formula I or a form, composition or medicament thereof.

The present invention provides a method of treating or ameliorating a syndrome, disorder or disease, in a subject in need thereof comprising administering to the subject an effective amount of the compound of Formula I or composition or medicament thereof in a combination therapy with one or more anti-inflammatory agents, or immunosuppressive agents, wherein said syndrome, disorder or disease is selected from the group consisting of: rheumatoid arthritis, and psoriasis.

The present invention provides a method of treating or ameliorating a syndrome, disorder or disease, wherein said syndrome, disorder or disease is rheumatoid arthritis, comprising administering to a subject in need thereof an effective amount of a compound of Formula I or a form, composition or medicament thereof.

The present invention provides a method of treating or ameliorating a syndrome, disorder or disease, wherein said syndrome, disorder or disease is psoriasis comprising administering to a subject in need thereof an effective amount of a compound of Formula I or a form, composition or medicament thereof.

The present invention provides a method of treating or ameliorating a syndrome, disorder or disease, wherein said syndrome, disorder or disease is chronic obstructive pulmonary disorder comprising administering to a subject in need thereof an effective amount of a compound of Formula I or a form, composition or medicament thereof.

The present invention provides a method of treating or ameliorating a syndrome, disorder or disease, wherein said syndrome, disorder or disease is psoriatic arthritis comprising administering to a subject in need thereof an effective amount of a compound of Formula I or a form, composition or medicament thereof.

The present invention provides a method of treating or ameliorating a syndrome, disorder or disease, wherein said syndrome, disorder or disease is ankylosing spondylitis comprising administering to a subject in need thereof an effective amount of a compound of Formula I or a form, composition or medicament thereof.

The present invention provides a method of treating or ameliorating an inflammatory bowel disease, wherein said inflammatory bowel disease is Crohn's disease comprising administering to a subject in need thereof an effective amount of a compound of Formula I or a form, composition or medicament thereof.

The present invention provides a method of treating or ameliorating an inflammatory bowel disease, wherein said inflammatory bowel disease is ulcerative colitis comprising administering to a subject in need thereof an effective amount of a compound of Formula I or a form, composition or medicament thereof.

The present invention provides a method of treating or ameliorating a syndrome, disorder or disease, wherein said syndrome, disorder or disease is neutrophilic asthma comprising administering to a subject in need thereof an effective amount of a compound of Formula I or a form, composition or medicament thereof.

The present invention provides a method of treating or ameliorating a syndrome, disorder or disease, wherein said syndrome, disorder or disease is steroid resistant asthma comprising administering to a subject in need thereof an effective amount of a compound of Formula I or a form, composition or medicament thereof.

The present invention provides a method of treating or ameliorating a syndrome, disorder or disease, wherein said syndrome, disorder or disease is multiple sclerosis comprising administering to a subject in need thereof an effective amount of a compound of Formula I or a form, composition or medicament thereof.

The present invention provides a method of treating or ameliorating a syndrome, disorder or disease, wherein said syndrome, disorder or disease is systemic lupus erythematosus comprising administering to a subject in need thereof an effective amount of a compound of Formula I or a form, composition or medicament thereof.

The invention also relates to methods of modulating RORγt activity in a mammal by administration of an effective amount of at least one compound of Formula I.

Definitions

The term "administering" with respect to the methods of the invention, means a method for therapeutically or prophylactically preventing, treating or ameliorating a syndrome, disorder or disease as described herein by using a compound of Formula I or a form, composition or medicament thereof. Such methods include administering an effective amount of said compound, compound form, composition or medicament at different times during the course of a therapy or concurrently in a combination form. The methods of the invention are to be understood as embracing all known therapeutic treatment regimens.

The term "subject" refers to a patient, which may be an animal, typically a mammal, typically a human, which has been the object of treatment, observation or experiment and is at risk of (or susceptible to) developing a syndrome, disorder or disease that is associated with aberrant RORγt expression or RORγt overexpression, or a patient with an inflammatory condition that accompanies syndromes, disorders or diseases associated with abberant RORγt expression or RORγt overexpression.

The term "effective amount" means that amount of active compound or pharmaceutical agent that elicits the biological or medicinal response in a tissue system, animal or human, that is being sought by a researcher, veterinarian, medical doctor, or other clinician, which includes preventing, treating or ameliorating the symptoms of a syndrome, disorder or disease being treated.

As used herein, the term "composition" is intended to encompass a product comprising the specified ingredients in the specified amounts, as well as any product which results, directly or indirectly, from combinations of the specified ingredients in the specified amounts.

The term "alkyl" refers to both linear and branched chain radicals of up to 12 carbon atoms, preferably up to 6 carbon atoms, unless otherwise indicated, and includes, but is not limited to, methyl, ethyl, propyl, isopropyl, butyl, isobutyl, sec-butyl, tert-butyl, pentyl, isopentyl, hexyl, isohexyl, heptyl, octyl, 2,2,4-trimethylpentyl, nonyl, decyl, undecyl and dodecyl. Any alkyl group may be optionally substituted with one $OCH_3$, one OH, or up to two fluorine atoms.

The term "$C_{(a-b)}$" (where a and b are integers referring to a designated number of carbon atoms) refers to an alkyl, alkenyl, alkynyl, alkoxy or cycloalkyl radical or to the alkyl portion of a radical in which alkyl appears as the prefix root containing from a to b carbon atoms inclusive. For example, $C_{(1-4)}$ denotes a radical containing 1, 2, 3 or 4 carbon atoms.

The term "cycloalkyl" refers to a saturated or partially unsaturated monocyclic or bicyclic hydrocarbon ring radical derived by the removal of one hydrogen atom from a single ring carbon atom. Typical cycloalkyl radicals include cyclopropyl, cyclobutyl, cyclopentyl, cyclopentenyl, cyclohexyl, cyclohexenyl, cycloheptyl and cyclooctyl. Additional examples include $C_{(3-6)}$cycloalkyl, $C_{(5-8)}$cycloalkyl, decahydronaphthalenyl, and 2,3,4,5,6,7-hexahydro-1H-indenyl.

Any cycloalkyl group may be optionally substituted with one $OCH_3$, one OH, or up to two fluorine atoms.

The term "heterocycloalkyl" refers to a saturated or partially unsaturated monocyclic or bicyclic hydrocarbon ring radical containing at least one ring atom selected from the group consisting O, N, or S, derived by the removal of one hydrogen atom from a single ring carbon atom or nitrogen atom. Typical heterocycloalkyl radicals include azetidinyl, pyrrolidinyl, piperazinyl, morpholinyl, thiomorpholinyl, oxetanyl and tetrahydrofuranyl. Sulfur atoms in the ring of the heterocycloalkyl group may be in any oxidation state.

As used herein, the term "thiophenyl" is intended to describe the radical formed by removing a hydrogen atom from the molecule with the structure:

Whenever a variable, such as "n" in —$(CX_2)_nO(CX_2)_n$—, appears more than one time in a chemical formula, each definition is considered to be independent.

Where an alkyl substituent, such as but not limited to $C_{(1-6)}$alkyl, appears more than once in a compound of Formula I, each substitution on said alkyl group is independently selected.

An alkyl group may be substituted as described in the specification. When an alkyl group is substituted with the diradical —$(CX_2)_m$— both termini of the diradical may be attached to either the same or different carbon atoms. For example, both

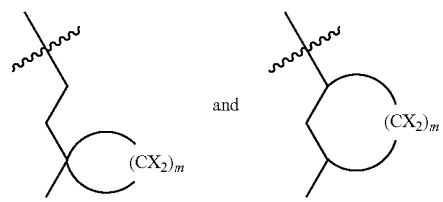

are examples of —$(CX_2)_m$— substitution on a butyl group. Examples of —$(CX_2)_m$— substitution include without limitation

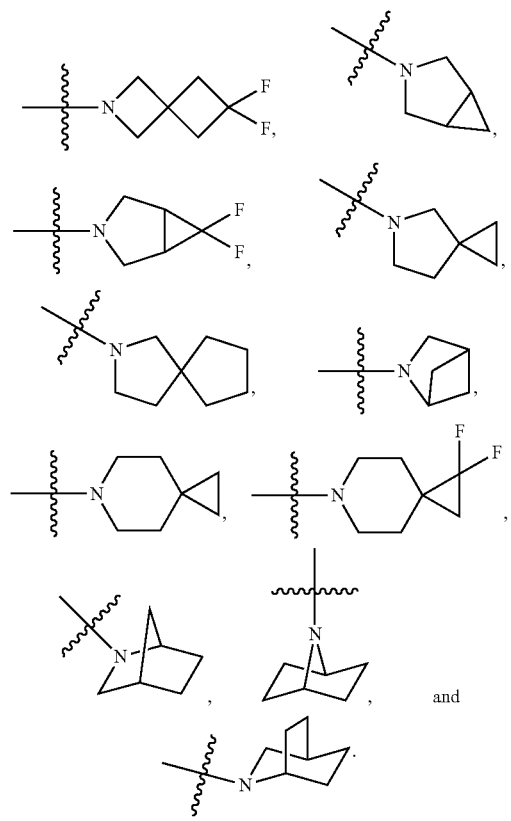

Similarly, —$(CX_2)_n$—, or —$(CX_2)_nO(CX_2)_n$— diradical substitution may occur on either the same or different ring carbons. Examples of —$(CX_2)_n$— substitution include without limitation

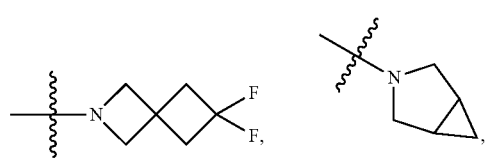

-continued

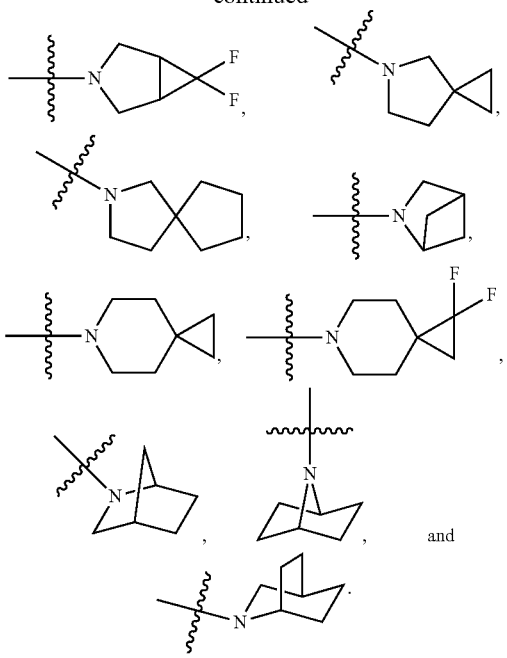

Examples of —(CX$_2$)$_n$O(CX$_2$)$_n$— substitution include without limitation

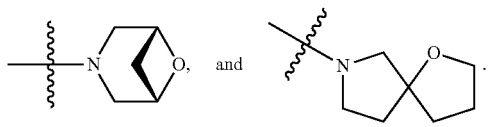 [SMILES: *N1C[C@H]2C[C@@H](C1)O2 ; *N1CCC2(CCCO2)C1]

Pharmaceutically Acceptable Salts

Pharmaceutically acceptable acidic/anionic salts include, and are not limited to acetate, benzenesulfonate, benzoate, bicarbonate, bitartrate, bromide, calcium edetate, camsylate, carbonate, chloride, citrate, dihydrochloride, edetate, edisylate, estolate, esylate, fumarate, glyceptate, gluconate, glutamate, glycollylarsanilate, hexylresorcinate, hydrabamine, hydrobromide, hydrochloride, hydroxynaphthoate, iodide, isethionate, lactate, lactobionate, malate, maleate, mandelate, mesylate, methylbromide, methylnitrate, methylsulfate, mucate, napsylate, nitrate, pamoate, pantothenate, phosphate/diphosphate, polygalacturonate, salicylate, stearate, subacetate, succinate, sulfate, tannate, tartrate, teoclate, tosylate and triethiodide. Organic or inorganic acids also include, and are not limited to, hydriodic, perchloric, sulfuric, phosphoric, propionic, glycolic, methanesulfonic, hydroxyethanesulfonic, oxalic, 2-naphthalenesulfonic, p-toluenesulfonic, cyclohexanesulfamic, saccharinic or trifluoroacetic acid.

Pharmaceutically acceptable basic/cationic salts include, and are not limited to aluminum, 2-amino-2-hydroxymethylpropane-1,3-diol (also known as tris(hydroxymethyl)aminomethane, tromethane or "TRIS"), ammonia, benzathine, t-butylamine, calcium, calcium gluconate, calcium hydroxide, chloroprocaine, choline, choline bicarbonate, choline chloride, cyclohexylamine, diethanolamine, ethylenediamine, lithium, LiOMe, L-lysine, magnesium, meglumine, NH$_3$, NH$_4$OH, N-methyl-D-glucamine, piperidine, potassium, potassium-t-butoxide, potassium hydroxide (aqueous), procaine, quinine, sodium, sodium carbonate, sodium-2-ethylhexanoate, sodium hydroxide, triethanolamine, or zinc.

Methods of Use

The present invention is directed to a method for preventing, treating or ameliorating a RORγt mediated inflammatory syndrome, disorder or disease comprising administering to a subject in need thereof an effective amount of a compound of Formula I or a form, composition or medicament thereof.

Since RORγt is an N-terminal isoform of RORγ, it is recognized that compounds of the present invention which are modulators of RORγt are likely to be modulators of RORγ as well. Therefore the mechanistic description "RORγt modulators" is intended to encompass RORγ modulators as well.

When employed as RORγt modulators, the compounds of the invention may be administered in an effective amount within the dosage range of about 0.5 mg to about 10 g, preferably between about 0.5 mg to about 5 g, in single or divided daily doses. The dosage administered will be affected by factors such as the route of administration, the health, weight and age of the recipient, the frequency of the treatment and the presence of concurrent and unrelated treatments.

It is also apparent to one skilled in the art that the therapeutically effective dose for compounds of the present invention or a pharmaceutical composition thereof will vary according to the desired effect. Therefore, optimal dosages to be administered may be readily determined by one skilled in the art and will vary with the particular compound used, the mode of administration, the strength of the preparation, and the advancement of the disease condition. In addition, factors associated with the particular subject being treated, including subject age, weight, diet and time of administration, will result in the need to adjust the dose to an appropriate therapeutic level. The above dosages are thus exemplary of the average case. There can, of course, be individual instances where higher or lower dosage ranges are merited, and such are within the scope of this invention.

The compounds of Formula I may be formulated into pharmaceutical compositions comprising any known pharmaceutically acceptable carriers. Exemplary carriers include, but are not limited to, any suitable solvents, dispersion media, coatings, antibacterial and antifungal agents and isotonic agents. Exemplary excipients that may also be components of the formulation include fillers, binders, disintegrating agents and lubricants.

The pharmaceutically-acceptable salts of the compounds of Formula I include the conventional non-toxic salts or the quaternary ammonium salts which are formed from inorganic or organic acids or bases. Examples of such acid addition salts include acetate, adipate, benzoate, benzenesulfonate, citrate, camphorate, dodecylsulfate, hydrochloride, hydrobromide, lactate, maleate, methanesulfonate, nitrate, oxalate, pivalate, propionate, succinate, sulfate and tartrate. Base salts include ammonium salts, alkali metal salts such as sodium and potassium salts, alkaline earth metal salts such as calcium and magnesium salts, salts with organic bases such as dicyclohexylamino salts and salts with amino acids such as arginine. Also, the basic nitrogen-containing groups may be quaternized with, for example, alkyl halides.

The pharmaceutical compositions of the invention may be administered by any means that accomplish their intended purpose. Examples include administration by parenteral, subcutaneous, intravenous, intramuscular, intraperitoneal, transdermal, buccal or ocular routes. Alternatively or concurrently, administration may be by the oral route. Suitable formulations for parenteral administration include aqueous solutions of the active compounds in water-soluble form, for example, water-soluble salts, acidic solutions, alkaline solutions, dextrose-water solutions, isotonic carbohydrate solutions and cyclodextrin inclusion complexes.

The present invention also encompasses a method of making a pharmaceutical composition comprising mixing a pharmaceutically acceptable carrier with any of the compounds of the present invention. Additionally, the present invention includes pharmaceutical compositions made by mixing a pharmaceutically acceptable carrier with any of the compounds of the present invention.

Polymorphs and Solvates

Furthermore, the compounds of the present invention may have one or more polymorph or amorphous crystalline forms and as such are intended to be included in the scope of the invention. In addition, the compounds may form solvates, for example with water (i.e., hydrates) or common organic solvents. As used herein, the term "solvate" means a physical association of the compounds of the present invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. The term "solvate" is intended to encompass both solution-phase and isolatable solvates. Non-limiting examples of suitable solvates include ethanolates, methanolates, and the like.

It is intended that the present invention include within its scope polymorphs and solvates of the compounds of the present invention. Thus, in the methods of treatment of the present invention, the term "administering" shall encompass the means for treating, ameliorating or preventing a syndrome, disorder or disease described herein with the compounds of the present invention or a polymorph or solvate thereof, which would obviously be included within the scope of the invention albeit not specifically disclosed.

In another embodiment, the invention relates to a compound as described in Formula I for use as a medicament.

In another embodiment, the invention relates to the use of a compound as described in Formula I for the preparation of a medicament for the treatment of a disease associated with an elevated or aberrant RORγt activity.

The present invention includes within its scope prodrugs of the compounds of this invention. In general, such prodrugs will be functional derivatives of the compounds which are readily convertible in vivo into the required compound. Thus, in the methods of treatment of the present invention, the term "administering" shall encompass the treatment of the various disorders described with the compound specifically disclosed or with a compound which may not be specifically disclosed, but which converts to the specified compound in vivo after administration to the patient. Conventional procedures for the selection and preparation of suitable prodrug derivatives are described, for example, in "Design of Prodrugs", Ed. H. Bundgaard, Elsevier, 1985.

Furthermore, it is intended that within the scope of the present invention, any element, in particular when mentioned in relation to a compound of Formula I, shall comprise all isotopes and isotopic mixtures of said element, either naturally occurring or synthetically produced, either with natural abundance or in an isotopically enriched form. For example, a reference to hydrogen includes within its scope $^1H$, $^2H$ (D), and $^3H$ (T). Similarly, references to carbon and oxygen include within their scope respectively $^{12}C$, $^{13}C$ and $^{14}C$ and $^{16}O$ and $^{18}O$. The isotopes may be radioactive or non-radioactive. Radiolabelled compounds of Formula I may comprise a radioactive isotope selected from the group of $^3H$, $^{11}C$, $^{18}F$, $^{122}I$, $^{123}I$, $^{125}I$, $^{131}I$, $^{75}Br$, $^{76}Br$, $^{77}Br$ and $^{82}Br$. Preferably, the radioactive isotope is selected from the group of $^3H$, $^{11}C$ and $^{18}F$.

Some compounds of the present invention may exist as atropisomers. Atropisomers are stereoisomers resulting from hindered rotation about single bonds where the steric strain barrier to rotation is high enough to allow for the isolation of the conformers. It is to be understood that all such conformers and mixtures thereof are encompassed within the scope of the present invention.

Where the compounds according to this invention have at least one stereo center, they may accordingly exist as enantiomers or diastereomers. It is to be understood that all such isomers and mixtures thereof are encompassed within the scope of the present invention.

Where the processes for the preparation of the compounds according to the invention give rise to mixture of stereoisomers, these isomers may be separated by conventional techniques such as preparative chromatography. The compounds may be prepared in racemic form, or individual enantiomers may be prepared either by enantiospecific synthesis or by resolution. The compounds may, for example, be resolved into their component enantiomers by standard techniques, such as the formation of diastereomeric pairs by salt formation with an optically active acid, such as (−)-di-p-toluoyl-D-tartaric acid and/or (+)-di-p-toluoyl-L-tartaric acid followed by fractional crystallization and regeneration of the free base. The compounds may also be resolved by formation of diastereomeric esters or amides, followed by chromatographic separation and removal of the chiral auxiliary. Alternatively, the compounds may be resolved using a chiral HPLC column.

During any of the processes for preparation of the compounds of the present invention, it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 1991. The protecting groups may be removed at a convenient subsequent stage using methods known from the art.

Abbreviations

Herein and throughout the application, the following abbreviations may be used.

Ac acetyl
APCI atmospheric pressure chemical ionisation
br broad
Bu butyl
Cy cyclohexyl
d doublet
dba dibenzylideneacetone
DABCO 1,4-diazabicyclo[2.2.2]octane
DAST diethylaminosulfur trifluoride
DCM dichloromethane
DIPEA N,N-diisopropylethylamine (Hünigs base)
DMA dimethylacetamide
DMAP 4-dimethylaminopyridine
DME ethylene glycol dimethyl ether
DMF N,N-dimethylformamide
DMSO dimethyl sulfoxide
dppf 1,1'-bis(diphenylphosphanyl) ferrocene EDC.HCl N-(3-dimethylaminopropyl)-N'-ethylcarbodiimide hydrochloride
ESI electrospray ionization
Et ethyl
$Et_2O$ diethyl ether
EtOAc ethyl acetate
FCC flash column chromatography
h hour
HATU O-(7-azabenzotriazol-1-yl)-N,N,N',N'-tetramethyluronium hexafluorophosphate
HOBt 1-hydroxybenzotriazole
HPLC high pressure liquid chromatography
Hz Hertz
IBX 2-iodoxybenzoic acid
Lawesson Reagent 2,4-bis(4-methoxyphenyl)-2,4-dithioxo-1,3,2,4-dithiadiphosphetane
LDA lithium diisopropyl amide
m multiplet
M molar (moles/liter)
Me methyl
min minutes
Ms methane sulfonyl
MS mass spectrometry
MTBE methyl tert-butyl ether
NBS N-bromosuccinimide
NMR nuclear magnetic resonance
PE petroleum ether
Ph phenyl
pin pinacolato
Piv pivaloyl ($Me_3CO$)
ppm parts per million
psi pounds per square inch
q quartet
rt room temperature
s singlet
SEM 2-(trimethylsilyl)ethoxymethyl
t triplet
TBAF tetrabutylammonium fluoride
TBAI tetrabutylammonium iodide
TEA triethylamine
TEMPO (2,2,6,6-tetramethylpiperidin-1-yl)oxidanyl
Tf trifluoromethanesulfonyl
TFAA trifluoroacetic acid anhydride
THF tetrahydrofuran
TLC thin layer chromatography
TMS trimethylsilyl
Ts p-toluenesulfonyl General Schemes The compounds of the present invention can be prepared by a combination of methods known in the art including the procedures described in Schemes I to XII below. The following reaction schemes are only meant to represent examples of the invention and are in no way meant to be a limit of the invention.

Scheme I describes the preparation of [1,3,4]-oxadiazoles and [1,3,4]-thiadiazoles of the present invention. α-Brominated ketones A-I can by cyclised using ethyl 2-amino-2-thioxoacetate to give thiazole intermediates A-II as described in WO2013/178362. Subsequent treatment with hydrazine followed by coupling to carboxylic acids $R^6COOH$ and cyclization with, e.g., TsCl or $Tf_2O$, affords the [1,3,4]-oxadiazole intermediates A-III (X=H). This sequence can alternatively be applied to a brominated A-II, which requires a bromination step prior to hydrazide formation. Pd catalyzed coupling with an appropriate aryl halide or aryl boronic ester (in case of a Suzuki procedure) affords compounds of structure A-IV. Intermediates A-III can be prepared by an alternative route that uses a different order of steps. Reaction of intermediates such as A-VIII with hydrazine followed by coupling to carboxylic acid $R^6COOH$ and cyclization with, e.g., TsCl, affords the [1,3,4]-oxadiazole intermediates A-IX. Palladium-catalyzed coupling with an appropriate alkyl zinc reagent then affords intermediates A-III. An alternative route uses a different order of steps, starting with a palladium-catalyzed coupling of intermediates A-II with an appropriate aryl halide. This is followed by hydrazine treatment, coupling to $R^6COOH$ and cyclization as previously described to afford intermediates A-IV. [1,3,4]-Thiadiazoles can be prepared in a similar fashion. Reaction of intermediates A-II with hydrazine followed by coupling to carboxylic acid $R^6COOH$ and treatment with Lawesson reagent at elevated temperature affords [1,3,4]-thiadiazoles A-VI. Palladium-catalyzed coupling with an appropriate aryl halide leads to compounds of structure A-VII.

Scheme I

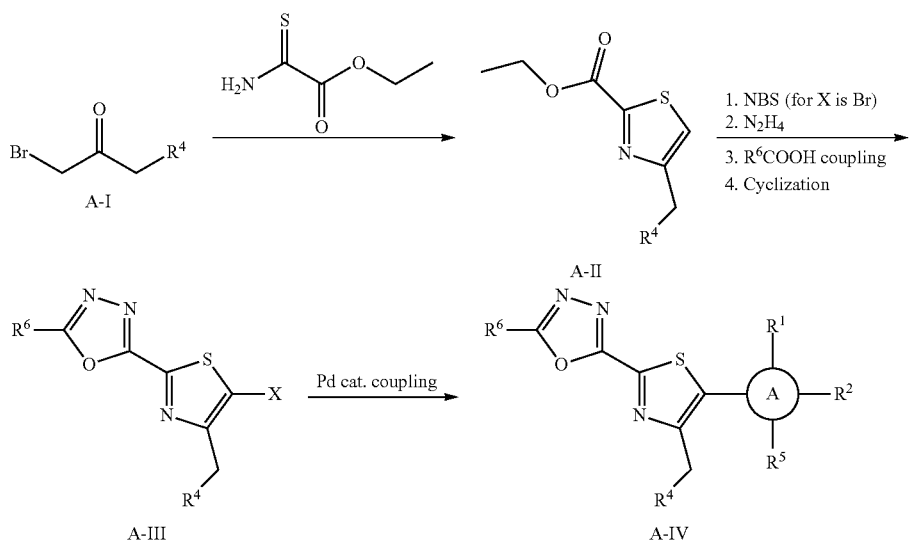

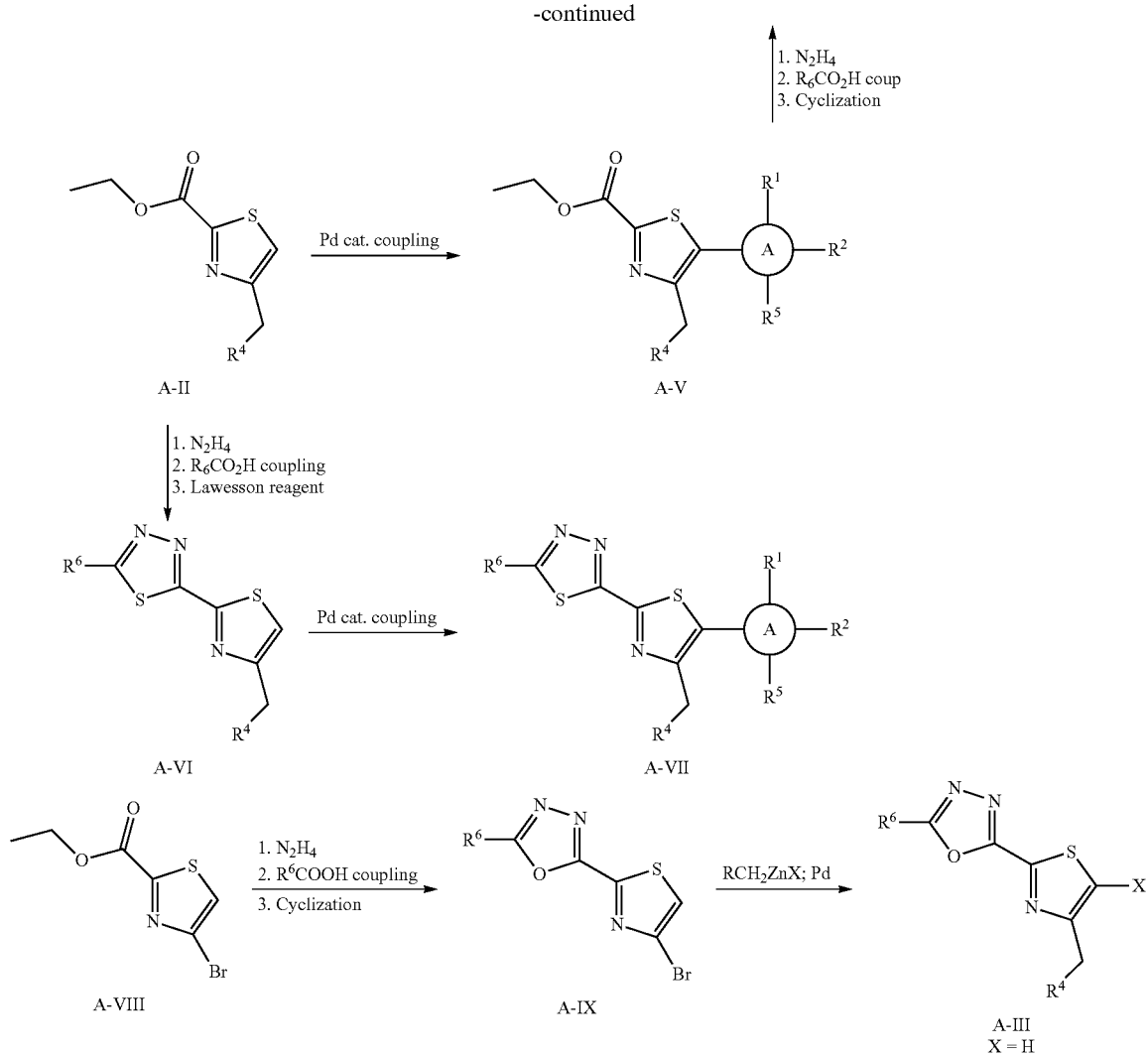

Scheme II illustrates the preparation of [1,3,4]-oxadiazoles of the present invention bearing an amine group $NA^1A^2$ as substituent $R^4$. 1-Bromo-3-hydroxypropan-2-one can be cyclized with ethyl 2-amino-2-thioxoacetate to give the thiazole intermediate B-I. Protection using SEMCl is followed by acyl hydrazide formation, $R^6COOH$ coupling and cyclization using, e.g., TsCl, to afford intermediates B-II. Deprotection using HCl is followed by palladium-catalyzed coupling with an appropriate aryl halide and selective oxidation using, e.g., $MnO_2$, to give the aldehyde intermediates B-III. Reductive amination leads to compounds of structure B-IV. Alternatively B-I can first be converted to B-V by a sequence of palladium-catalyzed coupling, $MnO_2$ oxidation and reductive amination. Compounds of structure B—IV can be obtained from B—V by applying the same three steps from ester to oxadiazole as described for preparation of B-II.

Scheme II

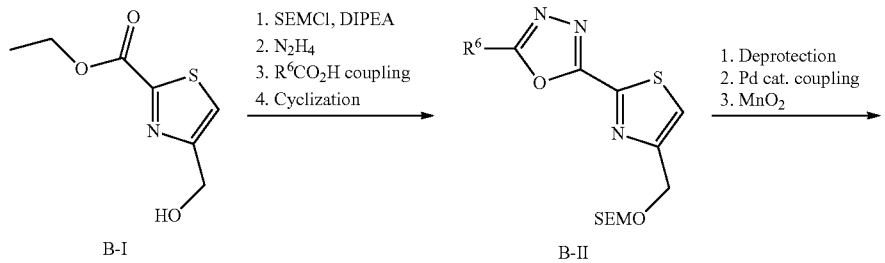

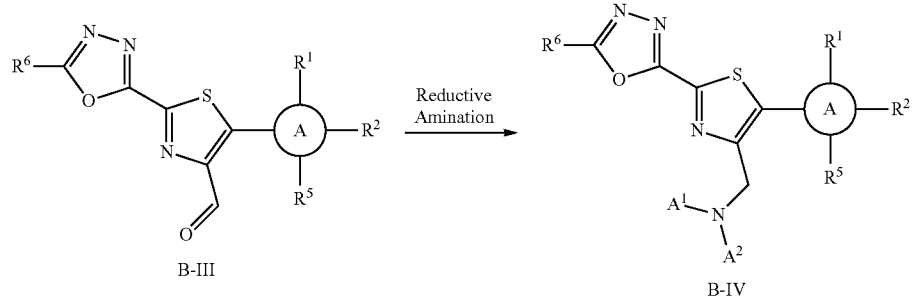

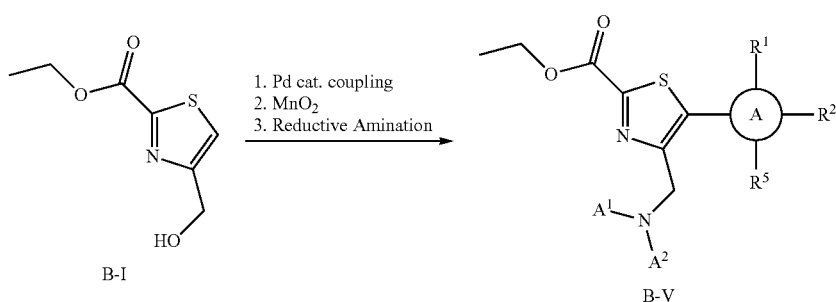

[1,2,4]-Oxadiazoles of the present invention can be prepared as shown in Scheme III. Thiazole ester intermediates A-II can be converted into C-I using a sequence of ester ammonolysis, dehydration with TFAA and amidoxime formation with hydroxylamine. The sequence is initiated with a bromination step in case of intermediates C-I with X=Br. Acylation of C-I with R⁶COOH and subsequent cyclization affords the [1,2,4]-oxadiazole intermediates C-II. Palladium-catalyzed coupling using appropriate aryl halides or aryl boronic acids or esters leads to compounds of structure C-III. Treatment of brominated thiazole intermediates A-II with an $R^6$ substituted amidoxime results in the formation of [1,2,4]-oxadiazole intermediates C-IV with an $R^6$ substituent in the 5-position. Suzuki coupling with an appropriate aryl boronic acid or ester leads to compounds of structure C-V.

Scheme III

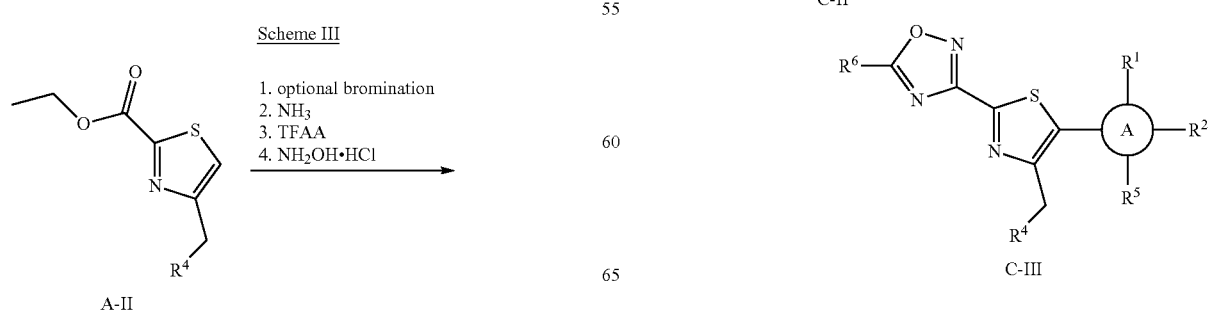

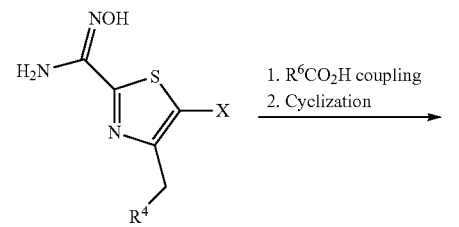

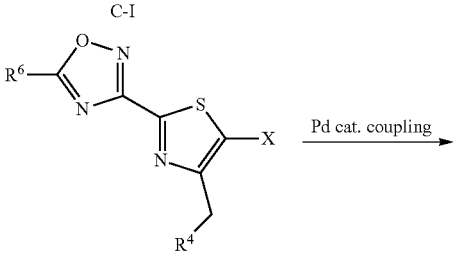

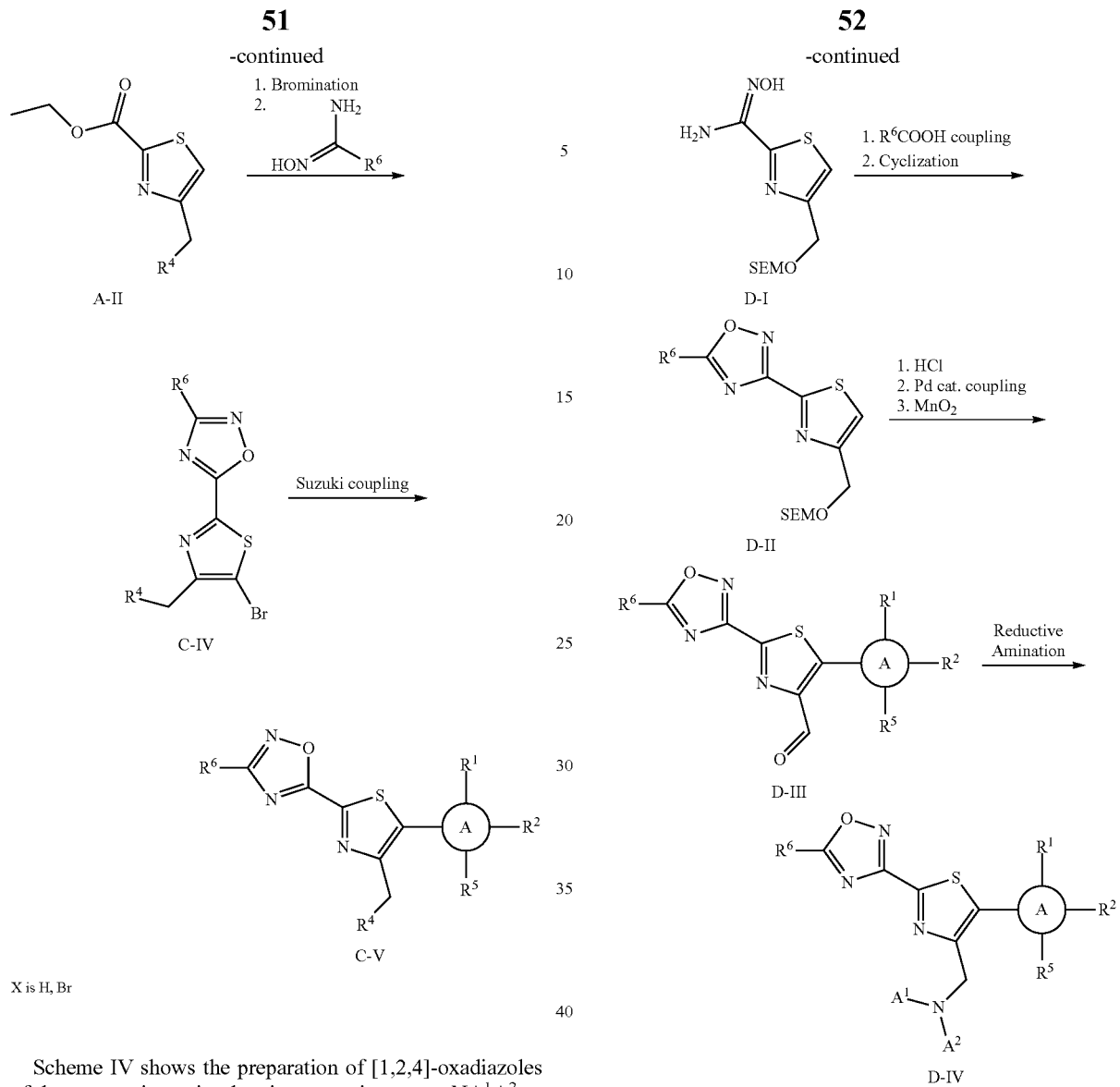

Scheme IV shows the preparation of [1,2,4]-oxadiazoles of the present invention bearing an amine group $NA^1A^2$ as substituent $R^4$. B-I is protected by using SEMCl followed by ammonolysis, dehydration with TFAA and amidoxime formation using hydroxylamine to give D-I. Acylation with $R^6COOH$ and cyclization affords intermediates D-II which are deprotected, coupled to an appropriate aryl halide using a palladium catalyst and oxidized with, e.g. $MnO_2$, to give aldehyde intermediates D-III. Reductive amination leads to compounds of structure D-IV.

The preparation of isoxazoles of the present invention is shown in Scheme V. Intermediates A-II can be reduced to alcohols using $NaBH_4$. IBX oxidation and treatment of the resulting aldehyde with hydroxylamine affords oxime intermediates E-I. Nitrile oxide formation and [3+2] cycloaddition with an $R^6$ substituted alkyne leads to isoxazoles E-II. Palladium-catalyzed coupling with an appropriate aryl halide affords compounds of structure E-III.

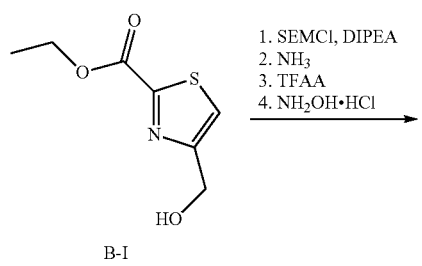

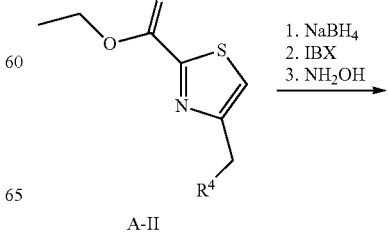

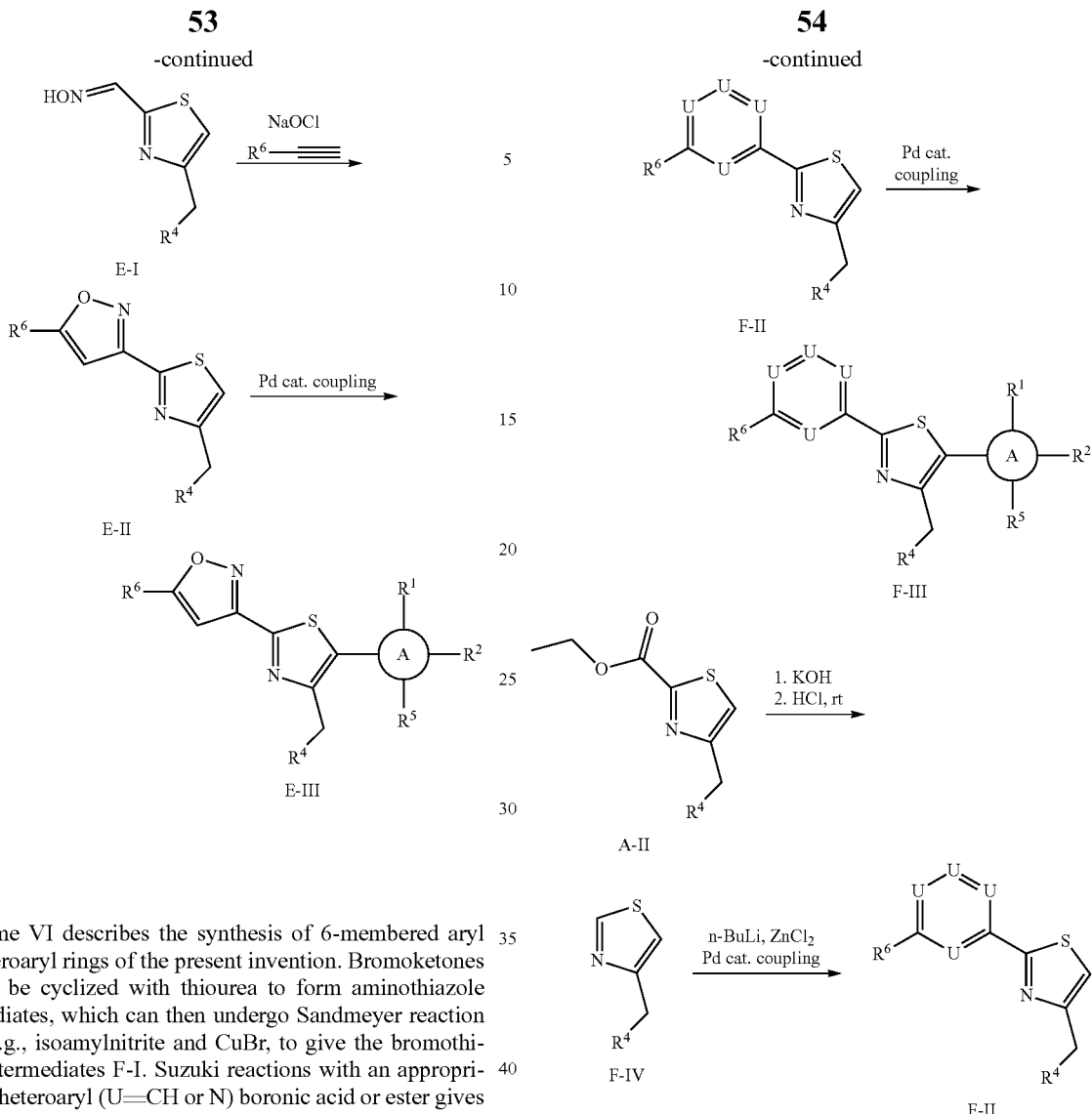

Scheme VI describes the synthesis of 6-membered aryl and heteroaryl rings of the present invention. Bromoketones A-I can be cyclized with thiourea to form aminothiazole intermediates, which can then undergo Sandmeyer reaction using, e.g., isoamylnitrite and CuBr, to give the bromothiazole intermediates F-I. Suzuki reactions with an appropriate aryl/heteroaryl (U=CH or N) boronic acid or ester gives intermediates F-II, which in a second palladium-catalyzed reaction with an appropriate aryl halide affords compounds of structure F-III. In an alternative route, intermediates A-II are saponified using KOH. After neutralization with HCl the resulting carboxylic acids are decarboxylated at rt to give intermediates F-IV, which are metallated with n-BuLi/ZnCl$_2$ followed by palladium-catalyzed coupling to give intermediates F-II.

Scheme VI

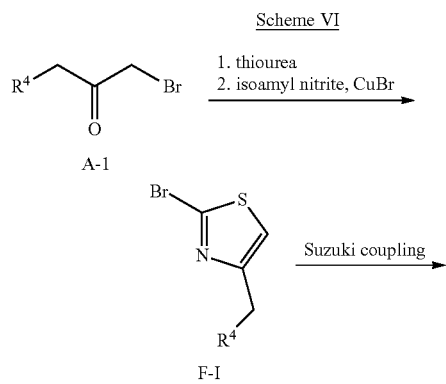

Scheme VII describes the synthesis of thiazole rings of the present invention. Suzuki reaction of intermediates F-I with an appropriate aryl boronic acid or ester gives intermediates G-I, which in a second palladium-catalyzed reaction with an appropriate aryl halide affords compounds of structure G-II.

Scheme VII

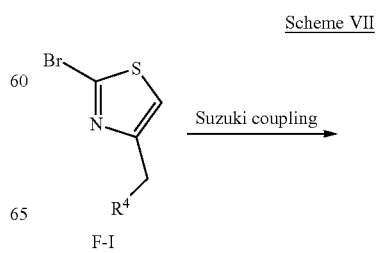

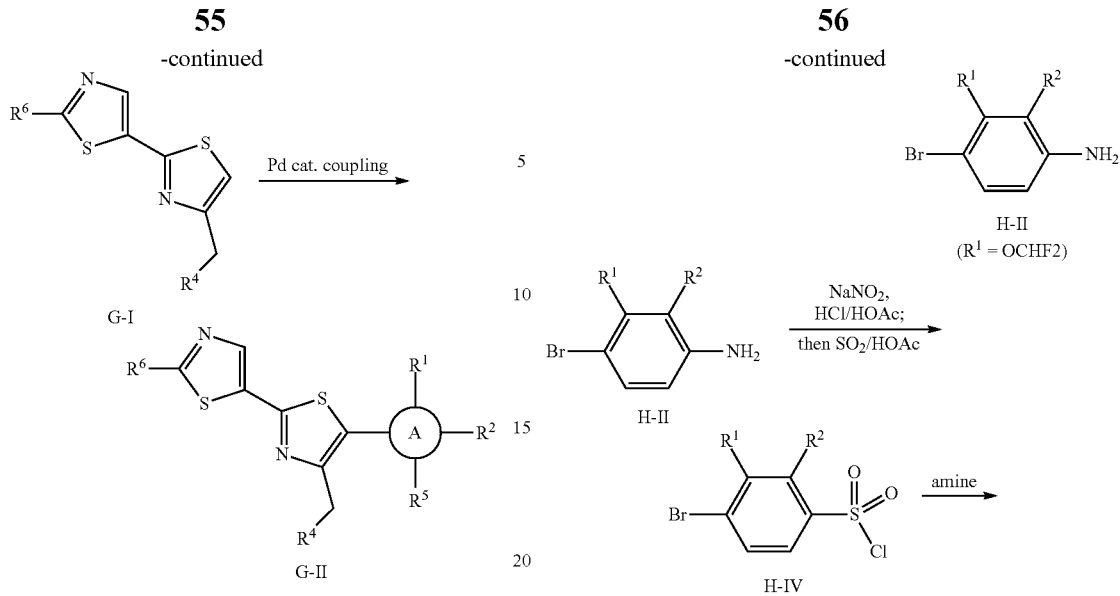

Scheme VIII describes the synthesis of sulfonamide-containing aryl bromide intermediates used in the above palladium-catalyzed coupling reactions. Aldehydes H-I are transformed into the anilines of structure H—II by a sequence of fluoronation, reduction, and bromination ($R^1$=CHF$_2$). Phenols H-III are transformed by a similar sequence of steps into anilines H-II ($R^1$=OCHF$_2$). Anilines H-II are treated sodium nitrite in acid followed by sulfur dioxide to furnish sulfonyl chlorides H-IV, which are coupled with amines to provide the aryl bromide sulfonamide intermediates H-V. Alternatively bromides H-VI are treated with sulfuric acid then with chlorinating reagents POCl$_3$ and PCl$_5$ to afford sulfonyl chlorides that are coupled with amines to provide the aryl bromide sulfonamide intermediates H-V. Isoquinolin-1(2H)-one H-VII is first brominated then treated with P$_2$S$_5$ to furnish 4-bromoisoquinoline-1(8H)-thione H-VIII. Subsequent oxidation and sulfonamide formation provides bromide H-IX.

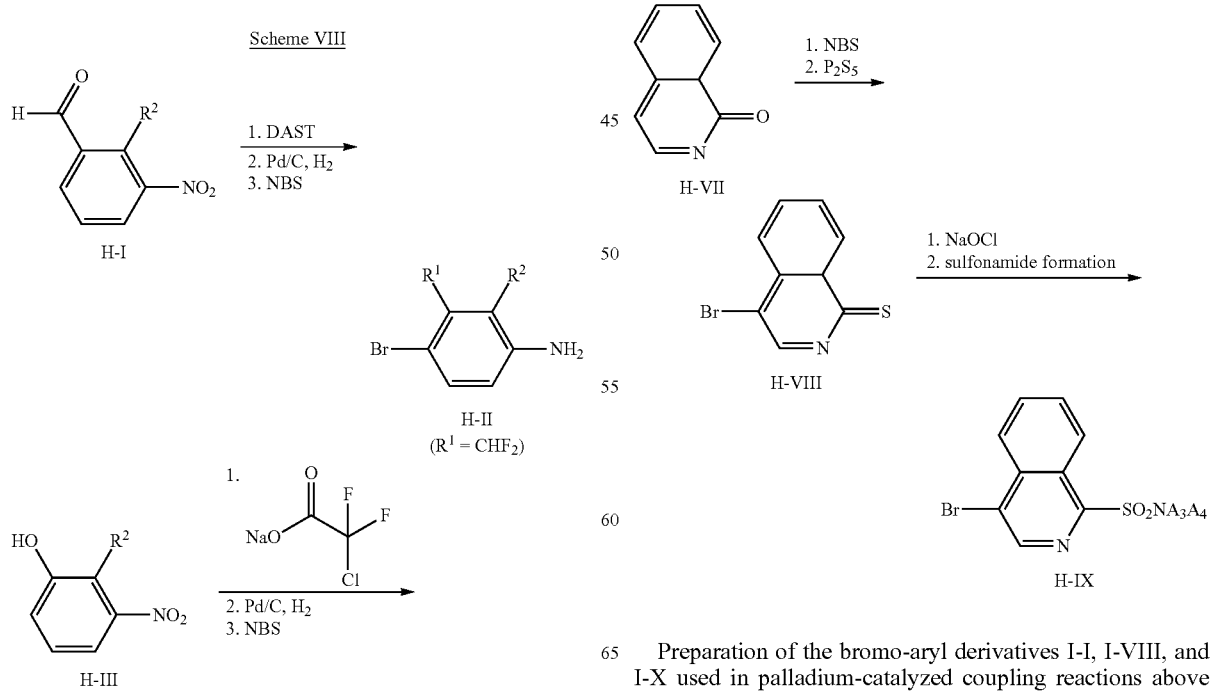

Preparation of the bromo-aryl derivatives I-I, I-VIII, and I-X used in palladium-catalyzed coupling reactions above are shown in Scheme IX. 1,4-Dibromo- or 1-bromo-4-iodoaromatics I-II can be used as reactants for a metallation reactions, e.g. a lithiation with n-butyl-lithium or Grignard formation using isopropyl magnesium chloride. The 1,4-dibromo aromatics should have identical substituents $R^1$ and $R^2$. The metallated species can react with 2,2,2-trifluoro-N-methoxy-N-methylacetamide to form 1-bromo-4-trifluoroacetyl derivates I-III. The trifluoromethyl alcohols I-I can be formed by reaction of intermediates I-III with $TMSCF_3$ in the presence of a fluoride source or by reaction with an alkyl Grignard reagent. Alternatively, the metallated species can react with hexafluoroactone to directly form hexafluoroisopropyl alcohols I-I. The intermediates I-III can also be formed from 1-bromo-4-alkoxycarbonyl aromatics I-IV by esterification and subsequent reaction with $TMSCF_3$ in the presence of a fluoride source. Alternatively, intermediates I-III can be formed from 1-bromo-4-formyl aromatics I-V by reaction with $TMSCF_3$ in the presence of a fluoride source and subsequent oxidation. The trifluoromethyl alcohols I-VIII can be formed by reaction of intermediates I-VII with $TMSCF_3$ in the presence of a fluoride source. 1,3-Dibromoaryl derivatives I-VI can be metallated, e.g. a lithiation with n-butyl-lithium, and subsequent reaction with the 2,2,2-trifluoro-N-methoxy-N-methylacetamide forms 1-bromo-3-trifluoroacetyl derivatives I-VII. 1,3-Dibromo aryl derivatives I-VI can undergo metallation, e.g. a lithiation with n-butyl-lithium, and subsequent reaction with methyl chloroformate to afford the methyl ester I-IX. Subsequent saponification and amide bond formation furnishes amides I-X.

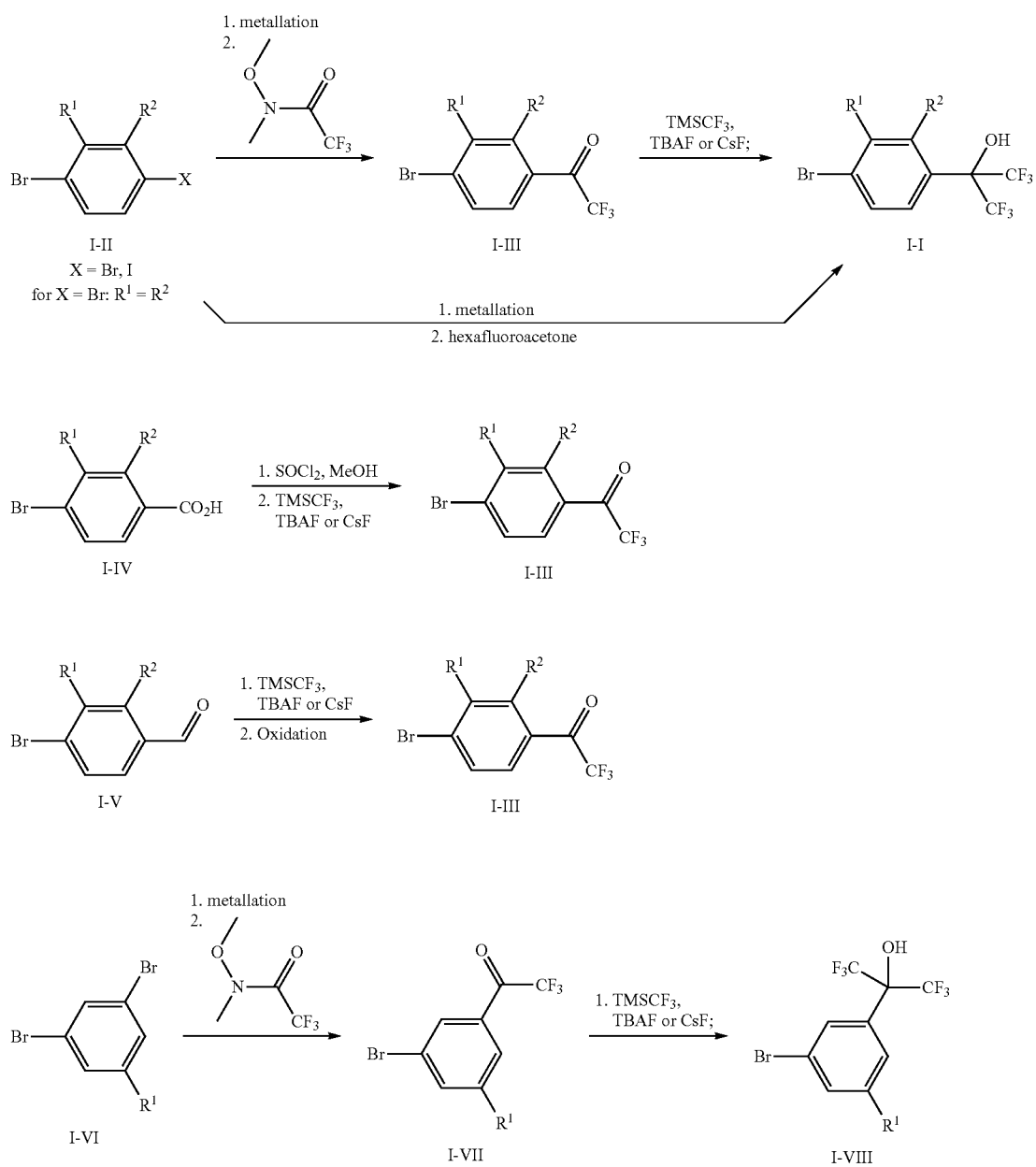

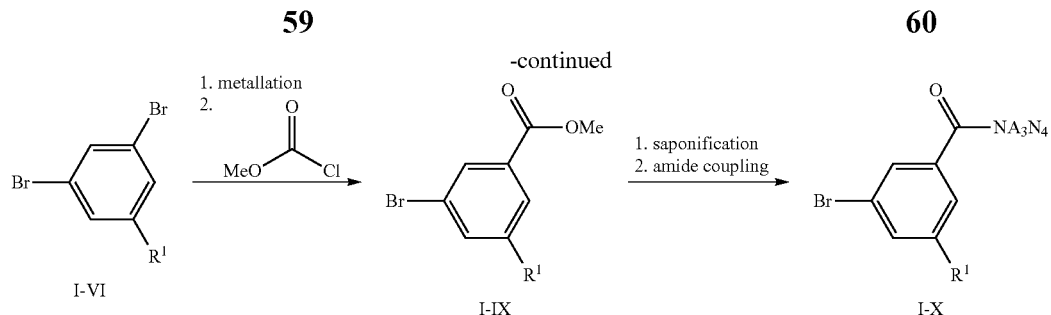

Scheme X describes the synthesis of bromo-aryl derivatives J-I and J-IV. Methyl ketones J-II can be treated with amines in the presence of a reducing agent, e.g. NaHB(OAc)$_3$, to afford aryl bromides J-I. Alternatively, benzaldehydes J-III can be reduced with sodium borohydride and subsequently converted to methanesulfonates, which upon treatment with amines furnish intermediates J-IV.

Scheme X

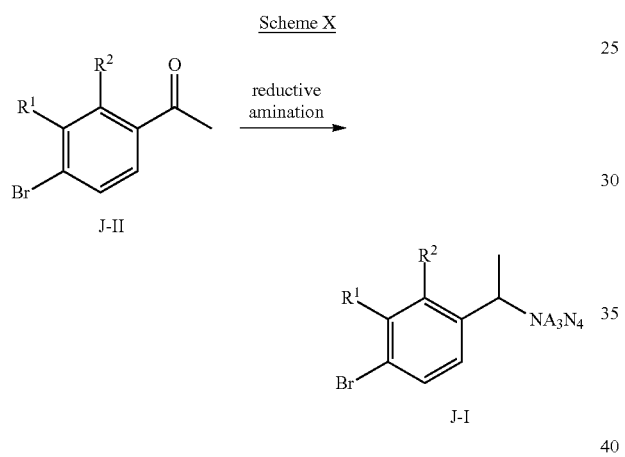

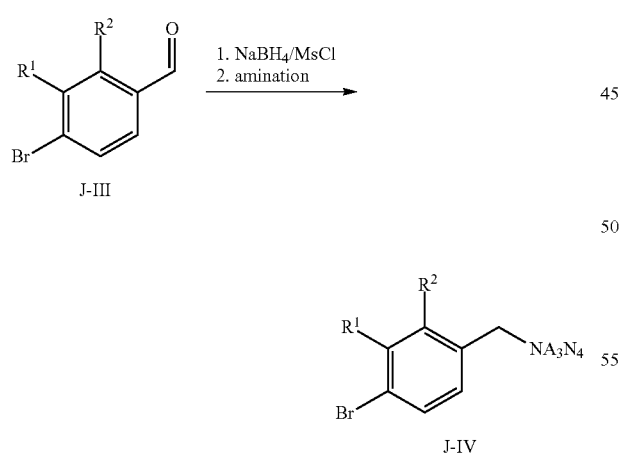

Scheme XI describes the synthesis of some amine intermediates used above in amide-forming reactions. Compounds K-I and K-III are treated with DAST, and then the tert-butoxycarbonyl groups are removed with HCl to provide the fluorinated amines K-II and K-IV as hydrochloride salts.

Scheme XI

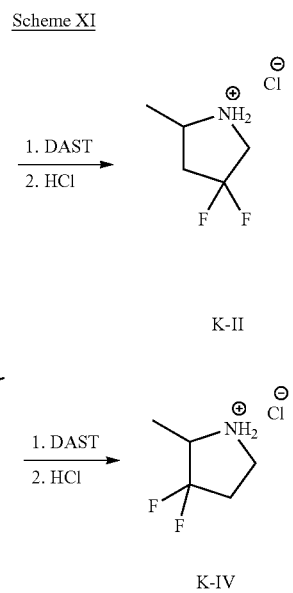

Scheme XII describes the synthesis of boronic esters L-I, L-III, and L-V used in the above thiazole arylation and heteroarylation reactions. Compounds H-V, L-II, and L-IV are treated with palladium reagents, such as Pd(dppf)Cl$_2$, in the presence of bis(pinacolato)diboron to afford boronic esters L-I, L-III, and L-V.

Scheme XII

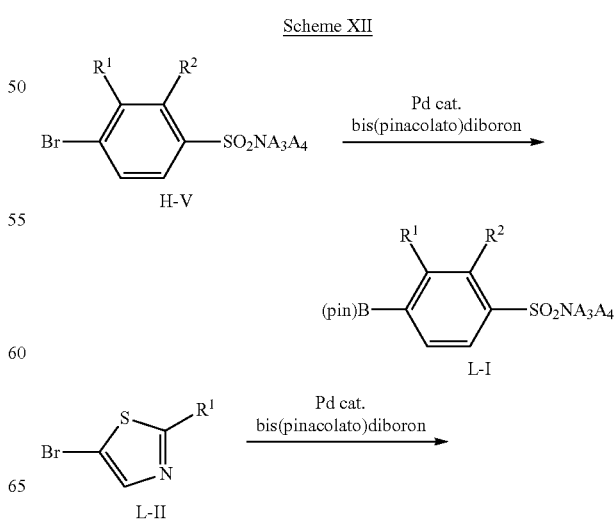

-continued

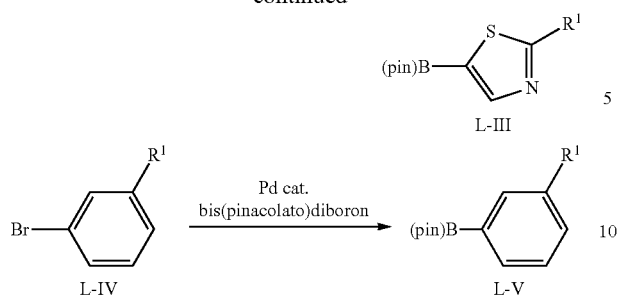

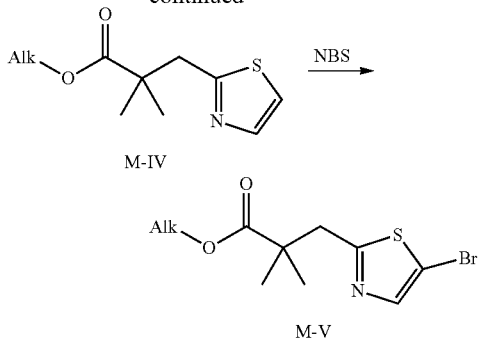

Scheme XIII illustrates the preparation of aryl and heteroaryl halides M-I, M-III and M-V. Isobutyrate esters can be deprotonated with a reagent such as LDA and subsequently reacted with a benzyl bromide to afford compounds of the structure M-I, or with diiodomethane to provide compounds M-II. Subsequent palladium mediated coupling of the corresponding zinc reagent generated from M-II with symmetrical heteroaryl dihalides, where X can equal Cl or Br and U=N or CH, then gives compounds of the general structure M-III. Lithiation of M-II, using n-BuLi, followed by palladium mediated coupling to 2-bromothiazole affords compounds M-IV. Bromination with NBS then yields compounds M-V.

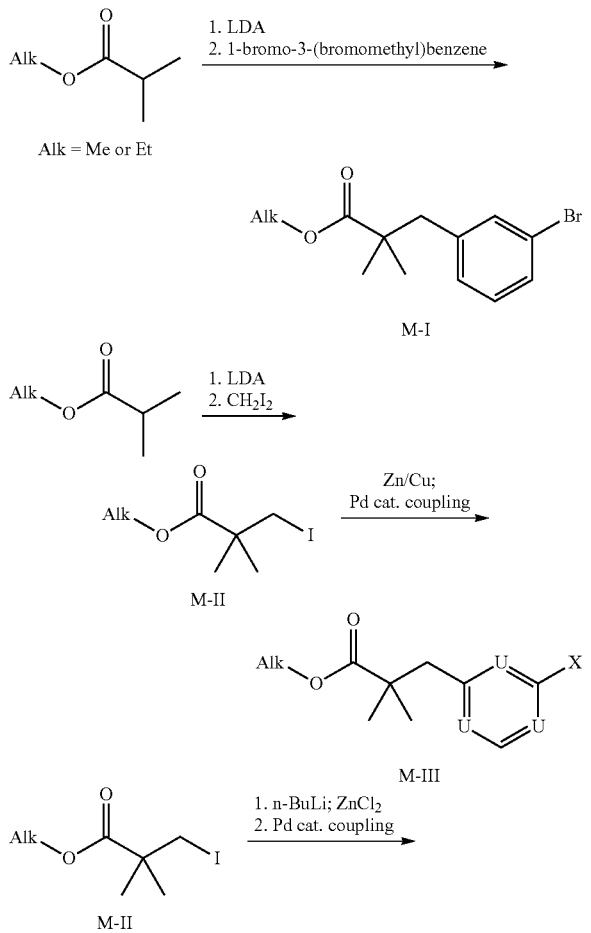

EXAMPLES

Compounds of the present invention can be prepared by methods known to those who are skilled in the art. The following examples are only meant to represent examples of the invention and are in no way meant to be a limit of the invention.

Intermediate 1: Step a

Cyclobutylmethyl 4-methylbenzenesulfonate

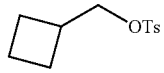

To a solution of cyclobutylmethanol (1.00 g, 11.6 mmol) and pyridine (1.4 mL) in DCM (15 mL) was slowly added TsCl (2.44 g, 12.8 mol) at 0° C. The solution was warmed to 20° C. and stirred at that temperature for 3 h. The reaction was poured into water (50 mL) and extracted with DCM (2×50 mL). The organic layer was washed with brine, dried over anhydrous Na₂SO₄, filtered and concentrated to dryness to afford the title compound as a colorless oil.

Intermediate 1: Step b

2-Cyclobutylacetonitrile

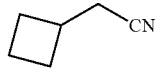

To a solution of cyclobutylmethyl 4-methylbenzenesulfonate (108 g, 450 mmol, Intermediate 1, step a) in DMSO (1000 mL) was added NaCN (33.1 g, 675 mmol) and the mixture was stirred at 80° C. overnight. The mixture was poured into water (2000 mL) and extracted with EtOAc (2×1000 mL). The combined organic layers were washed with brine, dried over anhydrous Na₂SO₄, filtered and concentrated to dryness. The residue was distilled to give the title compound as a yellow oil.

Intermediate 1: Step c

1-Cyclobutylpropan-2-one

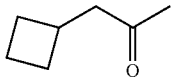

To a solution of 2-cyclobutylacetonitrile (1.00 g, 10.5 mmol, Intermediate 1, step b) in diethyl ether (10 mL) was added methylmagnesium iodide (10.5 mL, 3 M in diethylether) slowly at 0° C. under $N_2$ atmosphere. The mixture was stirred at rt overnight. The mixture was poured into ice (10 g) and 1 M aqueous HCl was added. The mixture was extracted with diethylether (2×15 mL). The combined organic layers were washed with brine, dried over anhydrous $Na_2SO_4$, filtered and concentrated to dryness to give the title compound as a yellow oil, which was used in the next step without further purification.

Intermediate 1: Step d

1-Bromo-3-cyclobutylpropan-2-one

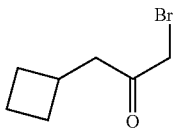

To a solution of 1-cyclobutylpropan-2-one (2.40 g, 21.4 mmol, Intermediate 1, step c) in MeOH (25 mL) was added $Br_2$ (0.88 mL, 17 mmol) dropwise at 0° C. and stirred at rt overnight. The mixture was extracted with EtOAc (2×30 mL). The combined organic layers were washed with brine, dried over anhydrous $Na_2SO_4$, filtered and concentrated to dryness to give the title compound as a yellow oil.

Intermediate 1

Ethyl 4-(cyclobutylmethyl)thiazole-2-carboxylate

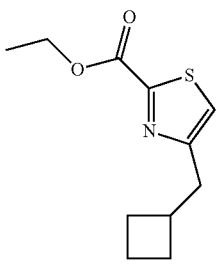

To a solution of 1-bromo-3-cyclobutylpropan-2-one (3.93 g, 20.7 mmol, Intermediate 1, step d) in EtOH (40 mL) was added ethyl 2-amino-2-thioxoacetate (3.30 g, 24.8 mmol) and the mixture was stirred at 85° C. for 3 h. The resulting mixture was poured into water and extracted with EtOAc (2×50 mL). The residue was purified by FCC on silica gel (PE/EtOAc=50/1) to give the title compound as a yellow oil.

Intermediate 1/1

Ethyl 4-(cyclopentylmethyl)thiazole-2-carboxylate

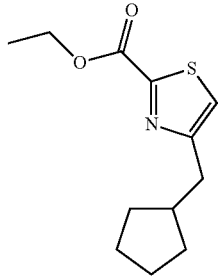 [SMILES: CCOC(=O)c1nc(CC2CCCC2)cs1]

The title compound was prepared as described for the synthesis of Intermediate 1, using in step d 1-cyclopentylpropan-2-one in place of 1-cyclobutylpropan-2-one.

Intermediate 1/2

Ethyl 4-(cyclohexylmethyl)thiazole-2-carboxylate

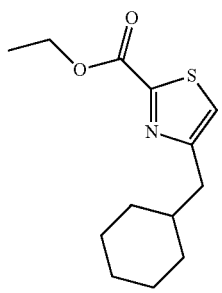 [SMILES: CCOC(=O)c1nc(CC2CCCCC2)cs1]

The title compound was prepared as described for the synthesis of Intermediate 1, using in step d 1-cyclohexylpropan-2-one in place of 1-cyclobutylpropan-2-one.

Intermediate 1/3

Ethyl 4-isobutylthiazole-2-carboxylate

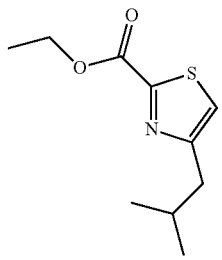

The title compound was prepared as described for the synthesis of Intermediate 1, using in step d 4-methylpentan-2-one in place of 1-cyclobutylpropan-2-one.

Intermediate 1/4

Ethyl 4-(2-methoxy-2-methylpropyl)thiazole-2-carboxylate

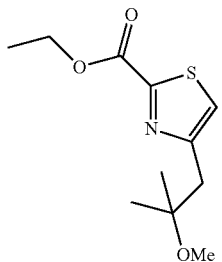 [SMILES: CCOC(=O)c1nc(CC(C)(C)OC)cs1]

The title compound was prepared as described for the synthesis of Intermediate 1, using in step d 4-methoxy-4-methylpentan-2-one in place of 1-cyclobutylpropan-2-one.

Intermediate 1/5

Ethyl 4-((1-methoxycyclobutyl)methyl)thiazole-2-carboxylate

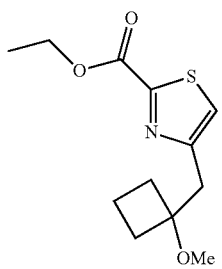 [SMILES: CCOC(=O)c1nc(CC2(OC)CCC2)cs1]

The title compound was prepared as described for the synthesis of Intermediate 1, using in step d 1-(1-methoxycyclobutyl)propan-2-one in place of 1-cyclobutylpropan-2-one.

Intermediate 1/6

Ethyl 4-(4-fluorobenzyl)thiazole-2-carboxylate

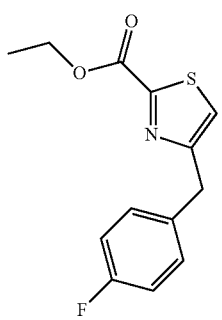 [SMILES: CCOC(=O)c1nc(Cc2ccc(F)cc2)cs1]

The title compound was prepared as described for the synthesis of Intermediate 1, using in step d 1-(4-fluorophenyl)propan-2-one in place of 1-cyclobutylpropan-2-one.

Intermediate 1/7

Ethyl 4-(hydroxymethyl)thiazole-2-carboxylate

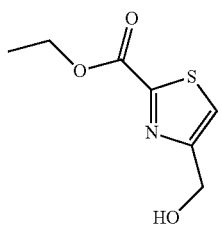

The title compound was prepared as described for the synthesis of Intermediate 1, using in the final step 1-bromo-3-hydroxypropan-2-one in place of 1-bromo-3-cyclobutylpropan-2-one.

Intermediate 1/8: Step a (3,3-Dimethylcyclobutyl)methyl 4-methylbenzenesulfonate

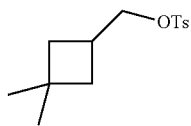

A solution of borane in THF (1.0 M, 43.0 mL, 42.9 mmol) was added to an ice-cooled solution of 3,3-dimethylcyclobutanecarboxylic acid (1.83 g, 14.3 mmol) in THF (5 mL) and the reaction mixture was heated under reflux for 6 h, cooled, quenched by the dropwise addition of MeOH, and concentrated under vacuum to afford a residue, which was dissolved in DCM (10 mL). Then TsCl (3.35 g, 18 mmol) and DMAP (360 mg, 3.0 mmol) were added and the mixture was stirred at rt overnight. Saturated aqueous NaHCO$_3$ was added and the mixture was extracted with EtOAc (3×50 mL). The combined organic layers were washed with brine, dried over anhydrous Na$_2$SO$_4$ and filtered. The filtrate was concentrated to dryness and the residue was purified by FCC on silica gel (PE/EtOAc=30:1) to give the title compound as a brown oil.

Intermediate 1/8: Step b 2-(3,3-Dimethylcyclobutyl)acetic acid

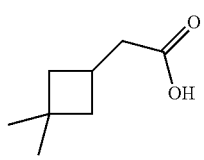

A suspension of (3,3-dimethylcyclobutyl)methyl 4-methylbenzenesulfonate (1.9 g, 7.1 mmol, Intermediate 1/8, step a), NaCN (0.69 g, 14 mmol) and TBAI (0.52 g, 1.4 mmol) in DMSO (20 mL) was heated at 80° C. overnight. The mixture was concentrated and the residue was diluted with H$_2$O and then extracted with EtOAc. The aqueous layer was washed with brine, dried over anhydrous Na$_2$SO$_4$, filtered and concentrated to dryness to afford an intermediate, which was treated with aqueous NaOH (8 N, 15 mmol) and heated to reflux overnight. The mixture was cooled to rt, and pH adjusted to pH 3 by addition of HCl. The mixture was extracted with EtOAc (50 mL×3), dried and concentrated to dryness to afford the title compound as an amber oil.

Intermediate 1/8: Step c 1-(3,3-Dimethylcyclobutyl)propan-2-one

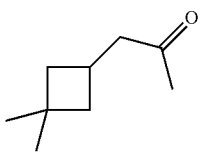

A suspension of 2-(3,3-dimethylcyclobutyl)acetic acid (320 mg, 2.25 mmol, Intermediate 1/8, step b), N,O-dimethylhydroxylamine (280 mg, 4.6 mmol), TEA (700 mg, 6.9 mmol) and HATU (1.31 g, 3.45 mmol) in MeCN (15 mL) was stirred at rt for 2 h. Water (20 mL) was added and the aqueous layer was extracted with EtOAc (20 mL×3). The combined organic layers were washed with brine, concentrated to dryness, redissolved in THF (30 mL) and cooled to −40° C. Methylmagnesium bromide (3 M in Et$_2$O, 2.5 mL, 7.5 mmol) was added and the mixture stirred for 2 h. The mixture was then allowed to warm to rt, quenched with saturated aqueous NH$_4$Cl (30 mL) and extracted with Et$_2$O (30 mL×3). The combined organic extracts were washed with brine and concentrated to dryness at 20° C. to afford the title compound as a brown residue, which was used directly in the next step.

Intermediate 1/8

Ethyl 4-((3,3-dimethylcyclobutyl)methyl)thiazole-2-carboxylate

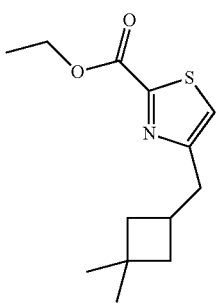 [SMILES: CCOC(=O)c1nc(CC2CC(C)(C)C2)cs1]

The title compound was prepared as described for the synthesis of Intermediate 1, using in step d 1-(3,3-dimethylcyclobutyl)propan-2-one (Intermediate 1/8, step c) in place of 1-cyclobutylpropan-2-one.

Intermediate 1/9

Ethyl 4-((3,3-difluorocyclobutyl)methyl)thiazole-2-carboxylate

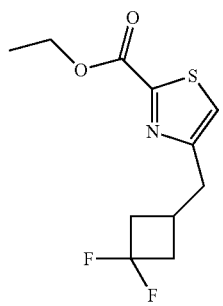 [SMILES: CCOC(=O)c1nc(CC2CC(F)(F)C2)cs1]

The title compound was prepared as described for the synthesis of Intermediate 1/8, using in step a 3,3-difluorocyclobutanecarboxylic acid in place of 3,3-dimethylcyclobutanecarboxylic acid.

Intermediate 1/10

Ethyl 4-(isopropoxymethyl)thiazole-2-carboxylate

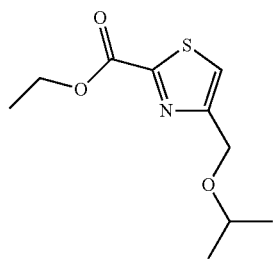

To a solution of 1,3-dibromopropan-2-one (10.0 g, 46.3 mmol) in isopropanol (40 mL) was added ethyl 2-amino-2-thioxoacetate (6.8 g, 50 mmol) and the mixture was stirred at 80° C. for 3 days, diluted with H$_2$O, and extracted with EtOAc (×3). The combined organic layers were washed with brine, dried over anhydrous Na$_2$SO$_4$, filtered, concentrated to dryness, and purified by FCC on silica gel (PE/EtOAc=3:1) to give the title compound as a brown oil.

Intermediate 2: Step a 4-(Cyclobutylmethyl)thiazole-2-carbohydrazide

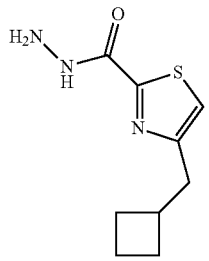 [SMILES: NNC(=O)c1nc(CC2CCC2)cs1]

To a mixture of ethyl 4-(cyclobutylmethyl)thiazole-2-carboxylate (1.65 g, 7.40 mmol, Intermediate 1) in EtOH (20 mL) hydrazine hydrate (4.2 mL) was added and the mixture was stirred at rt for 3 h. The mixture was poured into ice-water (50 mL), and a precipitate was formed. The precipitate was collected through filtration and dried under vacuum to give a residue, which was recrystallized from DCM and PE to afford the title compound.

Intermediate 2: Step b

Methyl 4-(2-(4-(cyclobutylmethyl)thiazole-2-carbonyl)hydrazinyl)-2,2-dimethyl-4-oxobutanoate

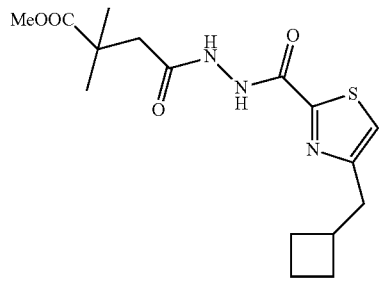 [SMILES: COC(=O)C(C)(C)CC(=O)NNC(=O)c1nc(CC2CCC2)cs1]

To a solution of 4-methoxy-3,3-dimethyl-4-oxobutanoic acid (750 mg, 4.69 mmol) in DCM (10 mL) was added SOCl$_2$ (0.9 mL, 9 mmol) followed by 3 drops of DMF at 0° C. The mixture was allowed to warm to rt and stirred for 4 h at this temperature. The solvent was removed under reduced pressure, and the residue was dissolved in freshly distilled DCM (2 mL). To a solution of 4-(cyclobutylmethyl)thiazole-2-carbohydrazide (1.10 g, 4.86 mmol, Intermediate 2, step a) and TEA (1.0 mL, 7.2 mmol) in DCM (15 mL) was added dropwise the above solution at 0° C. under nitrogen atmosphere. The resulting mixture was stirred at rt for 1 h. The reaction was quenched with H$_2$O (10 mL) and extracted with DCM (3×30 mL). The combined organic layers were washed with H$_2$O (30 mL) and brine (30 mL), dried over anhydrous Na$_2$SO$_4$, filtered and concentrated to dryness. The residue was recrystallized from DCM and PE to give the title compound as a white solid.

Intermediate 2

Methyl 3-(5-(4-(cyclobutylmethyl)thiazol-2-yl)-1,3,4-oxadiazol-2-yl)-2,2-dimethylpropanoate

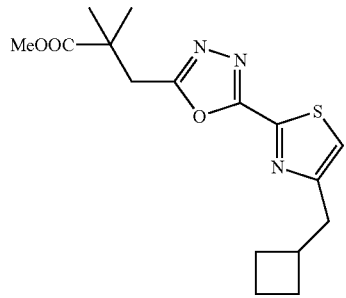 [SMILES: COC(=O)C(C)(C)Cc1nnc(-c2nc(CC3CCC3)cs2)o1]

To a mixture of methyl 4-(2-(4-(cyclobutylmethyl)thiazole-2-carbonyl)hydrazinyl)-2,2-dimethyl-4-oxobutanoate (1.27 g, 3.60 mmol, Intermediate 2, step b) and pyridine (0.90 mL, 11 mmol) in anhydrous DCM (15 mL) was added dropwise Tf$_2$O (1.25 mL, 7.2 mmol) at −10° C. under nitrogen atmosphere. The mixture was stirred at −10° C. for 1 h, at 0° C. for 1 h, and then at rt for 1 h. The mixture was concentrated to dryness and the residue was purified by FCC on silica gel (PE/EtOAc=10/1) to give the title compound as a yellow oil.

An Alternative Synthesis of Intermediate 2

Intermediate 2: Step aa

4-Bromothiazole-2-carbohydrazide

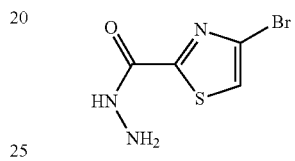

To a solution of ethyl 4-bromothiazole-2-carboxylate (900 g, 3.81 mol) in anhydrous EtOH (4.5 L) was added hydrazine hydrate (305 g, 80 wt % in water, 7.62 mol) dropwise at 15-25° C. in one hour under an inert atmosphere of nitrogen, and the reaction solution was stirred at 15-25° C. for an additional 12 h. The crude reaction mixture was filtered and the filter cake was washed with anhydrous EtOH (1 L). The filter cake was collected and dried at room temperature to afford the title compound as a light yellow solid.

Intermediate 2: Step bb

Methyl-3-(5-(4-bromothiazol-2-yl)-1,3,4-oxadiazol-2-yl)-2,2-dimethylpropanoate

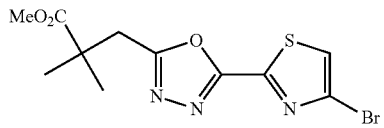 [SMILES: COC(=O)C(C)(C)Cc1nnc(-c2nc(Br)cs2)o1]

A flask was charged with EDC.HCl (1100 g, 5.73 mol,) and DMF (5 L). Then HOBt (77.4 g, 0.57 mol), 4-bromothiazole-2-carbohydrazide (1272 g, 5.73 mol, Intermediate 2, step aa) and DIPEA (2217 g, 17.18 mol) were added sequentially. A solution of 4-methoxy-3,3-dimethyl-4-oxobutanoic acid (1100 g, 6.87 mol) in DMF (1.3 L) was added dropwise at 5-25° C. over 40 minutes. The resulting solution was stirred at 25-37.5° C. and monitored by HPLC. After the consumption of 4-bromothiazole-2-carbohydrazide was complete, DIPEA (1603 g, 11.46 mol) was added followed by dropwise addition of a solution of TsCl (1540 g, 7.45 mol) in DMF (1.5 L) at 25-35° C. over 75 minutes. The resulting solution was stirred at 25-35° C. and monitored by HPLC. After completion of the reaction, the mixture was poured into ice water (40 L) and then acidified to pH 3-4 by the addition of concentrated aqueous HCl. The mixture was extracted with MTBE (2×20 L). The organic layers were combined and then washed with brine (15 L) Anhydrous Na₂SO₄ and activated carbon (380 g) were added to the organic layer, the suspension was stirred at room temperature for 12 h. The crude product was filtered and the filter cake was washed with MTBE (2.5 L). The filtrate was concentrated under vacuum to afford the crude solid product. To the crude solid was added isopropanol (6.5 L) and heptane (6.5 L) and the mixture was heated to 45-53° C. to form a clear solution. The solution was cooled down naturally to 20-25° C. The resultant solids were isolated by filtration and were washed with isopropanol/heptane (1:1). To the solids were added MTBE (8.6 L) and heptane (1.73 L) and the suspension was heated to 48° C. to form a clear solution. The solution was then cooled down naturally to 20-25° C. in 3 h. The resultant solids were isolated by filtration to afford the title compound as a colorless solid.

Intermediate 2

Methyl-3-(5-(4-(cyclobutylmethyl)thiazol-2-yl)-1,3,4-oxadiazol-2-yl)-2,2dimethylpropanoate

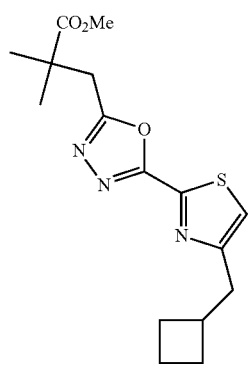 [SMILES: COC(=O)C(C)(C)Cc1nnc(-c2nc(CC3CCC3)cs2)o1]

A flask was charged with magnesium turnings (49.5 g, 2.04 mol), THF (250 mL) and 1,2-dibromoethane (4.7 g, 0.025 mol). The reaction suspension was cooled to 0-15° C. and a solution of cyclobutylmethyl bromide (300 g, 2.01 mol) in THF (3 L) was added dropwise at 10-20° C. over 2.5 h. After addition, the suspension was stirred at 10-20° C. for 12 h. After the reaction was complete, the content of the prepared Grignard reagent was triturated using a dilute HCl solution. A flask was charged with the above (cyclobutylmethyl) magnesium bromide in THF solution (1668 g, 11.9 wt %, 1.16 mol) under an inert atmosphere of nitrogen. A solution of ZnCl₂ (78.8 g, 0.58 mol) in THF (800 mL) was then added dropwise at -5-0° C. over 50 minutes and the resulting suspension was warmed to 20-25° C. over 2 h. A solution of methyl-3-(5-(4-bromothiazol-2-yl)-1,3,4-oxadiazol-2-yl)-2,2-dimethylpropanoate (200 g, 0.58 mol, Intermediate 2, step bb) in THF (400 mL) was the added followed by Pd(dppf)Cl₂ (12.8 g, 17.5 mmol). The resulting solution was stirred under nitrogen at 25-35° C. for 16 h and monitored by HPLC. After the reaction was complete, saturated aqueous NH₄Cl (1 L) was then added at 0-10° C. and the mixture was warmed to 20-25° C. The mixture was then filtered and the filter cake was washed with MTBE (250 mL). The filtrate was collected and the organic layer was washed with a sodium/potassium tartrate salt solution (15 wt. %). The insoluble solids were removed by filtration, and the organic layer was washed with brine (1 L) and concentrated. To the crude product was added MTBE (1.9 L) under an inert atmosphere of nitrogen. An aqueous KMnO₄ solution (0.1 M, 0.2 eq.) was then added dropwise at 0-10° C. over 30 minutes. The reaction mixture was stirred at 0-10° C. for 8 h then was filtered through Celite®. The filter cake was washed with MTBE and the organic layer was separated and concentrated under vacuum to afford the title compound as a light yellow oil.

Intermediate 2/1

Methyl 3-(5-(4-(cyclohexylmethyl)thiazol-2-yl)-1,3,4-oxadiazol-2-yl)-2,2-dimethylpropanoate

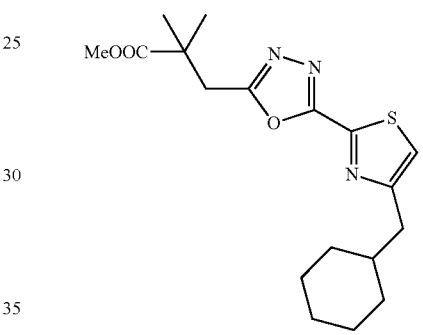

The title compound was prepared as described for the synthesis of Intermediate 2, using in step a ethyl 4-(cyclohexylmethyl)thiazole-2-carboxylate (Intermediate 1/2) in place of ethyl 4-(cyclobutylmethyl)thiazole-2-carboxylate.

Intermediate 2/2

Methyl 3-(5-(4-isobutylthiazole-2-yl)-1,3,4-oxadiazol-2-yl)-2,2-dimethylpropanoate

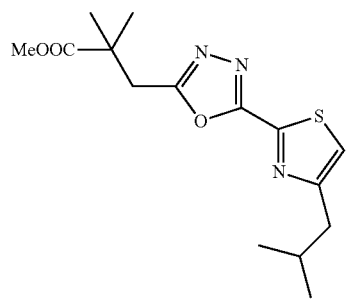 [SMILES: COC(=O)C(C)(C)Cc1nnc(-c2nc(CC(C)C)cs2)o1]

The title compound was prepared as described for the synthesis of Intermediate 2, using in step a ethyl 4-isobutylthiazole-2-carboxylate (Intermediate 1/3) in place of ethyl 4-(cyclobutylmethyl)thiazole-2-carboxylate.

Intermediate 2/3

Methyl 3-(5-(4-(2-methoxy-2-methylpropyl)thiazol-2-yl)-1,3,4-oxadiazol-2-yl)-2,2-dimethylpropanoate

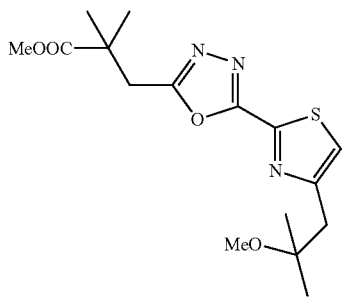 [SMILES: COC(=O)C(C)(C)Cc1nnc(-c2nc(CC(C)(C)OC)cs2)o1]

The title compound was prepared as described for the synthesis of Intermediate 2, using in step a ethyl 4-(2-methoxy-2-methylpropyl)thiazol-2-carboxylate (Intermediate 1/4) in place of ethyl 4-(cyclobutylmethyl)thiazole-2-carboxylate.

Intermediate 2/4

Methyl 3-(5-(4-(4-fluorobenzyl)thiazol-2-yl)-1,3,4-oxadiazol-2-yl)-2,2-dimethylpropanoate

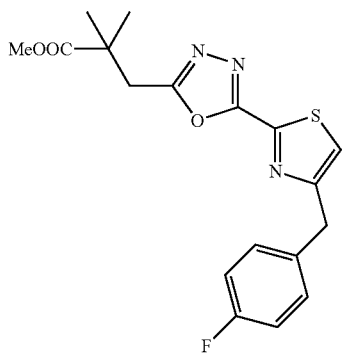 [SMILES: COC(=O)C(C)(C)Cc1nnc(-c2nc(Cc3ccc(F)cc3)cs2)o1]

The title compound was prepared as described for the synthesis of Intermediate 2, using in step a ethyl 4-(4-fluorobenzyl)thiazole-2-carboxylate (Intermediate 1/6) in place of ethyl 4-(cyclobutylmethyl)thiazole-2-carboxylate.

Intermediate 2/5: Step a

Ethyl 4-(((2-(trimethylsilyl)ethoxy)methoxy)methyl)thiazole-2-carboxylate

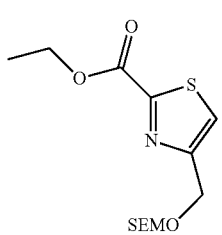

To a solution of ethyl 4-(hydroxymethyl)thiazole-2-carboxylate (375 mg, 2.00 mmol, Intermediate 1/7) in DCM (20 mL) was added DIPEA (516 mg, 4.00 mmol) at 0° C. SEMCl (670 mg, 4.0 mmol) was added dropwise over a period of 10 min and the mixture was stirred overnight at rt. The mixture was quenched with water and extracted with EtOAc (3×50 mL). The combined organic layers were washed with brine, dried, filtered and concentrated to dryness. The residue was purified by FCC on silica gel (PE/EtOAc=20:1) to obtain the title compound.

Intermediate 2/5: Step b 4-(((2-(Trimethylsilyl)ethoxy)methoxy)methyl)thiazole-2-carbohydrazide

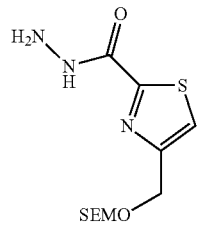

A solution of ethyl 4-(((2-(trimethylsilyl)ethoxy)methoxy)methyl)thiazole-2-carboxylate (3.17 g, 10.0 mmol, Intermediate 2/5, step a) and hydrazine monohydrate (2 mL) in EtOH (30 mL) was stirred at 50° C. for 4 h, concentrated to dryness, and purified by FCC on silica gel (EtOAc) to give the title compound as a colorless oil.

Intermediate 2/5: Step c

Methyl 2,2-dimethyl-4-oxo-4-(2-(4-(((2-(trimethylsilyl)ethoxy)methoxy)methyl)thiazole-2-carbonyl)hydrazinyl)butanoate

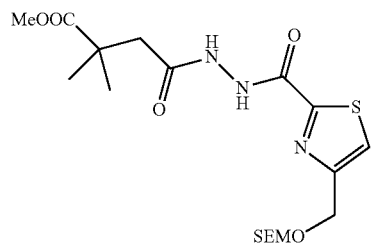

A solution of 4-(((2-(trimethylsilyl)ethoxy)methoxy)methyl)thiazole-2-carbohydrazide (2.7 g, 9.0 mmol, Intermediate 2/5, step b), 4-methoxy-3,3-dimethyl-4-oxobutanoic acid (1.76 g, 11.0 mmol), HATU (4.2 g, 11 mmol), and TEA (1.8 g, 18 mmol) in MeCN (40 mL) was stirred at rt for 2 h, poured into water (40 mL), and extracted with EtOAc (50 mL×4). The combined organic layers were washed with brine, dried over anhydrous $Na_2SO_4$, filtered, concentrated to dryness, and purified by FCC on silica gel (DCM/MeOH=10:1) to afford the title compound as a colorless oil.

Intermediate 2/5: Step d

Methyl 2,2-dimethyl-3-(5-(4-(((2-(trimethylsilyl)ethoxy)methoxy)methyl)thiazol-2-yl)-1,3,4-oxadiazol-2-yl)propanoate

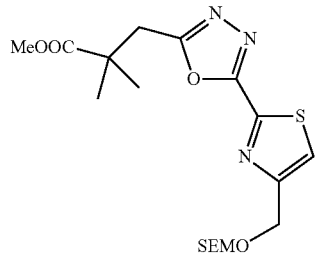

A mixture of methyl 2,2-dimethyl-4-oxo-4-(2-(4-(((2-(trimethylsilyl)ethoxy)methoxy)methyl)thiazole-2-carbonyl)hydrazinyl)butanoate (1.6 g, 3.6 mmol, Intermediate 2/5, step c), TsCl (1.4 g, 7.2 mmol) and TEA (720 mg, 7.2 mmol) in DCM (30 mL) was stirred at rt overnight, poured into water (10 mL), and extracted with EtOAc (8 mL×3). The combined organic layers were washed with brine, dried over anhydrous Na$_2$SO$_4$, filtered, concentrated to dryness, and purified by FCC on silica gel (EtOAc/PE=1:5) to give the title compound as a colorless oil.

Intermediate 2/5

Methyl 3-(5-(4-(hydroxymethyl)thiazol-2-yl)-1,3,4-oxadiazol-2-yl)-2,2-dimethylpropanoate

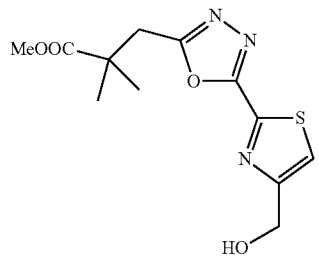 [SMILES: COC(=O)C(C)(C)Cc1nnc(-c2nc(CO)cs2)o1]

A solution of methyl 2,2-dimethyl-3-(5-(4-(((2-(trimethylsilyl)ethoxy)methoxy)methyl)thiazol-2-yl)-1,3,4-oxadiazol-2-yl)propanoate (1.38 g, 3.24 mmol, Intermediate 2/5, step d) in HCl/dioxane (4 N, 40 mL) was maintained at rt for 4 h and concentrated to dryness to afford the title compound.

Intermediate 2/6

Methyl 3-(5-(4-((3,3-dimethylcyclobutyl)methyl)thiazol-2-yl)-1,3,4-oxadiazol-2-yl)-2,2-dimethylpropanoate

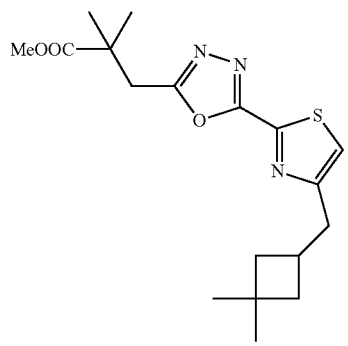 [SMILES: COC(=O)C(C)(C)Cc1nnc(-c2nc(CC3CC(C)(C)C3)cs2)o1]

The title compound was prepared as described for the synthesis of Intermediate 2, using in step a ethyl 4-((3,3-dimethylcyclobutyl)methyl)thiazole-2-carboxylate (Intermediate 1/8) in place of ethyl 4-(cyclobutylmethyl)thiazole-2-carboxylate.

Intermediate 2/7

Methyl 3-(5-(4-((3,3-difluorocyclobutyl)methyl)thiazol-2-yl)-1,3,4-oxadiazol-2-yl)-2,2-dimethylpropanoate

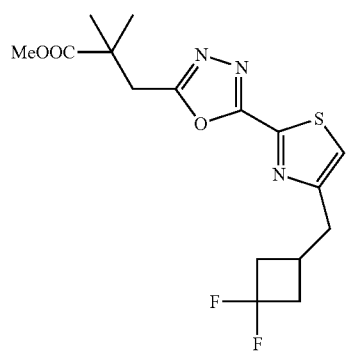 [SMILES: COC(=O)C(C)(C)Cc1nnc(-c2nc(CC3CC(F)(F)C3)cs2)o1]

The title compound was prepared as described for the synthesis of Intermediate 2, using in step a ethyl 4-((3,3-difluorocyclobutyl)methyl)thiazole-2-carboxylate (Intermediate 1/9) in place of ethyl 4-(cyclobutylmethyl)thiazole-2-carboxylate.

Intermediate 2/8: Step a 4-(Cyclohexylmethyl)thiazole-2-carbohydrazide

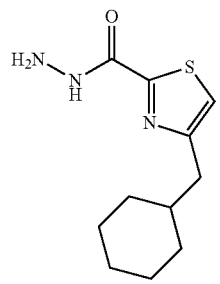 [SMILES: NNC(=O)c1nc(CC2CCCCC2)cs1]

To a solution of ethyl 4-(cyclohexylmethyl)thiazole-2-carboxylate (2.0 g, 7.9 mmol, Intermediate 1/2) in EtOH (10 mL) was added hydrazine hydrate (4.9 g, 98 mmol). The mixture was stirred at rt for 2 h. The resulting solution was concentrated to dryness and the residue was dissolved in EtOAc. The solution was washed with water twice, dried over anhydrous Na$_2$SO$_4$, filtered, and concentrated to dryness to give the title compound as a pale yellow oil.

Intermediate 2/8: Step b 1-(2-(4-(Cyclohexylmethyl)thiazole-2-carbonyl)hydrazinyl)-2-methyl-1-oxopropan-2-yl acetate

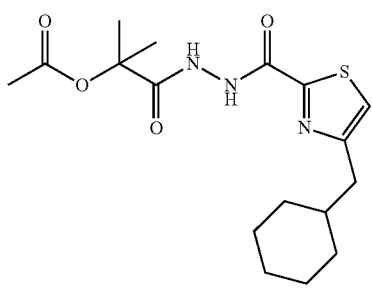 [SMILES: CC(=O)OC(C)(C)C(=O)NNC(=O)c1nc(CC2CCCCC2)cs1]

To a solution of 4-(cyclohexylmethyl)thiazole-2-carbohydrazide (1.7 g, 7.1 mmol, Intermediate 2/8, step a) and TEA (2.2 g, 21 mmol) in DCM (10 mL) was added 1-chloro-2-methyl-1-oxopropan-2-yl acetate (1.4 g, 8.5 mmol) dropwise at 0° C., and the solution was stirred at rt for 5 h. The resulting solution was washed with aqueous NaHCO$_3$, dried over anhydrous Na$_2$SO$_4$, filtered, and concentrated to dryness to give the title compound as a brown solid.

Intermediate 2/8

2-(5-(4-(Cyclohexylmethyl)thiazol-2-yl)-1,3,4-oxadiazol-2-yl)propan-2-yl acetate

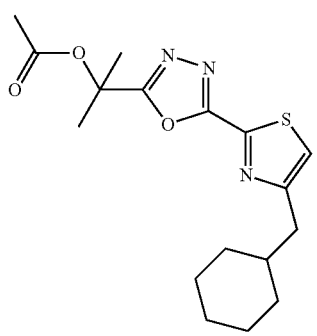 [SMILES: CC(=O)OC(C)(C)c1nnc(-c2nc(CC3CCCCC3)cs2)o1]

To a solution of 1-(2-(4-(cyclohexylmethyl)thiazole-2-carbonyl)hydrazinyl)-2-methyl-1-oxopropan-2-yl acetate (2.5 g, 6.8 mmol, Intermediate 2/8, step b) and TEA (2.1 g, 20 mmol) in DCM (20 mL) was added TsCl (2.0 g, 10 mmol) portionwise at 0° C., and the solution was stirred at rt for 2 h. The resulting solution was washed with water twice, dried over anhydrous Na$_2$SO$_4$, filtered, concentrated to dryness, and purified by FCC on silica gel (DCM/MeOH=50/1) to give the title compound as a colorless solid.

Intermediate 2/9

Methyl 3-(5-(4-(cyclopentylmethyl)thiazol-2-yl)-1,3,4-oxadiazol-2-yl)-2,2-dimethylpropanoate

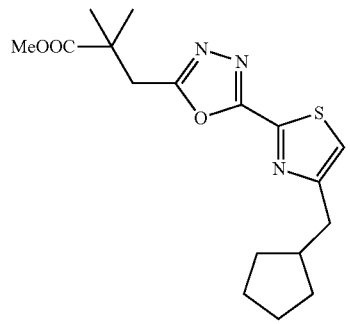 [SMILES: COC(=O)C(C)(C)Cc1nnc(-c2nc(CC3CCCC3)cs2)o1]

The title compound was prepared as described for the synthesis of Intermediate 2, using in step a ethyl 4-(cyclopentylmethyl)thiazole-2-carboxylate (Intermediate 1/1) in place of ethyl 4-(cyclobutylmethyl)thiazole-2-carboxylate.

Intermediate 2/10

Methyl 3-(5-(4-(isopropoxymethyl)thiazol-2-yl)-1,3,4-oxadiazol-2-yl)-2,2-dimethylpropanoate

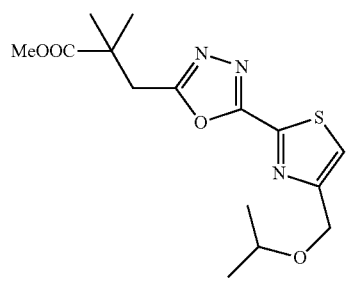 [SMILES: COC(=O)C(C)(C)Cc1nnc(-c2nc(COC(C)C)cs2)o1]

The title compound was prepared as described for the synthesis of Intermediate 2, using in step a ethyl 4-(isopropoxymethyl)thiazole-2-carboxylate (Intermediate 1/10) in place of ethyl 4-(cyclobutylmethyl)thiazole-2-carboxylate.

Intermediate 3: Step a 4-(Cyclobutylmethyl)thiazole-2-carboxamide

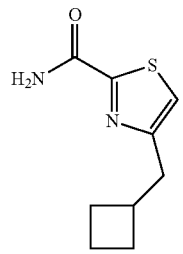

Ethyl 4-(cyclobutylmethyl)thiazole-2-carboxylate (0.84 g, 0.37 mmol, Intermediate 1) in a 7 M solution of NH$_3$ in MeOH (50 mL) was stirred at 60° C. for 12 h. The mixture was concentrated to dryness to afford the title compound as a white solid.

Intermediate 3: Step b 4-(Cyclobutylmethyl)thiazole-2-carbonitrile

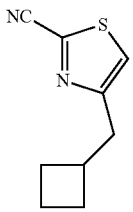

To a solution of 4-(cyclobutylmethyl)thiazole-2-carboxamide (0.72 g, 3.7 mmol, Intermediate 3, step a) in DCM (20 mL) was added pyridine (146 mg, 1.85 mmol) at 0° C. TFAA (1.55 g, 7.38 mmol) was added dropwise over a period of 10 min and the mixture was stirred for 1 h at this temperature. Water was added and the mixture was extracted with EtOAc (3×50 mL), washed with brine, dried over anhydrous Na$_2$SO$_4$, and concentrated to dryness. The residue was purified by preparative TLC (EtOAc) to afford the title compound.

Intermediate 3: Step c 4-(Cyclobutylmethyl)-N'-hydroxythiazole-2-carboximidamide

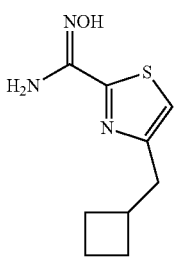

A suspension of 4-(cyclobutylmethyl)thiazole-2-carbonitrile (650 mg, 3.65 mmol, Intermediate 3, step b), NH$_2$OH.HCl (504 mg, 7.25 mmol) and Na$_2$CO$_3$ (2.32 g, 21.9 mmol) in a mixture of ethanol and water (20 mL, 5:1 v/v) was refluxed for 3 h. The mixture was concentrated to dryness, and the residue was diluted with water and extracted with EtOAc. The organic layer was washed with brine, dried over anhydrous Na$_2$SO$_4$, filtered and concentrated to dryness to afford the title compound, which was used in the next step without further purification.

Intermediate 3

Methyl 3-(3-(4-(cyclobutylmethyl)thiazol-2-yl)-1,2,4-oxadiazol-5-yl)-2,2-dimethylpropanoate

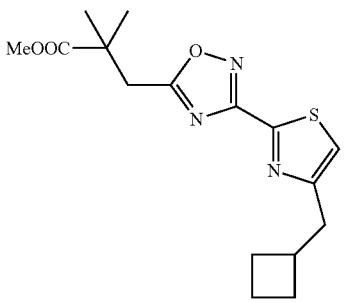 [SMILES: COC(=O)C(C)(C)Cc1nc(-c2nc(CC3CCC3)cs2)no1]

A mixture of 4-(cyclobutylmethyl)-N-hydroxythiazole-2-carboximidamide (698 mg, 3.30 mmol, Intermediate 3, step c), HATU (1.25 g, 3.29 mmol), DIPEA (1.65 mL, 9.49 mmol) and 4-methoxy-3,3-dimethyl-4-oxobutanoic acid (528 mg, 3.30 mmol) in DMF (10 mL) was stirred at rt for 1 h. The mixture was diluted with EtOAc, washed with water and brine, dried over anhydrous Na$_2$SO$_4$, filtered and concentrated to dryness. The residue was dissolved in DMF (5 mL) and heated at 120° C. for 12 h. Ice water was added and the mixture was extracted with EtOAc three times. The combined organic layers were washed with brine, dried over anhydrous Na$_2$SO$_4$ and filtered. The filtrate was concentrated to dryness and the residue was purified by FCC on silica gel (PE/EtOAc=5:1) to give the title compound as a colorless solid.

Intermediate 3/1

Methyl 3-(3-(4-(cyclohexylmethyl)thiazol-2-yl)-1,2,4-oxadiazol-5-yl)-2,2-dimethylpropanoate

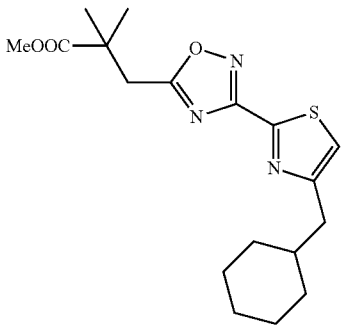 [SMILES: COC(=O)C(C)(C)Cc1nc(-c2nc(CC3CCCCC3)cs2)no1]

The title compound was prepared as described for the synthesis of Intermediate 3, using in step a ethyl 4-(cyclohexylmethyl)thiazole-2-carboxylate (Intermediate 1/2) in place of ethyl 4-(cyclobutylmethyl)thiazole-2-carboxylate.

Intermediate 3/2

Methyl 3-(3-(4-(2-methoxy-2-methylpropyl)thiazol-2-yl)-1,2,4-oxadiazol-5-yl)-2,2-dimethylpropanoate

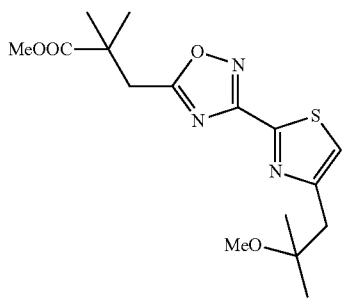 [SMILES: COC(=O)C(C)(C)Cc1nc(-c2nc(CC(C)(C)OC)cs2)no1]

The title compound was prepared as described for the synthesis of Intermediate 3, using in step a ethyl 4-(2-methoxy-2-methylpropyl)thiazole-2-carboxylate (Intermediate 1/4) in place of ethyl 4-(cyclobutylmethyl)thiazole-2-carboxylate.

Intermediate 3/3: Step a 4-(((2-(Trimethylsilyl)ethoxy)methoxy)methyl)thiazole-2-carboxamide

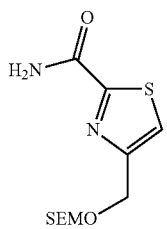

A solution of ethyl 4-(((2-(trimethylsilyl)ethoxy)methoxy)methyl)thiazole-2-carboxylate (3.17 g, 10.0 mmol, Intermediate 2/5, step a) in ammonia (7 N in MeOH, 50 mL) was stirred at 60° C. for 12 h and concentrated under vacuum to give the title compound as a white solid.

Intermediate 3/3: Step b 4-(((2-(Trimethylsilyl)ethoxy)methoxy)methyl)thiazole-2-carbonitrile

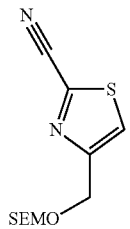

To a solution of 4-(((2-(trimethylsilyl)ethoxy)methoxy)methyl)thiazole-2-carboxamide (2.88 g, 10.0 mmol, Intermediate 3/3, step a) in DCM (100 mL) was added pyridine (1.46 g, 18.5 mmol) at 0° C. and then TFAA (4.19 g, 20.0 mmol) dropwise over 10 min. The mixture was stirred for 1 h at this temperature, quenched with water, extracted with EtOAc (3×50 mL), washed with brine, dried over anhydrous $Na_2SO_4$, filtered and concentrated to dryness to give the title compound.

Intermediate 3/3: Step c

N'-Hydroxy-4-(((2-(trimethylsilyl)ethoxy)methoxy)methyl)thiazole-2-carboximidamide

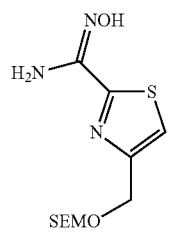

A suspension of 4-(((2-(trimethylsilyl)ethoxy)methoxy)methyl)thiazole-2-carbonitrile (986 mg, 3.65 mmol, Intermediate 3/3, step b), $NH_2OH \cdot HCl$ (504 mg, 7.25 mmol) and $Na_2CO_3$ (2.32 g, 21.9 mmol) in EtOH and water (20 mL, 5:1 v/v) was refluxed for 3 h, concentrated to dryness, redissolved in $H_2O$ and extracted with EtOAc. The organic layer was washed with saturated aqueous NaCl, dried over anhydrous $Na_2SO_4$, filtered and concentrated to dryness to afford the title compound.

Intermediate 3/3: Step d

Methyl 4-(((amino(4-(((2-(trimethylsilyl)ethoxy)methoxy)methyl)thiazol-2-yl)methylene)amino)oxy)-2,2-dimethyl-4-oxobutanoate

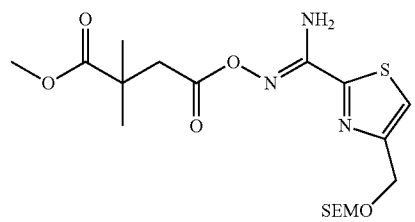

A mixture of N'-hydroxy-4-(((2-(trimethylsilyl)ethoxy)methoxy)methyl)thiazole-2-carboximidamide (1.0 g, 3.3 mmol, Intermediate 3/3, step c), 4-methoxy-3,3-dimethyl-4-oxobutanoic acid (528 mg, 3.30 mmol), HATU (1.25 g, 3.29 mmol), and DIPEA (1.65 mL, 9.49 mmol) in DMF (20 mL) was stirred at rt for 2 h, poured into water (120 mL) and extracted with EtOAc (100 mL×3). The combined organic layers were washed with brine, dried over anhydrous $Na_2SO_4$, concentrated to dryness, and purified by FCC on silica gel (PE/EtOAc=1:1) to afford the title compound as a yellow oil.

Intermediate 3/3: Step e

Methyl 2,2-dimethyl-3-(3-(4-(((2-(trimethylsilyl)ethoxy)methoxy)methyl)thiazol-2-yl)-1,2,4-oxadiazol-5-yl)propanoate

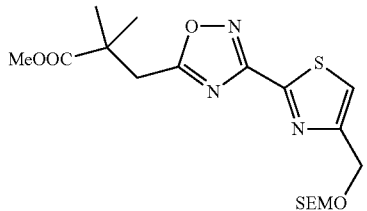

A solution of methyl 4-(((amino(4-(((2-(trimethylsilyl)ethoxy)methoxy)methyl)thiazol-2-yl)methylene)amino)oxy)-2,2-dimethyl-4-oxobutanoate (1.0 g, 2.2 mmol, Intermediate 3/3, step d) in DMF (10 mL) was stirred at 120° C. for 12 h, poured into water (120 mL) and extracted with EtOAc (100 mL×3). The combined organic layers were washed with brine, dried over anhydrous $Na_2SO_4$, filtered, concentrated to dryness, and purified by FCC on silica gel (PE/EtOAc=1:1) to afford the title compound.

Intermediate 3/3

Methyl 3-(3-(4-(hydroxymethyl)thiazol-2-yl)-1,2,4-oxadiazol-5-yl)-2,2-dimethylpropanoate

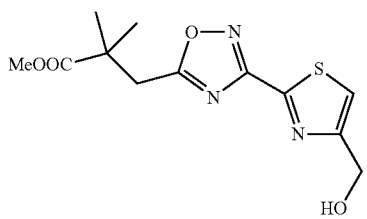 [SMILES: COC(=O)C(C)(C)Cc1nc(-c2nc(CO)cs2)no1]

Methyl 2,2-dimethyl-3-(3-(4-(((2-(trimethylsilyl)ethoxy)methoxy)methyl)thiazol-2-yl)-1,2,4-oxadiazol-5-yl)propanoate (350 mg, 0.82 mmol, Intermediate 3/3, step e) was treated with HCl/dioxane (11 mL, 4 M) for 1 h, quenched with $NH_3$/MeOH (7 mL, 7 M), poured into water (20 mL), and extracted with EtOAc (3×50 mL). The combined organic layers were concentrated to dryness to give the title compound.

Intermediate 3/4

Methyl 3-(3-(4-((1-methoxycyclobutyl)methyl)thiazol-2-yl)-1,2,4-oxadiazol-5-yl)-2,2-dimethylpropanoate

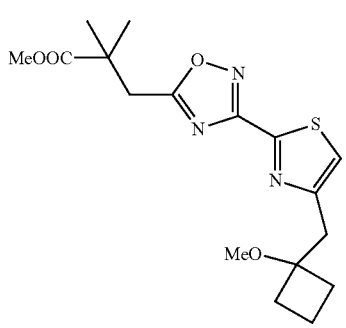 [SMILES: COC(=O)C(C)(C)Cc1nc(-c2nc(CC3(OC)CCC3)cs2)no1]

The title compound was prepared as described for the synthesis of Intermediate 3, using in step a ethyl 4-((1-methoxycyclobutyl)methyl)thiazole-2-carboxylate (Intermediate 1/5) in place of ethyl 4-(cyclobutylmethyl)thiazole-2-carboxylate.

Intermediate 4: Step a 1-(Difluoromethyl)-2-fluoro-3-nitrobenzene

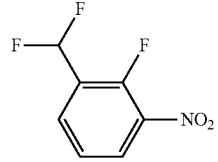

A solution of 2-fluoro-3-nitrobenzaldehyde (564 mg, 3.34 mmol) in DCM (20 mL) was cooled to −78° C. DAST (645 mg, 4.01 mmol) was added dropwise and the mixture was stirred at rt for 1 h. The mixture was poured into ice water, extracted with EtOAc (3×30 mL) and the combined organic layers were washed with brine and concentrated to dryness. The residue was purified by preparative TLC (PE/EtOAc=5:1) to give the title compound as a yellow solid.

Alternatively Intermediate 4, Step a was Prepared by the Following Route:

2-Fluoro-3-nitrobenzaldehyde (1.0 g, 5.92 mmol) and anhydrous DCM (10 mL) were added to a flask and the flask was cooled to −78° C. DAST (1.14 g, 7.07 mmol) was then added dropwise, maintaining the temperature below −65° C. After addition, the reaction mixture was warmed slowly to 15-20° C. and stirred at this temperature for 4 h. The reaction mixture was then poured into ice water (10 mL), and the aqueous layer was extracted with DCM (2×6 mL). The combined organic layers were washed with saturated aqueous $NaHCO_3$ (2×10 mL) and the aqueous wash was back extracted with DCM (2×5 mL). The combined organic layers were washed with brine, dried over $Na_2SO_4$, filtered and concentrated to dryness. The residue was purified by FCC on silica gel (PE/EtOAc=10/1) to afford the title compound.

Intermediate 4: Step b 3-(Difluoromethyl)-2-fluoroaniline

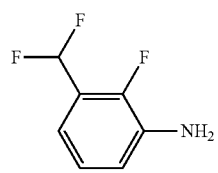

Palladium on carbon (10 wt %, 80 mg) was added to a solution of 1-(difluoromethyl)-2-fluoro-3-nitrobenzene (387 mg, 2.03 mmol, Intermediate 4, step a) in MeOH (20 mL). The mixture was stirred under a hydrogen atmosphere at rt overnight. The mixture was filtered through a pad of Celite® and the filtrate was concentrated to dryness to give the title compound, which was used in the next step directly.

Alternatively Intermediate 4, Step b was Prepared by the Following Route:

1-(Difluoromethyl)-2-fluoro-3-nitrobenzene (1 g, 5.92 mmol, Intermediate 4, step a) and anhydrous MeOH (10 mL) were added to a high pressure reaction bottle. The reaction vessel was treated with 10 wt % Pd/C (200 mg) in one portion under Ar. The resultant mixture was stirred at 10-20° C. under 30 psi of H$_2$ for 4 days. The reaction mixture was then filtered through Celite® and washed with MeOH (3×7.2 mL). The filtrate was dried over anhydrous Na$_2$SO$_4$, filtered and concentrated to dryness to afford the title compound as a brown oil.

Intermediate 4: Step c

4-Bromo-3-(difluoromethyl)-2-fluoroaniline

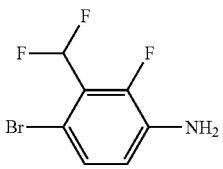 [SMILES: Nc1ccc(Br)c(C(F)F)c1F]

A solution of 3-(difluoromethyl)-2-fluoroaniline (319 mg, 1.98 mmol, Intermediate 4, step b) in DMF (10 mL) was cooled to 0° C. N-Bromosuccinimide (480 mg, 2.38 mmol) was added portionwise and the mixture was stirred at rt for 3 h. The mixture was poured into ice water and extracted with EtOAc (3×30 mL). The combined organic layers were washed with brine, dried over anhydrous Na$_2$SO$_4$ and filtered. The filtrate was concentrated to dryness and the residue was purified by FCC on silica gel (PE/EtOAc=5:1) to give the title compound as a white solid.

Alternatively Intermediate 4, Step c was Prepared by the Following Route:

A solution of 3-(difluoromethyl)-2-fluoroaniline (5 g, 31.0 mmol, Intermediate 4, step b) in anhydrous DMF (50 mL) was cooled to −5° C. and treated with NBS (5.8 g, 32.6 mmol) in portions under N$_2$. The resultant mixture was stirred for 1.5 h at −5° C. The reaction mixture was poured into ice water, and the aqueous layer was extracted with EtOAc. The combined organic layers were washed with water and brine, dried over Na$_2$SO$_4$, filtered and concentrated to dryness. The residue was purified by FCC on silica gel (1/100-1/5 EtOAc/PE) to afford the title compound.

Intermediate 4: Step d

4-Bromo-3-(difluoromethyl)-2-fluorobenzene-1-sulfonyl chloride

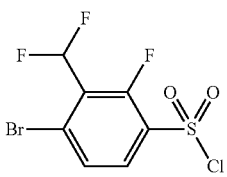 [SMILES: O=S(=O)(Cl)c1ccc(Br)c(C(F)F)c1F]

Sodium nitrite (143 mg, 2.07 mmol) dissolved in water (5 mL) was added dropwise to a −10° C. suspension of 4-bromo-3-(difluoromethyl)-2-fluoroaniline (331 mg, 1.38 mmol, Intermediate 4, step c) in HCl/HOAc (15 mL, 10:5 v/v). The mixture was stirred at −10° C. for 1 h and then poured into a complex of CuCl (0.1 g, 0.1 mmol), HOAc and SO$_2$ (saturated) at 0° C., warmed to rt and stirred overnight. The mixture was poured into ice water, and the precipitate was collected and dried to give the title compound as a colorless solid.

Alternatively Intermediate 4, Step d was Prepared by the Following Route:

A solution of 4-bromo-3-(difluoromethyl)-2-fluoroaniline (1.0 g, 4.17 mmol, Intermediate 4, step c) in acetic acid (7.5 mL) was treated with concentrated HCl (5 mL, 60 mmol) in portions at 10-15° C. and cooled to −5° C. A solution of NaNO$_2$ (0.345 g, 5 mmol) in water (7.5 mL) was added dropwise into the reaction vessel at −5-0° C. and stirred at this temperature for 1 h. The reaction mixture was added to a precooled mixture of saturated solution of SO$_2$ in acetic acid (~16 mL) and CuCl$_2$.H$_2$O (0.76 g, 5 mmol) in water (~3 mL) at −5-0° C. The resultant mixture was warmed slowly to 0-15° C. and stirred for 1 h. The mixture was poured into ice water (30 mL). The precipitate was filtered, the filtrate was extracted with DCM (2×20 mL), and the precipitate was dissolved with DCM (37.5 mL). The combined organic layers were washed with saturated aqueous Na$_2$CO$_3$, washed with brine, dried over Na$_2$SO$_4$, filtered and concentrated to dryness. The residue was purified by FCC on silica gel (PE/DCM=10/1-5/1) to afford the title compound.

Intermediate 4

(S)-4-Bromo-3-(difluoromethyl)-2-fluoro-N-(1,1,1-trifluorobutan-2-yl)benzenesulfonamide

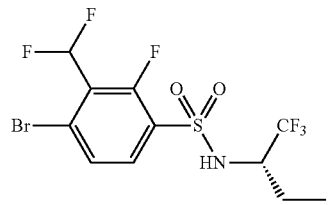

A solution of 4-bromo-3-(difluoromethyl)-2-fluorobenzene-1-sulfonyl chloride (246 mg, 0.761 mmol, Intermediate 4, step d), (S)-1,1,1-trifluorobutan-2-amine (106 mg, 0.835 mmol) and DMAP (0.1 g, 0.8 mmol) in pyridine (20 mL) was stirred at 90° C. for 2 h. The mixture was concentrated, water (20 mL) was added and the mixture was extracted with EtOAc (4×20 mL). The combined organic layers were washed with brine, dried over anhydrous Na$_2$SO$_4$, filtered and concentrated to dryness. The residue was purified by FCC on silica gel (PE/EtOAc=10:1) to afford the title compound as a colorless solid.

Alternatively Intermediate 4 was Prepared by the Following Route:

4-Bromo-3-(difluoromethyl)-2-fluorobenzene-1-sulfonyl chloride (0.5 g, 1.5 mmol, Intermediate 4, step d) was added in one portion under N$_2$ to a −5° C. solution of (S)-1,1,1-trifluorobutan-2-amine (0.19 g, 1.5 mmol) and pyridine (1.5 mL). The resultant mixture was stirred for 1 h at −5° C., and then stirred at about 10° C. for 20 h before 1 M aqueous HCl (10 mL) was added to the reaction mixture. The mixture was then extracted with EtOAc (2×10 mL). The combined organic layers were washed with 1 M aqueous HCl and concentrated to dryness. The residue was purified by FCC on silica gel (PE/EtOAc=10/1) to give the title compound.

Intermediate 4/1

(S)-4-Bromo-3-(difluoromethyl)-2-fluoro-N-(1,1,1-trifluoropropan-2-yl)benzenesulfonamide

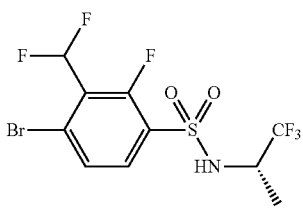 [SMILES: C[C@H](NS(=O)(=O)c1ccc(Br)c(C(F)F)c1F)C(F)(F)F]

The title compound was prepared as described for the synthesis of Intermediate 4 using in the final step (S)-1,1,1-trifluoropropan-2-amine in place of (S)-1,1,1-trifluorobutan-2-amine.

Intermediate 4/2

(S)-4-Bromo-2,3-dichloro-N-(1,1,1-trifluoropropan-2-yl)benzenesulfonamide

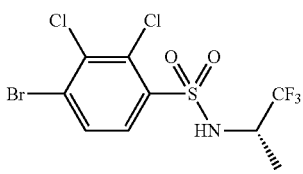 [SMILES: C[C@H](NS(=O)(=O)c1ccc(Br)c(Cl)c1Cl)C(F)(F)F]

The title compound was prepared as described for the synthesis of Intermediate 4, using in step d 4-bromo-2,3-dichloroaniline in place of 4-bromo-3-(difluoromethyl)-2-fluoroaniline and in the final step using (5)-1,1,1-trifluoropropan-2-amine in place of (5)-1,1,1-trifluorobutan-2-amine.

Intermediate 4/3

(S)-4-Bromo-2,3-dichloro-N-(1,1,1-trifluorobutan-2-yl)benzenesulfonamide

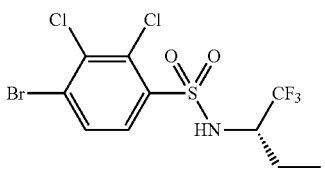

The title compound was prepared as described for the synthesis of Intermediate 4/2 using (5)-1,1,1-trifluorobutan-2-amine in place of (S)-1,1,1-trifluoropropan-2-amine.

Intermediate 4/4

4-Bromo-2,3-dichloro-N-(2,2,2-trifluoroethyl)benzenesulfonamide

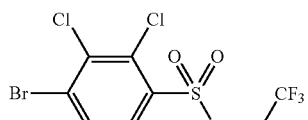

The title compound was prepared as described for the synthesis of Intermediate 4/2 using 2,2,2-trifluoroethanamine in place of (S)-1,1,1-trifluoropropan-2-amine.

Intermediate 4/5

4-Bromo-N-(tert-butyl)-2,3-dichlorobenzenesulfonamide

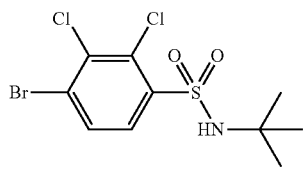 [SMILES: CC(C)(C)NS(=O)(=O)c1ccc(Br)c(Cl)c1Cl]

The title compound was prepared as described for the synthesis of Intermediate 4/2 using 2-methylpropan-2-amine in place of (S)-1,1,1-trifluoropropan-2-amine.

Intermediate 4/6

4-Bromo-N-(tert-butyl)naphthalene-1-sulfonamide

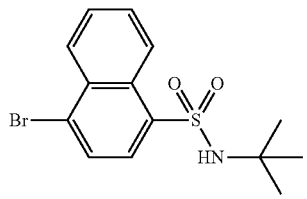 [SMILES: CC(C)(C)NS(=O)(=O)c1ccc(Br)c2ccccc12]

The title compound was prepared as described for the synthesis of Intermediate 4, using in the final step 4-bromonaphthalene-1-sulfonyl chloride in place of 4-bromo-3-(difluoromethyl)-2-fluorobenzene-1-sulfonyl chloride and 2-methylpropan-2-amine in place of (S)-1,1,1-trifluorobutan-2-amine.

Intermediate 4/7

(S)-4-Bromo-N-(1,1,1-trifluoropropan-2-yl)naphthalene-1-sulfonamide

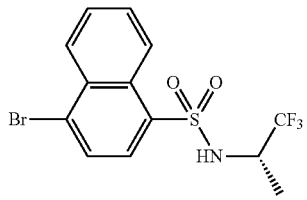 [SMILES: C[C@H](NS(=O)(=O)c1ccc(Br)c2ccccc12)C(F)(F)F]

The title compound was prepared as described for the synthesis of Intermediate 4/6, using (5)-1,1,1-trifluoropropan-2-amine in place of 2-methylpropan-2-amine.

Intermediate 4/8

(S)-4-Bromo-N-(1,1,1-trifluorobutan-2-yl)naphthalene-1-sulfonamide

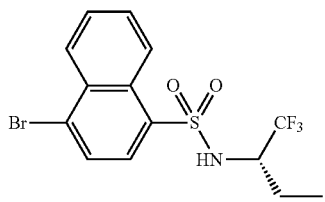 [SMILES: CC[C@H](NS(=O)(=O)c1ccc(Br)c2ccccc12)C(F)(F)F]

The title compound was prepared as described for the synthesis of Intermediate 4/6, using (5)-1,1,1-trifluorobutan-2-amine in place of 2-methylpropan-2-amine.

Intermediate 4/9

(S)-4-Bromo-2-fluoro-N-(1,1,1-trifluorobutan-2-yl)-3-(trifluoromethyl)benzenesulfonamide

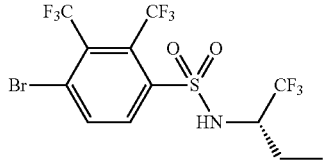 [SMILES: CC[C@H](NS(=O)(=O)c1ccc(Br)c(C(F)(F)F)c1C(F)(F)F)C(F)(F)F]

The title compound was prepared as described for the synthesis of Intermediate 4, using in step c 2-fluoro-3-(trifluoromethyl)aniline in place of 3-(difluoromethyl)-2-fluoroaniline.

Intermediate 4/10

(S)-4-Bromo-3-chloro-N-(1,1,1-trifluoropropan-2-yl)benzenesulfonamide

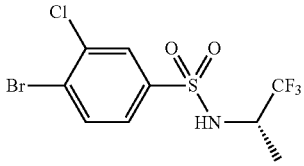 [SMILES: C[C@H](NS(=O)(=O)c1ccc(Br)c(Cl)c1)C(F)(F)F]

The title compound was prepared as described for the synthesis of Intermediate 4, using in the final step 4-bromo-3-chlorobenzene-1-sulfonyl chloride in place of 4-bromo-3-(difluoromethyl)-2-fluorobenzene-1-sulfonyl chloride and (S)-1,1,1-trifluoropropan-2-amine in place of (S)-1,1,1-trifluorobutan-2-amine.

Intermediate 4/11

(S)-4-Bromo-3-chloro-N-(1,1,1-trifluorobutan-2-yl)benzenesulfonamide

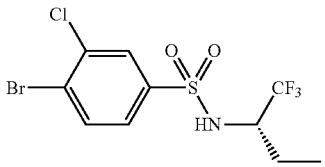

The title compound was prepared as described for the synthesis of Intermediate 4/10, using (5)-1,1,1-trifluorobutan-2-amine in place of (S)-1,1,1-trifluoropropan-2-amine.

Intermediate 4/12

(S)-4-Bromo-3-(trifluoromethyl)-N-(1,1,1-trifluoropropan-2-yl)benzenesulfonamide

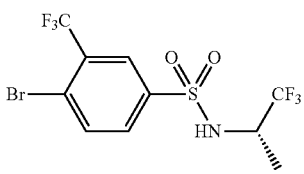 [SMILES: C[C@H](NS(=O)(=O)c1ccc(Br)c(C(F)(F)F)c1)C(F)(F)F]

The title compound was prepared as described for the synthesis of Intermediate 4, using in the final step 4-bromo-3-(trifluoromethyl)benzene-1-sulfonyl chloride in place of 4-bromo-3-(difluoromethyl)-2-fluorobenzene-1-sulfonyl chloride and (5)-1,1,1-trifluoropropan-2-amine in place of (S)-1,1,1-trifluorobutan-2-amine.

Intermediate 4/13

(S)-4-Bromo-N-(1,1,1-trifluorobutan-2-yl)-3-(trifluoromethoxy)benzenesulfonamide

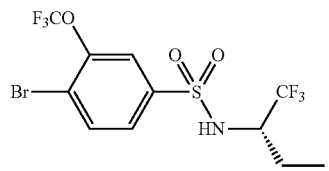 [SMILES: CC[C@H](NS(=O)(=O)c1ccc(Br)c(OC(F)(F)F)c1)C(F)(F)F]

The title compound was prepared as described for the synthesis of Intermediate 4, using in step c 3-(trifluoromethoxy)aniline in place of 3-(difluoromethyl)-2-fluoroaniline.

Intermediate 4/14

(S)-4-Bromo-3-(trifluoromethoxy)-N-(1,1,1-trifluoropropan-2-yl)benzenesulfonamide

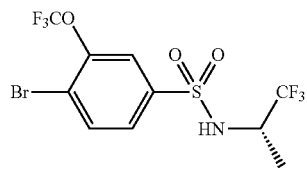 [SMILES: C[C@H](NS(=O)(=O)c1ccc(Br)c(OC(F)(F)F)c1)C(F)(F)F]

The title compound was prepared as described for the synthesis of Intermediate 4/13 using (5)-1,1,1-trifluoropropan-2-amine in place of (S)-1,1,1-trifluorobutan-2-amine.

Intermediate 4/15

(S)-4-Bromo-2-chloro-3-(difluoromethyl)-N-(1,1,1-trifluorobutan-2-yl)benzenesulfonamide

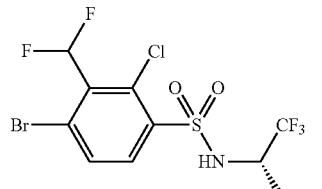

The title compound was prepared as described for the synthesis of Intermediate 4, using in step a 2-chloro-3-nitrobenzaldehyde in place of 2-fluoro-3-nitrobenzaldehyde.

Intermediate 4/16: Step a

5-Bromoisoquinoline-8-sulfonic acid

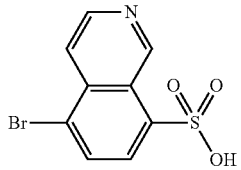 [SMILES: O=S(=O)(O)c1ccc(Br)c2ccncc12]

A solution of 5-bromoisoquinoline (2.07 g, 10.0 mmol) in fuming $H_2SO_4$ (40 mL) was heated to 200° C. and stirred for 4 h. The mixture was cooled to rt and poured into ice. A precipitate was formed, which was collected by filtration and dried under reduced pressure to give the title compound, which was used in the next step without further purification.

Intermediate 4/16: Step b

5-Bromoisoquinoline-8-sulfonyl chloride

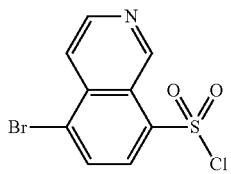 [SMILES: O=S(=O)(Cl)c1ccc(Br)c2ccncc12]

To a solution of 5-bromoisoquinoline-8-sulfonic acid (2.85 g, 9.89 mmol, Intermediate 4/16, step a) in $POCl_3$ (40 mL) was added $PCl_5$ (2.5 g, 12 mmol) and the mixture was heated to 110° C. and stirred for 4 h. The mixture was concentrated to dryness to give the title compound as a brown solid, which was used in the next step without further purification.

Intermediate 4/16

(S)-5-Bromo-N-(1,1,1-trifluoropropan-2-yl)isoquinoline-8-sulfonamide

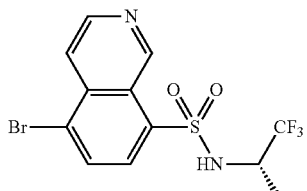

A solution of 5-bromoisoquinoline-8-sulfonyl chloride (1.5 g, 4.9 mmol, Intermediate 4/16, step b), (S)-1,1,1-trifluoropropan-2-amine (1.67 g, 14.8 mmol) and DMAP (2.4 g, 10 mmol) in pyridine (50 mL) was heated to 90° C. and stirred at this temperature overnight. The mixture was concentrated, water (50 mL) and EtOAc (50 mL) were added and the aqueous layer was extracted with EtOAc twice. The combined organic layers were washed with brine, dried over anhydrous Na$_2$SO$_4$, filtered and concentrated to dryness. The brown residue was purified by FCC on silica gel (PE/EtOAc=3:1) to give the title compound.

Intermediate 4/17

(S)-8-Chloro-N-(1,1,1-trifluoropropan-2-yl)isoquinoline-5-sulfonamide

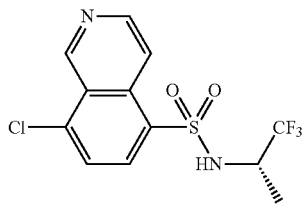 [SMILES: C[C@H](NS(=O)(=O)c1ccc(Cl)c2cnccc12)C(F)(F)F]

The title compound was prepared as described for the synthesis of Intermediate 4/16, using in step a 8-chloroisoquinoline in place of 5-bromoisoquinoline.

Intermediate 4/18

(S)-5-Bromo-N-(1,1,1-trifluorobutan-2-yl)isoquinoline-8-sulfonamide

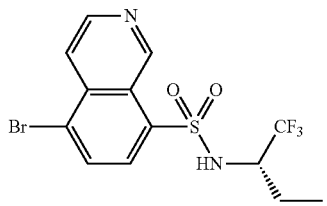 [SMILES: CC[C@H](NS(=O)(=O)c1ccc(Br)c2ccncc12)C(F)(F)F]

The title compound was prepared as described for the synthesis of Intermediate 4/16, using in the final step (S)-1,1,1-trifluorobutan-2-amine in place of (S)-1,1,1-trifluoropropan-2-amine.

Intermediate 4/19: Step a

4-Bromoisoquinolin-1(2H)-one

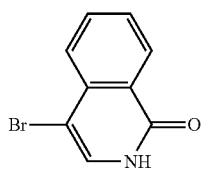

A solution of isoquinolin-1(2H)-one (150 mg, 1.03 mmol) in DMF (5 mL) was treated with NBS (184 mg, 1.03 mmol). The mixture was stirred at rt for 2 h and then poured into H$_2$O (15 mL). The formed precipitate was collected by filtration, washed with water and dried by lyophilization to give the title compound as a white solid.

Intermediate 4/19: Step b

4-Bromoisoquinoline-1(2H)-thione

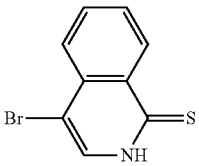 [SMILES: O=c1[nH]cc(Br)c2ccccc12]

A mixture of 4-bromoisoquinolin-1(2H)-one (200 mg, 0.90 mmol, Intermediate 4/19, step a) and P$_2$S$_5$ (220 mg, 1.0 mmol) in pyridine (1 mL) was heated at 130° C. for 3 h. The mixture was cooled to rt and water (3 mL) was added slowly. A precipitate was formed, which was collected by filtration, washed with water and dried by lyophilization to give the title compound as a yellow solid.

Intermediate 4/19

(S)-4-Bromo-N-(1,1,1-trifluoropropan-2-yl)isoquinoline-1-sulfonamide

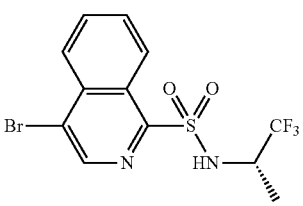 [SMILES: C[C@H](NS(=O)(=O)c1ncc(Br)c2ccccc12)C(F)(F)F]

To a mixture of 4-bromoisoquinoline-1(2H)-thione (690 mg, 2.87 mmol, Intermediate 4/19, step b), DCM (15 mL), aqueous HCl (1 M, 15 mL) at −5° C. was added aqueous NaOCl solution (6% w/w). The mixture was stirred for 10 min and then loaded in a separation funnel. The DCM phase was separated and injected into a mixture of (S)-1,1,1-trifluoropropan-2-amine (325 mg, 2.87 mmol), DMAP (322 mg, 2.87 mmol) and pyridine (15 mL). The resulting mixture was heated at 80° C. overnight. After cooling to rt, EtOAc (100 mL) was added and the mixture was washed with aqueous HCl (1 M, 3×30 mL). The organic phase was separated, dried over anhydrous Na$_2$SO$_4$, filtered and concentrated to dryness to give a brown residue. The residue was purified by FCC on silica gel (PE/EtOAc=10:1) to give the title compound as a white solid.

Intermediate 4/20

(S)-4-Bromo-2-chloro-3-(difluoromethyl)-N-(1,1,1-trifluoropropan-2-yl)benzenesulfonamide

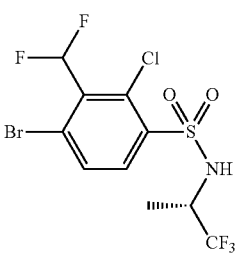 [SMILES: C[C@H](NS(=O)(=O)c1ccc(Br)c(C(F)F)c1Cl)C(F)(F)F]

The title compound was prepared as described for the synthesis of Intermediate 4 using in step a 2-chloro-3-nitrobenzaldehyde in place of 2-fluoro-3-nitrobenzaldehyde and in the final step (S)-1,1,1-trifluoropropan-2-amine in place of (S)-1,1,1-trifluorobutan-2-amine.

Intermediate 4/21

(S)-4-Bromo-2-(difluoromethyl)-3-fluoro-N-(1,1,1-trifluorobutan-2-yl)benzenesulfonamide

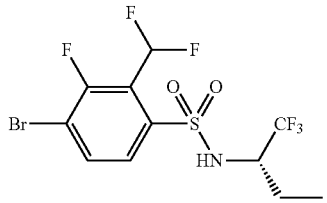 [SMILES: CC[C@H](NS(=O)(=O)c1ccc(Br)c(F)c1C(F)F)C(F)(F)F]

The title compound was prepared as described for the synthesis of Intermediate 4, using in step a 2-fluoro-6-nitrobenzaldehyde in place of 2-fluoro-3-nitrobenzaldehyde.

Intermediate 4/22

(R)-4-Bromo-3-(difluoromethyl)-2-fluoro-N-(1,1,1-trifluorobutan-2-yl)benzenesulfonamide

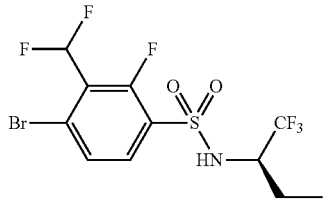 [SMILES: CC[C@@H](NS(=O)(=O)c1ccc(Br)c(C(F)F)c1F)C(F)(F)F]

A solution of (R)-1,1,1-trifluorobutan-2-amine (982 mg, 7.73 mmol) in pyridine (3 mL) was cooled to −5° C. Then 4-bromo-3-(difluoromethyl)-2-fluorobenzene-1-sulfonyl chloride (2.5 g, 7.73 mmol, Intermediate 4, step d) was added and the resulting mixture was stirred at −5° C. for 1 h then warmed to 10° C. for 20 h. 1 N aqueous HCl (20 mL) was then added and the mixture was extracted with EtOAc (2×20 mL). The combined organic layers were washed with 1 N aqueous HCl and concentrated to dryness. The residue was purified by FCC on silica gel (PE/EtOAc=10:1) to afford the title compound as a white solid.

Intermediate 5

4-(1-(4-Bromonaphthalen-1-yl)ethyl)-3,3-dimethylmorpholine

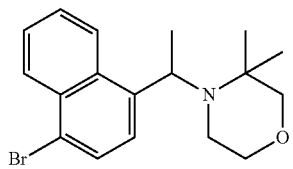

A solution of 1-(4-bromonaphthalen-1-yl)ethanone (2.49 g, 10.0 mmol), 3,3-dimethylmorpholine (1.27 g, 11.0 mmol), and AcOH (5 drops) in DCM (30 mL) was stirred at rt for 30 min. Then NaBH(OAc)$_3$ (4.24 g, 20.0 mmol) was added, and the suspension was stirred at rt overnight. Saturated aqueous NaHCO$_3$ solution was added to adjust the pH to 8, and the two layers were separated. The organic layer was washed with water and brine, dried over anhydrous Na$_2$SO$_4$, filtered, concentrated to dryness and purified by FCC on silica gel (PE/EtOAc=2/1) to give the title compound as a pale yellow solid.

Intermediate 6: Step a 1-(4-Bromo-2,3-dichlorophenyl)-2,2,2-trifluoroethanone

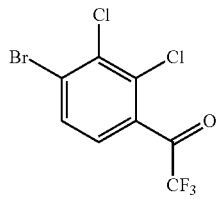 [SMILES: O=C(c1ccc(Br)c(Cl)c1Cl)C(F)(F)F]

To a solution of 1-bromo-2,3-dichloro-4-iodobenzene (3.52 g, 10.0 mmol) in anhydrous THF (20 mL) was added n-BuLi (2.5 M in hexane, 4.4 mL, 11 mmol) at −78° C. under nitrogen, and the solution was stirred at this temperature for 30 min. The resulting solution was slowly added to a solution of 2,2,2-trifluoro-N-methoxy-N-methyl-acetamide (2.35 g, 14.8 mmol) in anhydrous THF (25 mL) at −78° C., and the solution was stirred for an additional 2 h. The solution was quenched with saturated aqueous NH$_4$Cl and extracted with EtOAc twice. The combined organic layers were washed with water and brine, dried over anhydrous Na$_2$SO$_4$, filtered, and concentrated to dryness. The residue was purified by FCC on silica gel (PE/EtOAc=100/1) to give the title compound as a pale yellow oil.

Alternate Synthesis of Intermediate 6: Step a

Isopropylmagnesium chloride lithium chloride complex (78.7 mL, 1.3 M in THF, 102 mmol) was added dropwise to a −85-78° C. solution of 1-bromo-2,3-dichloro-4-iodobenzene (30.0 g, 85.3 mmol) in THF (240 mL). Then 2,2,2-trifluoro-N-methoxy-N-methylacetamide (20.1 g, 128 mmol) was added one portion. The mixture was allowed to warm to 20-25° C. and stirred for 4 h. The reaction was quenched with saturated aqueous NH$_4$Cl (120 mL) and then diluted with EtOAc (150 mL). The layers were separated, and the aqueous layer was extracted with EtOAc (90 mL). The combined organic layers were washed with water (60 mL) and brine (60 mL) successively and concentrated under vacuum to give the title compound as a brown solid, which was used in the next step without further purification.

Intermediate 6

2-(4-Bromo-2,3-dichlorophenyl)-1,1,1,3,3,3-hexafluoropropan-2-ol

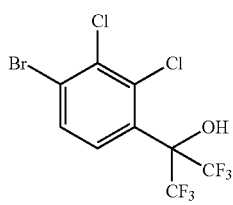

To a solution of 1-(4-bromo-2,3-dichlorophenyl)-2,2,2-trifluoroethanone (1.99 g, 6.18 mmol, Intermediate 6, step a) and TMSCF$_3$ (4.38 g, 30.9 mmol) in anhydrous THF (30 mL) was added a solution of TBAF (2.45 g, 9.27 mmol) in anhydrous THF (25 mL) at 0° C., and the solution was stirred at rt overnight. The resulting solution was quenched with 1 N aqueous HCl, diluted with EtOAc, and the two layers were separated. The organic layer was washed with water and brine, dried over anhydrous Na$_2$SO$_4$, filtered, concentrated to dryness and purified by FCC on silica gel (PE/EtOAc=5/1) to give the title compound as a yellow oil.

Alternate Synthesis of Intermediate 6

A solution of TBAF (14.3 g, 46.6 mmol) in THF (40 mL) was added dropwise to a stirring −15-10° C. solution of 1-(4-bromo-2,3-dichlorophenyl)-2,2,2-trifluoroethanone (10.0 g, 31.1 mmol, Intermediate 6, step a) and TMSCF$_3$ (22.1 g, 155 mmol) in THF (10 mL). Then the reaction was quenched with 2 N aqueous HCl (78 mL), diluted with EtOAc (50 mL), and the layers were separated. The organic layer was washed with water (40 mL) and brine (40 mL) successively and concentrated. The residue was dissolved with heptane (50 mL), and DABCO (1.7 g, 15.2 mmol) was added one portion. The mixture was stirred overnight, filtered, and the cake was washed with heptane (10 mL×2). The cake was dissolved with EtOAc (100 mL), washed with 1 N aqueous HCl (30 mL×3), and concentrated to dryness to give the title compound as a brown liquid.

Intermediate 7: Step a

4-Bromo-2,3-dichlorobenzyl methanesulfonate

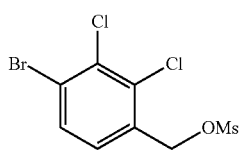 [SMILES: CS(=O)(=O)OCc1ccc(Br)c(Cl)c1Cl]

To a solution of 4-bromo-2,3-dichloro-benzaldehyde (2.00 g, 7.88 mmol) in MeOH (15 mL) was added NaBH$_4$ (756 mg, 20.0 mmol) slowly, and the suspension was stirred at rt for 1 h. The resulting suspension was quenched with saturated aqueous NH$_4$Cl, concentrated under reduced pressure and diluted with EtOAc and water. The organic layer was washed with brine, dried over anhydrous Na$_2$SO$_4$, filtered and concentrated to dryness to give a residue. To this residue was added DCM (20 mL), TEA (2.02 g, 20.0 mmol) and MsCl (2.30 g, 20.1 mmol), and the mixture was stirred for 1 h. The resulting solution was quenched with water, and the organic layer was dried over anhydrous Na$_2$SO$_4$, filtered, concentrated under reduced pressure and purified by preparative TLC (PE/EtOAc=100/1) to give the title compound as a colorless solid.

Intermediate 7

4-(4-Bromo-2,3-dichlorobenzyl)-3,3-dimethylmorpholine

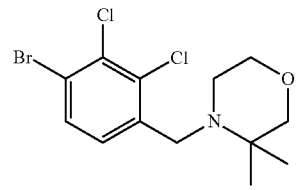 [SMILES: CC1(C)COCCN1Cc1ccc(Br)c(Cl)c1Cl]

A suspension of 4-bromo-2,3-dichlorobenzyl methanesulfonate (735 mg, 2.20 mmol, Intermediate 7, step a), 3,3-dimethyl-morpholine (512 mg, 4.45 mmol) and K$_2$CO$_3$ (828 mg, 6.00 mmol) in MeCN (10 mL) was refluxed overnight. The suspension was cooled to rt, filtered, concentrated to dryness and purified by FCC on silica gel (PE/EtOAc=5/1) to give the title compound as a colorless solid.

Intermediate 7/1

4-((4-Bromonaphthalen-1-yl)methyl)-3,3-dimethylmorpholine

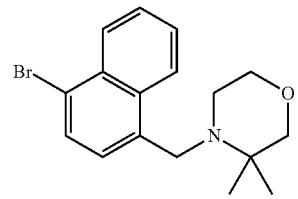 [SMILES: CC1(C)COCCN1Cc1ccc(Br)c2ccccc12]

The title compound was prepared as described for the synthesis of Intermediate 7, using in step a 4-bromo-1-naphthaldehyde in place of 4-bromo-2,3-dichloro-benzaldehyde.

Intermediate 8: Step a

1-(3-Bromo-5-(tert-butyl)phenyl)-2,2,2-trifluoroethanone

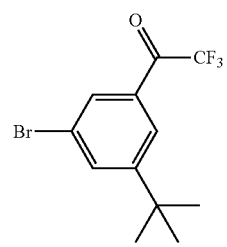 [SMILES: CC(C)(C)c1cc(Br)cc(C(=O)C(F)(F)F)c1]

To a solution of 1,3-dibromo-5-(tert-butyl)benzene (5.84 g, 20.0 mmol) in anhydrous THF (60 mL) was added n-BuLi (2.5 M in THF, 10 mL, 25 mmol) at −78° C. under nitrogen and the solution was stirred for 40 min. Then 2,2,2-trifluoro-N-methoxy-N-methyl-acetamide (3.93 g, 25.0 mmol) was added slowly at this temperature, and the solution was warmed to rt and stirred overnight, quenched with saturated NH$_4$Cl and extracted with EtOAc twice. The combined organic layers were washed with water and brine, dried over anhydrous Na$_2$SO$_4$, filtered and concentrated to dryness. The residue was purified by FCC on silica gel (PE) followed by preparative HPLC to give the title compound as a yellow oil.

Intermediate 8

2-(3-Bromo-5-(tert-butyl)phenyl)-1,1,1,3,3,3-hexafluoropropan-2-ol

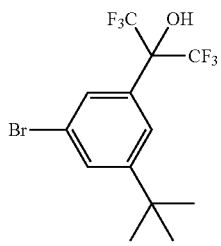 [SMILES: CC(C)(C)c1cc(Br)cc(C(O)(C(F)(F)F)C(F)(F)F)c1]

To a solution of 1-(3-bromo-5-(tert-butyl)phenyl)-2,2,2-trifluoroethanone (3.77 g, 12.2 mmol, Intermediate 8, step a) and TMSCF$_3$ (2.33 mL, 15.0 mmol) in dry DME (50 mL) was added anhydrous CsF (60.8 mg, 0.40 mmol) at rt under nitrogen, and the mixture was stirred for 3 h at rt. Then an additional portion of TMSCF$_3$ (1.00 mL, 6.44 mmol) was added, and the mixture stirred for 2 h, diluted with 2 N aqueous HCl, stirred for 18 h at rt and extracted with EtOAc twice. The combined organic layers were washed with water and brine, dried over anhydrous Na$_2$SO$_4$, filtered and concentrated to dryness. The residue was purified by FCC on silica gel (PE/EtOAc=10/1) followed by preparative HPLC to give the title compound as a colorless oil.

Intermediate 9: Step a 1,3-Dibromo-5-(3,3,3-trifluoroprop-1-en-2-yl)benzene

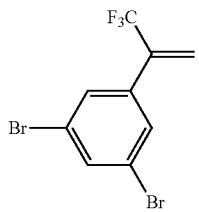

To a stirred mixture of methyltriphenylphosphonium bromide (3.34 g, 9.35 mmol) in anhydrous THF (10 mL) was added t-BuOK (1.04 g, 9.35 mmol) under N$_2$ atmosphere at −40° C., and the mixture was stirred for 30 min at this temperature. Then a solution of 1-(3,5-dibromophenyl)-2,2,2-trifluoroethanone (2.99 g, 9.01 mmol) in anhydrous THF (30 mL) was added dropwise. The solution was stirred at rt overnight, quenched with aqueous NH$_4$Cl at 0° C. and extracted with EtOAc. The organic layer was concentrated to dryness and the residue was purified by FCC on silica gel (PE) to give the title compound as a colorless solid.

Intermediate 9: Step b 1,3-Dibromo-5-(1-(trifluoromethyl)cyclopropyl)benzene

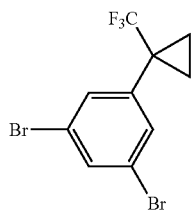 [SMILES: FC(F)(F)C1(c2cc(Br)cc(Br)c2)CC1]

To a suspension of 1,3-dibromo-5-(3,3,3-trifluoroprop-1-en-2-yl)benzene (1.80 g, 5.46 mmol; Intermediate 9, step a) and Pd(OAc)$_2$ (300 mg, 1.3 mmol) in anhydrous THF (10 mL) at 0° C. was added a solution of CH$_2$N$_2$ in Et$_2$O (2 M, 20 mL, 40 mmol) dropwise and the mixture was stirred at rt overnight, filtered and concentrated to dryness. This procedure was repeated four times and the crude product was purified by FCC on silica gel (PE) to give the title compound as a colorless oil.

Intermediate 9: Step c

Methyl 3-bromo-5-(1-(trifluoromethyl)cyclopropyl)benzoate

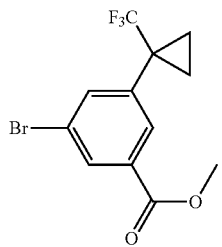 [SMILES: COC(=O)c1cc(Br)cc(C2(C(F)(F)F)CC2)c1]

To a solution of 1,3-dibromo-5-(1-(trifluoromethyl)cyclopropyl)benzene (3.44 g, 10.0 mmol, Intermediate 9, step b) in THF (40 mL) was added n-BuLi (2.5 M, 4.40 mL, 11.0 mmol) at −78° C. and the mixture was stirred at this temperature for 1 h. Methyl chloroformate (1.04 g, 11.0 mmol) was added slowly. The mixture was allowed to reach rt in 2 h, quenched with saturated aqueous NH$_4$Cl and extracted with EtOAc three times. The combined organic layers were washed with brine, dried over anhydrous MgSO$_4$, filtered and concentrated to dryness. The residue was purified by FCC on silica gel (PE/EtOAc=50/1) to give the title compound as a colorless oil.

Intermediate 9: Step d

3-Bromo-5-(1-(trifluoromethyl)cyclopropyl)benzoic acid

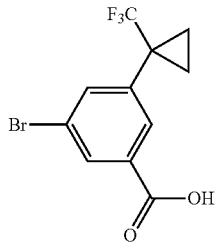 [SMILES: O=C(O)c1cc(Br)cc(C2(C(F)(F)F)CC2)c1]

To a solution of methyl 3-bromo-5-(1-(trifluoromethyl)cyclopropyl)benzoate (1.0 g, 3.1 mmol, Intermediate 9, step c) in a mixture of THF/water (12 mL, 5:1 v/v) was added LiOH.H$_2$O (1.26 g, 30.0 mmol) and the solution was stirred overnight at rt, partially concentrated and the pH was adjusted to pH=4 with 1 N aqueous HCl. The precipitate formed was collected by filtration and dried in vacuo to give the title compound as a colorless solid.

Intermediate 9

(S)-3-Bromo-5-(1-(trifluoromethyl)cyclopropyl)-N-(1,1,1-trifluoropropan-2-yl)benzamide

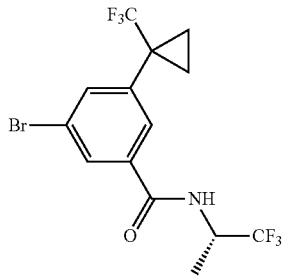 [SMILES: C[C@H](NC(=O)c1cc(Br)cc(C2(C(F)(F)F)CC2)c1)C(F)(F)F]

A solution of (S)-1,1,1-trifluoropropan-2-amine hydrochloride (449 mg, 3.00 mmol), 3-bromo-5-(1-(trifluoromethyl)cyclopropyl)benzoic acid (880 mg, 2.85 mmol, Intermediate 9, step d), DIPEA (775 mg, 6.00 mmol) and HATU (1.14 g, 3.00 mmol) in DMF (10 mL) was stirred overnight at rt. The mixture was concentrated to dryness and the residue was purified by FCC on silica gel (PE/EtOAc=10/1) to give the title compound as a colorless solid.

Intermediate 10

(S)-3-Bromo-5-(1-methylcyclopropyl)-N-(1,1,1-trifluoropropan-2-yl)benzamide

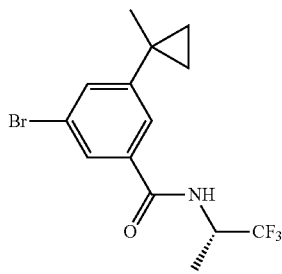 [SMILES: C[C@H](NC(=O)c1cc(Br)cc(C2(C)CC2)c1)C(F)(F)F]

The title compound was prepared as described for the synthesis of Intermediate 9, using in the final step 3-bromo-5-(1-methylcyclopropyl)benzoic acid (prepared as described in WO2013/079223, Preparative Example P33c) in place of 3-bromo-5-(1-(trifluoromethyl)cyclopropyl)benzoic acid.

Intermediate 11: Step a

1-Bromo-2-(difluoromethyl)-4-iodobenzene

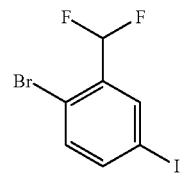 [SMILES: FC(F)c1cc(I)ccc1Br]

Diethylaminosulfur trifluoride (77.8 g, 482 mmol) was added to a solution of 2-bromo-5-iodobenzaldehyde (100 g, 322 mmol) and DCM (1 L) at 0° C. The resultant mixture was stirred at room temperature for 2 h before quenching with ice/water (1 L) and extracting with DCM (800 mL×3). The combined organic extracts were washed with brine, dried over anhydrous Na$_2$SO$_4$, filtered and concentrated to dryness to give the crude product, which was purified by FCC on silica gel (PE/EtOAc=50:1) to afford the title compound.

Intermediate 11: Step b 1-(4-Bromo-3-(difluoromethyl)phenyl)-2,2,2-trifluoroethanone

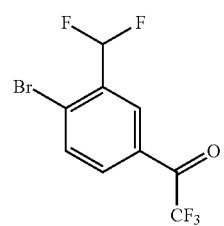

Isopropylmagnesium chloride lithium chloride complex (194 mL, 1.3 M in THF, 252 mmol) was added dropwise to a solution of 1-bromo-2-(difluoromethyl)-4-iodobenzene (70.0 g, 210 mmol, Intermediate 11, step a) and anhydrous THF (200 mL) at −78° C. The resultant mixture was stirred at −78° C. for 30 minutes and then treated with 2,2,2-trifluoro-N-methoxy-N-methylacetamide (49.5 g, 315 mmol). The resultant mixture was stirred at −78° C. under N$_2$ for 1 h before it was quenched with saturated aqueous NH$_4$Cl (600 mL) solution and extracted with EtOAc (800 mL×3). The combined organic extracts were dried over anhydrous Na$_2$SO$_4$, filtered, and concentrated to dryness to give the crude product, which was purified by FCC on silica gel (PE/EtOAc=10:1 to 4:1) to afford the title compound.

Intermediate 11

2-(4-Bromo-3-(difluoromethyl)phenyl)-1,1,1,3,3,3-hexafluoropropan-2-ol

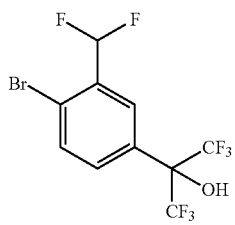 [SMILES: OC(c1ccc(Br)c(C(F)F)c1)(C(F)(F)F)C(F)(F)F]

Tetrabutylammonium fluoride (470 mL, 1 M in THF, 470 mmol) was added dropwise to a solution of 1-(4-bromo-3-(difluoromethyl)phenyl)-2,2,2-trifluoroethanone (95.0 g, 313 mmol, Intermediate 11, step b), TMSCF₃ (223 g, 1.6 mol), and anhydrous THF (100 mL) at −15° C. The resultant mixture was stirred at −15-10° C. for 30 minutes and then was allowed to warm to rt over 2 h before it was quenched with 2 N aqueous HCl (400 mL) and extracted with EtOAc (800 mL×3). The combined organic extracts were dried over anhydrous Na₂SO₄, filtered, and concentrated to dryness to give the crude product, which was purified by FCC on silica gel (PE/EtOAc=100:1 to 20:1) to afford the title compound.

Intermediate 12: Step a

Ethyl 2,2-dimethyl-3-(thiazol-2-yl)propanoate

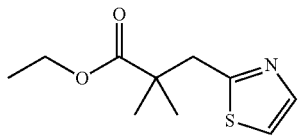

To a solution of ethyl 3-iodo-2,2-dimethylpropanoate (2.5 g, 10 mmol, Intermediate 14, step a) in THF (50 mL) was added dropwise n-BuLi (4.8 mL, 12 mmol, 2.5 M in THF) at −78° C. under an Ar atmosphere and the mixture was stirred for 1 h at that temperature. A 0.5 M solution of ZnCl₂ in THF (24 mL, 12 mmol) was added, and the mixture was stirred for 30 min at −78° C. The solution was allowed to warm to rt and stirred for 1 h. 2-Bromothiazole (1.6 g, 10 mmol), Pd₂(dba)₃ (0.45 g, 0.49 mmol) and dppf (0.54 g, 0.98 mmol) were added, and the mixture was stirred for 20 h at 60° C. After cooling, the mixture was treated with water (50 mL) and extracted with EtOAc (3×50 mL). The combined organic layers were washed with brine, dried over Na₂SO₄ and concentrated to dryness. The residue was purified by FCC on silica gel (PE/EtOAc=15:1) to give the title compound as a colorless liquid.

Intermediate 12: Step b

Ethyl 3-(5-bromothiazol-2-yl)-2,2-dimethylpropanoate

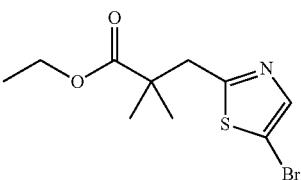

To a solution of ethyl 2,2-dimethyl-3-(thiazol-2-yl)propanoate (1.1 g, 5.2 mmol, Intermediate 12, step a) in CH₃CN (30 mL) was added NBS (1.1 g, 6.2 mmol). The mixture was stirred 3 h at reflux temperature, cooled to rt and quenched with aqueous Na₂SO₃ (50 mL). The mixture was extracted with EtOAc (3×50 mL) and the combined organic layers were concentrated to dryness. The residue was purified by FCC on silica gel (PE/EtOAc=30:1) to give the title compound as a colorless liquid.

Intermediate 12

Ethyl 2,2-dimethyl-3-(5-(4,4,5,5-tetramethyl-1,3,2-dioxaborolan-2-yl)thiazol-2-yl)propanoate

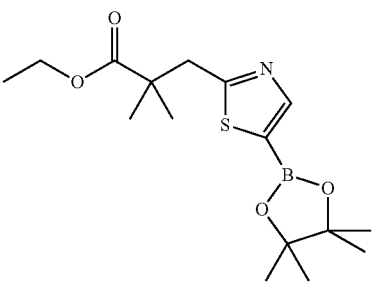 [SMILES: CCOC(=O)C(C)(C)Cc1ncc(B2OC(C)(C)C(C)(C)O2)s1]

To a solution of ethyl 3-(5-bromothiazol-2-yl)-2,2-dimethylpropanoate (616 mg, 2.12 mmol, Intermediate 12, step b), bis(pinacolato)diboron (646 mg, 2.54 mmol) and KOAc (519 mg, 5.30 mmol) in 1,4-dioxane (10 mL) was added Pd(dppf)Cl₂ (50 mg, 68 μmol) and the solution was stirred at 90° C. overnight. The mixture was allowed to cool to rt and partitioned between EtOAc and water. The organic layer was washed with water and brine, dried over Na₂SO₄, filtered and concentrated to dryness. The residue was purified by FCC on silica gel (PE/EA=10:1) to give the title compound as a colorless solid.

Intermediate 13

4-(Cyclobutylmethyl)thiazole

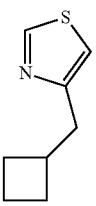

A mixture of ethyl 4-(cyclobutylmethyl)thiazole-2-carboxylate (300 mg, 1.3 mmol, Intermediate 1) and KOH (230 mg, 3.9 mmol) in ethanol (10 mL) and water (3 mL) was stirred for 4 h at rt. The pH was adjusted to pH 3 with 1 M aqueous HCl and the mixture was extracted with EtOAc (3×50 mL). The combined organic layers were dried over $Na_2SO_4$, filtered and concentrated to dryness. The residue was treated with HCl/dioxane (15 mL) at rt for 1 h. Water was added and the mixture was extracted with EtOAc (3×50 mL). The combined organic layers were washed with brine, dried over $Na_2SO_4$, filtered and concentrated to dryness. The residue was purified by preparative TLC (PE/EtOAc=50:1) to afford the title compound.

Intermediate 14: Step a

Ethyl 3-iodo-2,2-dimethylpropanoate

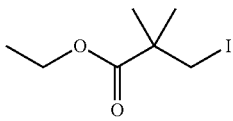

To a solution of ethyl isobutyrate (15 g, 130 mmol) in THF at −78° C. was added slowly LDA (2 M in hexane, 71 mL, 142 mmol). The mixture was stirred at −78° C. for 1 h, then $CH_2I_2$ (24.9 g, 92.9 mmol) was added. The mixture was warmed to rt overnight, poured into saturated aqueous $NH_4Cl$ (100 mL) and extracted with EtOAc. The combined organic layers were dried over anhydrous $Na_2SO_4$, filtered and concentrated to dryness. The residue was purified by fractional distillation to afford the title compound as a colorless liquid.

Intermediate 14: Step b

Ethyl 3-(6-bromopyridin-2-yl)-2,2-dimethylpropanoate

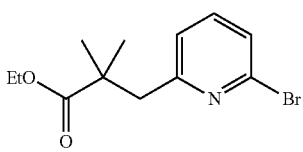 [SMILES: CCOC(=O)C(C)(C)Cc1cccc(Br)n1]

A suspension of Zn—Cu couple (690 mg, 10.5 mmol) in toluene/DMA (6 mL, 11:1 v/v) was purged with Ar for 15 min. Ethyl 3-iodo-2,2-dimethylpropanoate (340 mg, 1.35 mmol, Intermediate 14, step a) was added to the suspension, and the resulting mixture was heated at 110° C. for 3 h. The mixture was cooled to 70° C., and 2,6-dibromopyridine (320 mg, 1.35 mmol) and $Pd(PPh_3)_4$ (47 mg, 0.040 mmol) were added. The mixture was stirred at 80° C. for 16 h, allowed to cool, filtered and concentrated to dryness. The residue was purified by preparative TLC (PE/EtOAc=8:1) to give the title compound.

Intermediate 14

Ethyl 3-(6-(4-(cyclobutylmethyl)thiazol-2-yl)pyridin-2-yl)-2,2-dimethylpropanoate

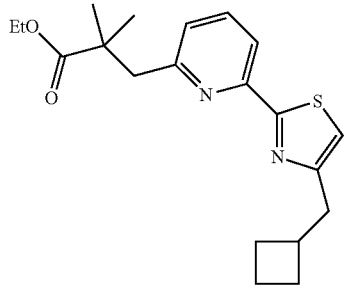 [SMILES: CCOC(=O)C(C)(C)Cc1cccc(-c2nc(CC3CCC3)cs2)n1]

To a solution of 4-(cyclobutylmethyl)thiazole (180 mg, 1.17 mmol, Intermediate 13) in THF (8 mL) at −78° C. was added n-BuLi (1.6 M in hexane, 1.5 mL, 2.4 mmol). The mixture was stirred at −78° C. for 2 h and then a solution of $ZnCl_2$ in THF (1 M, 5.9 mL, 5.9 mmol) was added. The mixture was stirred at −78° C. for 1.5 h and then allowed to warm to rt. Ethyl 3-(6-bromopyridin-2-yl)-2,2-dimethylpropanoate (337 mg, 1.17 mmol, Intermediate 14, step b) and $Pd(PPh_3)_4$ (135 mg, 117 μmol) were added and the mixture was stirred at 60° C. overnight. The mixture was allowed to cool to rt, diluted with EtOAc (50 mL) and washed with saturated aqueous $NH_4Cl$ (3×15 mL). The organic layer was dried over anhydrous $Na_2SO_4$, filtered, and concentrated to dryness to give a residue, which was purified by preparative TLC (PE/EtOAc=15/1) to give the title compound.

Intermediate 15: Step a

Ethyl 3-(6-chloropyrimidin-4-yl)-2,2-dimethylpropanoate

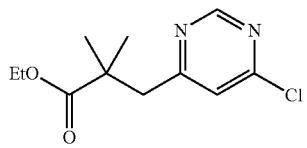 [SMILES: CCOC(=O)C(C)(C)Cc1cc(Cl)ncn1]

The title compound was prepared as described for the synthesis of Intermediate 14, step b, using 4,6-dichloropyrimidine in place of 2,6-dibromopyridine.

Intermediate 15

Ethyl 3-(6-(4-(Cyclobutylmethyl)thiazol-2-yl)pyrimidin-4-yl)-2,2-dimethylpropanoate

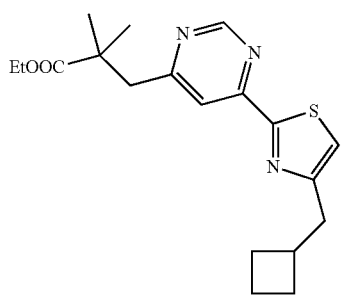 [SMILES: CCOC(=O)C(C)(C)Cc1cc(-c2nc(CC3CCC3)cs2)ncn1]

The title compound was prepared as described for the synthesis of Intermediate 14, using in the final step ethyl 3-(6-chloropyrimidin-4-yl)-2,2-dimethylpropanoate (Intermediate 15, step a) in place of ethyl 3-(6-bromopyridin-2-yl)-2,2-dimethylpropanoate.

Intermediate 16: Step a (S)-tert-Butyl 4,4-difluoro-2-methylpyrrolidine-1-carboxylate

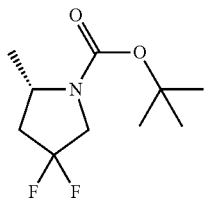

Under a nitrogen atmosphere, DAST (0.60 mL, 4.4 mmol) was added to a solution of (S)-tert-butyl 2-methyl-4-oxopyrrolidine-1-carboxylate (420 mg, 2.10 mmol) in DCM (5.0 mL) under ice cooling and the resultant mixture was stirred for 16 h at rt and quenched with saturated aqueous NaHCO$_3$. The organic layer was dried over anhydrous Na$_2$SO$_4$, filtered, concentrated to dryness, and purified by FCC on silica gel (PE/EtOAc=70/1) to give the title compound as a yellow oil.

Intermediate 16

(S)-4,4-Difluoro-2-methylpyrrolidine hydrochloride

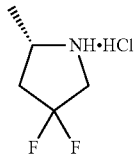

To a solution of (S)-tert-butyl 4,4-difluoro-2-methylpyrrolidine-1-carboxylate (250 mg, 1.13 mmol, Intermediate 16, step a) in 1,4-dioxane (2 mL) was added a solution of HCl in 1,4-dioxane (4 M, 5.0 mL) at 0° C. The mixture was stirred at rt for 1 h and concentrated to dryness to give the title compound as a red solid.

Intermediate 17

(S)-3,3-Difluoro-2-methylpyrrolidine hydrochloride

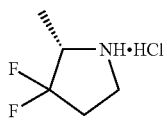

The title compound was prepared as described for the synthesis of Intermediate 16 using in step a (S)-tert-butyl 2-methyl-3-oxopyrrolidine-1-carboxylate in place of (S)-tert-butyl 2-methyl-4-oxopyrrolidine-1-carboxylate.

Intermediate 18

N-(tert-Butyl)-4-(4,4,5,5-tetramethyl-1,3,2-dioxaborolan-2-yl)naphthalene-1-sulfonamide

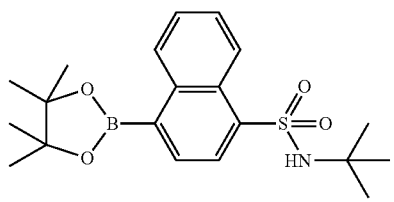 [SMILES: CC(C)(C)NS(=O)(=O)c1ccc(B2OC(C)(C)C(C)(C)O2)c2ccccc12]

A mixture of 4-bromo-N-(tert-butyl)naphthalene-1-sulfonamide (55.0 g, 161 mmol, Intermediate 4/6), bis(pinacolato)diboron (42.0 g, 165 mmol), K$_2$CO$_3$ (92.0 g, 667 mmol) and Pd(dppf)Cl$_2$ (5.0 g, 6.1 mmol) in 1,4-dioxane (600 mL) was stirred under nitrogen at 90° C. overnight. The resulting solution was allowed to cool to rt, concentrated to dryness and the residue was purified by FCC on silica gel (PE/EtOAc=10/1) to give the title compound as a pale yellow solid.

Example 1: Step a 2-(5-(5-(4-(N-(tert-Butyl)sulfamoyl)-3-(trifluoromethyl)phenyl)-4-(cyclohexylmethyl)thiazol-2-yl)-1,3,4-oxadiazol-2-yl)propan-2-yl acetate

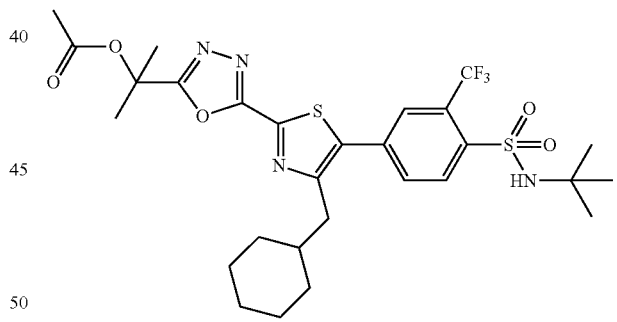

A mixture of 2-(5-(4-(cyclohexylmethyl)thiazol-2-yl)-1,3,4-oxadiazol-2-yl)propan-2-yl acetate (150 mg, 0.43 mmol, Intermediate 2/8), 4-bromo-N-(tert-butyl)-2-(trifluoromethyl)benzenesulfonamide (155 mg, 0.430 mmol, prepared as described for Intermediate 4, using 2-(trifluoromethyl)aniline in place of 3-(difluoromethyl)-2-fluoroaniline in step c), KOAc (126 mg, 1.28 mmol), PPh$_3$ (113 mg, 0.431 mmol), Pd(OAc)$_2$ (50 mg, 0.22 mmol) and DMF (5 mL) was purged with N$_2$ and heated at 120° C. overnight. The resulting solution was allowed to cool to rt and diluted with EtOAc. The solution was washed with water three times, dried over anhydrous Na$_2$SO$_4$, filtered, concentrated to dryness, and purified by FCC on silica gel (DCM/MeOH=100/1) to give the title compound as a colorless solid.

Example 1: N-(tert-Butyl)-4-(4-(cyclohexylmethyl)-2-(5-(2-hydroxypropan-2-yl)-1,3,4-oxadiazol-2-yl)thiazol-5-yl)-2-(trifluoromethyl)benzenesulfonamide

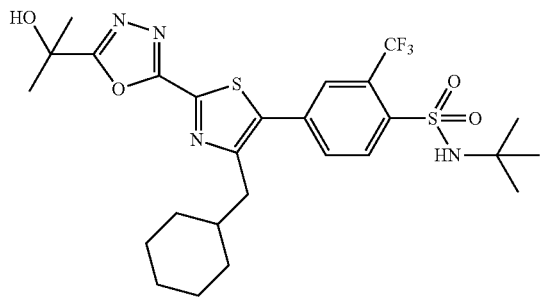 [SMILES: CC(C)(C)NS(=O)(=O)c1ccc(-c2sc(-c3nnc(C(C)(C)O)o3)nc2CC2CCCCC2)cc1C(F)(F)F]

A solution of 2-(5-(5-(4-(N-(tert-butyl)sulfamoyl)-3-(trifluoromethyl)phenyl)-4-(cyclohexylmethyl)thiazol-2-yl)-1,3,4-oxadiazol-2-yl)propan-2-yl acetate (250 mg, 0.398 mmol, Example 1, step a) and LiOH.H$_2$O (52 mg, 1.2 mmol) in a mixture of MeOH (10 mL) and water (2 mL) was stirred at rt for 1 h. The resulting mixture was concentrated to dryness, and the resulting residue was dissolved in EtOAc. The solution was washed with water twice, dried over anhydrous Na$_2$SO$_4$, filtered, concentrated to dryness, and purified by preparative HPLC to give the title compound as a colorless solid. $^1$H NMR (400 MHz, CDCl$_3$): δ ppm 8.40 (d, J=8.0 Hz, 1H), 7.93 (s, 1H), 7.78-7.75 (m, 1H), 4.74 (s, 1H), 2.75 (d, J=8.0 Hz, 2H), 2.64 (s, 1H), 1.89-1.88 (m, 1H), 1.82 (s, 6H), 1.66-1.64 (m, 4H), 1.30 (s, 9H), 1.29-1.12 (m, 4H), 0.93-0.88 (m, 2H). MS (APCI): m/z 585.2 [M–H]$^-$.

Example 1/1: N-(tert-Butyl)-4-(4-(cyclohexylmethyl)-2-(5-(2-hydroxypropan-2-yl)-1,3,4-oxadiazol-2-yl)thiazol-5-yl)naphthalene-1-sulfonamide

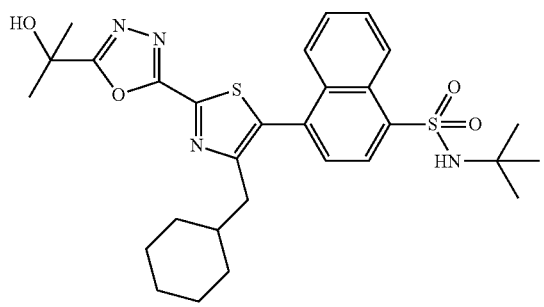 [SMILES: CC(C)(C)NS(=O)(=O)c1ccc(-c2sc(-c3nnc(C(C)(C)O)o3)nc2CC2CCCCC2)c2ccccc12]

The title compound was prepared as described for the synthesis of Example 1 using in step a 4-bromo-N-(tert-butyl)naphthalene-1-sulfonamide (Intermediate 4/6) in place of 4-bromo-N-(tert-butyl)-2-(trifluoromethyl)benzenesulfonamide. $^1$H NMR (300 MHz, CDCl$_3$): δ ppm 8.71 (d, J=8.1 Hz, 1H), 8.37 (d, J=8.1 Hz, 1H), 7.77-7.70 (m, 2H), 7.62-7.56 (m, 2H), 4.69 (s, 1H), 2.72 (s, 1H), 2.45 (br s, 2H), 1.82 (s, 6H), 1.54-1.50 (m, 6H), 1.25 (s, 9H), 0.95-1.20 (m, 3H), 0.61-0.69 (m, 2H). MS (ESI): m/z 569.2 [M+H]$^+$.

Example 2: Step a

5-Bromo-4-(cyclohexylmethyl)thiazole-2-carbohydrazide

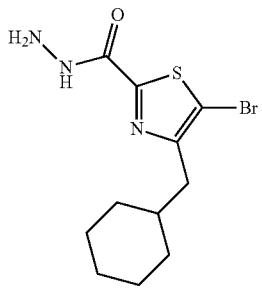 [SMILES: NNC(=O)c1nc(CC2CCCCC2)c(Br)s1]

To a solution of ethyl 5-bromo-4-(cyclohexylmethyl)thiazole-2-carboxylate (1.00 g, 3.01 mmol, prepared as described in WO2013/178362, Example 6, step 3) in EtOH (15 mL) was added aqueous 85% hydrazine hydrate (1.24 g, 21.1 mmol), and the solution was stirred at rt for 1 h. The resulting solution was concentrated to dryness and purified by FCC on silica gel (EtOAc/PE=1/3) to give the title compound as a colorless solid.

Example 2: Step b

2-(5-Bromo-4-(cyclohexylmethyl)thiazol-2-yl)-5-methyl-1,3,4-oxadiazole

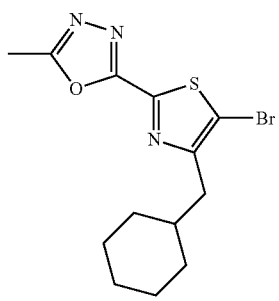 [SMILES: Cc1nnc(-c2nc(CC3CCCCC3)c(Br)s2)o1]

A solution of 5-bromo-4-(cyclohexylmethyl)thiazole-2-carbohydrazide (250 mg, 0.786 mmol, Example 2, step a) in Ac$_2$O (5 mL) was heated at 45° C. for 1 h under nitrogen. The resulting solution was cooled to rt, poured into saturated aqueous NaHCO$_3$ and extracted with EtOAc twice. The combined organic layers were washed with brine, dried over anhydrous Na$_2$SO$_4$, filtered and concentrated to dryness. Pyridine (154 mg, 1.94 mmol) and DCM (25 mL) were then added, followed by Tf$_2$O (460 mg, 1.63 mmol) under N$_2$ at −10° C., and the solution was stirred at −10° C. for 1 h, at 0° C. for 1 h, and at rt for 30 min. The resulting solution was concentrated to dryness and purified by FCC on silica gel (EtOAc/PE=1/10) to give the title compound as a colorless solid.

Example 2: N-(tert-Butyl)-4-(4-(cyclohexylmethyl)-2-(5-methyl-1,3,4-oxadiazol-2-yl)thiazol-5-yl)naphthalene-1-sulfonamide

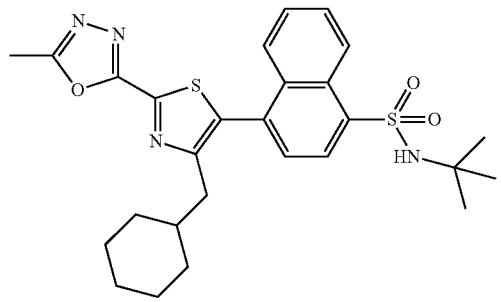 [SMILES: Cc1nnc(-c2nc(CC3CCCCC3)c(-c3ccc(S(=O)(=O)NC(C)(C)C)c4ccccc34)s2)o1]

A solution of 2-(5-bromo-4-(cyclohexylmethyl)thiazol-2-yl)-5-methyl-1,3,4-oxadiazole (100 mg, 0.292 mmol, Example 2, step b), N-(tert-butyl)-4-(4,4,5,5-tetramethyl-1,3,2-dioxaborolan-2-yl)naphthalene-1-sulfonamide (142 mg, 0.366 mmol, Intermediate 18), Pd(dppf)Cl$_2$ (24 mg, 0.029 mmol) and Na$_2$CO$_3$ (2 M in water, 1.6 mL, 3.2 mmol) in DME (5 mL) was purged with nitrogen for 15 min and heated at reflux temperature overnight. After cooling to rt, the resulting solution was diluted with EtOAc and water. The layers were separated, and the aqueous layer was extracted with EtOAc. The combined organic layers were washed with brine, dried over anhydrous Na$_2$SO$_4$, filtered, concentrated to dryness, and purified by FCC on silica gel (EtOAc/PE=1/1) to give the title compound as an off-white solid. $^1$H NMR (400 MHz, CD$_3$OD): δ ppm 8.84 (d, J=8.0 Hz, 1H), 8.35 (d, J=8.0 Hz, 1H), 7.80-7.64 (m, 4H), 2.69 (s, 3H), 2.50-2.45 (m, 2H), 1.70-1.66 (m, 1H), 1.52-1.50 (m, 5H), 1.10 (s, 9H), 1.07-0.97 (m, 3H), 0.72-0.67 (m, 2H). MS (ESI): m/z 525.2 [M+H]$^+$.

Example 3: Step a

Methyl 3-(5-(5-(4-(N-(tert-butyl)sulfamoyl)-2,3-dichlorophenyl)-4-(cyclobutylmethyl)thiazol-2-yl)-1,3,4-oxadiazol-2-yl)-2,2-dimethylpropanoate

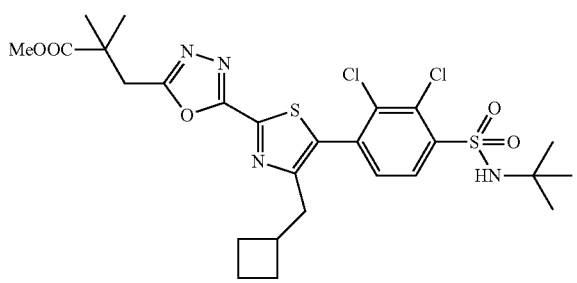 [SMILES: COC(=O)C(C)(C)Cc1nnc(-c2nc(CC3CCC3)c(-c3ccc(S(=O)(=O)NC(C)(C)C)c(Cl)c3Cl)s2)o1]

A mixture of methyl 3-(5-(4-(cyclobutylmethyl)thiazol-2-yl)-1,3,4-oxadiazol-2-yl)-2,2-dimethylpropanoate (200 mg, 600 µmol, Intermediate 2), 4-bromo-N-(tert-butyl)-2,3-dichlorobenzenesulfonamide (323 mg, 0.900 mmol, Intermediate 4/5), Pd(OAc)$_2$ (80 mg, 0.4 mmol), KOAc (156 mg, 1.50 mmol) and PPh$_3$ (60 mg, 0.2 mmol) in DMF (15 mL) was stirred at 95° C. for 24 h under nitrogen atmosphere. After cooling to rt, the mixture was diluted with EtOAc (75 mL), washed with water (3×50 mL) and brine (50 mL), dried over anhydrous Na$_2$SO$_4$, filtered and concentrated to dryness. The residue was purified by FCC on silica gel (PE/EtOAc=6/1) to give the title compound as a yellow oil.

Example 3: 3-(5-(5-(4-(N-(tert-Butyl)sulfamoyl)-2,3-dichlorophenyl)-4-(cyclobutylmethyl)thiazol-2-yl)-1,3,4-oxadiazol-2-yl)-2,2-dimethylpropanoic acid

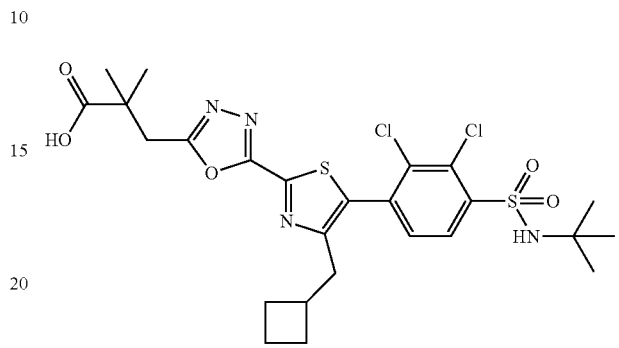

To a solution of methyl 3-(5-(5-(4-(N-(tert-butyl)sulfamoyl)-2,3-dichlorophenyl)-4-(cyclobutylmethyl)thiazol-2-yl)-1,3,4-oxadiazol-2-yl)-2,2-dimethylpropanoate (178 mg, 0.289 mmol, Example 3, step a) in a mixture of THF, MeOH and H$_2$O (15 mL, 1:1:1 v/v/v) was added LiOH.H$_2$O (122 mg, 2.89 mmol). The resultant mixture was stirred at rt overnight. The pH was adjusted to pH 2 with 1 M aqueous HCl and the precipitate was collected by filtration. The precipitate was washed with diethyl ether and dried to give the title compound as a colorless solid. $^1$H NMR (300 MHz, DMSO-d$_6$): δ ppm 12.57 (br s, 1H). 8.13 (d, J=8.3 Hz, 1H), 8.06 (s, 1H), 7.75 (d, J=8.3 Hz, 1H), 3.21 (s, 2H), 2.71-2.55 (m, 3H), 1.94-1.45 (m, 6H), 1.27 (s, 6H), 1.17 (s, 9H). MS (ESI): m/z 601.1 [M+H]$^+$.

Example 3/1: 3-(5-(5-(4-(N-(tert-Butyl)sulfamoyl)naphthalen-1-yl)-4-(cyclohexylmethyl)thiazol-2-yl)-1,3,4-oxadiazol-2-yl)-2,2-dimethylpropanoic acid

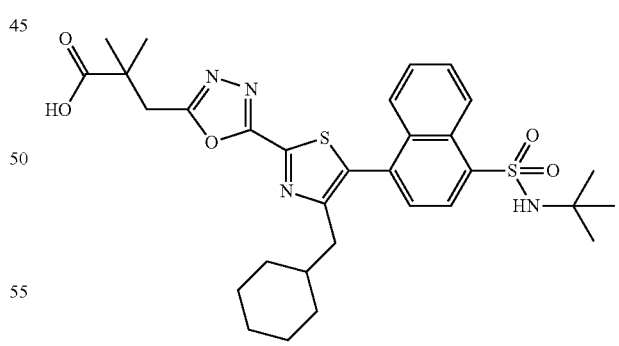

The title compound was prepared as described for the synthesis of Example 3, using in step a methyl 3-(5-(4-(cyclohexylmethyl)thiazol-2-yl)-1,3,4-oxadiazol-2-yl)-2,2-dimethylpropanoate (Intermediate 2/1) in place of methyl 3-(5-(4-(cyclobutylmethyl)thiazol-2-yl)-1,3,4-oxadiazol-2-yl)-2,2-dimethylpropanoate and 4-bromo-N-(tert-butyl) naphthalene-1-sulfonamide (Intermediate 4/6) in place of 4-bromo-N-(tert-butyl)-2,3-dichlorobenzenesulfonamide.
$^1$H NMR (300 MHz, CDCl$_3$): δ ppm 8.72 (d, J=8.1 Hz, 1H), 8.37 (d, J=8.1 Hz, 1H), 8.25 (br s, 1H), 7.77-7.69 (m, 2H), 7.61-7.55 (m, 2H), 5.14 (s, 1H), 3.30 (s, 2H), 2.44 (m, 2H), 1.76 (m, 1H), 1.60-1.47 (m, 4H), 1.44 (s, 6H), 1.22 (s, 9H), 1.15-0.80 (m, 4H), 0.71-0.54 (m, 2H). MS (ESI): m/z 611.3 [M+H]⁺.

Example 3/2: 3-(5-(5-(4-(N-(tert-Butyl)sulfamoyl)-2,3-dichlorophenyl)-4-(cyclohexylmethyl)thiazol-2-yl)-1,3,4-oxadiazol-2-yl)-2,2-dimethylpropanoic acid

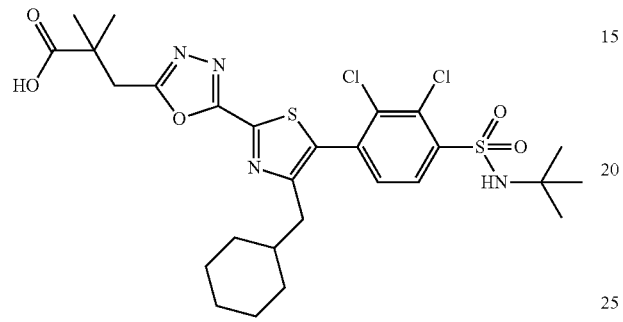

The title compound was prepared as described for the synthesis of Example 3, using in step a 3-(5-(4-(cyclohexylmethyl)thiazol-2-yl)-1,3,4-oxadiazol-2-yl)-2,2-dimethylpropanoic acid (Intermediate 2/1) instead of methyl 3-(5-(4-(cyclobutylmethyl)thiazol-2-yl)-1,3,4-oxadiazol-2-yl)-2,2-dimethylpropanoate. ¹H NMR (300 MHz, DMSO-d₆): δ ppm 12.53 (br s, 1H), 8.11 (d, J=8.3 Hz, 1H), 8.03 (s, 1H), 7.72 (d, J=8.3 Hz, 1H), 3.20 (s, 2H), 1.69-1.55 (m, 2H), 1.53-1.46 (m, 6H), 1.26 (s, 6H), 1.14-0.99 (m, 12H), 0.78-0.71 (m, 2H). MS (ESI): m/z 629.1 [M+H]⁺.

Example 3/3: (S)-3-(5-(5-(4-(Cyclobutylmethyl)-5-(4-(N-(1,1,1-trifluoropropan-2-yl)sulfamoyl)naphthalen-1-yl)thiazol-2-yl)-1,3,4-oxadiazol-2-yl)-2,2-dimethylpropanoic acid

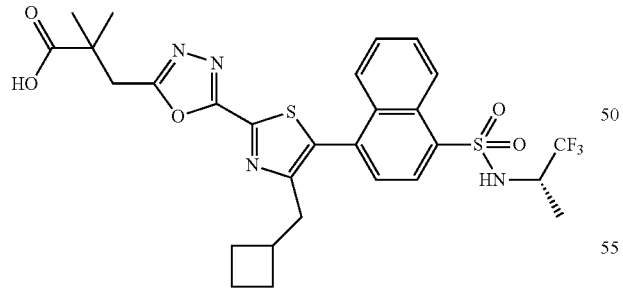

The title compound was prepared as described for the synthesis of Example 3, using in step a (5)-4-bromo-N-(1,1,1-trifluoropropan-2-yl)naphthalene-1-sulfonamide (Intermediate 4/7) in place of 4-bromo-N-(tert-butyl)-2,3-dichlorobenzenesulfonamide. ¹H NMR (300 MHz, DMSO-d₆): δ ppm 12.58 (br s, 1H), 9.05 (br s, 1H), 8.75 (d, J=8.7 Hz, 1H), 8.30 (d, J=7.5 Hz, 1H), 7.86-7.69 (m, 4H), 4.12-4.01 (m, 1H), 3.24 (s, 2H), 2.63-2.54 (m, 2H), 1.87-1.13 (m, 13H), 1.05 (d, J=6.9 Hz, 3H). MS (ESI): m/z 632.2 [M+H]⁺.

Example 3/4: (S)-3-(5-(4-(Cyclobutylmethyl)-5-(2,3-dichloro-4-(N-(1,1,1-trifluorobutan-2-yl)sulfamoyl)phenyl)thiazol-2-yl)-1,3,4-oxadiazol-2-yl)-2,2-dimethylpropanoic acid

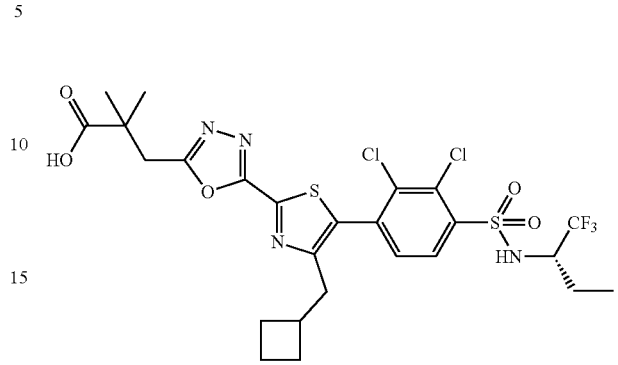

The title compound was prepared as described for the synthesis of Example 3, using in step a (5)-4-bromo-2,3-dichloro-N-(1,1,1-trifluorobutan-2-yl)benzenesulfonamide (Intermediate 4/3) in place of 4-bromo-N-(tert-butyl)-2,3-dichlorobenzenesulfonamide. ¹H NMR (300 MHz, CDCl₃): δ ppm 8.08 (d, J=8.4 Hz, 1H), 7.45 (d, J=8.4 Hz, 1H), 5.33 (d, J=10.2 Hz, 1H), 3.94-3.88 (m, 1H), 2.74-2.72 (m, 3H), 3.28 (s, 2H), 1.97-1.51 (m, 7H), 1.44 (s, 6H), 1.28-1.25 (m, 2H), 1.11 (t, J=7.5 Hz, 3H). MS (ESI): m/z 655.1 [M+H]⁺.

Example 3/5: 3-(5-(4-(Cyclobutylmethyl)-5-(2,3-dichloro-4-(N-(2,2,2-trifluoroethyl)sulfamoyl)phenyl)thiazol-2-yl)-1,3,4-oxadiazol-2-yl)-2,2-dimethylpropanoic acid

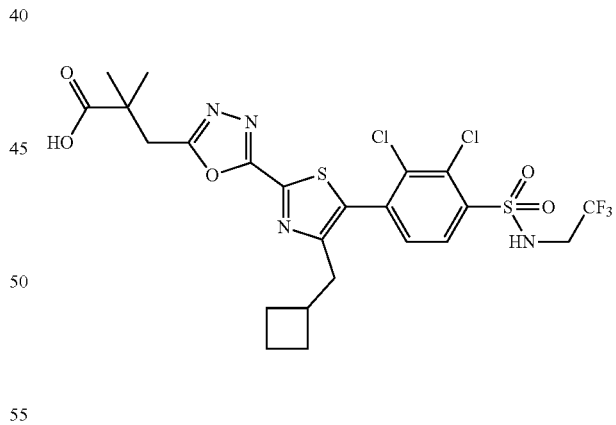

The title compound was prepared as described for the synthesis of Example 3, using in step a 4-bromo-2,3-dichloro-N-(2,2,2-trifluoroethyl)benzenesulfonamide (Intermediate 4/4) in place of 4-bromo-N-(tert-butyl)-2,3-dichlorobenzenesulfonamide. ¹H NMR (300 MHz, CDCl₃): δ ppm 8.11 (d, J=8.4 Hz, 1H), 7.47 (d, J=8.4 Hz, 1H), 5.65 (br s, 1H), 3.85-3.79 (m, 2H), 3.28 (s, 2H), 2.75-2.70 (m, 3H), 2.01-1.53 (m, 6H), 1.43 (s, 6H). MS (ESI): m/z 627.0 [M+H]⁺.

Example 3/6: 3-(5-(4-(Cyclobutylmethyl)-5-(2,3-dichloro-4-((3,3-dimethylmorpholino)methyl)phenyl)thiazol-2-yl)-1,3,4-oxadiazol-2-yl)-2,2-dimethylpropanoic acid

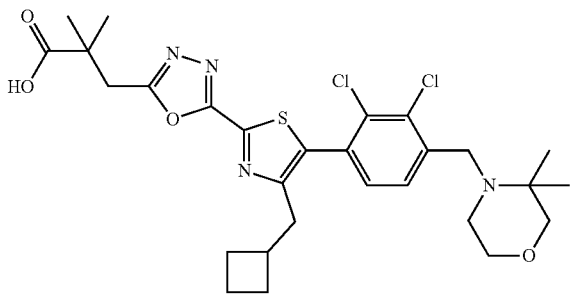 [SMILES: CC(C)(Cc1nnc(-c2nc(CC3CCC3)c(-c3ccc(CN4CCOCC4(C)C)c(Cl)c3Cl)s2)o1)C(=O)O]

The title compound was prepared as described for the synthesis of Example 3, using in step a 4-(4-bromo-2,3-dichlorobenzyl)-3,3-dimethylmorpholine (Intermediate 7) in place of 4-bromo-N-(tert-butyl)-2,3-dichlorobenzenesulfonamide. $^1$H NMR (300 MHz, CDCl$_3$): δ ppm 7.69 (d, J=8.1 Hz, 1H), 7.29-7.26 (m, 1H), 3.76-3.72 (m, 4H), 3.44 (s, 2H), 3.27 (s, 2H), 2.74-2.73 (m, 3H), 2.56-2.50 (m, 2H), 1.98-1.52 (m, 6H), 1.41 (s, 6H), 1.14 (s, 6H). MS (ESI): m/z 593.2 [M+H]$^+$.

Example 3/7: 3-(5-(4-(Cyclobutylmethyl)-5-(4-((3,3-dimethylmorpholino)methyl)naphthalen-1-yl)thiazol-2-yl)-1,3,4-oxadiazol-2-yl)-2,2-dimethylpropanoic acid

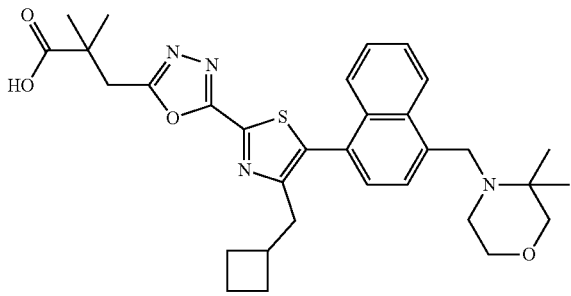

The title compound was prepared as described for the synthesis of Example 3, using in step a 4-((4-bromonaphthalen-1-yl)methyl)-3,3-dimethylmorpholine (Intermediate 7/1) in place of 4-bromo-N-(tert-butyl)-2,3-dichlorobenzenesulfonamide. $^1$H NMR (300 MHz, CDCl$_3$): δ ppm 8.38 (d, J=9.0 Hz, 1H), 7.71-7.44 (m, 5H), 4.08 (s, 2H), 3.70-3.67 (m, 2H), 3.48 (s, 2H), 3.29 (s, 2H), 2.70-2.68 (m, 3H), 2.53-2.50 (m, 2H), 1.91-1.43 (m, 6H), 1.40 (s, 6H), 1.23 (s, 6H). MS (ESI): m/z 575.2 [M+H]$^+$.

Example 3/8: Step a

Methyl 3-(5-(4-(cyclobutylmethyl)-5-(4-(1-(3,3-dimethylmorpholino)ethyl)naphthalen-1-yl)thiazol-2-yl)-1,3,4-oxadiazol-2-yl)-2,2-dimethylpropanoate

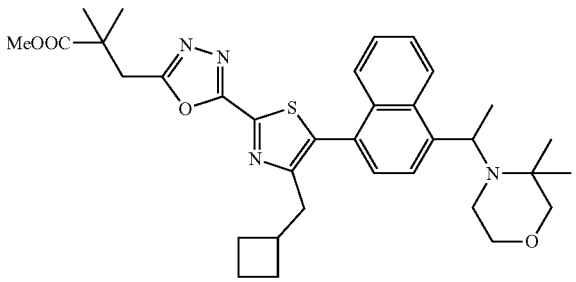 [SMILES: COC(=O)C(C)(C)Cc1nnc(-c2nc(CC3CCC3)c(-c3ccc(C(C)N4CCOCC4(C)C)c4ccccc34)s2)o1]

The title compound was prepared as described for the synthesis of Example 3, using in step a 4-(1-(4-bromonaphthalen-1-yl)ethyl)-3,3-dimethylmorpholine (Intermediate 5) in place of 4-bromo-N-(tert-butyl)-2,3-dichlorobenzenesulfonamide.

Example 3/8a and 3/8b: Step b

Methyl 3-(5-(4-(cyclobutylmethyl)-5-(4-(1-(3,3-dimethylmorpholino)ethyl)naphthalen-1-yl)thiazol-2-yl)-1,3,4-oxadiazol-2-yl)-2,2-dimethylpropanoate

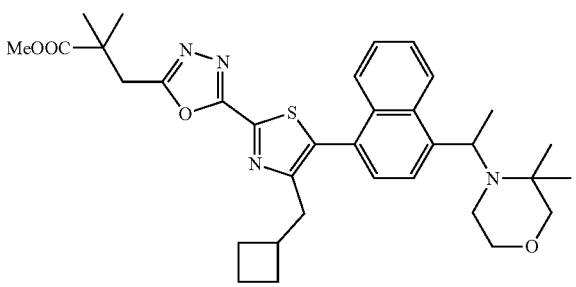 [SMILES: COC(=O)C(C)(C)Cc1nnc(-c2nc(CC3CCC3)c(-c3ccc(C(C)N4CCOCC4(C)C)c4ccccc34)s2)o1]

Chiral HPLC separation (Chiralpak OD-H column, hexane: EtOH=80/20) of methyl 3-(5-(4-(cyclobutylmethyl)-5-(4-(1-(3,3-dimethylmorpholino)ethyl)naphthalen-1-yl)thiazol-2-yl)-1,3,4-oxadiazol-2-yl)-2,2-dimethylpropanoate (Example 3/8, step a) afforded Example 3/8a, step b (faster eluting enantiomer with a retention time of 7.060 min) and Example 3/8b, step b (slower eluting enantiomer with a retention time of 8.037 min).

Example 3/8a and 3/8b: 3-(5-(4-(Cyclobutylmethyl)-5-(4-(1-(3,3-dimethylmorpholino)ethyl)naphthalen-1-yl)thiazol-2-yl)-1,3,4-oxadiazol-2-yl)-2,2-dimethylpropanoic acid

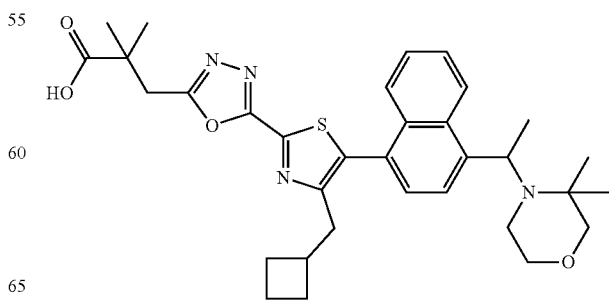

Example 3/8a was prepared as described for the synthesis of Example 3, using in the final step methyl 3-(5-(4-(cyclobutylmethyl)-5-(4-(1-(3,3-dimethylmorpholino)ethyl)naphthalen-1-yl)thiazol-2-yl)-1,3,4-oxadiazol-2-yl)-2,2-dimethylpropanoate (Example 3/8a, step b) instead of methyl 3-(5-(5-(4-(N-(tert-butyl)sulfamoyl)-2,3-dichlorophenyl)-4-(cyclobutylmethyl)thiazol-2-yl)-1,3,4-oxadiazol-2-yl)-2,2-dimethylpropanoate. ¹H NMR (300 MHz, CDCl₃): δ ppm 8.30 (d, J=8.4 Hz, 1H), 7.81 (d, J=7.2 Hz, 1H), 7.69-7.66 (m, 1H), 7.57-7.55 (m, 1H), 7.50-7.44 (m, 2H), 5.02-4.99 (m, 1H), 3.94-3.90 (m, 1H), 3.73-3.68 (m, 1H), 3.39-3.37 (m, 2H), 3.29 (s, 2H), 3.18-3.09 (m, 1H), 2.74-2.67 (m, 4H), 1.90-1.86 (m, 2H), 1.69-1.58 (m, 2H), 1.50 (d, J=6.9 Hz, 3H), 1.46-1.43 (m, 2H), 1.40 (s, 6H), 1.25 (s, 3H), 0.89 (s, 3H). MS (ESI): m/z 589.3 [M+H]⁺.

Example 3/8b was prepared as described for the synthesis of Example 3, using in the final step methyl 3-(5-(4-(cyclobutylmethyl)-5-(4-(1-(3,3-dimethylmorpholino)ethyl)naphthalen-1-yl)thiazol-2-yl)-1,3,4-oxadiazol-2-yl)-2,2-dimethylpropanoate (Example 3/8b, step b) instead of methyl 3-(5-(5-(4-(N-(tert-butyl)sulfamoyl)-2,3-dichlorophenyl)-4-(cyclobutylmethyl)thiazol-2-yl)-1,3,4-oxadiazol-2-yl)-2,2-dimethylpropanoate. ¹H NMR (300 MHz, CDCl₃) δ ppm 8.30 (d, J=8.4 Hz, 1H), 7.81 (d, J=7.2 Hz, 1H), 7.69-7.66 (m, 1H), 7.57-7.55 (m, 1H), 7.50-7.44 (m, 2H), 5.02-4.99 (m, 1H), 3.94-3.90 (m, 1H), 3.73-3.68 (m, 1H), 3.39-3.37 (m, 2H), 3.29 (s, 2H), 3.18-3.09 (m, 1H), 2.74-2.67 (m, 4H), 1.90-1.86 (m, 2H), 1.69-1.58 (m, 2H), 1.50 (d, J=6.9 Hz, 3H), 1.46-1.43 (m, 2H), 1.40 (s, 6H), 1.25 (s, 3H), 0.89 (s, 3H). MS (ESI): m/z 589.3 [M+H]⁺.

Example 3/9: (S)-3-(5-(4-(Cyclobutylmethyl)-5-(2,3-dichloro-4-(N-(1,1,1-trifluoropropan-2-yl)sulfamoyl)phenyl)thiazol-2-yl)-1,3,4-oxadiazol-2-yl)-2,2-dimethylpropanoic acid

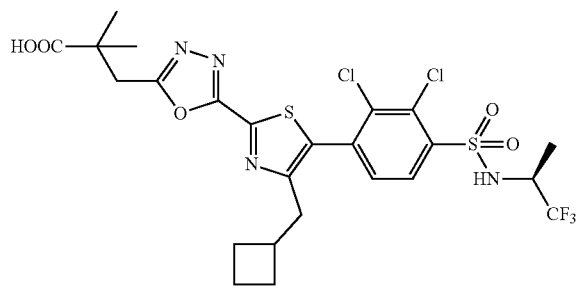 [SMILES: C[C@H](NS(=O)(=O)c1ccc(-c2sc(-c3nnc(CC(C)(C)C(=O)O)o3)nc2CC2CCC2)c(Cl)c1Cl)C(F)(F)F]

The title compound was prepared as described for the synthesis of Example 3, using in step a (5)-4-bromo-2,3-dichloro-N-(1,1,1-trifluoropropan-2-yl)benzenesulfonamide (Intermediate 4/2) in place of 4-bromo-N-(tert-butyl)-2,3-dichlorobenzenesulfonamide. ¹H NMR (400 MHz, CDCl₃): δ ppm 8.11 (d, J=8.2 Hz, 1H), 7.47 (d, J=8.2 Hz, 1H), 5.51 (d, J=10.0 Hz, 1H), 4.13-4.07 (m, 1H), 3.29 (s, 2H), 2.75-2.63 (m, 3H), 1.99-1.93 (m, 2H), 1.79-1.69 (m, 2H), 1.56-1.43 (m, 11H). MS (ESI): m/z 641.0 [M+H]⁺.

Example 3/10: (S)-3-(5-(5-(2-Chloro-4-(N-(1,1,1-trifluoropropan-2-yl)sulfamoyl)phenyl)-4-(cyclobutylmethyl)thiazol-2-yl)-1,3,4-oxadiazol-2-yl)-2,2-dimethylpropanoic acid

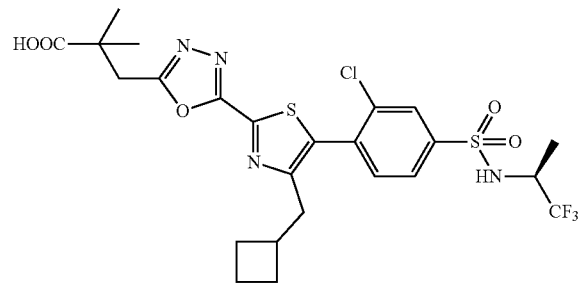 [SMILES: C[C@H](NS(=O)(=O)c1ccc(-c2sc(-c3nnc(CC(C)(C)C(=O)O)o3)nc2CC2CCC2)c(Cl)c1)C(F)(F)F]

The title compound was prepared as described for the synthesis of Example 3, using in step a (S)-4-bromo-3-chloro-N-(1,1,1-trifluoropropan-2-yl)benzenesulfonamide (Intermediate 4/10) in place of 4-bromo-N-(tert-butyl)-2,3-dichlorobenzenesulfonamide. ¹H NMR (400 MHz, CDCl₃): δ ppm 8.03 (s, 1H), 7.86-7.84 (m, 1H), 7.55 (d, J=8.0 Hz, 1H), 4.13-4.06 (m, 1H), 3.27 (s, 2H), 2.76-2.62 (m, 3H), 1.96-1.90 (m, 2H), 1.78-1.64 (m, 2H), 1.51-1.39 (m, 11H). MS (ESI): m/z 607.2 [M+H]⁺.

Example 3/11: (S)-3-(5-(4-(Cyclobutylmethyl)-5-(2-(trifluoromethoxy)-4-(N-(1,1,1-trifluoropropan-2-yl)sulfamoyl)phenyl)thiazol-2-yl)-1,3,4-oxadiazol-2-yl)-2,2-dimethylpropanoic acid

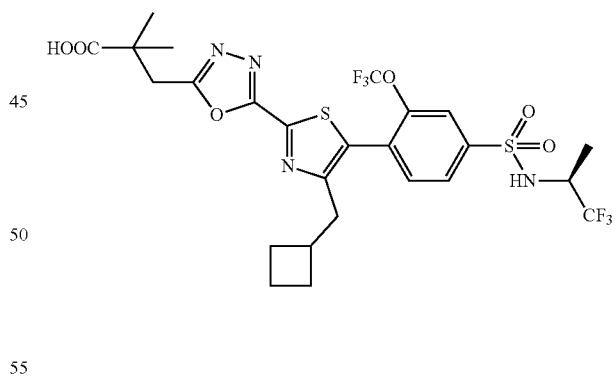

The title compound was prepared as described for the synthesis of Example 3, using in step a (5)-4-bromo-3-(trifluoromethoxy)-N-(1,1,1-trifluoropropan-2-yl)benzenesulfonamide (Intermediate 4/14) in place of 4-bromo-N-(tert-butyl)-2,3-dichlorobenzenesulfonamide. ¹H NMR (400 MHz, CDCl₃): δ ppm 7.94-7.90 (m, 2H), 7.67 (d, J=8.0 Hz, 1H), 5.42 (d, J=9.2 Hz, 1H), 4.13-4.09 (m, 1H), 3.29 (s, 2H), 2.81-2.68 (m, 3H), 1.99-1.93 (m, 2H), 1.81-1.67 (m, 2H), 1.56-1.51 (m, 2H), 1.44-1.42 (m, 9H). MS (ESI): m/z 657.1 [M+H]⁺.

Example 3/12: (S)-3-(5-(4-(Cyclobutylmethyl)-5-(2-(trifluoromethyl)-4-(N-(1,1,1-trifluoropropan-2-yl)sulfamoyl)phenyl)thiazol-2-yl)-1,3,4-oxadiazol-2-yl)-2,2-dimethylpropanoic acid

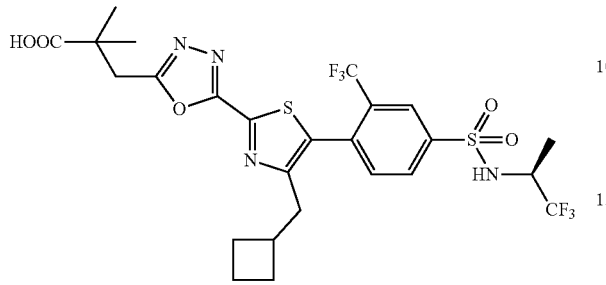

The title compound was prepared as described for the synthesis of Example 3, using in step a (S)-4-bromo-3-(trifluoromethyl)-N-(1,1,1-trifluoropropan-2-yl)benzenesulfonamide (Intermediate 4/12) in place of 4-bromo-N-(tert-butyl)-2,3-dichlorobenzenesulfonamide. $^1$H NMR (400 MHz, CDCl$_3$): δ ppm 8.30 (s, 1H), 8.15-8.12 (m, 1H), 7.60 (d, J=8.4 Hz, 1H), 5.35 (d, J=9.2 Hz, 1H), 4.16-4.10 (m, 1H), 3.28 (s, 2H), 2.72-2.64 (m, 3H), 1.96-1.67 (m, 4H), 1.54-1.52 (m, 2H), 1.46-1.31 (m, 9H). MS (ESI): m/z 641.1 [M+H]$^+$.

Example 3/13: (S)-3-(5-(5-(2,3-Dichloro-4-(N-(1,1,1-trifluoropropan-2-yl)sulfamoyl)phenyl)-4-isobutylthiazole-2-yl)-1,3,4-oxadiazol-2-yl)-2,2-dimethylpropanoic acid

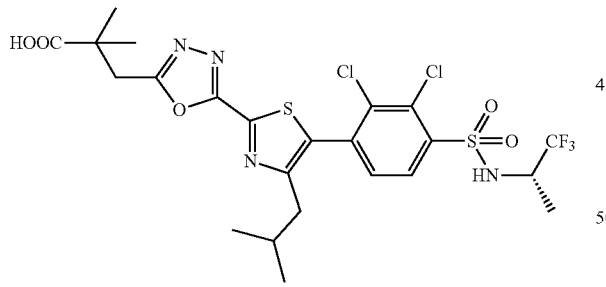

The title compound was prepared as described for the synthesis of Example 3, using in step a methyl 3-(5-(4-isobutylthiazole-2-yl)-1,3,4-oxadiazol-2-yl)-2,2-dimethylpropanoate (Intermediate 2/2) in place of methyl 3-(5-(4-(cyclobutylmethyl)thiazol-2-yl)-1,3,4-oxadiazol-2-yl)-2,2-dimethylpropanoate and (S)-4-bromo-2,3-dichloro-N-(1,1,1-trifluoropropan-2-yl)benzenesulfonamide (Intermediate 4/2) in place of 4-bromo-N-(tert-butyl)-2,3-dichlorobenzenesulfonamide. $^1$H NMR (400 MHz, CDCl$_3$): δ ppm 12.59 (br s, 1H), 9.24 (d, J=8.8 Hz, 1H), 8.11 (d, J=8.2 Hz, 1H), 7.78 (d, J=8.2 Hz, 1H), 4.21-4.15 (m, 1H), 3.22 (s, 2H), 2.49-2.46 (m, 2H), 2.03-1.96 (m, 1H), 1.28-1.27 (m, 9H), 0.77 (d, J=6.4 Hz, 6H). MS (ESI): m/z 629.0 [M+H]$^+$.

Example 3/14: (S)-3-(5-(4-Isobutyl-5-(2-(trifluoromethoxy)-4-(N-(1,1,1-trifluoropropan-2-yl)sulfamoyl)phenyl)thiazol-2-yl)-1,3,4-oxadiazol-2-yl)-2,2-dimethylpropanoic acid

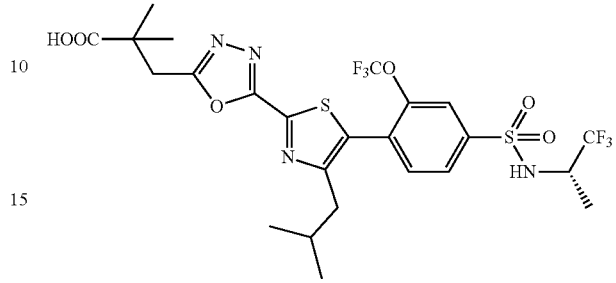

The title compound was prepared as described for the synthesis of Example 3, using in step a methyl 3-(5-(4-isobutylthiazole-2-yl)-1,3,4-oxadiazol-2-yl)-2,2-dimethylpropanoate (Intermediate 2/2) in place of methyl 3-(5-(4-(cyclobutylmethyl)thiazol-2-yl)-1,3,4-oxadiazol-2-yl)-2,2-dimethylpropanoate and (S)-4-bromo-3-(trifluoromethoxy)-N-(1,1,1-trifluoropropan-2-yl)benzenesulfonamide (Intermediate 4/14) in place of 4-bromo-N-(tert-butyl)-2,3-dichlorobenzenesulfonamide. $^1$H NMR (400 MHz, CDCl$_3$): δ ppm 7.93-7.89 (m, 2H), 7.66 (d, J=8.4 Hz, 1H), 5.27 (d, J=9.2 Hz, 1H), 4.15-4.06 (m, 1H), 3.29 (s, 2H), 2.57 (d, J=7.2 Hz, 1H), 2.17-2.11 (m, 1H), 1.44-1.42 (m, 9H), 0.80 (d, J=6.8 Hz, 6H). MS (ESI): m/z 645.2 [M+H]$^+$.

Example 3/15: (S)-3-(5-(4-(Cyclohexylmethyl)-5-(1-(N-(1,1,1-trifluoropropan-2-yl)sulfamoyl)isoquinolin-4-yl)thiazol-2-yl)-1,3,4-oxadiazol-2-yl)-2,2-dimethylpropanoic acid

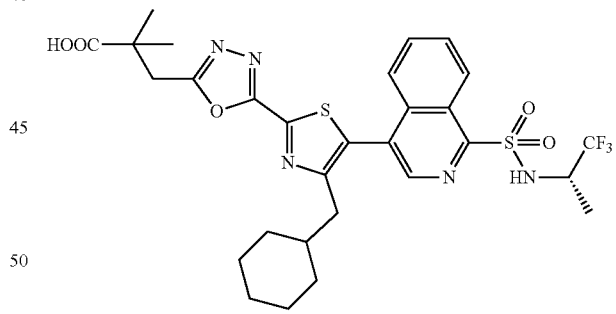

The title compound was prepared as described for the synthesis of Example 3, using in step a methyl 3-(5-(4-(cyclohexylmethyl)thiazol-2-yl)-1,3,4-oxadiazol-2-yl)-2,2-dimethylpropanoate (Intermediate 2/1) in place of methyl 3-(5-(4-(cyclobutylmethyl)thiazol-2-yl)-1,3,4-oxadiazol-2-yl)-2,2-dimethylpropanoate and (S)-4-bromo-N-(1,1,1-trifluoropropan-2-yl)isoquinoline-1-sulfonamide (Intermediate 4/19) in place of 4-bromo-N-(tert-butyl)-2,3-dichlorobenzenesulfonamide. $^1$H NMR (400 MHz, CDCl$_3$): δ ppm 9.02-9.00 (m, 1H), 8.49 (s, 1H), 7.87-7.83 (m, 2H), 7.80-7.77 (m, 1H), 5.58 (d, J=8.8 Hz, 1H), 4.28-4.23 (m, 1H), 3.31 (s, 2H), 2.50-2.48 (m, 2H), 1.84-1.78 (m, 1H), 1.61 (d, J=7.2 Hz, 3H), 1.57-1.54 (m, 5H), 1.48 (s, 6H), 1.18-0.97 (m, 3H), 0.72-0.64 (m, 2H). MS (ESI): m/z 651.9 [M+H]$^+$.

Example 3/16: (S)-3-(5-(4-(Cyclobutylmethyl)-5-(8-(N-(1,1,1-trifluoropropan-2-yl)sulfamoyl)isoquinolin-5-yl)thiazol-2-yl)-1,3,4-oxadiazol-2-yl)-2,2-dimethylpropanoic acid

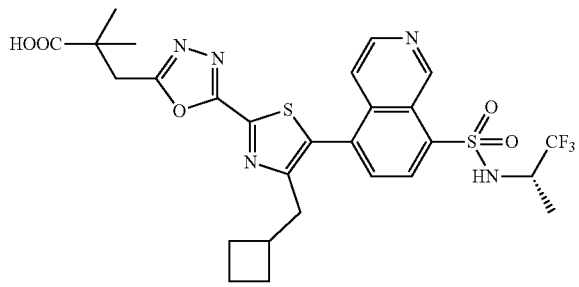 [SMILES: C[C@H](NS(=O)(=O)c1ccc(-c2sc(-c3nnc(CC(C)(C)C(=O)O)o3)nc2CC2CCC2)c2ccncc12)C(F)(F)F]

The title compound was prepared as described for the synthesis of Example 3, using in step a (5)-5-bromo-N-(1,1,1-trifluoropropan-2-yl)isoquinoline-8-sulfonamide (Intermediate 4/16) in place of 4-bromo-N-(tert-butyl)-2,3-dichlorobenzenesulfonamide. $^1$H NMR (400 MHz, DMSO-$d_6$): δ ppm 12.59 (br s, 1H), 10.15 (br s, 1H), 9.33 (d, J=9.2 Hz, 1H), 8.76-8.75 (m, 1H), 8.37 (d, J=7.4 Hz, 1H), 8.08 (d, J=7.4 Hz, 1H), 7.72 (s, 1H), 4.20-4.17 (m, 1H), 3.25 (s, 2H), 2.69-2.58 (m, 3H), 1.84-1.79 (m, 2H), 1.68-1.52 (m, 2H), 1.38-1.34 (m, 8H), 1.10 (d, J=6.8 Hz, 3H). MS (ESI): m/z 624.1 [M+H]$^+$.

Example 3/17: (S)-3-(5-(4-(Cyclobutylmethyl)-5-(5-(N-(1,1,1-trifluoropropan-2-yl)sulfamoyl)isoquinolin-8-yl)thiazol-2-yl)-1,3,4-oxadiazol-2-yl)-2,2-dimethylpropanoic acid

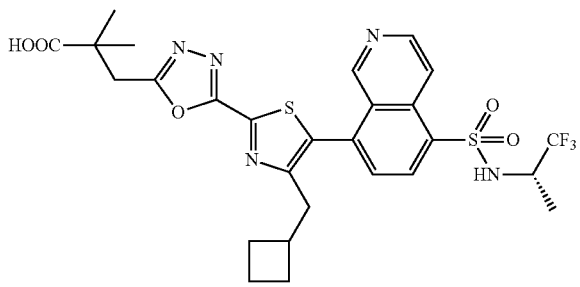 [SMILES: C[C@H](NS(=O)(=O)c1ccc(-c2sc(-c3nnc(CC(C)(C)C(=O)O)o3)nc2CC2CCC2)c2cnccc12)C(F)(F)F]

The title compound was prepared as described for the synthesis of Example 3, using in step a (5)-8-chloro-N-(1,1,1-trifluoropropan-2-yl)isoquinoline-5-sulfonamide (Intermediate 4/17) in place of 4-bromo-N-(tert-butyl)-2,3-dichlorobenzenesulfonamide. $^1$H NMR (400 MHz, DMSO-$d_6$): δ ppm 12.59 (br s, 1H), 9.25-9.20 (m, 2H), 8.83 (d, J=6.0 Hz, 1H), 8.57 (dd, J=0.8, 6.4 Hz, 1H), 8.51-8.49 (m, 1H), 7.95 (d, J=7.6 Hz, 1H), 4.20-4.15 (m, 1H), 3.25 (s, 2H), 2.66-2.56 (m, 3H), 1.86-1.82 (m, 2H), 1.55-1.52 (m, 2H), 1.41-1.30 (m, 8H), 1.07 (d, J=6.8 Hz, 3H). MS (ESI): m/z 624.2 [M+H]$^+$.

Example 3/18: (S)-3-(5-(4-(Cyclobutylmethyl)-5-(4-(N-(1,1,1-trifluorobutan-2-yl)sulfamoyl)-2-(trifluoromethoxy)phenyl)thiazol-2-yl)-1,3,4-oxadiazol-2-yl)-2,2-dimethylpropanoic acid

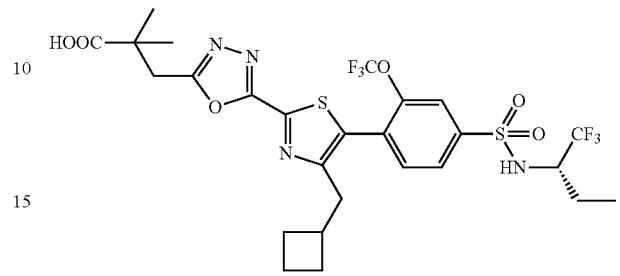

The title compound was prepared as described for the synthesis of Example 3, using in step a (5)-4-bromo-N-(1,1,1-trifluorobutan-2-yl)-3-(trifluoromethoxy)benzenesulfonamide (Intermediate 4/13) in place of 4-bromo-N-(tert-butyl)-2,3-dichlorobenzenesulfonamide. $^1$H NMR (400 MHz, CDCl$_3$): δ ppm 7.94-7.90 (m, 2H), 7.66 (d, J=6.8 Hz, 1H), 5.37 (br s, 1H), 3.93-3.90 (m, 1H), 3.28 (s, 2H), 2.80 (d, J=5.6 Hz, 2H), 2.71-2.68 (m, 1H), 1.96-1.92 (m, 3H), 1.78-1.71 (m, 2H), 1.56-1.50 (m, 3H), 1.43 (s, 6H), 1.07 (t, J=6.0 Hz, 3H). MS (ESI): m/z 671.2 [M+H]$^+$.

Example 3/19: (S)-3-(5-(5-(2-Chloro-4-(N-(1,1,1-trifluorobutan-2-yl)sulfamoyl)phenyl)-4-(cyclobutylmethyl)thiazol-2-yl)-1,3,4-oxadiazol-2-yl)-2,2-dimethylpropanoic acid

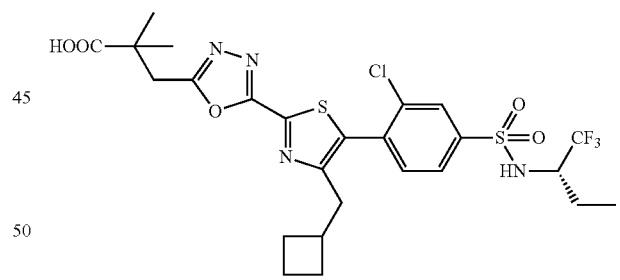

The title compound was prepared as described for the synthesis of Example 3, using in step a (S)-4-bromo-3-chloro-N-(1,1,1-trifluorobutan-2-yl)benzenesulfonamide (Intermediate 4/11) in place of 4-bromo-N-(tert-butyl)-2,3-dichlorobenzenesulfonamide. $^1$H NMR (400 MHz, DMSO-$d_6$): δ ppm 8.80 (br s, 1H), 8.09 (d, J=1.2 Hz, 1H), 7.93 (dd, J=1.2, 6.4 Hz, 1H), 7.84 (d, J=6.4 Hz, 1H), 4.08-4.05 (m, 1H), 3.21 (s, 2H), 2.69 (d, J=5.6 Hz, 2H), 2.58-2.55 (m, 1H), 1.93-1.87 (m, 2H), 1.75-1.61 (m, 3H), 1.49-1.40 (m, 3H), 1.27 (s, 6H), 0.63 (t, J=6.0 Hz, 3H). MS (ESI): m/z 621.1 [M+H]$^+$.

Example 3/20: (S)-3-(5-(4-(Cyclohexylmethyl)-5-(4-(N-(1,1,1-trifluoropropan-2-yl)sulfamoyl)naphthalen-1-yl)thiazol-2-yl)-1,3,4-oxadiazol-2-yl)-2,2-dimethylpropanoic acid

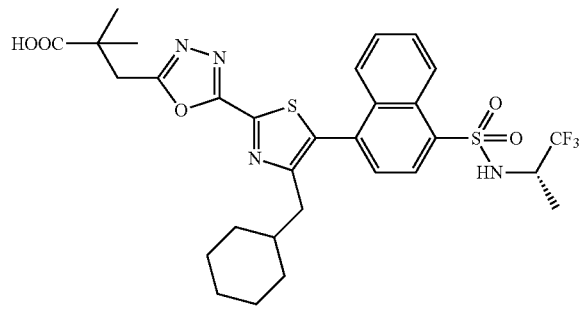 [SMILES: C[C@H](NS(=O)(=O)c1ccc(-c2sc(-c3nnc(CC(C)(C)C(=O)O)o3)nc2CC2CCCCC2)c2ccccc12)C(F)(F)F]

The title compound was prepared as described for the synthesis of Example 3, using in step a methyl 3-(5-(4-(cyclohexylmethyl)thiazol-2-yl)-1,3,4-oxadiazol-2-yl)-2,2-dimethylpropanoate (Intermediate 2/1) in place of methyl 3-(5-(4-(cyclobutylmethyl)thiazol-2-yl)-1,3,4-oxadiazol-2-yl)-2,2-dimethylpropanoate and (S)-4-bromo-N-(1,1,1-trifluoropropan-2-yl)naphthalene-1-sulfonamide (Intermediate 4/7) in place of 4-bromo-N-(tert-butyl)-2,3-dichlorobenzenesulfonamide. $^1$H NMR (400 MHz, CDCl$_3$): δ ppm 8.67 (d, J=6.8 Hz, 1H), 8.34 (d, J=6.0 Hz, 1H), 7.79-7.73 (m, 2H), 7.64-7.57 (m, 2H), 5.11 (d, J=7.6 Hz, 1H), 4.06-4.01 (m, 1H), 3.30 (s, 2H), 2.44 (m, 2H), 1.74-1.73 (m, 1H), 1.52-1.48 (m, 5H), 1.43 (s, 6H), 1.39-1.30 (m, 3H), 1.12-0.93 (m, 3H), 0.65-0.58 (m, 2H). MS (ESI): m/z 650.9 [M+H]$^+$.

Example 3/21: (S)-3-(5-(4-(Cyclohexylmethyl)-5-(2-(trifluoromethoxy)-4-(N-(1,1,1-trifluoropropan-2-yl)sulfamoyl)phenyl)thiazol-2-yl)-1,3,4-oxadiazol-2-yl)-2,2-dimethylpropanoic acid

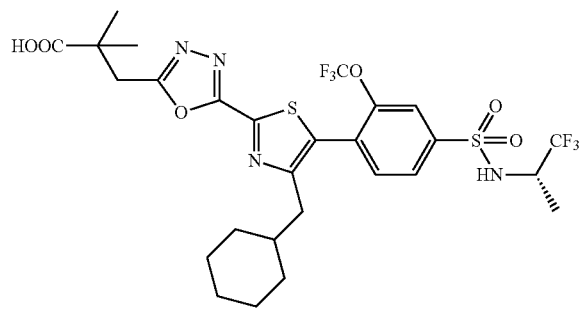 [SMILES: C[C@H](NS(=O)(=O)c1ccc(-c2sc(-c3nnc(CC(C)(C)C(=O)O)o3)nc2CC2CCCCC2)c(OC(F)(F)F)c1)C(F)(F)F]

The title compound was prepared as described for the synthesis of Example 3, using in step a methyl 3-(5-(4-(cyclohexylmethyl)thiazol-2-yl)-1,3,4-oxadiazol-2-yl)-2,2-dimethylpropanoate (Intermediate 2/1) in place of methyl 3-(5-(4-(cyclobutylmethyl)thiazol-2-yl)-1,3,4-oxadiazol-2-yl)-2,2-dimethylpropanoate and (S)-4-bromo-3-(trifluoromethoxy)-N-(1,1,1-trifluoropropan-2-yl)benzenesulfonamide (Intermediate 4/14) in place of 4-bromo-N-(tert-butyl)-2,3-dichlorobenzenesulfonamide. $^1$H NMR (400 MHz, CDCl$_3$): δ ppm 7.93-7.88 (m, 2H), 7.65 (d, J=6.8 Hz, 1H), 5.19-5.16 (m, 1H), 4.12-4.08 (m, 1H), 3.29 (s, 2H), 2.57 (d, J=6.8 Hz, 2H), 1.81-1.78 (m, 1H), 1.60-1.54 (m, 5H), 1.44-1.42 (m, 9H), 1.17-1.03 (m, 3H), 0.78-0.72 (m, 2H). MS (ESI): m/z 684.8 [M+H]$^+$.

Example 3/22: (S)-3-(5-(4-(Cyclohexylmethyl)-5-(8-(N-(1,1,1-trifluoropropan-2-yl)sulfamoyl)isoquinolin-5-yl)thiazol-2-yl)-1,3,4-oxadiazol-2-yl)-2,2-dimethylpropanoic acid

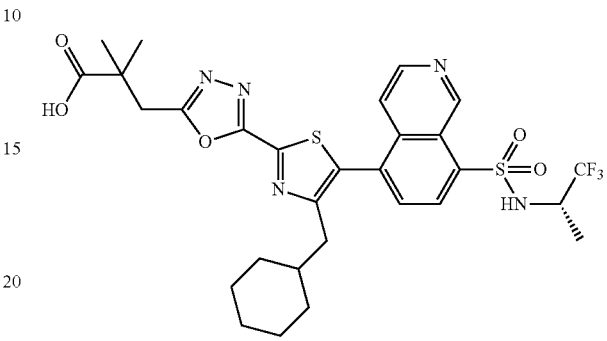

The title compound was prepared as described for the synthesis of Example 3, using in step a methyl 3-(5-(4-(cyclohexylmethyl)thiazol-2-yl)-1,3,4-oxadiazol-2-yl)-2,2-dimethylpropanoate (Intermediate 2/1) in place of methyl 3-(5-(4-(cyclobutylmethyl)thiazol-2-yl)-1,3,4-oxadiazol-2-yl)-2,2-dimethylpropanoate and (S)-5-bromo-N-(1,1,1-trifluoropropan-2-yl)isoquinoline-8-sulfonamide (Intermediate 4/16) in place of 4-bromo-N-(tert-butyl)-2,3-dichlorobenzenesulfonamide. $^1$H NMR (400 MHz, CDCl$_3$): δ ppm 10.12 (s, 1H), 9.34 (d, J=8.8 Hz, 1H), 8.73 (d, J=6.0 Hz, 1H), 8.37 (d, J=7.6 Hz, 1H), 8.07 (d, J=7.6 Hz, 1H), 7.73 (d, J=6.0 Hz, 1H), 4.22-4.16 (m, 1H), 3.25 (s, 2H), 2.44-2.38 (m, 2H), 1.65-1.61 (m, 1H), 1.48-1.43 (m, 5H), 1.31 (s, 6H), 1.11-0.93 (m, 6H), 0.64-0.57 (m, 2H). MS (ESI): m/z 652.2 [M+H]$^+$.

Example 3/23: (S)-3-(5-(4-(Cyclohexylmethyl)-5-(8-(N-(1,1,1-trifluorobutan-2-yl)sulfamoyl)isoquinolin-5-yl)thiazol-2-yl)-1,3,4-oxadiazol-2-yl)-2,2-dimethylpropanoic acid

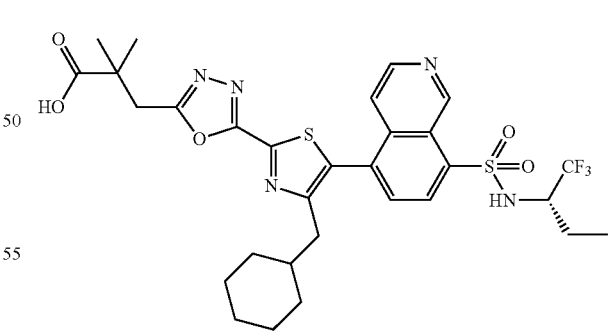

The title compound was prepared as described for the synthesis of Example 3, using in step a methyl 3-(5-(4-(cyclohexylmethyl)thiazol-2-yl)-1,3,4-oxadiazol-2-yl)-2,2-dimethylpropanoate (Intermediate 2/1) in place of methyl 3-(5-(4-(cyclobutylmethyl)thiazol-2-yl)-1,3,4-oxadiazol-2-yl)-2,2-dimethylpropanoate and (S)-5-bromo-N-(1,1,1-trifluorobutan-2-yl)isoquinoline-8-sulfonamide (Intermediate 4/18) in place of 4-bromo-N-(tert-butyl)-2,3-dichlorobenzenesulfonamide. $^1$H NMR (400 MHz, CDCl$_3$): δ ppm 10.38 (s, 1H), 8.70 (d, J=6.0 Hz, 1H), 8.43 (d, J=7.6 Hz, 1H), 7.90-7.86 (m, 2H), 7.72 (d, J=6.0 Hz, 1H), 3.84-3.82 (m, 1H), 3.32 (s, 2H), 2.43-2.42 (m, 2H), 1.87-1.46 (m, 14H), 1.14-0.94 (m, 6H), 0.55-0.65 (m, 2H). MS (ESI): m/z 666.3 [M+H]$^+$.

Example 3/24: (S)-3-(5-(4-(Cyclohexylmethyl)-5-(2-(difluoromethyl)-3-fluoro-4-(N-(1,1,1-trifluoropropan-2-yl)sulfamoyl)phenyl)thiazol-2-yl)-1,3,4-oxadiazol-2-yl)-2,2-dimethylpropanoic acid

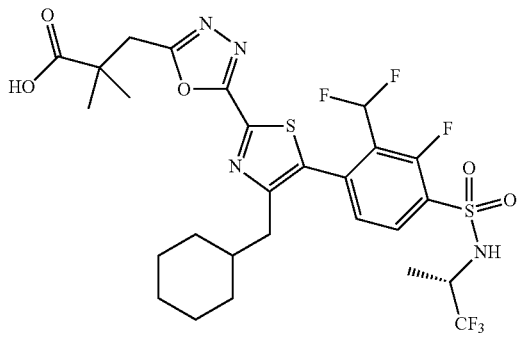 [SMILES: C[C@H](NS(=O)(=O)c1ccc(-c2sc(-c3nnc(CC(C)(C)C(=O)O)o3)nc2CC2CCCCC2)c(C(F)F)c1F)C(F)(F)F]

The title compound was prepared as described for the synthesis of Example 3, using in step a methyl 3-(5-(4-(cyclohexylmethyl)thiazol-2-yl)-1,3,4-oxadiazol-2-yl)-2,2-dimethylpropanoate (Intermediate 2/1) in place of methyl 3-(5-(4-(cyclobutylmethyl)thiazol-2-yl)-1,3,4-oxadiazol-2-yl)-2,2-dimethylpropanoate and (S)-4-bromo-3-(difluoromethyl)-2-fluoro-N-(1,1,1-trifluoropropan-2-yl)benzenesulfonamide (Intermediate 4/1) in place of 4-bromo-N-(tert-butyl)-2,3-dichlorobenzenesulfonamide. $^1$H NMR (400 MHz, DMSO-d$_6$): δ ppm 12.57 (br s, 1H), 9.34 (d, J=8.8 Hz, 1H), 8.10 (t, J=7.6 Hz, 1H), 7.57 (d, J=8.0 Hz, 1H), 7.04 (t, J=51.6 Hz, 1H), 4.22-4.17 (m, 1H), 3.23 (s, 2H), 2.46-2.42 (m, 2H), 1.67-1.52 (m, 6H), 1.28 (s, 6H), 1.24-1.00 (m, 6H), 0.76-0.71 (m, 2H). MS (ESI): m/z 668.8 [M+H]$^+$.

Example 3/25: (S)-3-(5-(5-(3-Chloro-2-(difluoromethyl)-4-(N-(1,1,1-trifluorobutan-2-yl)sulfamoyl)phenyl)-4-(cyclobutylmethyl)thiazol-2-yl)-1,3,4-oxadiazol-2-yl)-2,2-dimethylpropanoic acid

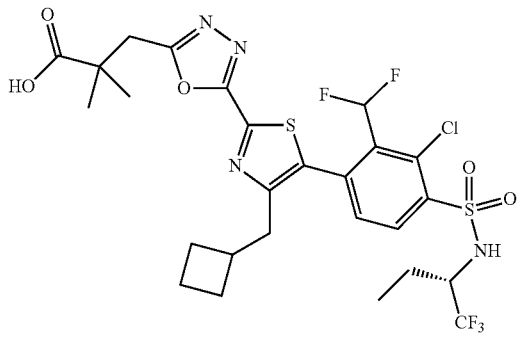 [SMILES: CC[C@H](NS(=O)(=O)c1ccc(-c2sc(-c3nnc(CC(C)(C)C(=O)O)o3)nc2CC2CCC2)c(C(F)F)c1Cl)C(F)(F)F]

The title compound was prepared as described for the synthesis of Example 3, using in step a (5)-4-bromo-2-chloro-3-(difluoromethyl)-N-(1,1,1-trifluorobutan-2-yl)benzenesulfonamide (Intermediate 4/15) in place of 4-bromo-N-(tert-butyl)-2,3-dichlorobenzenesulfonamide.
$^1$H NMR (400 MHz, CDCl$_3$): δ ppm 8.27 (d, J=6.4 Hz, 1H), 7.43 (d, J=6.8 Hz, 1H), 6.97 (t, J=42.2 Hz, 1H), 5.38 (d, J=8.0 Hz, 1H), 3.91-3.86 (m, 1H), 3.29 (s, 2H), 2.80-2.65 (m, 3H), 1.95-1.91 (m, 3H), 1.81-1.43 (m, 11H), 1.12 (t, J=6.0 Hz, 3H). MS (ESI): m/z 670.8 [M+H]$^+$.

Example 3/26: (S)-3-(5-(4-(Cyclohexylmethyl)-5-(2-(difluoromethyl)-3-fluoro-4-(N-(1,1,1-trifluorobutan-2-yl)sulfamoyl)phenyl)thiazol-2-yl)-1,3,4-oxadiazol-2-yl)-2,2-dimethylpropanoic acid

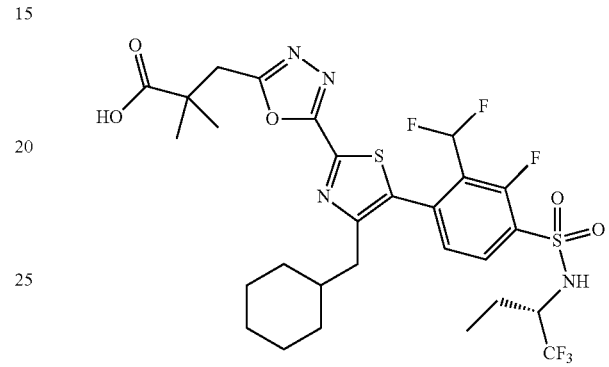

The title compound was prepared as described for the synthesis of Example 3, using in step a methyl 3-(5-(4-(cyclohexylmethyl)thiazol-2-yl)-1,3,4-oxadiazol-2-yl)-2,2-dimethylpropanoate (Intermediate 2/1) in place of methyl 3-(5-(4-(cyclobutylmethyl)thiazol-2-yl)-1,3,4-oxadiazol-2-yl)-2,2-dimethylpropanoate and (S)-4-bromo-3-(difluoromethyl)-2-fluoro-N-(1,1,1-trifluorobutan-2-yl)benzenesulfonamide (Intermediate 4) in place of 4-bromo-N-(tert-butyl)-2,3-dichlorobenzenesulfonamide. $^1$H NMR (400 MHz, CDCl$_3$): δ ppm 8.06 (t, J=7.6 Hz, 1H), 7.30 (d, J=8.0 Hz, 1H), 6.67 (t, J=52.4 Hz, 1H), 5.29 (d, J=9.6 Hz, 1H), 4.01-3.88 (m, 1H), 3.29 (s, 2H), 2.47 (br s, 2H), 1.97-1.90 (m, 1H), 1.81-1.76 (m, 1H), 1.66-1.52 (m, 6H), 1.44 (s, 6H), 1.21-1.04 (m, 6H), 0.78-0.71 (m, 2H). MS (ESI): m/z 683.3 [M+H]$^+$.

Example 3/27: (S)-3-(5-(4-(2-Methoxy-2-methylpropyl)-5-(4-(N-(1,1,1-trifluorobutan-2-yl)sulfamoyl)naphthalen-1-yl)thiazol-2-yl)-1,3,4-oxadiazol-2-yl)-2,2-dimethylpropanoic acid

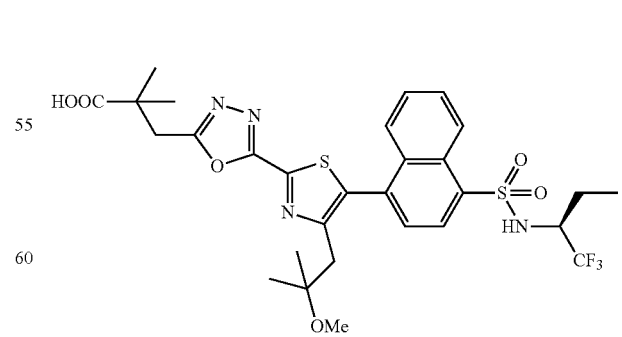

The title compound was prepared as described for the synthesis of Example 3, using in step a methyl 3-(5-(4-(2-methoxy-2-methylpropyl)thiazol-2-yl)-1,3,4-oxadiazol-2- yl)-2,2-dimethylpropanoate (Intermediate 2/3) in place of methyl 3-(5-(4-(cyclobutylmethyl)thiazol-2-yl)-1,3,4-oxadiazol-2-yl)-2,2-dimethylpropanoate and (S)-4-bromo-N-(1,1,1-trifluorobutan-2-yl)naphthalene-1-sulfonamide (Intermediate 4/8) in place of 4-bromo-N-(tert-butyl)-2,3-dichlorobenzenesulfonamide. ¹H NMR (400 MHz, CDCl₃): δ ppm 8.68 (d, J=6.4 Hz, 1H), 8.33 (d, J=6.0 Hz, 1H), 7.72-7.81 (m, 2H), 7.61-7.64 (m, 2H), 5.13 (d, J=8.0 Hz, 1H), 3.85-3.87 (m, 1H), 3.30 (s, 2H), 2.67-3.01 (m, 5H), 1.81-1.87 (m, 1H), 1.47-1.57 (m, 1H), 1.43 (s, 6H), 0.96-1.04 (m, 9H). MS (ESI): m/z 655.2 [M+H]⁺.

Example 3/28: (S)-3-(5-(4-(2-Methoxy-2-methylpropyl)-5-(4-(N-(1,1,1-trifluoropropan-2-yl)sulfamoyl)naphthalen-1-yl)thiazol-2-yl)-1,3,4-oxadiazol-2-yl)-2,2-dimethylpropanoic acid

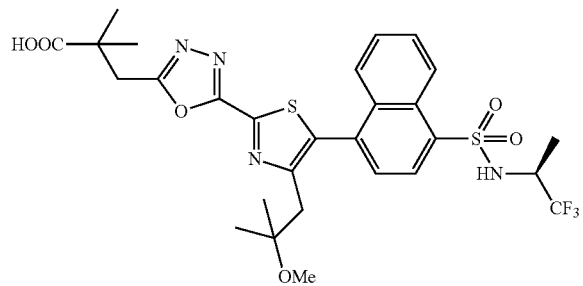 [SMILES: COC(C)(C)Cc1nc(-c2nnc(CC(C)(C)C(=O)O)o2)sc1-c1ccc(S(=O)(=O)N[C@@H](C)C(F)(F)F)c2ccccc12]

The title compound was prepared as described for the synthesis of Example 3, using in step a methyl 3-(5-(4-(2-methoxy-2-methylpropyl)thiazol-2-yl)-1,3,4-oxadiazol-2-yl)-2,2-dimethylpropanoate (Intermediate 2/3) in place of methyl 3-(5-(4-(cyclobutylmethyl)thiazol-2-yl)-1,3,4-oxadiazol-2-yl)-2,2-dimethylpropanoate and (S)-4-bromo-N-(1,1,1-trifluoropropan-2-yl)naphthalene-1-sulfonamide (Intermediate 4/7) in place of 4-bromo-N-(tert-butyl)-2,3-dichlorobenzenesulfonamide. ¹H NMR (400 MHz, CDCl₃): δ ppm 8.66 (d, J=8.8 Hz, 1H), 8.34 (d, J=7.6 Hz, 1H), 7.82-7.73 (m, 2H), 7.64-7.61 (m, 2H), 5.03 (d, J=9.6 Hz, 1H), 4.05-4.00 (m, 1H), 3.30 (s, 2H), 2.87-2.81 (m, 5H), 1.44 (s, 6H), 1.32 (d, J=7.2 Hz, 3H), 1.05 (s, 6H). MS (ESI): 641.3 [M+H]⁺.

Example 3/29: (S)-3-(5-(5-(2,3-Dichloro-4-(N-(1,1,1-trifluoropropan-2-yl)sulfamoyl)phenyl)-4-((3,3-dimethylcyclobutyl)methyl)thiazol-2-yl)-1,3,4-oxadiazol-2-yl)-2,2-dimethylpropanoic acid

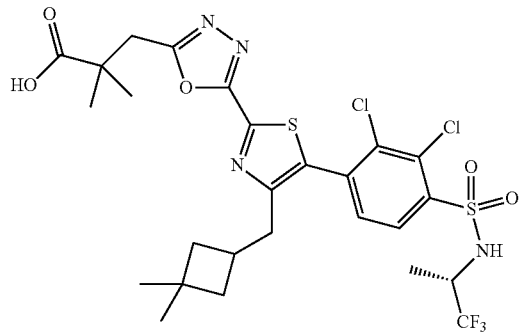 [SMILES: C[C@H](NS(=O)(=O)c1ccc(-c2sc(-c3nnc(CC(C)(C)C(=O)O)o3)nc2CC2CC(C)(C)C2)c(Cl)c1Cl)C(F)(F)F]

The title compound was prepared as described for the synthesis of Example 3, using in step a methyl 3-(5-(4-((3,3-dimethylcyclobutyl)methyl)thiazol-2-yl)-1,3,4-oxadiazol-2-yl)-2,2-dimethylpropanoate (Intermediate 2/6) in place of methyl 3-(5-(4-(cyclobutylmethyl)thiazol-2-yl)-1,3,4-oxadiazol-2-yl)-2,2-dimethylpropanoate and (S)-4-bromo-2,3-dichloro-N-(1,1,1-trifluoropropan-2-yl)benzenesulfonamide (Intermediate 4/2) in place of 4-bromo-N-(tert-butyl)-2,3-dichlorobenzenesulfonamide. ¹H NMR (400 MHz, CDCl₃): δ ppm 8.11 (d, J=8.0 Hz, 1H), 7.47 (d, J=8.0 Hz, 1H), 4.11-4.06 (m, 1H), 3.26 (s, 2H), 2.72 (d, J=7.2 Hz, 2H), 2.58-2.52 (m, 1H), 1.78-1.73 (m, 2H), 1.45 (d, J=7.2 Hz, 3H), 1.35-1.25 (m, 8H), 1.03 (s, 3H), 0.91 (s, 3H). MS (ESI): m/z 669.1 [M+H]⁺.

Example 3/30: (S)-3-(5-(5-(2,3-Dichloro-4-(N-(1,1,1-trifluorobutan-2-yl)sulfamoyl)phenyl)-4-((3,3-difluorocyclobutyl)methyl)thiazol-2-yl)-1,3,4-oxadiazol-2-yl)-2,2-dimethylpropanoic acid

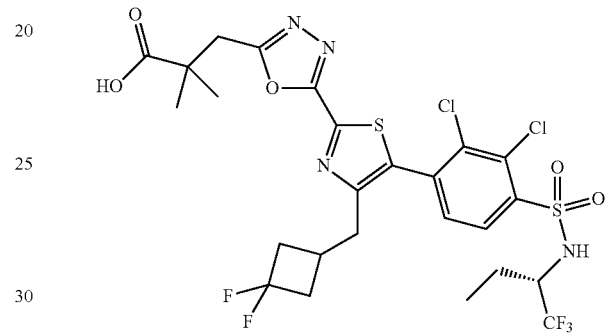

The title compound was prepared as described for the synthesis of Example 3, using in step a methyl 3-(5-(4-((3,3-difluorocyclobutyl)methyl)thiazol-2-yl)-1,3,4-oxadiazol-2-yl)-2,2-dimethylpropanoate (Intermediate 2/7) in place of methyl 3-(5-(4-(cyclobutylmethyl)thiazol-2-yl)-1,3,4-oxadiazol-2-yl)-2,2-dimethylpropanoate and (S)-4-bromo-2,3-dichloro-N-(1,1,1-trifluorobutan-2-yl)benzenesulfonamide (Intermediate 4/3) in place of 4-bromo-N-(tert-butyl)-2,3-dichlorobenzenesulfonamide. ¹H NMR (400 MHz, CDCl₃): δ ppm 8.10 (d, J=8.0 Hz, 1H), 7.45 (d, J=8.0 Hz, 1H), 5.41 (d, J=10.0 Hz, 1H), 3.89-3.85 (m, 1H), 3.29 (s, 2H), 2.81 (d, J=7.2 Hz, 2H), 2.67-2.56 (m, 3H), 2.22-2.12 (m, 2H), 1.94-1.89 (m, 1H), 1.66-1.58 (m, 1H), 1.44 (s, 6H), 1.11 (t, J=7.2 Hz, 3H). MS (ESI): m/z 691.0 [M+H]⁺.

Example 3/31: (S)-3-(5-(4-((3,3-Difluorocyclobutyl)methyl)-5-(4-(N-(1,1,1-trifluoropropan-2-yl)sulfamoyl)naphthalen-1-yl)thiazol-2-yl)-1,3,4-oxadiazol-2-yl)-2,2-dimethylpropanoic acid

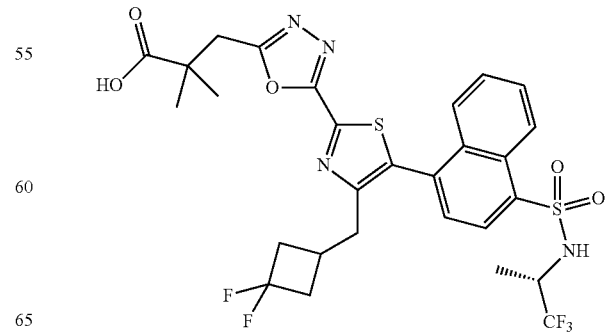

The title compound was prepared as described for the synthesis of Example 3, using in step a methyl 3-(5-(4-((3,3-difluorocyclobutyl)methyl)thiazol-2-yl)-1,3,4-oxadiazol-2-yl)-2,2-dimethylpropanoate (Intermediate 2/7) in place of methyl 3-(5-(4-(cyclobutylmethyl)thiazol-2-yl)-1,3,4-oxadiazol-2-yl)-2,2-dimethylpropanoate and (S)-4-bromo-N-(1,1,1-trifluoropropan-2-yl)naphthalene-1-sulfonamide (Intermediate 4/7) in place of 4-bromo-N-(tert-butyl)-2,3-dichlorobenzenesulfonamide. ¹H NMR (400 MHz, CDCl₃): δ ppm 8.69 (d, J=8.4 Hz, 1H), 8.36 (d, J=8.0 Hz, 1H), 7.79-7.58 (m, 4H), 5.14 (d, J=9.6 Hz, 1H), 4.06-4.00 (m, 1H), 3.31 (s, 2H), 2.74-2.50 (m, 5H), 2.07-2.00 (m, 2H), 1.45 (s, 6H), 1.33 (d, J=7.2 Hz, 3H). MS (ESI): m/z 659.1 [M+H]⁺.

Example 3/32: (S)-3-(5-(5-(2-(Difluoromethyl)-3-fluoro-4-(N-(1,1,1-trifluorobutan-2-yl)sulfamoyl)phenyl)-4-(4-fluorobenzyl)thiazol-2-yl)-1,3,4-oxadiazol-2-yl)-2,2-dimethylpropanoic acid

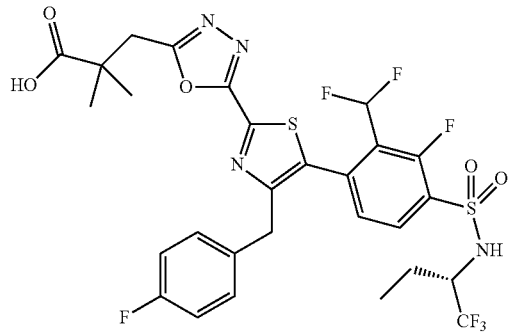 [SMILES: CC[C@H](NS(=O)(=O)c1ccc(-c2sc(-c3nnc(CC(C)(C)C(=O)O)o3)nc2Cc2ccc(F)cc2)c(C(F)F)c1F)C(F)(F)F]

The title compound was prepared as described for the synthesis of Example 3, using in step a methyl 3-(5-(4-(4-fluorobenzyl)thiazol-2-yl)-1,3,4-oxadiazol-2-yl)-2,2-dimethylpropanoate (Intermediate 2/4) in place of methyl 3-(5-(4-(cyclobutylmethyl)thiazol-2-yl)-1,3,4-oxadiazol-2-yl)-2,2-dimethylpropanoate and (S)-4-bromo-3-(difluoromethyl)-2-fluoro-N-(1,1,1-trifluorobutan-2-yl)benzenesulfonamide (Intermediate 4) in place of 4-bromo-N-(tert-butyl)-2,3-dichlorobenzenesulfonamide. ¹H NMR (400 MHz, CDCl₃): δ ppm 7.99 (t, J=7.8 Hz, 1H), 7.15 (d, J=8.0 Hz, 1H), 7.00-6.86 (m, 4H), 6.66 (t, J=52.8 Hz, 1H), 5.37 (d, J=10.4 Hz, 1H), 3.99-3.90 (m, 3H), 3.28 (s, 2H), 1.97-1.91 (m, 1H), 1.67-1.52 (m, 1H), 1.43 (s, 6H), 1.13 (t, J=7.2 Hz, 3H). MS (ESI): m/z 695.2 [M+H]⁺.

Example 3/33: (S)-3-(5-(5-(2,3-Dichloro-4-(N-(1,1,1-trifluoropropan-2-yl)sulfamoyl)phenyl)-4-(4-fluorobenzyl)thiazol-2-yl)-1,3,4-oxadiazol-2-yl)-2,2-dimethylpropanoic acid

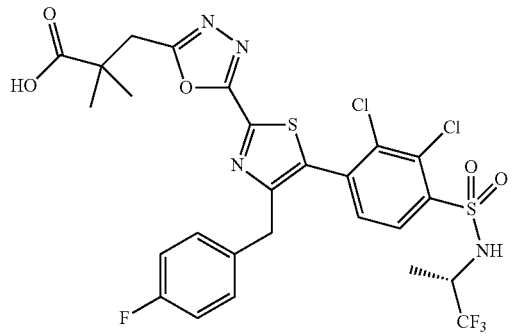 [SMILES: C[C@H](NS(=O)(=O)c1ccc(-c2sc(-c3nnc(CC(C)(C)C(=O)O)o3)nc2Cc2ccc(F)cc2)c(Cl)c1Cl)C(F)(F)F]

The title compound was prepared as described for the synthesis of Example 3, using in step a methyl 3-(5-(4-(4-fluorobenzyl)thiazol-2-yl)-1,3,4-oxadiazol-2-yl)-2,2-dimethylpropanoate (Intermediate 2/4) in place of methyl 3-(5-(4-(cyclobutylmethyl)thiazol-2-yl)-1,3,4-oxadiazol-2-yl)-2,2-dimethylpropanoate and (S)-4-bromo-2,3-dichloro-N-(1,1,1-trifluoropropan-2-yl)benzenesulfonamide (Intermediate 4/2) in place of 4-bromo-N-(tert-butyl)-2,3-dichlorobenzenesulfonamide. ¹H NMR (400 MHz, DMSO-d₆): δ ppm 12.57 (br s, 1H), 9.22 (d, J=9.2 Hz, 1H), 8.08 (d, J=8.4 Hz, 1H), 7.77 (d, J=8.4 Hz, 1H), 7.10-7.01 (m, 4H), 4.19-4.15 (m, 1H), 4.02 (s, 2H), 3.21 (s, 2H), 1.27-1.25 (m, 9H). MS (ESI): m/z 681.0 [M+H]⁺.

Example 3/34: 3-(5-(4-(Cyclobutylmethyl)-5-(2,3-dichloro-4-(1,1,1,3,3,3-hexafluoro-2-hydroxypropan-2-yl)phenyl)thiazol-2-yl)-1,3,4-oxadiazol-2-yl)-2,2-dimethylpropanoic acid

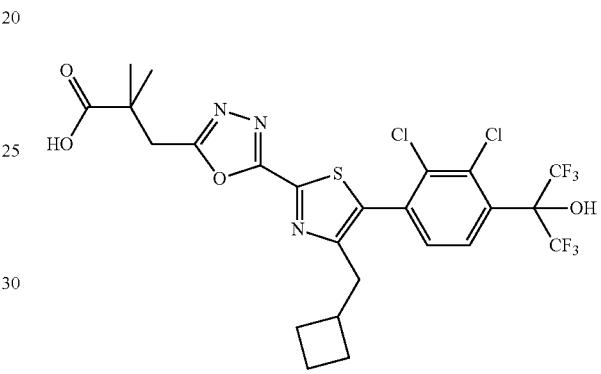

The title compound was prepared as described for the synthesis of Example 3, using in step a 2-(4-bromo-2,3-dichlorophenyl)-1,1,1,3,3,3-hexafluoropropan-2-ol (Intermediate 6) in place of 4-bromo-N-(tert-butyl)-2,3-dichlorobenzenesulfonamide. ¹H NMR (300 MHz, CD₃OD): δ ppm 8.04-7.91 (m, 1H), 7.60-7.56 (m, 1H), 3.27-3.25 (m, 2H), 2.87-2.68 (m, 3H), 2.01-1.95 (m, 2H), 1.84-1.57 (m, 4H), 1.37 (s, 6H). MS (ESI): m/z 632.0 [M+H]⁺.

Example 3/35: (S)-3-(5-(4-(Cyclobutylmethyl)-5-(3-(1-methylcyclopropyl)-5-((1,1,1-trifluoropropan-2-yl)carbamoyl)phenyl)thiazol-2-yl)-1,3,4-oxadiazol-2-yl)-2,2-dimethylpropanoic acid

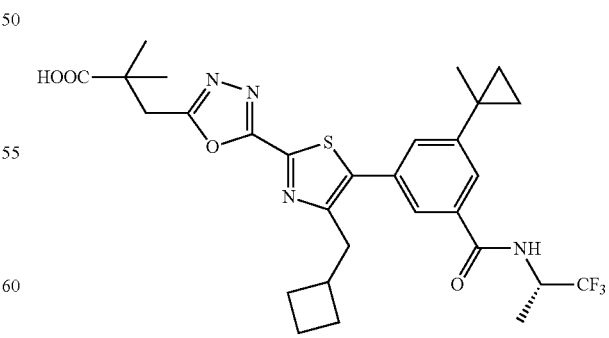

The title compound was prepared as described for the synthesis of Example 3, using in step a (5)-3-bromo-5-(1-methylcyclopropyl)-N-(1,1,1-trifluoropropan-2-yl)benzamide (Intermediate 10) in place of 4-bromo-N-(tert-butyl)-

2,3-dichlorobenzenesulfonamide. ¹H NMR (300 MHz, CDCl₃): δ ppm 7.78 (s, 1H), 7.67 (s, 1H), 7.39 (s, 1H), 7.03 (d, J=7.2 Hz, 1H), 5.01-4.95 (m, 1H), 3.22 (s, 2H), 2.81-2.79 (m, 2H), 2.73-2.64 (m, 1H), 1.98-1.95 (m, 2H), 1.77-1.57 (m, 4H), 1.49-1.45 (m, 6H), 1.34-1.33 (m, 6H), 0.93-0.90 (m, 2H), 0.86-0.83 (m, 2H). MS (ESI): m/z 591.1 [M+H]⁺.

Example 3/36: 3-(5-(5-(3-(tert-Butyl)-5-(1,1,1,3,3,3-hexafluoro-2-hydroxypropan-2-yl)phenyl)-4-(cyclobutylmethyl)thiazol-2-yl)-1,3,4-oxadiazol-2-yl)-2,2-dimethylpropanoic acid

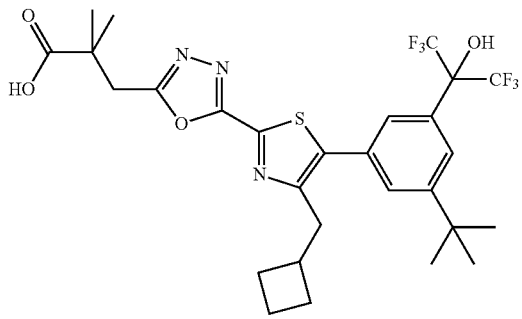 [SMILES: CC(C)(Cc1nnc(-c2nc(CC3CCC3)c(-c3cc(C(C)(C)C)cc(C(O)(C(F)(F)F)C(F)(F)F)c3)s2)o1)C(=O)O]

The title compound was prepared as described for the synthesis of Example 3, using in step a 2-(3-bromo-5-(tert-butyl)phenyl)-1,1,1,3,3,3-hexafluoropropan-2-ol (Intermediate 8) in place of 4-bromo-N-(tert-butyl)-2,3-dichlorobenzenesulfonamide. ¹H NMR (CDCl₃, 300 MHz): δ ppm 7.80 (m, 1H), 7.66-7.65 (m, 1H), 7.55 (s, 1H), 3.27-3.25 (d, J=4.8 Hz, 2H), 2.95-2.75 (m, 3H), 2.03-1.98 (m, 2H), 1.77-1.65 (m, 5H), 1.41 (s, 6H), 1.38 (s, 9H). MS (ESI): m/z 620.2 [M+H]⁺.

Example 3/37: (S)-3-(5-(4-(Cyclobutylmethyl)-5-(3-(1-(trifluoromethyl)cyclopropyl)-5-((1,1,1-trifluoropropan-2-yl)carbamoyl)phenyl)thiazol-2-yl)-1,3,4-oxadiazol-2-yl)-2,2-dimethylpropanoic acid

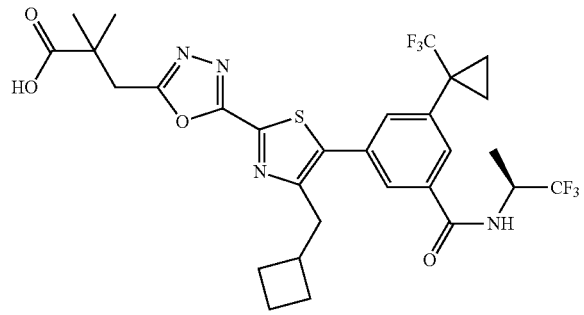 [SMILES: C[C@H](NC(=O)c1cc(-c2sc(-c3nnc(CC(C)(C)C(=O)O)o3)nc2CC2CCC2)cc(C2(C(F)(F)F)CC2)c1)C(F)(F)F]

The title compound was prepared as described for the synthesis of Example 3, using in step a (5)-3-bromo-5-(1-(trifluoromethyl)cyclopropyl)-N-(1,1,1-trifluoropropan-2-yl)benzamide (Intermediate 9) in place of 4-bromo-N-(tert-butyl)-2,3-dichlorobenzenesulfonamide. ¹H NMR (CDCl₃, 300 MHz): δ ppm 7.99 (s, 1H), 7.87 (s, 1H), 7.64 (s, 1H), 7.15 (d, J=9.9 Hz, 1H), 5.05-4.92 (m, 1H), 3.21 (s, 2H), 2.82-2.80 (m, 2H), 2.78-2.65 (m, 1H), 1.98-1.95 (m, 2H), 1.77-1.54 (m, 4H), 1.50-1.42 (m, 5H), 1.32 (s, 6H), 1.11 (s, 2H). MS (ESI): m/z 645.2 [M+H]⁺.

Example 3/38: (S)-3-(5-(4-(Cyclopentylmethyl)-5-(2-(difluoromethyl)-3-fluoro-4-(N-(1,1,1-trifluorobutan-2-yl)sulfamoyl)phenyl)thiazol-2-yl)-1,3,4-oxadiazol-2-yl)-2,2-dimethylpropanoic acid

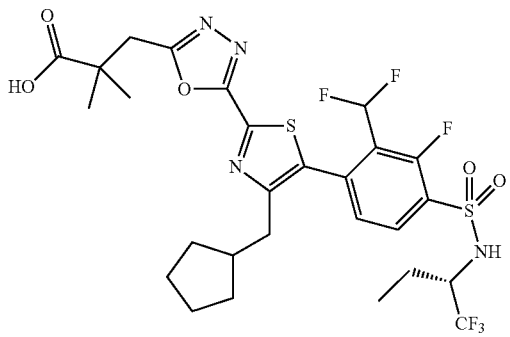 [SMILES: CC[C@H](NS(=O)(=O)c1ccc(-c2sc(-c3nnc(CC(C)(C)C(=O)O)o3)nc2CC2CCCC2)c(C(F)F)c1F)C(F)(F)F]

The title compound was prepared as described for the synthesis of Example 3, using in step a methyl 3-(5-(4-(cyclopentylmethyl)thiazol-2-yl)-1,3,4-oxadiazol-2-yl)-2,2-dimethylpropanoate (Intermediate 2/9) in place of methyl 3-(5-(4-(cyclobutylmethyl)thiazol-2-yl)-1,3,4-oxadiazol-2-yl)-2,2-dimethylpropanoate and (S)-4-bromo-3-(difluoromethyl)-2-fluoro-N-(1,1,1-trifluorobutan-2-yl)benzenesulfonamide (Intermediate 4) in place of 4-bromo-N-(tert-butyl)-2,3-dichlorobenzenesulfonamide. ¹H NMR (400 MHz, CDCl₃): δ ppm 8.08-8.04 (m, 1H), 7.31 (d, J=8.0 Hz, 1H), 6.67 (t, J=52.4 Hz, 1H), 3.94-3.89 (m, 1H), 3.27 (s, 2H), 2.61 (br s, 2H), 2.28-2.20 (m, 1H), 1.95-1.90 (m, 1H), 1.66-1.58 (m, 3H), 1.52-1.45 (m, 4H), 1.40 (s, 6H), 1.11 (t, J=7.6 Hz, 3H), 0.99-0.95 (m, 2H). MS (ESI): m/z 669.0 [M+H]⁺.

Example 3/39: (S)-3-(5-(4-(Isopropoxymethyl)-5-(4-(N-(1,1,1-trifluorobutan-2-yl)sulfamoyl)naphthalen-1-yl)thiazol-2-yl)-1,3,4-oxadiazol-2-yl)-2,2-dimethylpropanoic acid

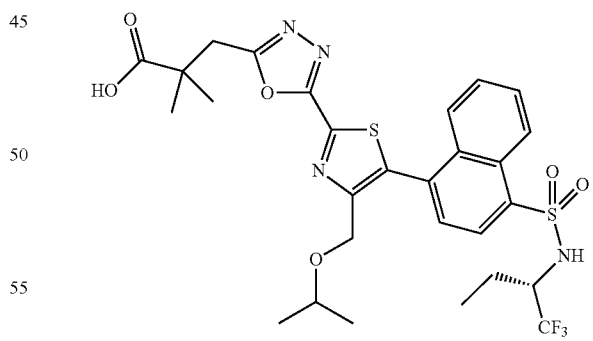

The title compound was prepared as described for the synthesis of Example 3, using in step a methyl 3-(5-(4-(isopropoxymethyl)thiazol-2-yl)-1,3,4-oxadiazol-2-yl)-2,2-dimethylpropanoate (Intermediate 2/10) in place of methyl 3-(5-(4-(cyclobutylmethyl)thiazol-2-yl)-1,3,4-oxadiazol-2-yl)-2,2-dimethylpropanoate and (S)-4-bromo-N-(1,1,1-trifluorobutan-2-yl)naphthalene-1-sulfonamide (Intermediate 4/8) in place of 4-bromo-N-(tert-butyl)-2,3-dichlorobenzenesulfonamide. ¹H NMR (400 MHz, DMSO-d₆): δ ppm 12.61 (s, 1H), 9.00 (d, J=8.8 Hz, 1H), 8.80 (d, J=8.4 Hz, 1H), 8.26 (d, J=7.6 Hz, 1H), 7.88-7.69 (m, 4H), 4.35-4.29 (m, 2H), 3.92-3.88 (m, 1H), 3.37-3.34 (m, 2H), 3.25 (s, 1H), 1.65-1.40 (m, 2H), 1.29 (s, 6H), 0.80 (d, J=6.4 Hz, 6H), 0.59 (t, J=7.2 Hz, 3H). MS (ESI): m/z 640.9 [M+H]$^+$.

Example 3/40: (S)-3-(5-(5-(3-Chloro-2-(difluoromethyl)-4-(N-(1,1,1-trifluoropropan-2-yl)sulfamoyl)phenyl)-4-(cyclopentylmethyl)thiazol-2-yl)-1,3,4-oxadiazol-2-yl)-2,2-dimethylpropanoic acid

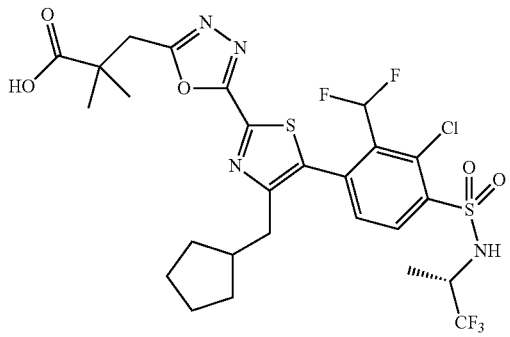 [SMILES: C[C@H](NS(=O)(=O)c1ccc(-c2sc(-c3nnc(CC(C)(C)C(=O)O)o3)nc2CC2CCCC2)c(C(F)F)c1Cl)C(F)(F)F]

The title compound was prepared as described for the synthesis of Example 3, using in step a methyl 3-(5-(4-(cyclopentylmethyl)thiazol-2-yl)-1,3,4-oxadiazol-2-yl)-2,2-dimethylpropanoate (Intermediate 2/9) in place of methyl 3-(5-(4-(cyclobutylmethyl)thiazol-2-yl)-1,3,4-oxadiazol-2-yl)-2,2-dimethylpropanoate and (S)-4-Bromo-2-chloro-3-(difluoromethyl)-N-(1,1,1-trifluoropropan-2-yl)benzenesulfonamide (Intermediate 4/20) in place of 4-bromo-N-(tert-butyl)-2,3-dichlorobenzenesulfonamide. $^1$H NMR (500 MHz, DMSO-d$_6$): δ ppm 12.58 (br s, 1H), 9.24 (d, J=7.0 Hz, 1H), 8.27 (d, J=8.0 Hz, 1H), 7.71 (d, J=8.0 Hz, 1H), 7.22 (t, J=52.0 Hz, 1H), 4.17 (s, 1H), 3.23 (s, 2H), 2.64-2.18 (m, 3H), 1.61 (br s, 2H), 1.42-1.41 (m, 4H), 1.28-1.25 (m, 9H), 1.25-1.00 (m, 2H). MS (ESI): m/z 671.0 [M+H]$^+$.

Example 3/41: (S)-3-(5-(4-(Cyclopentylmethyl)-5-(3-(difluoromethyl)-2-fluoro-4-(N-(1,1,1-trifluorobutan-2-yl)sulfamoyl)phenyl)thiazol-2-yl)-1,3,4-oxadiazol-2-yl)-2,2-dimethylpropanoic acid

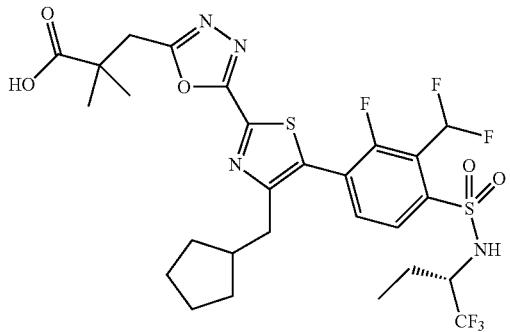 [SMILES: CC[C@H](NS(=O)(=O)c1ccc(-c2sc(-c3nnc(CC(C)(C)C(=O)O)o3)nc2CC2CCCC2)c(F)c1C(F)F)C(F)(F)F]

The title compound was prepared as described for the synthesis of Example 3, using in step a methyl 3-(5-(4-(cyclopentylmethyl)thiazol-2-yl)-1,3,4-oxadiazol-2-yl)-2,2-dimethylpropanoate (Intermediate 2/9) in place of methyl 3-(5-(4-(cyclobutylmethyl)thiazol-2-yl)-1,3,4-oxadiazol-2-yl)-2,2-dimethylpropanoate and (S)-4-bromo-2-(difluoromethyl)-3-fluoro-N-(1,1,1-trifluorobutan-2-yl)benzenesulfonamide (Intermediate 4/21) in place of 4-bromo-N-(tert-butyl)-2,3-dichlorobenzenesulfonamide. $^1$H NMR (500 MHz, DMSO-d$_6$): δ ppm 12.58 (br s, 1H), 9.32 (br s, 1H), 7.97-7.92 (m, 2H), 7.77 (t, J=51.0 Hz, 1H), 3.95-3.93 (m, 1H), 3.22 (s, 2H), 2.68 (d, J=7.0 Hz, 2H), 2.20-2.15 (m, 1H), 1.70-1.42 (m, 8H), 1.28 (m, 6H), 0.99-0.94 (m, 2H), 0.77 (t, J=7.5 Hz, 3H). MS (ESI): m/z 669.2 [M+H]$^+$.

Example 3/42: 3-(5-(5-(2-(Difluoromethyl)-4-(1,1,1,3,3,3-hexafluoro-2-hydroxypropan-2-yl)phenyl)-4-(4-fluorobenzyl)thiazol-2-yl)-1,3,4-oxadiazol-2-yl)-2,2-dimethylpropanoic acid

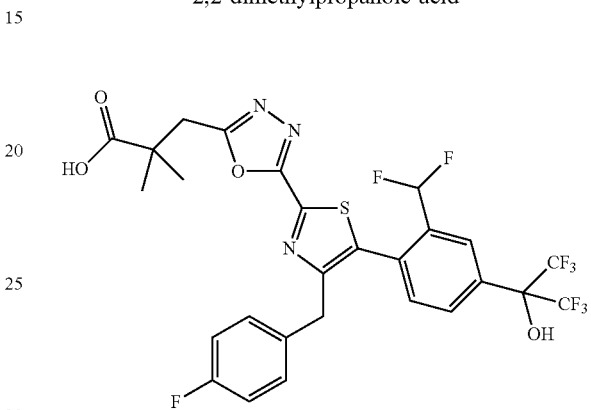

The title compound was prepared as described for the synthesis of Example 3, using in step a methyl 3-(5-(4-(4-fluorobenzyl)thiazol-2-yl)-1,3,4-oxadiazol-2-yl)-2,2-dimethylpropanoate (Intermediate 2/4) in place of methyl 3-(5-(4-(cyclobutylmethyl)thiazol-2-yl)-1,3,4-oxadiazol-2-yl)-2,2-dimethylpropanoate and 2-(4-bromo-3-(difluoromethyl)phenyl)-1,1,1,3,3,3-hexafluoropropan-2-ol (Intermediate 11) in place of 4-bromo-N-(tert-butyl)-2,3-dichlorobenzenesulfonamide. $^1$H NMR (500 MHz, DMSO-d$_6$): δ ppm 12.57 (m, 1H), 9.20 (m, 1H), 8.04 (m, 1H), 7.92 (d, J=8.5 Hz, 1H), 7.68 (d, J=8.5 Hz, 1H), 7.08-6.87 (m, 5H), 3.98 (s, 2H), 3.21 (m, 2H), 1.27 (m, 6H). MS (ESI): m/z 654.2 [M+H]$^+$.

Example 3/43: Step a (R)-Methyl 3-(5-(4-(cyclobutylmethyl)-5-(2-(difluoromethyl)-3-fluoro-4-(N-(1,1,1-trifluorobutan-2-yl)sulfamoyl)phenyl)thiazol-2-yl)-1,3,4-oxadiazol-2-yl)-2,2-dimethylpropanoate

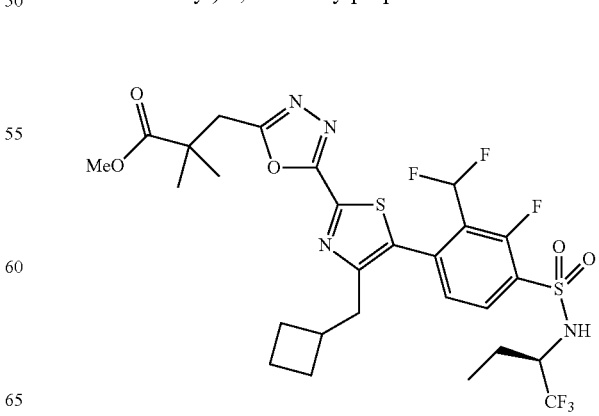

To a solution of methyl 3-(5-(4-(cyclobutylmethyl)thiazol-2-yl)-1,3,4-oxadiazol-2-yl)-2,2-dimethylpropanoate (500 mg, 1.49 mmol, Intermediate 2) and (R)-4-bromo-3-(difluoromethyl)-2-fluoro-N-(1,1,1-trifluorobutan-2-yl)benzenesulfonamide (700 mg, 1.69 mmol, Intermediate 4/22) in DME (20 mL) was added potassium carbonate (400 mg, 2.89 mmol), pivalic acid (85 mg, 0.83 mmol), tricyclohexylphosphine tetrafluoroborate (100 mg, 0.27 mmol), and palladium acetate (100 mg, 0.45 mmol). The mixture was stirred at 115° C. for 2 h. After cooling to room temperature, water (25 mL) and EtOAc (15 mL) were added. The layers were mixed and separated and the aqueous layer was further extracted with additional ethyl acetate (3×15 mL). The combined organic layers were washed with water (3×10 mL) and then brine (10 mL). After concentration, the resulting residue was purified by FCC on silica gel (PE/EtOAc=15:1 ramping to 3:1) to provide the title compound.

Example 3/43: (R)-3-(5-(4-(cyclobutylmethyl)-5-(2-(difluoromethyl)-3-fluoro-4-(N-(1,1,1-trifluorobutan-2-yl)sulfamoyl)phenyl)thiazol-2-yl)-1,3,4-oxadiazol-2-yl)-2,2-dimethylpropanoic acid

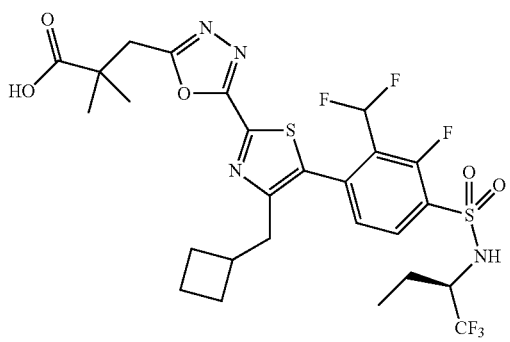 [SMILES: CC[C@@H](NS(=O)(=O)c1ccc(-c2sc(-c3nnc(CC(C)(C)C(=O)O)o3)nc2CC2CCC2)c(C(F)F)c1F)C(F)(F)F]

A mixture of (R)-methyl 3-(5-(4-(cyclobutylmethyl)-5-(2-(difluoromethyl)-3-fluoro-4-(N-(1,1,1-trifluorobutan-2-yl)sulfamoyl)phenyl)thiazol-2-yl)-1,3,4-oxadiazol-2-yl)-2,2-dimethylpropanoate (600 mg, 0.90 mmol, Example 3/43, step a) and LiOH (190 mg, 7.93 mmol) in MeOH (6 mL), THF (6 mL), and water (3 mL) was stirred at room temperature for 6 h. After concentration, the residue was partitioned between water (12 mL) and EtOAc (6 mL). The layers were separated and the aqueous layer was extracted with additional EtOAc (2×6 mL). The combined organic layers were washed with brine and concentrated to dryness. Dissolution into EtOAc (5 mL), treatment with heptane (20 mL), and concentration to dryness provided the title compound as a solid. $^1$H NMR (400 MHz, CDCl$_3$) δ 8.11-8.02 (m, 1H), 7.30 (d, J=8.2 Hz, 1H), 6.67 (t, J=52.5 Hz, 1H), 5.34-5.23 (m, 1H), 3.98-3.87 (m, 1H), 3.28 (s, 2H), 2.78-2.50 (m, 3H), 2.01-1.47 (m, 8H), 1.43 (s, 6H), 1.12 (t, J=7.4 Hz, 3H). MS (ESI): m/z 655.1 [M+H]$^+$.

Example 4: Step a (S)-Ethyl 5-(2,3-dichloro-4-(N-(1,1,1-trifluorobutan-2-yl)sulfamoyl)phenyl)-4-(2-methoxy-2-methylpropyl)thiazole-2-carboxylate

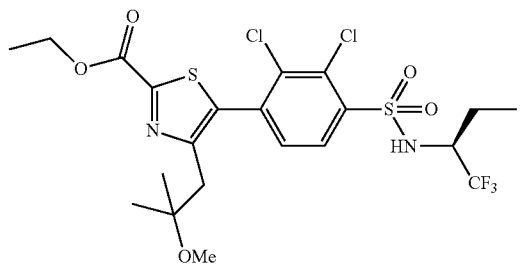 [SMILES: CCOC(=O)c1nc(CC(C)(C)OC)c(-c2ccc(S(=O)(=O)N[C@@H](CC)C(F)(F)F)c(Cl)c2Cl)s1]

To a solution of ethyl 4-(2-methoxy-2-methylpropyl)thiazole-2-carboxylate (490 mg, 2.02 mmol, Intermediate 1/4) and (S)-4-bromo-2,3-dichloro-N-(1,1,1-trifluorobutan-2-yl)benzenesulfonamide (830 mg, 2.00 mmol, Intermediate 4/3) in DMA (30 mL) was added P(Cy)$_3$.HBF$_4$ (200 mg, 0.54 mmol), pivalic acid (200 mg, 2.0 mmol), Pd(OAc)$_2$ (200 mg, 0.90 mmol), and K$_2$CO$_3$ (550 mg, 4.0 mmol) under N$_2$ atmosphere. The mixture was heated to 110° C. and stirred overnight. The mixture was allowed to cool to rt and then water (50 mL) and EtOAc (50 mL) were added. The layers were separated, the aqueous layer was extracted with EtOAc (3×50 mL) and the combined organic layers were concentrated to dryness. The residue was purified by preparative TLC (PE/EtOAc=1:1) to afford the title compound as a brown oil.

Example 4: Step b (S)-2,3-Dichloro-4-(2-(hydrazinecarbonyl)-4-(2-methoxy-2-methylpropyl)thiazol-5-yl)-N-(1,1,1-trifluorobutan-2-yl)benzenesulfonamide

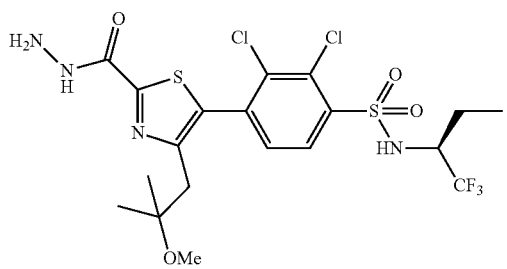 [SMILES: CC[C@H](NS(=O)(=O)c1ccc(-c2sc(C(=O)NN)nc2CC(C)(C)OC)c(Cl)c1Cl)C(F)(F)F]

A mixture of (S)-ethyl 5-(2,3-dichloro-4-(N-(1,1,1-trifluorobutan-2-yl)sulfamoyl)phenyl)-4-(2-methoxy-2-methylpropyl)thiazole-2-carboxylate (550 mg, 0.96 mmol, Example 4, step a) and hydrazine monohydrate (0.5 mL) in ethanol (10 mL) was stirred at 50° C. for 4 h. The mixture was concentrated to dryness and the residue was purified by preparative TLC (EtOAc) to give the title compound as a brown solid.

Example 4: Step c (S)-Methyl 4-(2-(5-(2,3-dichloro-4-(N-(1,1,1-trifluorobutan-2-yl)sulfamoyl)phenyl)-4-(2-methoxy-2-methylpropyl)thiazole-2-carbonyl)hydrazinyl)-2,2-dimethyl-4-oxobutanoate

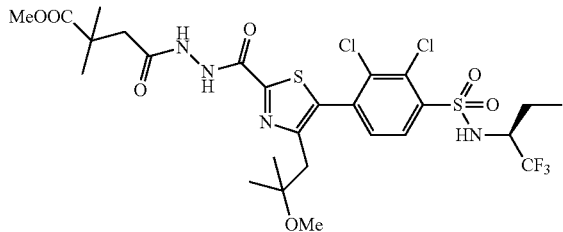 [SMILES: CC[C@H](NS(=O)(=O)c1ccc(-c2sc(C(=O)NNC(=O)CC(C)(C)C(=O)OC)nc2CC(C)(C)OC)c(Cl)c1Cl)C(F)(F)F]

A solution of (S)-2,3-dichloro-4-(2-(hydrazinecarbonyl)-4-(2-methoxy-2-methylpropyl)thiazol-5-yl)-N-(1,1,1-trifluorobutan-2-yl)benzenesulfonamide (440 mg, 0.78 mmol, Example 4, step b), 4-methoxy-3,3-dimethyl-4-oxobutanoic acid (220 mg, 1.4 mmol), HATU (530 mg, 1.4 mmol), and TEA (0.5 mL) in acetonitrile (10 mL) was stirred at rt for 2 h. The mixture was poured into water (20 mL) and extracted with EtOAc (4×30 mL). The combined organic layers were washed with brine, dried over anhydrous $Na_2SO_4$, filtered and concentrated to dryness. The residue was purified by preparative TLC (DCM/MeOH=10:1) to afford the title compound as a colorless solid.

Example 4: Step d (S)-Methyl 3-(5-(5-(2,3-dichloro-4-(N-(1,1,1-trifluorobutan-2-yl)sulfamoyl)phenyl)-4-(2-methoxy-2-methylpropyl)thiazol-2-yl)-1,3,4-oxadiazol-2-yl)-2,2-dimethylpropanoate

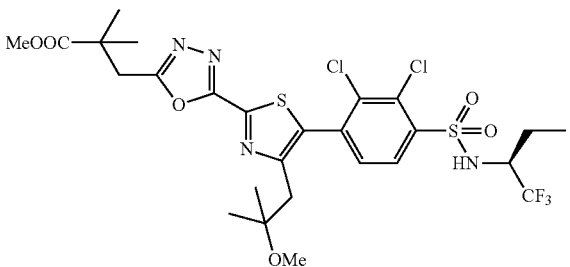 [SMILES: CC[C@H](NS(=O)(=O)c1ccc(-c2sc(-c3nnc(CC(C)(C)C(=O)OC)o3)nc2CC(C)(C)OC)c(Cl)c1Cl)C(F)(F)F]

A mixture of (S)-methyl 4-(2-(5-(2,3-dichloro-4-(N-(1,1,1-trifluorobutan-2-yl)sulfamoyl)phenyl)-4-(2-methoxy-2-methylpropyl)thiazole-2-carbonyl)hydrazinyl)-2,2-dimethyl-4-oxobutanoate (159 mg, 0.226 mmol, Example 4, step c), TsCl (87 mg, 0.46 mmol) and TEA (0.1 mL) in DCM (5 mL) was stirred at rt overnight. The mixture was poured into water (10 mL) and extracted with EtOAc (3×8 mL). The combined organic layers were washed with brine, dried over anhydrous $Na_2SO_4$, filtered and concentrated to dryness. The residue was purified by preparative TLC (EtOAc/PE=4:1) to give the title compound as a colorless solid.

Example 4: (S)-3-(5-(5-(2,3-Dichloro-4-(N-(1,1,1-trifluorobutan-2-yl)sulfamoyl)phenyl)-4-(2-methoxy-2-methylpropyl)thiazol-2-yl)-1,3,4-oxadiazol-2-yl)-2,2-dimethylpropanoic acid

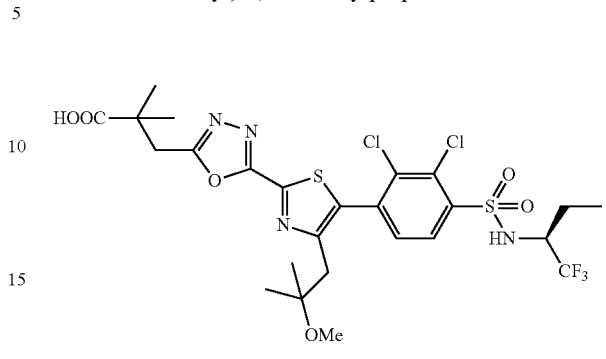

A mixture of (S)-methyl 3-(5-(5-(2,3-dichloro-4-(N-(1,1,1-trifluorobutan-2-yl)sulfamoyl)phenyl)-4-(2-methoxy-2-methylpropyl)thiazol-2-yl)-1,3,4-oxadiazol-2-yl)-2,2-dimethylpropanoate (91 mg, 0.13 mmol, Example 4, step d) and $LiOH \cdot H_2O$ (11 mg, 0.26 mmol) in MeOH (4 mL) and water (2 mL) was stirred at rt overnight. The mixture was concentrated to dryness, water was added (10 mL) and the aqueous layer was extracted with EtOAc (3×8 mL). The combined organic layers were washed with brine, dried over anhydrous $Na_2SO_4$, filtered and concentrated to dryness. The residue was purified by preparative HPLC to give the title compound as a colorless solid. $^1$H NMR (400 MHz, DMSO-$d_6$): δ ppm 12.58 (br s, 1H), 9.19 (d, J=9.2 Hz, 1H), 8.08 (d, J=8.0 Hz, 1H), 7.78 (d, J=8.0 Hz, 1H), 3.95-3.89 (m, 1H), 3.22 (s, 2H), 2.89 (s, 3H), 2.84 (s, 2H), 1.72-1.54 (m, 2H), 1.28 (s, 6H), 1.01 (s, 6H), 0.87 (t, J=7.2 Hz, 3H). MS (ESI): m/z 673.0 [M+H]$^+$.

Example 4/1: (S)-3-(5-(4-(Cyclobutylmethyl)-5-(2-(difluoromethyl)-3-fluoro-4-(N-(1,1,1-trifluorobutan-2-yl)sulfamoyl)phenyl)thiazol-2-yl)-1,3,4-oxadiazol-2-yl)-2,2-dimethylpropanoic acid

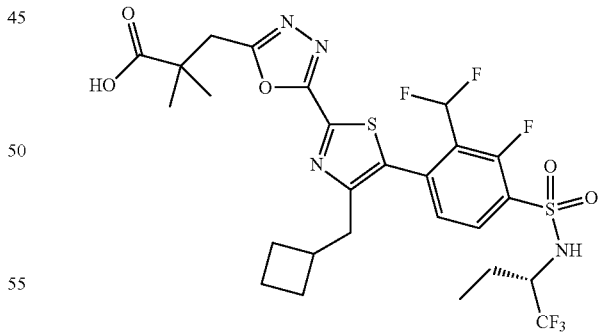

The title compound was prepared as described for the synthesis of Example 4 using in step a ethyl 4-(cyclobutylmethyl)thiazole-2-carboxylate (Intermediate 1) in place of 4-(2-methoxy-2-methylpropyl)thiazole-2-carboxylate and (S)-4-bromo-3-(difluoromethyl)-2-fluoro-N-(1,1,1-trifluorobutan-2-yl)benzenesulfonamide (Intermediate 4) in place of (S)-4-bromo-2,3-dichloro-N-(1,1,1-trifluorobutan-2-yl)benzenesulfonamide. $^1$H NMR (400 MHz, CDCl$_3$): δ ppm 8.07 (t, J=7.6 Hz, 1H), 7.30 (d, J=8.0 Hz, 1H), 6.68 (t, J=52.8

Hz, 1H), 5.41 (d, J=10.0 Hz, 1H), 3.95-3.88 (m, 1H), 3.29 (s, 2H), 2.70-2.59 (m, 3H), 1.96-1.54 (m, 8H), 1.43 (s, 6H), 1.11 (t, J=7.2 Hz, 3H). MS (ESI): m/z 655.1 [M+H]$^+$.

An Alternative Synthesis of Example 4/1

The title compound was prepared as described for the synthesis of Example 3/43 using in step a (S)-4-bromo-3-(difluoromethyl)-2-fluoro-N-(1,1,1-trifluorobutan-2-yl)benzenesulfonamide (Intermediate 4) in place of (R)-4-bromo-3-(difluoromethyl)-2-fluoro-N-(1,1,1-trifluorobutan-2-yl)benzenesulfonamide.

Example 4/2: (S)-3-(5-(4-((3,3-Difluorocyclobutyl)methyl)-5-(4-(N-(1,1,1-trifluorobutan-2-yl)sulfamoyl)naphthalen-1-yl)thiazol-2-yl)-1,3,4-oxadiazol-2-yl)-2,2-dimethylpropanoic acid

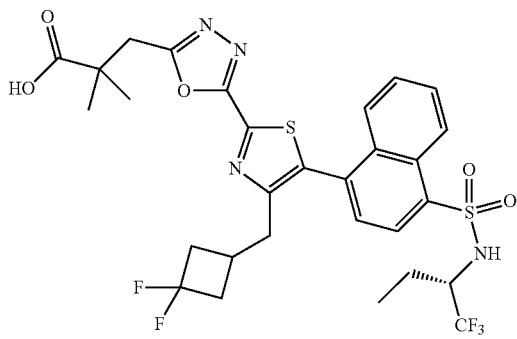 [SMILES: CC[C@H](NS(=O)(=O)c1ccc(-c2sc(-c3nnc(CC(C)(C)C(=O)O)o3)nc2CC2CC(F)(F)C2)c2ccccc12)C(F)(F)F]

The title compound was prepared as described for the synthesis of Example 4 using in step a ethyl 4-(3,3-difluorocyclobutyl)methyl)thiazole-2-carboxylate (Intermediate 1/9) in place of 4-(2-methoxy-2-methylpropyl)thiazole-2-carboxylate and (S)-4-bromo-N-(1,1,1-trifluorobutan-2-yl)naphthalene-1-sulfonamide (Intermediate 4/8) in place of (S)-4-bromo-2,3-dichloro-N-(1,1,1-trifluorobutan-2-yl)benzenesulfonamide. $^1$H NMR (400 MHz, CDCl$_3$): δ ppm 8.71 (d, J=8.8 Hz, 1H), 8.32 (d, J=7.6 Hz, 1H), 7.33-7.71 (m, 2H), 7.63-7.54 (m, 2H), 5.25 (br s, 1H), 3.86 (t, J=3.2 Hz, 1H), 3.29 (s, 2H), 2.73 (br s, 2H), 2.50-2.47 (m, 3H), 2.03-1.97 (m, 2H), 1.89-1.82 (m, 1H), 1.59-1.52 (m, 1H), 1.40 (s, 6H), 0.97 (t, J=6.8 Hz, 3H). MS (ESI): m/z 673.1 [M+H]$^+$.

Example 5: Step a trans-Methyl 3-(2-(4-(cyclobutylmethyl)thiazole-2-carbonyl)hydrazinecarbonyl)cyclobutanecarboxylate

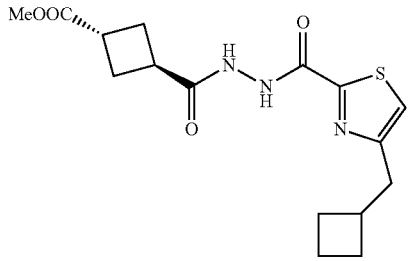 [SMILES: COC(=O)[C@H]1C[C@H](C(=O)NNC(=O)c2nc(CC3CCC3)cs2)C1]

A solution of 4-(cyclobutylmethyl)thiazole-2-carbohydrazide (260 mg, 1.23 mmol, Intermediate 2, step a), trans-3-(methoxycarbonyl)cyclobutanecarboxylic acid (395 mg, 2.5 mmol), HATU (950 mg, 2.5 mmol), and TEA (0.8 mL) in acetonitrile (12 mL) was stirred at rt for 2 h. The mixture was poured into water (30 mL) and extracted with EtOAc (4×30 mL). The combined organic layers were washed with brine, dried over anhydrous Na$_2$SO$_4$, filtered and concentrated to dryness. The residue was purified by FCC on silica gel (PE/EtOAc=1:2) to afford the title compound as a yellow solid.

Example 5: Step b trans-Methyl 3-(5-(4-(cyclobutylmethyl)thiazol-2-yl)-1,3,4-oxadiazol-2-yl)cyclobutanecarboxylate

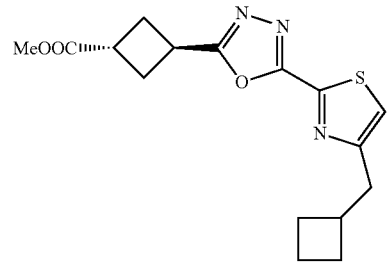 [SMILES: COC(=O)[C@H]1C[C@H](c2nnc(-c3nc(CC4CCC4)cs3)o2)C1]

A mixture of trans-methyl 3-(2-(4-(cyclobutylmethyl)thiazole-2-carbonyl)hydrazinecarbonyl)cyclobutanecarboxylate (185 mg, 0.526 mmol, Example 5, step a), TsCl (475 mg, 2.49 mmol) and TEA (0.8 mL) in DCM (5 mL) was stirred at rt overnight. The mixture was poured into water (20 mL) and extracted with EtOAc (3×25 mL). The combined organic layers were washed with brine, dried over anhydrous Na$_2$SO$_4$, filtered and concentrated to dryness. The residue was purified by FCC on silica gel (PE/EtOAc=2:1) to give the title compound as a yellow oil.

Example 5: trans-3-(5-(4-(Cyclobutylmethyl)-5-(2,3-dichloro-4-(N—((S)-1,1,1-trifluoropropan-2-yl)sulfamoyl)phenyl)thiazol-2-yl)-1,3,4-oxadiazol-2-yl)cyclobutanecarboxylic acid

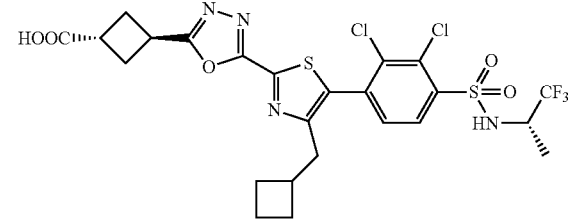 [SMILES: C[C@H](NS(=O)(=O)c1ccc(-c2sc(-c3nnc([C@H]4C[C@H](C(=O)O)C4)o3)nc2CC2CCC2)c(Cl)c1Cl)C(F)(F)F]

The title compound was prepared as described for the synthesis of Example 3, using in step a trans-methyl 3-(5-(4-(cyclobutylmethyl)thiazol-2-yl)-1,3,4-oxadiazol-2-yl)cyclobutanecarboxylate (Example 5, step b) in place of methyl 3-(5-(4-(cyclobutylmethyl)thiazol-2-yl)-1,3,4-oxadiazol-2-yl)-2,2-dimethylpropanoate and (S)-4-bromo-2,3-dichloro-N-(1,1,1-trifluoropropan-2-yl)benzenesulfonamide (Intermediate 4/2) in place of 4-bromo-N-(tert-butyl)-2,3-dichlorobenzenesulfonamide. $^1$H NMR (400 MHz, CDCl$_3$): δ ppm 8.11 (d, J=8.0 Hz, 1H), 7.47 (d, J=8.4 Hz, 1H), 5.42 (br s, 1H), 4.14-3.98 (m, 2H), 3.46-3.42 (m, 1H), 2.87-2.83

(m, 4H), 2.75-2.64 (m, 3H), 1.99-1.95 (m, 2H), 1.82-1.68 (m, 2H), 1.57-1.47 (m, 2H), 1.44 (d, J=6.8 Hz, 3H). MS (ESI): m/z 639.0 [M+H]$^+$.

Example 6: Step a (S)-Ethyl 5-(2,3-dichloro-4-(N-(1,1,1-trifluorobutan-2-yl)sulfamoyl)phenyl)-4-(hydroxymethyl)thiazole-2-carboxylate

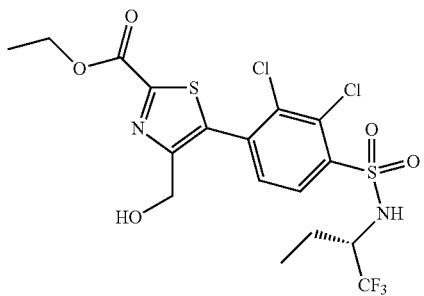 [SMILES: CCOC(=O)c1nc(CO)c(-c2ccc(S(=O)(=O)N[C@@H](CC)C(F)(F)F)c(Cl)c2Cl)s1]

A mixture of ethyl 4-(hydroxymethyl)thiazole-2-carboxylate (0.94 g, 5.0 mmol, Intermediate 1/7), (S)-4-bromo-2,3-dichloro-N-(1,1,1-trifluorobutan-2-yl)benzenesulfonamide (2.1 g, 5.0 mmol, Intermediate 4/3), Pd(OAc)$_2$ (400 mg, 1.8 mmol), P(Cy)$_3$.HBF$_4$ (400 mg, 1.1 mmol), PivOH (400 mg, 3.9 mmol), and Na$_2$CO$_3$ (1.1 g, 10 mmol) in DMA (30 mL) was heated at 90° C. overnight, cooled to rt, poured into water (150 mL), and extracted with EtOAc (70 mL×3). The combined organic layers were washed with brine, dried over anhydrous Na$_2$SO$_4$, filtered, concentrated to dryness, and purified by FCC on silica gel (PE/EtOAc=2:1) to give the title compound as a brown solid.

Example 6: Step b (S)-Ethyl 5-(2,3-dichloro-4-(N-(1,1,1-trifluorobutan-2-yl)sulfamoyl)phenyl)-4-formylthiazole-2-carboxylate

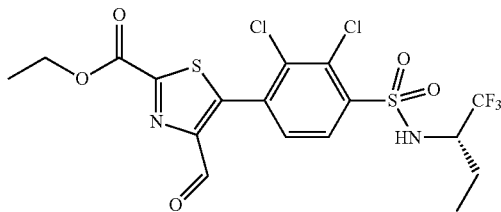 [SMILES: CCOC(=O)c1nc(C=O)c(-c2ccc(S(=O)(=O)N[C@@H](CC)C(F)(F)F)c(Cl)c2Cl)s1]

A solution of (S)-ethyl 5-(2,3-dichloro-4-(N-(1,1,1-trifluorobutan-2-yl)sulfamoyl)phenyl)-4-(hydroxymethyl)thiazole-2-carboxylate (520 mg, 1.0 mmol, Example 6, step a) and MnO$_2$ (870 mg, 10.0 mmol) in DCM (10 mL) was stirred at rt overnight. The reaction mixture was filtered through a pad of Celite®, and the filtrate was concentrated to dryness to give the title compound as a brown oil, which was used directly in the next step.

Example 6: Step c (S)-Ethyl 5-(2,3-dichloro-4-(N-(1,1,1-trifluorobutan-2-yl)sulfamoyl)phenyl)-4-((3,3-difluoropiperidin-1-yl)methyl)thiazole-2-carboxylate

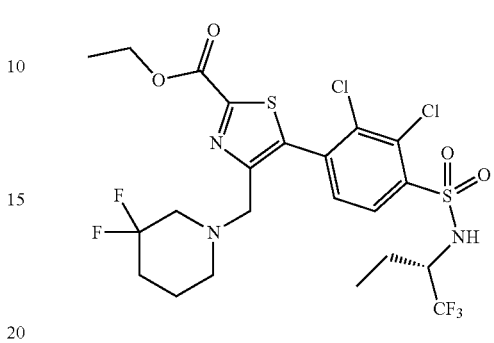

A solution of crude (S)-ethyl 5-(2,3-dichloro-4-(N-(1,1,1-trifluorobutan-2-yl)sulfamoyl)phenyl)-4-formylthiazole-2-carboxylate (477 mg, 0.919 mmol, Example 6, step b), 3,3-difluoropiperidine (220 mg, 1.84 mmol), and HOAc (3 drops) in MeOH (10 mL) was stirred at rt overnight. NaBH(OAc)$_3$ (390 mg, 1.84 mmol) was added and the mixture was stirred at rt for 2 h. The reaction mixture was then diluted with water (20 mL) and extracted with EtOAc (20 mL×3). The combined organic layers were washed with brine, dried over anhydrous Na$_2$SO$_4$, filtered, concentrated to dryness, and purified by FCC on silica gel (PE/EtOAc=3:2) to give the title compound as a brown gel.

Example 6: Step d (S)-2,3-Dichloro-4-(4-((3,3-difluoropiperidin-1-yl)methyl)-2-(hydrazinecarbonyl)thiazol-5-yl)-N-(1,1,1-trifluorobutan-2-yl)benzenesulfonamide

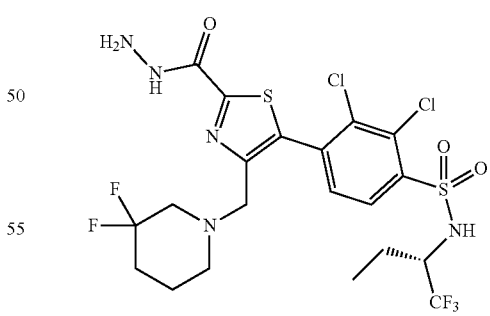

A solution of (S)-ethyl 5-(2,3-dichloro-4-(N-(1,1,1-trifluorobutan-2-yl)sulfamoyl)phenyl)-4-((3,3-difluoropiperidin-1-yl)methyl)thiazole-2-carboxylate (350 mg, 0.56 mmol, Example 6, step c) and hydrazine hydrate (0.4 mL) in EtOH (10 mL) was stirred at 50° C. for 4 h, concentrated to dryness, and purified by preparative TLC (EtOAc) to give the title compound as a brown solid.

Example 6: Step e (S)-2,3-Dichloro-4-(4-((3,3-difluoropiperidin-1-yl)methyl)-2-(2-(2-hydroxy-2-methylpropanoyl)hydrazinecarbonyl)thiazol-5-yl)-N-(1,1,1-trifluorobutan-2-yl)benzenesulfonamide

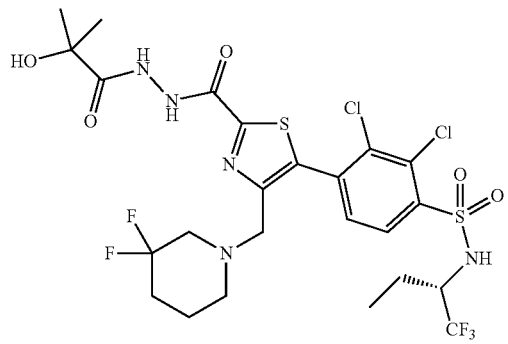 [SMILES: CC[C@H](NS(=O)(=O)c1ccc(-c2sc(C(=O)NNC(=O)C(C)(C)O)nc2CN2CCCC(F)(F)C2)c(Cl)c1Cl)C(F)(F)F]

A solution of (S)-2,3-dichloro-4-(4-((3,3-difluoropiperidin-1-yl)methyl)-2-(hydrazinecarbonyl)thiazol-5-yl)-N-(1,1,1-trifluorobutan-2-yl)benzenesulfonamide (130 mg, 0.21 mmol, Example 6, step d), 2-hydroxy-2-methylpropanoic acid (42 mg, 0.40 mmol), HATU (114 mg, 300 μmol), and TEA (0.1 mL) in MeCN (5 mL) was stirred at rt for 2 h. The reaction mixture was then poured into water (20 mL) and extracted with EtOAc (20 mL×4). The combined organic layers were washed with brine, dried over anhydrous $Na_2SO_4$, filtered, concentrated to dryness, and purified by preparative TLC (DCM/MeOH=10:1) to afford the title compound as a colorless solid.

Example 6: (S)-2,3-Dichloro-4-(4-((3,3-difluoropiperidin-1-yl)methyl)-2-(5-(2-hydroxypropan-2-yl)-1,3,4-oxadiazol-2-yl)thiazol-5-yl)-N-(1,1,1-trifluorobutan-2-yl)benzenesulfonamide

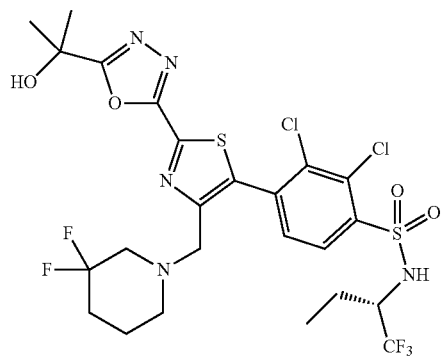 [SMILES: CC[C@H](NS(=O)(=O)c1ccc(-c2sc(-c3nnc(C(C)(C)O)o3)nc2CN2CCCC(F)(F)C2)c(Cl)c1Cl)C(F)(F)F]

A solution of (S)-2,3-dichloro-4-(4-((3,3-difluoropiperidin-1-yl)methyl)-2-(2-(2-hydroxy-2-methylpropanoyl)hydrazinecarbonyl)thiazol-5-yl)-N-(1,1,1-trifluorobutan-2-yl)benzenesulfonamide (75 mg, 0.11 mmol, Example 6, step e), TsCl (42 mg, 0.22 mmol), and TEA (0.05 mL) in DCM (10 mL) was stirred at rt overnight. The reaction mixture was then poured into water (10 mL) and extracted with EtOAc (8 mL×3). The combined organic layers were washed with brine, dried over anhydrous $Na_2SO_4$, filtered, concentrated to dryness, and purified by preparative TLC (EtOAc/PE=4:1) to give the title compound as a colorless solid. $^1$H NMR (400 MHz, DMSO-$d_6$): δ ppm 9.02 (br s, 1H), 8.05 (d, J=8.0 Hz, 1H), 7.82 (d, J=8.0 Hz, 1H), 6.13 (s, 1H), 3.95-3.85 (m, 1H), 3.71 (s, 2H), 2.58-2.54 (m, 2H), 2.30-2.26 (m, 2H), 1.79-1.55 (m, 10H), 1.45-1.35 (m, 2H), 0.87 (t, J=7.2 Hz, 3H). MS (ESI): m/z 678.0 [M+H]$^+$.

Example 7: Step a (S)-Methyl 4-(2-(5-(2,3-dichloro-4-(N-(1,1,1-trifluorobutan-2-yl)sulfamoyl)phenyl)-4-((3,3-difluoropiperidin-1-yl)methyl)thiazole-2-carbonyl)hydrazinyl)-2,2-dimethyl-4-oxobutanoate

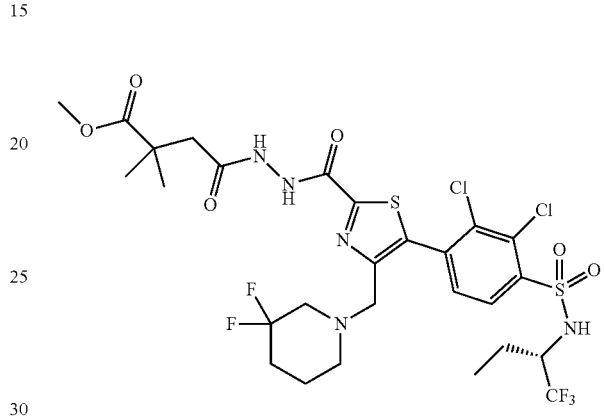

A solution of (S)-2,3-dichloro-4-(4-((3,3-difluoropiperidin-1-yl)methyl)-2-(hydrazinecarbonyl)thiazol-5-yl)-N-(1,1,1-trifluorobutan-2-yl)benzenesulfonamide (130 mg, 0.21 mmol, Example 6, step d), 4-methoxy-3,3-dimethyl-4-oxobutanoic acid (64 mg, 0.40 mmol), HATU (150 mg, 0.40 mmol), and TEA (0.1 mL) in MeCN (5 mL) was stirred at rt for 2 h. The reaction mixture was then poured into water (20 mL) and extracted with EtOAc (20 mL×3). The combined organic layers were washed with brine, dried over anhydrous $Na_2SO_4$, filtered, concentrated to dryness, and purified by preparative TLC (DCM/MeOH=10:1) to afford the title compound as a colorless solid.

Example 7: Step b (S)-Methyl 3-(5-(5-(2,3-dichloro-4-(N-(1,1,1-trifluorobutan-2-yl)sulfamoyl)phenyl)-4-((3,3-difluoropiperidin-1-yl)methyl)thiazol-2-yl)-1,3,4-oxadiazol-2-yl)-2,2-dimethylpropanoate

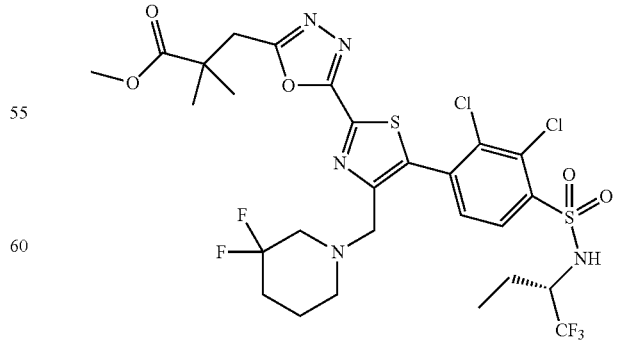

A solution of (S)-methyl 4-(2-(5-(2,3-dichloro-4-(N-(1,1,1-trifluorobutan-2-yl)sulfamoyl)phenyl)-4-((3,3-difluoropiperidin-1-yl)methyl)thiazole-2-carbonyl)hydrazinyl)-2,2- dimethyl-4-oxobutanoate (105 mg, 0.140 mmol, Example 7, step a), TsCl (42 mg, 0.22 mmol), and TEA (0.05 mL) in DCM (10 mL) was stirred at rt overnight. The reaction mixture was then poured into water (10 mL) and extracted with EtOAc (8 mL×3). The combined organic layers were washed with brine, dried over anhydrous Na₂SO₄, filtered, concentrated to dryness, and purified by preparative TLC (EtOAc/PE=2:1) to give the title compound as a colorless solid.

Example 7: (S)-3-(5-(5-(2,3-Dichloro-4-(N-(1,1,1-trifluorobutan-2-yl)sulfamoyl)phenyl)-4-((3,3-difluoropiperidin-1-yl)methyl)thiazol-2-yl)-1,3,4-oxadiazol-2-yl)-2,2-dimethylpropanoic acid

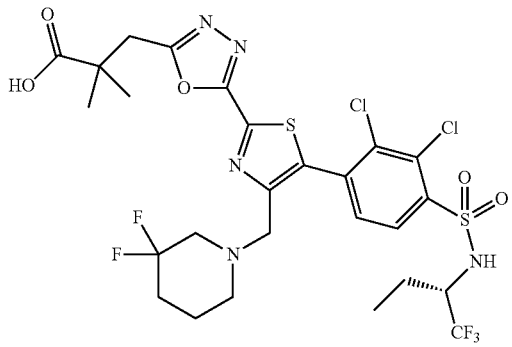 [SMILES: CC[C@H](NS(=O)(=O)c1ccc(-c2sc(-c3nnc(CC(C)(C)C(=O)O)o3)nc2CN2CCCC(F)(F)C2)c(Cl)c1Cl)C(F)(F)F]

A solution of (S)-methyl 3-(5-(5-(2,3-dichloro-4-(N-(1,1,1-trifluorobutan-2-yl)sulfamoyl)phenyl)-4-((3,3-difluoropiperidin-1-yl)methyl)thiazol-2-yl)-1,3,4-oxadiazol-2-yl)-2,2-dimethylpropanoate (63 mg, 96 μmol, Example 7, step b) and LiOH.H₂O (11 mg, 0.27 mmol) in MeOH (4 mL) and water (2 mL) was stirred at rt overnight. The reaction mixture was then concentrated to dryness, diluted with water (10 mL), adjusted to pH 7 with 0.1 M aqueous HCl and extracted with EtOAc (8 mL×3). The combined organic layers were washed with brine, dried over anhydrous Na₂SO₄, filtered, concentrated to dryness, and purified by preparative HPLC to give the title compound as a colorless solid. $^1$H NMR (400 MHz, CDCl₃): δ ppm 8.10 (d, J=8.0 Hz, 1H), 7.57 (d, J=8.4 Hz, 1H), 5.56 (d, J=10.0 Hz, 1H), 4.08 (s, 2H), 3.90-3.87 (m, 1H), 3.27 (s, 2H), 3.12 (t, J=2.8 Hz, 2H), 2.95 (br s, 2H), 1.99-1.80 (m, 5H), 1.66-1.60 (m, 1H), 1.39 (s, 6H), 1.11 (t, J=7.2 Hz, 3H). MS (ESI): m/z 720.0 [M+H]⁺.

Example 8: Step a (S)-Methyl 3-(5-(4-(hydroxymethyl)-5-(4-(N-(1,1,1-trifluorobutan-2-yl)sulfamoyl)naphthalen-1-yl)thiazol-2-yl)-1,3,4-oxadiazol-2-yl)-2,2-dimethylpropanoate

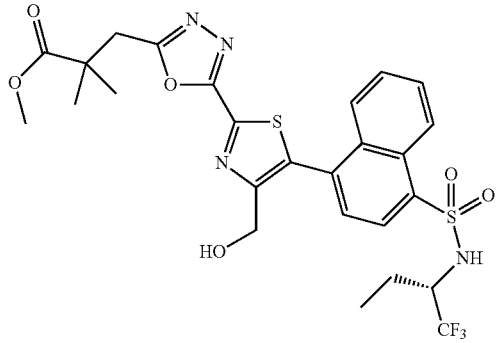 [SMILES: CC[C@H](NS(=O)(=O)c1ccc(-c2sc(-c3nnc(CC(C)(C)C(=O)OC)o3)nc2CO)c2ccccc12)C(F)(F)F]

To a solution of (S)-4-bromo-N-(1,1,1-trifluorobutan-2-yl)naphthalene-1-sulfonamide (790 mg, 2.0 mmol, Intermediate 4/8) and methyl 3-(5-(4-(hydroxymethyl)thiazol-2-yl)-1,3,4-oxadiazol-2-yl)-2,2-dimethylpropanoate (600 mg, 2.0 mmol, Intermediate 2/5) in DMA (30 mL) was added P(Cy)₃.HBF₄ (160 mg, 0.44 mmol), PivOH (160 mg, 1.6 mmol), Pd(OAc)₂ (160 mg, 0.71 mmol), and K₂CO₃ (560 mg, 4 mmol) under a N₂ atmosphere, and the mixture was stirred at 110° C. overnight. The reaction mixture was then allowed to cool to rt, diluted with water (60 mL), and extracted with EtOAc (60 mL×4). The combined organic layers were concentrated to dryness and purified by preparative TLC (PE/EtOAc=1:1) to afford the title compound as a brown solid.

Example 8: Step b (S)-Methyl 3-(5-(4-formyl-5-(4-(N-(1,1,1-trifluorobutan-2-yl)sulfamoyl)naphthalen-1-yl)thiazol-2-yl)-1,3,4-oxadiazol-2-yl)-2,2-dimethylpropanoate

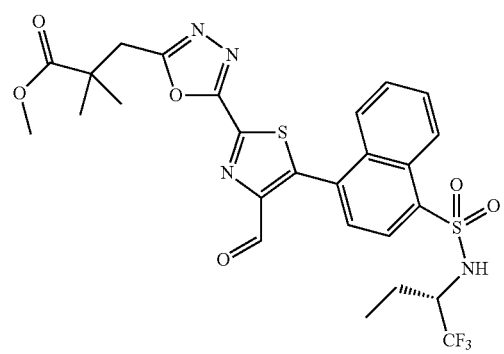 [SMILES: CC[C@H](NS(=O)(=O)c1ccc(-c2sc(-c3nnc(CC(C)(C)C(=O)OC)o3)nc2C=O)c2ccccc12)C(F)(F)F]

To a solution of (S)-methyl 3-(5-(4-(hydroxymethyl)-5-(4-(N-(1,1,1-trifluorobutan-2-yl)sulfamoyl)naphthalen-1-yl)thiazol-2-yl)-1,3,4-oxadiazol-2-yl)-2,2-dimethylpropanoate (620 mg, 1.0 mmol, Example 8, step a) in DCM (20 mL) was added activated MnO₂ (440 mg, 5.0 mmol) and the black suspension was stirred at rt for 2 h. The reaction mixture was then filtered through a pad of Celite® and concentrated to dryness to give the crude title compound as a brown solid, which was used directly in the next step.

Example 8: Step c

Methyl 3-(5-(4-(((R)-3-fluoropiperidin-1-yl)methyl)-5-(4-(N—((S)-1,1,1-trifluorobutan-2-yl)sulfamoyl) naphthalen-1-yl)thiazol-2-yl)-1,3,4-oxadiazol-2-yl)-2,2-dimethylpropanoate

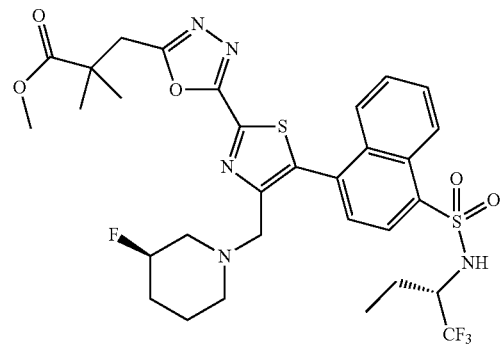 [SMILES: CC[C@H](NS(=O)(=O)c1ccc(-c2sc(-c3nnc(CC(C)(C)C(=O)OC)o3)nc2CN2CCC[C@@H](F)C2)c2ccccc12)C(F)(F)F]

To a solution of (S)-methyl 3-(5-(4-formyl-5-(4-(N-(1,1,1-trifluorobutan-2-yl)sulfamoyl)naphthalen-1-yl)thiazol-2-yl)-1,3,4-oxadiazol-2-yl)-2,2-dimethylpropanoate (240 mg, 0.39 mmol, Example 8, step b) in THF (8 mL) was added (R)-3-fluoropiperidine (83 mg, 0.80 mmol) and HOAc (3 drops) and the mixture was stirred at rt overnight. NaBH(OAc)₃ (170 mg, 0.80 mmol) was added in portions and the mixture was stirred for 4 h. The reaction mixture was then diluted with ice and extracted with EtOAc (20 mL×3). The combined organic layers were washed with brine, dried over anhydrous Na₂SO₄, filtered, concentrated to dryness, and purified by preparative TLC (PE/EtOAc=2/3) to give the title compound as a colorless solid.

Example 8: 3-(5-(4-(((R)-3-Fluoropiperidin-1-yl)methyl)-5-(4-(N—((S)-1,1,1-trifluorobutan-2-yl)sulfamoyl)naphthalen-1-yl)thiazol-2-yl)-1,3,4-oxadiazol-2-yl)-2,2-dimethylpropanoic acid

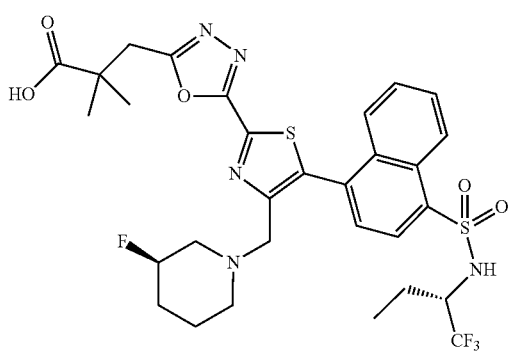 [SMILES: CC[C@H](NS(=O)(=O)c1ccc(-c2sc(-c3nnc(CC(C)(C)C(=O)O)o3)nc2CN2CCC[C@@H](F)C2)c2ccccc12)C(F)(F)F]

A solution of methyl 3-(5-(4-(((R)-3-fluoropiperidin-1-yl)methyl)-5-(4-(N—((S)-1,1,1-trifluorobutan-2-yl)sulfamoyl)naphthalen-1-yl)thiazol-2-yl)-1,3,4-oxadiazol-2-yl)-2,2-dimethylpropanoate (80 mg, 0.12 mmol, Example 8, step c) and LiOH.H₂O (25 mg, 0.60 mmol) in MeOH (4 mL) and water (2 mL) was stirred at rt overnight. The reaction mixture was then concentrated to dryness, diluted with water (10 mL), and extracted with EtOAc (8 mL×3). The combined organic layers were washed with brine, dried over anhydrous Na₂SO₄, filtered, concentrated to dryness, and purified by preparative HPLC to give the title compound as a colorless solid. ¹H NMR (400 MHz, CD₃OD): δ ppm 8.87 (d, J=6.4 Hz, 1H), 8.35 (d, J=6.0 Hz, 1H), 7.87-7.69 (m, 4H), 4.31 (d, J=38.4 Hz, 1H), 3.88-3.85 (m, 1H), 3.58 (s, 2H), 3.28 (s, 2H), 2.66-2.60 (m, 1H), 2.33-2.25 (m, 2H), 2.13-2.12 (m, 1H), 1.76-1.53 (m, 4H), 1.45-1.37 (m, 7H), 1.25-1.23 (m, 1H), 0.79 (t, J=6.0 Hz, 3H). MS (ESI): m/z 684.0 [M+H]⁺.

Example 8/1: (S)-3-(5-(4-((3,3-Difluoropiperidin-1-yl)methyl)-5-(4-(N-(1,1,1-trifluorobutan-2-yl)sulfamoyl)naphthalen-1-yl)thiazol-2-yl)-1,3,4-oxadiazol-2-yl)-2,2-dimethylpropanoic acid

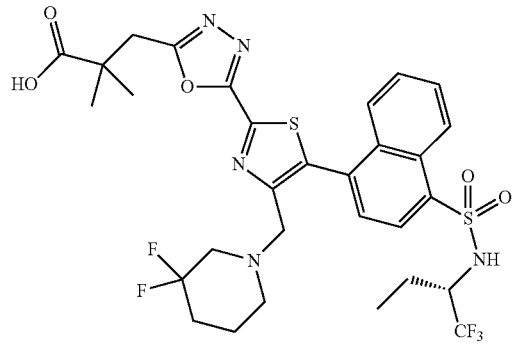 [SMILES: CC[C@H](NS(=O)(=O)c1ccc(-c2sc(-c3nnc(CC(C)(C)C(=O)O)o3)nc2CN2CCCC(F)(F)C2)c2ccccc12)C(F)(F)F]

The title compound was prepared as described for the synthesis of Example 8, using in step c 3,3-difluoropiperidine in place of (R)-3-fluoropiperidine. ¹H NMR (400 MHz, CDCl₃): δ ppm 8.70 (d, J=6.8 Hz, 1H), 8.35 (d, J=6.0 Hz, 1H), 7.79-7.75 (m, 2H), 7.70-7.65 (m, 2H), 5.35 (d, J=6.8 Hz, 1H), 4.22-4.14 (m, 2H), 3.89-3.86 (m, 1H), 3.34-3.24 (m, 4H), 3.12 (s, 2H), 1.99-1.83 (m, 5H), 1.61-1.55 (m, 1H), 1.43 (s, 6H), 0.99 (t, J=6.0 Hz, 3H). MS (ESI): m/z 702.1 [M+H]⁺.

Example 8/2: 3-(5-(5-(2,3-Dichloro-4-(1,1,1,3,3,3-hexafluoro-2-hydroxypropan-2-yl)phenyl)-4-((3,3-difluoropiperidin-1-yl)methyl)thiazol-2-yl)-(1,3,4-oxadiazol-2-yl)-2,2-dimethylpropanoic acid

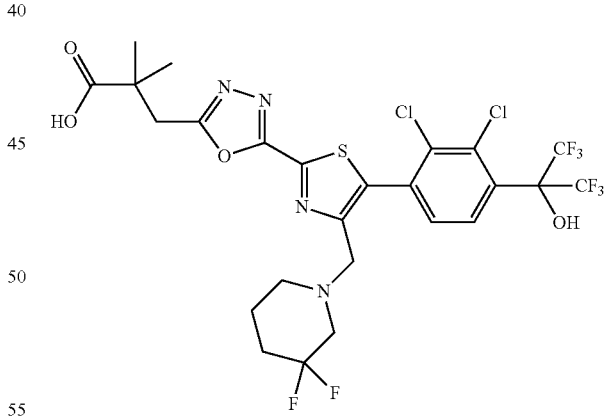

The title compound was prepared as described for the synthesis of Example 8, using in step a 2-(4-bromo-2,3-dichlorophenyl)-1,1,1,3,3,3-hexafluoropropan-2-ol (Intermediate 6) in place of (S)-4-bromo-N-(1,1,1-trifluorobutan-2-yl)naphthalene-1-sulfonamide and in step c 3,3-difluoropiperidine in place of (R)-3-fluoropiperidine. ¹H NMR (400 MHz, CDCl₃): δ ppm 7.85 (br s, 1H), 7.49 (d, J=7.2 Hz, 1H), 4.23 (s, 2H), 3.40-3.27 (m, 4H), 3.11 (br s, 2H), 2.00-1.95 (m, 2H), 1.95-1.85 (m, 2H), 1.40 (s, 6H). MS (ESI): m/z 697.1 [M+H]⁺.

Example 8/3: (R)-3-(5-(5-(2,3-Dichloro-4-(1,1,1,3,3,3-hexafluoro-2-hydroxypropan-2-yl)phenyl)-4-((3-fluoropiperidin-1-yl)methyl)thiazol-2-yl)-1,3,4-oxadiazol-2-yl)-2,2-dimethylpropanoic acid

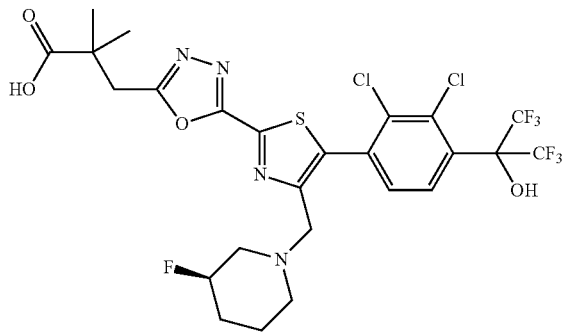 [SMILES: CC(C)(Cc1nnc(-c2nc(CN3CCC[C@@H](F)C3)c(-c3ccc(C(O)(C(F)(F)F)C(F)(F)F)c(Cl)c3Cl)s2)o1)C(=O)O]

The title compound was prepared as described for the synthesis of Example 8, using in step a 2-(4-bromo-2,3-dichlorophenyl)-1,1,1,3,3,3-hexafluoropropan-2-ol (Intermediate 6) in place of (S)-4-bromo-N-(1,1,1-trifluorobutan-2-yl)naphthalene-1-sulfonamide. $^1$H NMR (400 MHz, CDCl$_3$): δ ppm 7.75 (br s, 1H), 7.44 (d, J=8.4 Hz, 1H), 4.49-4.35 (m, 1H), 4.28 (br s, 1H), 3.69-3.57 (m, 2H), 3.26 (s, 2H), 2.55-2.21 (m, 4H), 1.65-1.59 (m, 3H), 1.31 (s, 6H), 1.30-1.27 (m, 1H). MS (ESI): m/z 679.1 [M+H]$^+$.

Example 9: Step a

Methyl 3-(5-(4-(cyclobutylmethyl)thiazol-2-yl)-1,3,4-thiadiazol-2-yl)-2,2-dimethylpropanoate

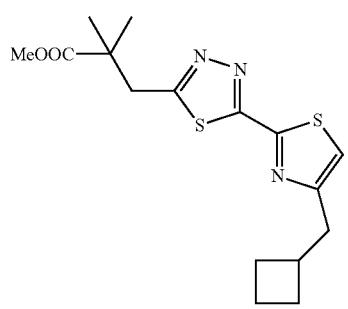 [SMILES: COC(=O)C(C)(C)Cc1nnc(-c2nc(CC3CCC3)cs2)s1]

A mixture of methyl 4-(2-(4-(cyclobutylmethyl)thiazole-2-carbonyl)hydrazinyl)-2,2-dimethyl-4-oxobutanoate (220 mg, 0.63 mmol, Intermediate 2, step b) and Lawesson reagent (283 mg, 0.700 mmol) in toluene (2.5 mL) was stirred at 110° C. overnight. The mixture was poured into water (10 mL) and extracted with EtOAc (3×15 mL). The combined organic layers were washed with brine, dried over anhydrous Na$_2$SO$_4$, filtered, and concentrated to dryness. The residue was purified by preparative TLC (PE/EtOAc=2:1) to give the title compound as a yellow solid.

Example 9: (S)-3-(5-(4-(Cyclobutylmethyl)-5-(2,3-dichloro-4-(N-(1,1,1-trifluoropropan-2-yl)sulfamoyl)phenyl)thiazol-2-yl)-1,3,4-thiadiazol-2-yl)-2,2-dimethylpropanoic acid

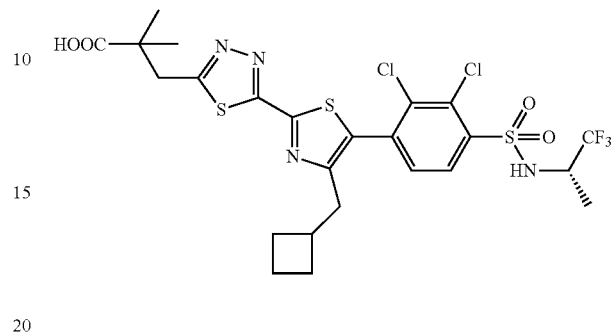

The title compound was prepared as described for the synthesis of Example 3, using in step a methyl 3-(5-(4-(cyclobutylmethyl)thiazol-2-yl)-1,3,4-thiadiazol-2-yl)-2,2-dimethylpropanoate (Example 9, step a) in place of methyl 3-(5-(4-(cyclobutylmethyl)thiazol-2-yl)-1,3,4-oxadiazol-2-yl)-2,2-dimethylpropanoate and (S)-4-bromo-2,3-dichloro-N-(1,1,1-trifluoropropan-2-yl)benzenesulfonamide (Intermediate 4/2) in place of 4-bromo-N-(tert-butyl)-2,3-dichlorobenzenesulfonamide. $^1$H NMR (400 MHz, CDCl$_3$): δ ppm 8.09 (d, J=8.0 Hz, 1H), 7.46 (d, J=8.0 Hz, 1H), 5.51 (d, J=10.0 Hz, 1H), 4.13-4.07 (m, 1H), 3.48 (s, 2H), 2.66-2.62 (m, 3H), 2.00-1.96 (m, 2H), 1.79-1.69 (m, 2H), 1.56-1.52 (m, 2H), 1.43 (d, J=7.2 Hz, 3H), 1.40 (s, 6H). MS (ESI) m/z 657.0 [M+H]$^+$.

Example 10: Step a

5-Bromo-4-(cyclohexylmethyl)thiazole-2-carboxamide

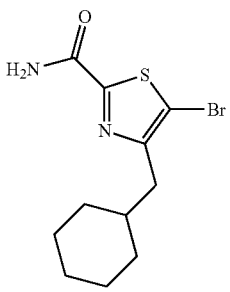

A stream of NH$_3$ gas was passed through anhydrous EtOH (70 mL) at −20° C. for 7 min. Then a solution of ethyl 5-bromo-4-(cyclohexylmethyl)thiazole-2-carboxylate (1.00 g, 3.00 mmol, prepared as described in WO2013/178362, Example 6, step 3) in EtOH (5 mL) was added, and the solution was stirred at 80° C. overnight. The resulting solution was concentrated to dryness to give the title compound as a pale yellow solid.

Example 10: Step b

5-Bromo-4-(cyclohexylmethyl)thiazole-2-carbonitrile

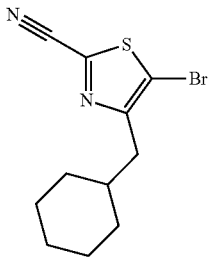 [SMILES: N#Cc1nc(CC2CCCCC2)c(Br)s1]

To a solution of 5-bromo-4-(cyclohexylmethyl)thiazole-2-carboxamide (660 mg, 2.17 mmol, Example 10, step a) and TEA (1.01 g, 10.9 mmol) in anhydrous DCM (5 mL) at 0° C. under $N_2$ was added TFAA (1.37 g, 6.51 mmol) and the solution was stirred at 0° C. for 2 h. The resulting solution was quenched with water and extracted with DCM twice. The combined organic layers were washed with brine, dried over anhydrous $Na_2SO_4$, filtered and concentrated to dryness to give the title compound as a yellow solid.

Example 10: Step c

5-Bromo-4-(cyclohexylmethyl)-N'-hydroxythiazole-2-carboximidamide

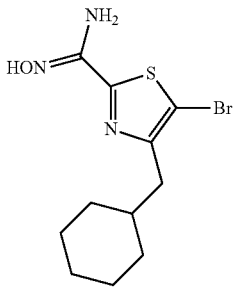

To a solution of 5-bromo-4-(cyclohexylmethyl)thiazole-2-carbonitrile (600 mg, 2.10 mmol, Example 10, step b) and TEA (636 mg, 6.30 mmol) in anhydrous EtOH (5 mL) was added hydroxylamine hydrochloride (438 mg, 6.30 mmol), and the solution was heated to reflux overnight. After it was allowed to cool to rt, the resulting solution was concentrated to dryness and purified by FCC on silica gel (PE/EtOAc=10/1) to give the title compound as a colorless solid.

Example 10: Step d

N'-Acetoxy-5-bromo-4-(cyclohexylmethyl)thiazole-2-carboximidamide

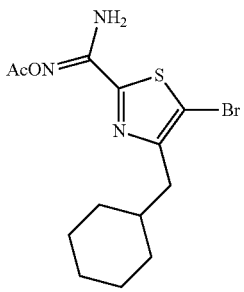

To a stirred solution of 5-bromo-4-(cyclohexylmethyl)-N-hydroxythiazole-2-carboximidamide (460 mg, 1.44 mmol, Example 10, step c) in pyridine (5 mL) was added $Ac_2O$ (300 mg, 2.89 mmol), and the solution was heated at 50° C. overnight. After it was allowed to cool to rt, the resulting solution was concentrated to dryness and purified by FCC on silica gel (PE/EtOAc=6/1) to give the title compound as an off-white solid.

Example 10: Step e 3-(5-Bromo-4-(cyclohexylmethyl)thiazol-2-yl)-5-methyl-1,2,4-oxadiazole

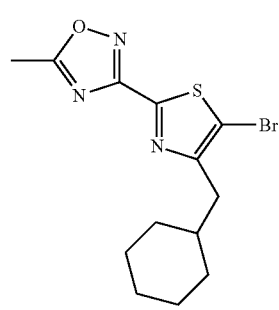 [SMILES: Cc1nc(-c2nc(CC3CCCCC3)c(Br)s2)no1]

To a solution of N-acetoxy-5-bromo-4-(cyclohexylmethyl)thiazole-2-carboximidamide (472 mg, 1.31 mmol, Example 10, step d) in a mixture of DMF (5 mL) and water (1 mL) was added NaOAc (108 mg, 1.31 mmol), and the solution was heated at reflux temperature for 5 h. After it was allowed to cool to rt, the solution was quenched with water and extracted with DCM twice. The combined organic layers were washed with brine, dried over anhydrous $Na_2SO_4$, filtered, concentrated to dryness, and purified by FCC on silica gel (PE/EtOAc=8/1) to give the title compound as a colorless solid.

Example 10: N-(tert-Butyl)-4-(4-(cyclohexylmethyl)-2-(5-methyl-1,2,4-oxadiazol-3-yl)thiazol-5-yl)naphthalene-1-sulfonamide

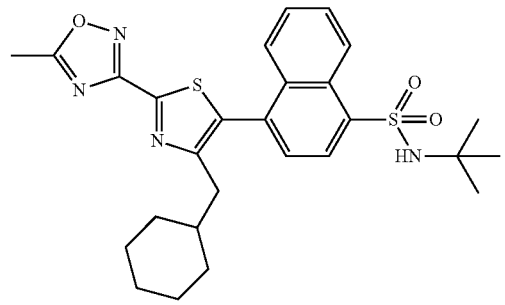 [SMILES: Cc1nc(-c2nc(CC3CCCCC3)c(-c3ccc(S(=O)(=O)NC(C)(C)C)c4ccccc34)s2)no1]

A solution of 3-(5-bromo-4-(cyclohexylmethyl)thiazol-2-yl)-5-methyl-1,2,4-oxadiazole (100 mg, 0.29 mmol, Example 10, step e), N-(tert-butyl)-4-(4,4,5,5-tetramethyl-1,3,2-dioxaborolan-2-yl)naphthalene-1-sulfonamide (142 mg, 0.365 mmol, Intermediate 18), 2 M aqueous $Na_2CO_3$ (2.4 mL), and $Pd(dppf)Cl_2$ (24 mg, 30 μmol) in DME (5 mL) was heated to reflux temperature overnight under nitrogen. The resulting solution was allowed to cool to rt and diluted with EtOAc. The layers were separated, and the organic layer was washed with brine, dried over anhydrous $Na_2SO_4$, filtered, concentrated to dryness, and purified by FCC on silica gel (PE/EtOAc=2/1) to give the title compound as a colorless solid. $^1$H NMR ($CD_3OD$, 400 MHz): δ ppm 8.75 (d, J=8.4 Hz, 1H), 8.26 (d, J=7.6 Hz, 1H), 7.71-7.55 (m, 4H), 2.62 (s, 3H), 2.38 (br s, 2H), 1.60-1.57 (m, 1H), 1.44-1.38 (m, 5H), 1.05 (s, 9H), 1.00-0.87 (m, 3H), 0.61-0.53 (m, 2H). MS (ESI): m/z 525.2 [M+H]$^+$.

Example 11: Step a (S)-Methyl 3-(3-(4-(cyclobutylmethyl)-5-(2,3-dichloro-4-(N-(1,1,1-trifluoropropan-2-yl)sulfamoyl)phenyl)thiazol-2-yl)-1,2,4-oxadiazol-5-yl)-2,2-dimethylpropanoate

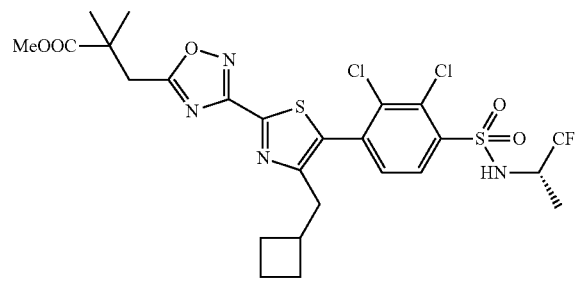

A solution of methyl 3-(3-(4-(cyclobutylmethyl)thiazol-2-yl)-1,2,4-oxadiazol-5-yl)-2,2-dimethylpropanoate (145 mg, 0.432 mmol, Intermediate 3), (S)-4-bromo-2,3-dichloro-N-(1,1,1-trifluoropropan-2-yl)benzenesulfonamide (170 mg, 0.43 mmol, Intermediate 4/2), $K_2CO_3$ (120 mg, 0.86 mmol), Pd(OAc)$_2$ (23 mg, 0.10 mmol), P(Cy)$_3$.HBF$_4$ (20 mg, 58 µmol), and PivOH (10 mg, 86 µmol) in DMA (2 mL) was heated under argon at 95° C. overnight. The reaction mixture was then allowed to cool to rt, partitioned between EtOAc and water, and the layers were separated. The organic layer was washed with water and brine, dried over anhydrous $Na_2SO_4$, filtered, concentrated to dryness, and purified by preparative TLC (EtOAc) to give the title compound as a light-yellow solid.

Example 11: (S)-3-(3-(4-(Cyclobutylmethyl)-5-(2,3-dichloro-4-(N-(1,1,1-trifluoropropan-2-yl)sulfamoyl)phenyl)thiazol-2-yl)-1,2,4-oxadiazol-5-yl)-2,2-dimethylpropanoic acid

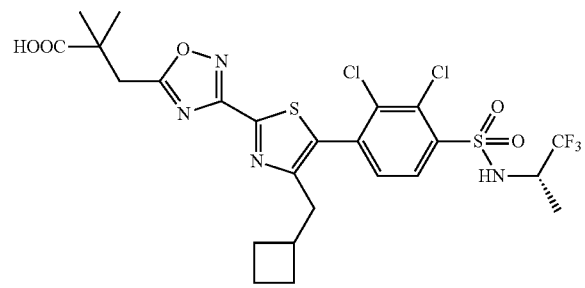

A mixture of (S)-methyl 3-(3-(4-(cyclobutylmethyl)-5-(2,3-dichloro-4-(N-(1,1,1-trifluoropropan-2-yl)sulfamoyl)phenyl)thiazol-2-yl)-1,2,4-oxadiazol-5-yl)-2,2-dimethylpropanoate (126 mg, 0.192 mmol, Example 11, step a) and LiOH.H$_2$O (43 mg, 1.0 mmol) in MeOH (2 mL) and water (1 mL) was stirred at rt overnight. The mixture was concentrated and aqueous HCl (1 M, 10 mL) was added. The aqueous phase was extracted with EtOAc (3×8 mL) and the combined organic layers were washed with brine, dried over anhydrous $Na_2SO_4$, filtered, and concentrated to dryness. The residue was purified by preparative HPLC to give the title compound as a colorless solid. $^1$H NMR (400 MHz, CDCl$_3$): δ ppm 8.10 (d, J=8.0 Hz, 1H), 7.47 (d, J=8.0 Hz, 1H), 5.51 (d, J=8.4 Hz, 1H), 4.13-4.07 (m, 1H), 3.30 (s, 2H), 2.76-2.67 (m, 3H), 1.96-1.93 (m, 2H), 1.80-1.68 (m, 2H), 1.54-1.42 (m, 11H). MS (ESI): m/z 641.2 [M+H]$^+$.

Example 11/1: (S)-3-(3-(4-(Cyclobutylmethyl)-5-(2-(trifluoromethoxy)-4-(N-(1,1,1-trifluoropropan-2-yl)sulfamoyl)phenyl)thiazol-2-yl)-1,2,4-oxadiazol-5-yl)-2,2-dimethylpropanoic acid

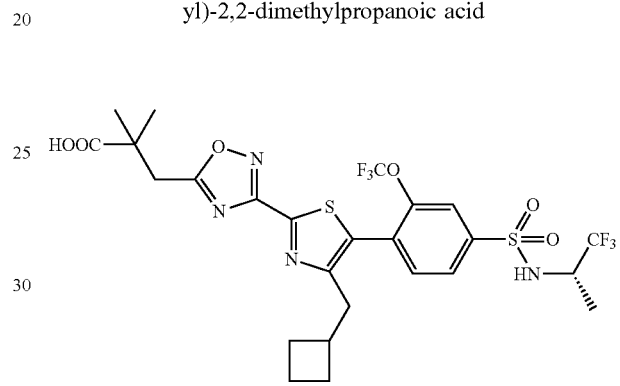

The title compound was prepared as described for the synthesis of Example 11, using in step a (S)-4-bromo-3-(trifluoromethoxy)-N-(1,1,1-trifluoropropan-2-yl)benzenesulfonamide (Intermediate 4/14) in place of (S)-4-bromo-2,3-dichloro-N-(1,1,1-trifluoropropan-2-yl)benzenesulfonamide. $^1$H NMR (400 MHz, CD$_3$OD): δ ppm 8.03-7.99 (m, 2H), 7.84 (d, J=6.4 Hz, 1H), 4.20-4.15 (m, 1H), 3.32 (s, 2H), 2.84 (d, J=6.4 Hz, 2H), 2.76-2.69 (m, 1H), 1.99-1.95 (m, 2H), 1.84-1.70 (m, 2H), 1.62-1.55 (m, 2H), 1.41 (s, 6H), 1.26 (d, J=5.6 Hz, 3H). MS (ESI): m/z 656.7 [M+H]$^+$.

Example 11/2: (S)-3-(3-(4-(Cyclohexylmethyl)-5-(8-(N-(1,1,1-trifluoropropan-2-yl)sulfamoyl)isoquinolin-5-yl)thiazol-2-yl)-1,2,4-oxadiazol-5-yl)-2,2-dimethylpropanoic acid

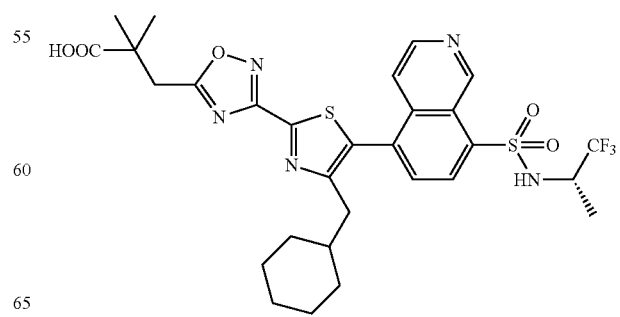

The title compound was prepared as described for the synthesis of Example 11, using in step a methyl 3-(3-(4-(cyclohexylmethyl)thiazol-2-yl)-1,2,4-oxadiazol-5-yl)-2,2-dimethylpropanoate (Intermediate 3/1) in place of methyl 3-(3-(4-(cyclobutylmethyl)thiazol-2-yl)-1,2,4-oxadiazol-5-yl)-2,2-dimethylpropanoate and (S)-5-bromo-N-(1,1,1-trifluoropropan-2-yl)iso quino line-8-sulfonamide (Intermediate 4/16) in place of (S)-4-bromo-2,3-dichloro-N-(1,1,1-trifluoropropan-2-yl)benzenesulfonamide. $^1$H NMR (400 MHz, DMSO-d$_6$): δ ppm 10.11 (s, 1H), 9.34 (d, J=7.6 Hz, 1H), 8.73 (d, J=4.8 Hz, 1H), 8.37 (d, J=6.0 Hz, 1H), 8.07 (d, J=6.0 Hz, 1H), 7.73 (d, J=4.4 Hz, 1H), 4.22-4.16 (m, 1H), 3.30 (s, 2H), 2.42 (s, 2H), 1.64-1.62 (m, 1H), 1.51-1.45 (m, 5H), 1.30 (s, 6H), 1.10-0.90 (m, 6H), 0.61-0.58 (m, 2H). MS (ESI) m/z 652.2 [M+H]$^+$.

Example 11/3: (S)-3-(3-(4-(Cyclohexylmethyl)-5-(5-(N-(1,1,1-trifluoropropan-2-yl)sulfamoyl)isoquinolin-8-yl)thiazol-2-yl)-1,2,4-oxadiazol-5-yl)-2,2-dimethylpropanoic acid

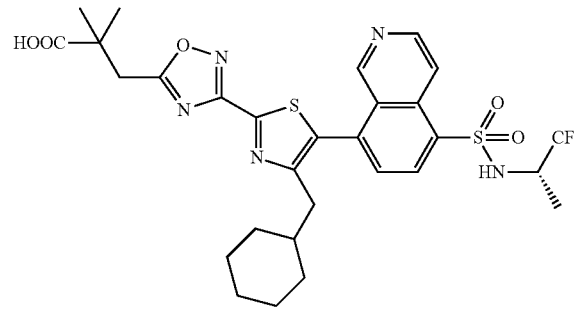

The title compound was prepared as described for the synthesis of Example 11, using in step a methyl 3-(3-(4-(cyclohexylmethyl)thiazol-2-yl)-1,2,4-oxadiazol-5-yl)-2,2-dimethylpropanoate (Intermediate 3/1) in place of methyl 3-(3-(4-(cyclobutylmethyl)thiazol-2-yl)-1,2,4-oxadiazol-5-yl)-2,2-dimethylpropanoate and (S)-8-chloro-N-(1,1,1-trifluoropropan-2-yl)isoquinoline-5-sulfonamide (Intermediate 4/17) in place of (S)-4-bromo-2,3-dichloro-N-(1,1,1-trifluoropropan-2-yl)benzenesulfonamide. $^1$H NMR (400 MHz, CD$_3$OD): δ ppm 9.31 (s, 1H), 8.83-8.78 (m, 2H), 8.68 (d, J=7.6 Hz, 1H), 7.99-7.96 (m, 1H), 4.17-4.10 (m, 1H), 3.37 (s, 2H), 2.60-2.40 (m, 2H), 1.78-1.74 (m, 1H), 1.58-1.52 (m, 5H), 1.42 (s, 6H), 1.27 (d, J=6.8 Hz, 3H), 1.17-0.99 (m, 3H), 0.70-0.64 (m, 2H). MS (ESI): m/z 652.2 [M+H]$^+$.

Example 11/4: (S)-3-(3-(4-(Cyclohexylmethyl)-5-(2-(trifluoromethoxy)-4-(N-(1,1,1-trifluoropropan-2-yl)sulfamoyl)phenyl)thiazol-2-yl)-1,2,4-oxadiazol-5-yl)-2,2-dimethylpropanoic acid

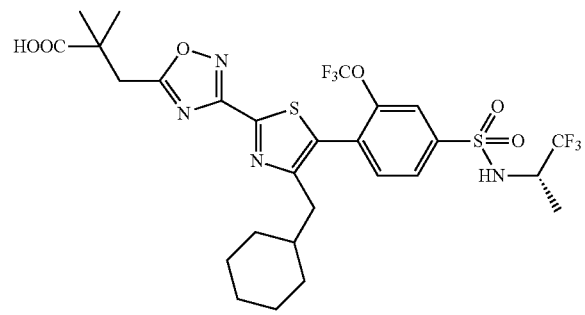 [SMILES: C[C@H](NS(=O)(=O)c1ccc(-c2sc(-c3noc(CC(C)(C)C(=O)O)n3)nc2CC2CCCCC2)c(OC(F)(F)F)c1)C(F)(F)F]

The title compound was prepared as described for the synthesis of Example 11, using in step a methyl 3-(3-(4-(cyclohexylmethyl)thiazol-2-yl)-1,2,4-oxadiazol-5-yl)-2,2-dimethylpropanoate (Intermediate 3/1) in place of methyl 3-(3-(4-(cyclobutylmethyl)thiazol-2-yl)-1,2,4-oxadiazol-5-yl)-2,2-dimethylpropanoate and (S)-4-bromo-3-(trifluoromethoxy)-N-(1,1,1-trifluoropropan-2-yl)benzenesulfonamide (Intermediate 4/14) in place of (S)-4-bromo-2,3-dichloro-N-(1,1,1-trifluoropropan-2-yl) benzenesulfonamide. $^1$H NMR (400 MHz, CDCl$_3$): δ ppm 7.92-7.90 (m, 2H), 7.63 (d, J=6.4 Hz, 1H), 5.17 (d, J=8.0 Hz, 1H), 4.14-4.09 (m, 1H), 3.32 (s, 2H), 2.61 (d, J=5.6 Hz, 2H), 1.88-1.84 (m, 1H), 1.63-1.55 (m, 5H), 1.46-1.44 (m, 9H), 1.21-1.04 (m, 3H), 0.79-0.72 (m, 2H). MS (ESI): m/z 685.1 [M+H]$^+$.

Example 11/5: (S)-3-(3-(4-(Cyclobutylmethyl)-5-(1-(N-(1,1,1-trifluoropropan-2-yl)sulfamoyl)isoquinolin-4-yl)thiazol-2-yl)-1,2,4-oxadiazol-5-yl)-2,2-dimethylpropanoic acid

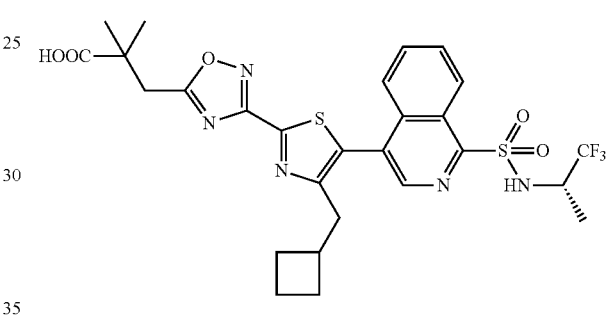

The title compound was prepared as described for the synthesis of Example 11, using in step a (S)-4-bromo-N-(1,1,1-trifluoropropan-2-yl)isoquinoline-1-sulfonamide (Intermediate 4/19) in place of (S)-4-bromo-2,3-dichloro-N-(1,1,1-trifluoropropan-2-yl)benzenesulfonamide. $^1$H NMR (400 MHz, CDCl$_3$): δ ppm 9.02-9.00 (m, 1H), 8.49 (s, 1H), 7.85-7.77 (m, 3H), 5.68 (d, J=8.8 Hz, 1H), 4.28-4.21 (m, 1H), 3.31 (s, 2H), 2.71 (s, 3H), 1.92-1.87 (m, 2H), 1.73-1.69 (m, 1H), 1.62-1.58 (m, 4H), 1.45-1.42 (m, 8H). MS (ESI): m/z 624.2 [M+H]$^+$.

Example 11/6: (S)-3-(3-(4-(Cyclobutylmethyl)-5-(2-(difluoromethyl)-3-fluoro-4-(N-(1,1,1-trifluorobutan-2-yl)sulfamoyl)phenyl)thiazol-2-yl)-1,2,4-oxadiazol-5-yl)-2,2-dimethylpropanoic acid

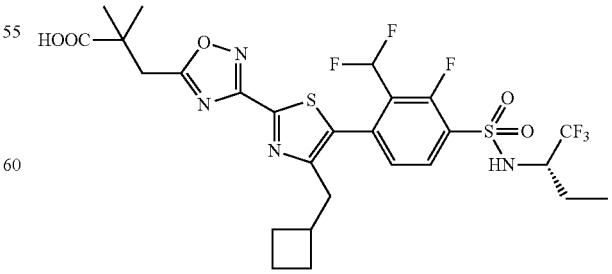

The title compound was prepared as described for the synthesis of Example 11, using in step a (S)-4-bromo-3-

(difluoromethyl)-2-fluoro-N-(1,1,1-trifluorobutan-2-yl)benzenesulfonamide (Intermediate 4) in place of (S)-4-bromo-2,3-dichloro-N-(1,1,1-trifluoropropan-2-yl)benzenesulfonamide. ¹H NMR (400 MHz, CD₃OD): δ ppm 8.14 (t, J=7.6 Hz, 1H), 7.48 (d, J=8.4 Hz, 1H), 6.85 (t, J=52 Hz, 1H), 3.96-3.90 (m, 1H), 3.28 (s, 2H), 2.73-2.67 (m, 3H), 2.00-1.95 (m, 2H), 1.88-1.57 (m, 6H), 1.37 (s, 6H), 0.99 (t, J=7.2 Hz, 3H). MS (ESI): m/z 655.1 [M+H]⁺.

Example 11/7: (S)-3-(3-(4-(Cyclobutylmethyl)-5-(3-fluoro-4-(N-(1,1,1-trifluorobutan-2-yl)sulfamoyl)-2-(trifluoromethyl)phenyl)thiazol-2-yl)-1,2,4-oxadiazol-5-yl)-2,2-dimethylpropanoic acid

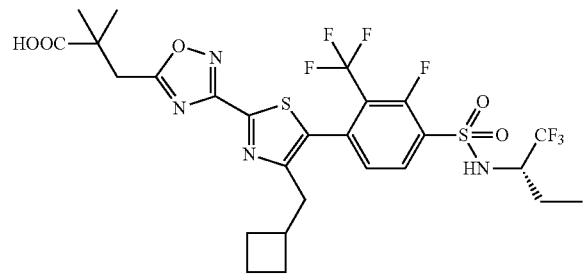 [SMILES: CC[C@H](NS(=O)(=O)c1ccc(-c2sc(-c3noc(CC(C)(C)C(=O)O)n3)nc2CC2CCC2)c(C(F)(F)F)c1F)C(F)(F)F]

The title compound was prepared as described for the synthesis of Example 11, using in step a (S)-4-bromo-2-fluoro-N-(1,1,1-trifluorobutan-2-yl)-3-(trifluoromethyl)benzenesulfonamide (Intermediate 4/9) in place of (S)-4-bromo-2,3-dichloro-N-(1,1,1-trifluoropropan-2-yl)benzenesulfonamide. ¹H NMR (400 MHz, CD₃OD): δ ppm 8.23 (t, J=7.6 Hz, 1H), 7.53 (d, J=8.0 Hz, 1H), 3.97-3.93 (m, 1H), 3.29 (s, 2H), 2.77-2.58 (m, 3H), 2.01-1.51 (m, 8H), 1.38 (s, 6H), 1.07-0.97 (m, 3H). MS (ESI): m/z 673.1 [M+H]⁺.

Example 11/8: (S)-3-(3-(5-(2,3-Dichloro-4-(N-(1,1,1-trifluorobutan-2-yl)sulfamoyl)phenyl)-4-(2-methoxy-2-methylpropyl)thiazol-2-yl)-1,2,4-oxadiazol-5-yl)-2,2-dimethylpropanoic acid

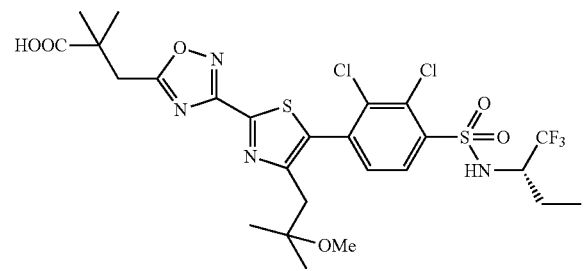 [SMILES: CC[C@H](NS(=O)(=O)c1ccc(-c2sc(-c3noc(CC(C)(C)C(=O)O)n3)nc2CC(C)(C)OC)c(Cl)c1Cl)C(F)(F)F]

The title compound was prepared as described for the synthesis of Example 11, using in step a methyl 3-(3-(4-(2-methoxy-2-methylpropyl)thiazol-2-yl)-1,2,4-oxadiazol-5-yl)-2,2-dimethylpropanoate (Intermediate 3/2) in place of methyl 3-(3-(4-(cyclobutylmethyl)thiazol-2-yl)-1,2,4-oxadiazol-5-yl)-2,2-dimethylpropanoate and (S)-4-bromo-2,3-dichloro-N-(1,1,1-trifluorobutan-2-yl)benzenesulfonamide (Intermediate 4/3) in place of (S)-4-bromo-2,3-dichloro-N-(1,1,1-trifluoropropan-2-yl)benzenesulfonamide. ¹H NMR (400 MHz, CDCl₃): δ ppm 8.06 (d, J=6.4 Hz, 1H), 7.50 (d, J=6.4 Hz, 1H), 5.47 (m, 1H), 3.87 (m, 1H), 3.26 (m 2H), 2.99 (s, 3H), 2.87 (s, 2H), 1.92-1.88 (m, 1H), 1.64-1.56 (m, 1H), 1.32 (s, 6H), 1.12-1.06 (m, 9H). MS (ESI): m/z 673.1 [M+H]⁺.

Example 11/9: (S)-3-(3-(4-(Cyclohexylmethyl)-5-(3-(1-methylcyclopropyl)-5-((1,1,1-trifluoropropan-2-yl)carbamoyl)phenyl)thiazol-2-yl)-1,2,4-oxadiazol-5-yl)-2,2-dimethylpropanoic acid

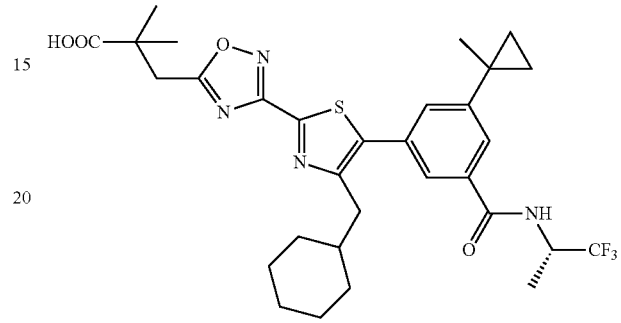

The title compound was prepared as described for the synthesis of Example 11, using in step a methyl 3-(3-(4-(cyclohexylmethyl)thiazol-2-yl)-1,2,4-oxadiazol-5-yl)-2,2-dimethylpropanoate (Intermediate 3/1) in place of methyl 3-(3-(4-(cyclobutylmethyl)thiazol-2-yl)-1,2,4-oxadiazol-5-yl)-2,2-dimethylpropanoate and (S)-3-bromo-5-(1-methylcyclopropyl)-N-(1,1,1-trifluoropropan-2-yl)benzamide (Intermediate 10) in place of (S)-4-bromo-2,3-dichloro-N-(1,1,1-trifluoropropan-2-yl)benzenesulfonamide. ¹H NMR (400 MHz, CDCl₃): δ ppm 7.75 (s, 1H), 7.63 (s, 1H), 7.43 (s, 1H), 6.60-6.54 (m, 1H), 5.00-4.93 (m, 1H), 3.25 (s, 2H), 2.58 (d, J=6.0 Hz, 2H), 1.75-1.44 (m, 12H), 1.35 (s, 6H), 1.06-1.01 (m, 3H), 0.99-0.90 (m, 2H), 0.88-0.80 (m, 4H). MS 619.3 (ESI) m/z [M+H]⁺.

Example 11/10: (S)-3-(3-(5-(2,3-Dichloro-4-(N-(1,1,1-trifluorobutan-2-yl)sulfamoyl)phenyl)-4-((1-methoxycyclobutyl)methyl)thiazol-2-yl)-1,2,4-oxadiazol-5-yl)-2,2-dimethylpropanoic acid

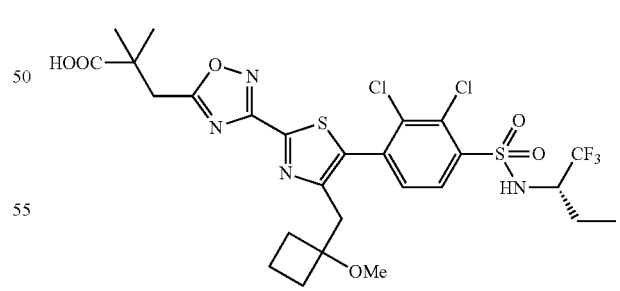

The title compound was prepared as described for the synthesis of Example 11, using in step a methyl 3-(3-(4-((1-methoxycyclobutyl)methyl)thiazol-2-yl)-1,2,4-oxadiazol-5-yl)-2,2-dimethylpropanoate (Intermediate 3/4) in place of methyl 3-(3-(4-(cyclobutylmethyl)thiazol-2-yl)-1,2,4-oxadiazol-5-yl)-2,2-dimethylpropanoate and (S)-4-bromo-2,3-dichloro-N-(1,1,1-trifluorobutan-2-yl)benzenesulfonamide (Intermediate 4/3) in place of (S)-4-bromo-2,3-dichloro-N-

(1,1,1-trifluoropropan-2-yl)benzenesulfonamide. ¹H NMR (400 MHz, CDCl₃): δ ppm 8.06 (d, J=8.2 Hz, 1H), 7.54 (d, J=8.2 Hz, 1H), 5.57 (d, J=9.6 Hz, 1H), 3.87 (s, 1H), 3.29 (s, 2H), 3.06 (s, 2H), 2.88 (s, 3H), 2.09-2.04 (m, 4H), 1.91-1.86 (m, 1H), 1.65-1.50 (m, 3H), 1.40 (s, 6H), 1.11-1.08 (m, 3H). MS (ESI): 685.0 [M+H]⁺.

Example 11/11: (S)-3-(3-(5-(3-Chloro-2-(difluoromethyl)-4-(N-(1,1,1-trifluoropropan-2-yl)sulfamoyl)phenyl)-4-(cyclobutylmethyl)thiazol-2-yl)-1,2,4-oxadiazol-5-yl)-2,2-dimethylpropanoic acid

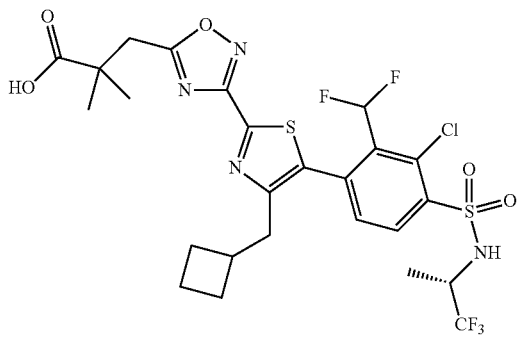 [SMILES: C[C@H](NS(=O)(=O)c1ccc(-c2sc(-c3noc(CC(C)(C)C(=O)O)n3)nc2CC2CCC2)c(C(F)F)c1Cl)C(F)(F)F]

The title compound was prepared as described for the synthesis of Example 11, using in step a (S)-4-bromo-2-chloro-3-(difluoromethyl)-N-(1,1,1-trifluoropropan-2-yl)benzenesulfonamide (Intermediate 4/20) in place of (S)-4-bromo-2,3-dichloro-N-(1,1,1-trifluoropropan-2-yl)benzenesulfonamide. ¹H NMR (500 MHz, DMSO-d₆): δ ppm 8.24 (d, J=8.0 Hz, 1H), 7.63 (d, J=8.5 Hz, 1H), 7.21 (t, J=52.5 Hz, 1H), 4.06-4.04 (m, 1H), 3.24 (s, 2H), 2.69-2.63 (m, 3H), 1.90 (br s, 2H), 1.75-1.62 (m, 2H), 1.54-1.47 (m, 2H), 1.26 (s, 6H), 1.20 (d, J=7.0 Hz, 3H). MS (ESI): m/z 657.1 [M+H]⁺.

Example 12: Step a (S)-Methyl 3-(3-(5-(2-(difluoromethyl)-3-fluoro-4-(N-(1,1,1-trifluorobutan-2-yl)sulfamoyl)phenyl)-4-(hydroxymethyl)thiazol-2-yl)-1,2,4-oxadiazol-5-yl)-2,2-dimethylpropanoate

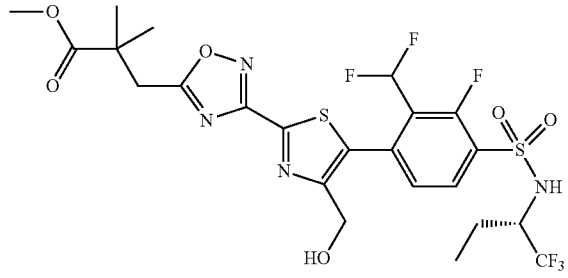 [SMILES: CC[C@H](NS(=O)(=O)c1ccc(-c2sc(-c3noc(CC(C)(C)C(=O)OC)n3)nc2CO)c(C(F)F)c1F)C(F)(F)F]

To a solution of methyl 3-(3-(4-(hydroxymethyl)thiazol-2-yl)-1,2,4-oxadiazol-5-yl)-2,2-dimethylpropanoate (122 mg, 0.410 mmol, Intermediate 3/3), (S)-4-bromo-3-(difluoromethyl)-2-fluoro-N-(1,1,1-trifluorobutan-2-yl)benzenesulfonamide (169 mg, 0.408 mmol, Intermediate 4), and Na₂CO₃ (87 mg, 0.82 mmol) in DMA (2 mL) was added P(Cy)₃·HBF₄ (45 mg, 0.12 mmol), PivOH (15 mg, 0.15 mmol), and Pd(OAc)₂ (40 mg, 0.18 mmol) under Ar. The solution was stirred at 95° C. overnight and then allowed to cool to rt. The reaction mixture was then diluted with EtOAc and water, and the layers were separated. The organic layer was washed with water and brine, dried over anhydrous Na₂SO₄, filtered, concentrated to dryness, and purified by FCC on silica gel (PE/EtOAc=1:4) to give the title compound as a yellow solid.

Example 12: Step b (S)-Methyl 3-(3-(5-(2-(difluoromethyl)-3-fluoro-4-(N-(1,1,1-trifluorobutan-2-yl)sulfamoyl)phenyl)-4-formylthiazol-2-yl)-1,2,4-oxadiazol-5-yl)-2,2-dimethylpropanoate

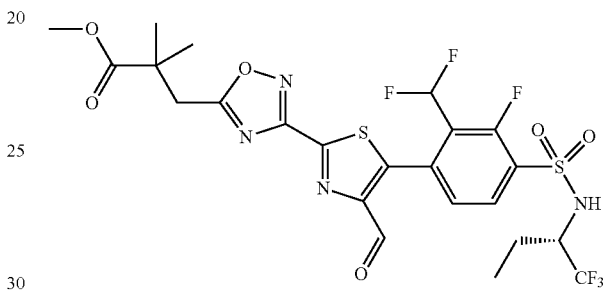

To a solution of (S)-methyl 3-(3-(5-(2-(difluoromethyl)-3-fluoro-4-(N-(1,1,1-trifluorobutan-2-yl)sulfamoyl)phenyl)-4-(hydroxymethyl)thiazol-2-yl)-1,2,4-oxadiazol-5-yl)-2,2-dimethylpropanoate (315 mg, 500 μmol, Example 12, step a) in DCM (8 mL) was added activated MnO₂ (260 mg, 3.00 mmol) and the mixture was stirred at rt for 2 h, filtered through a pad of Celite®, and concentrated to dryness to give the title compound as a yellow solid.

Example 12: Step c (S)-Methyl 3-(3-(5-(2-(difluoromethyl)-3-fluoro-4-(N-(1,1,1-trifluorobutan-2-yl)sulfamoyl)phenyl)-4-((3,3-difluoropiperidin-1-yl)methyl)thiazol-2-yl)-1,2,4-oxadiazol-5-yl)-2,2-dimethylpropanoate

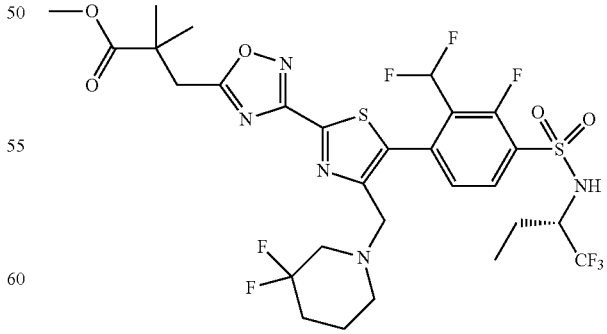

To a solution of (S)-methyl 3-(3-(5-(2-(difluoromethyl)-3-fluoro-4-(N-(1,1,1-trifluorobutan-2-yl)sulfamoyl)phenyl)-4-formylthiazol-2-yl)-1,2,4-oxadiazol-5-yl)-2,2-dimethylpropanoate (240 mg, 0.38 mmol, Example 12, step b)

in THF (5 mL) was added 3,3-difluoropiperidine (92 mg, 0.76 mmol) and HOAc (3 drops) and the mixture was stirred at rt overnight. NaBH(OAc)₃ (180 mg, 0.84 mmol) was added portionwise and stirring was continued for an additional 4 h. The reaction mixture was then diluted with ice and extracted with EtOAc (15 mL×3). The combined organic layers were washed with brine, dried over anhydrous Na₂SO₄, filtered, concentrated to dryness, and purified by preparative TLC (PE/EtOAc=1/1) to give the title compound as a solid.

Example 12: (S)-3-(3-(5-(2-(Difluoromethyl)-3-fluoro-4-(N-(1,1,1-trifluorobutan-2-yl)sulfamoyl)phenyl)-4-((3,3-difluoropiperidin-1-yl)methyl)thiazol-2-yl)-1,2,4-oxadiazol-5-yl)-2,2-dimethylpropanoic acid

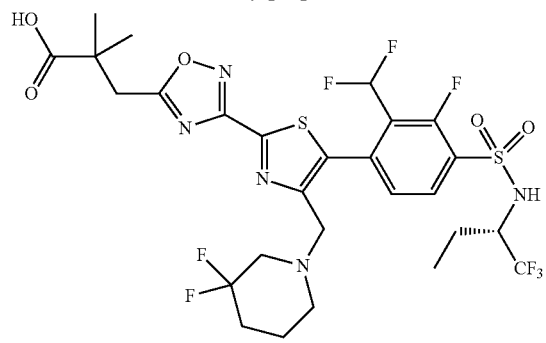

A solution of (S)-methyl 3-(3-(5-(2-(difluoromethyl)-3-fluoro-4-(N-(1,1,1-trifluorobutan-2-yl)sulfamoyl)phenyl)-4-((3,3-difluoropiperidin-1-yl)methyl)thiazol-2-yl)-1,2,4-oxadiazol-5-yl)-2,2-dimethylpropanoate (90 mg, 0.12 mmol, Example 12, step c) and LiOH.H₂O (27 mg, 0.64 mmol) in MeOH (8 mL) and water (4 mL) was stirred at rt overnight. The reaction mixture was then concentrated to dryness, diluted with water (15 mL), adjusted to pH 7 with aqueous HCl (2 N) and extracted with EtOAc (8 mL×3). The combined organic layers were washed with brine, dried over anhydrous Na₂SO₄, filtered, concentrated to dryness, and purified by preparative HPLC to give the title compound as a colorless solid. ¹H NMR (400 MHz, CDCl₃): δ ppm 8.03 (t, J=7.6 Hz, 1H), 7.41 (d, J=8.4 Hz, 1H), 6.76 (t, J=52.8 Hz, 1H), 3.93 (br s, 1H), 3.64 (s, 2H), 3.28 (s, 2H), 2.56 (t, J=11.6 Hz, 2H), 2.36 (br s, 2H), 1.95-1.89 (m, 1H), 1.82-1.56 (m, 5H), 1.38 (s, 6H), 1.11 (t, J=7.6 Hz, 3H). MS (ESI): m/z 720.1 [M+H]⁺.

Example 12/1: (S)-3-(3-(5-(2,3-Dichloro-4-(N-(1,1,1-trifluorobutan-2-yl)sulfamoyl)phenyl)-4-((3,3-difluoropiperidin-1-yl)methyl)thiazol-2-yl)-1,2,4-oxadiazol-5-yl)-2,2-dimethylpropanoic acid

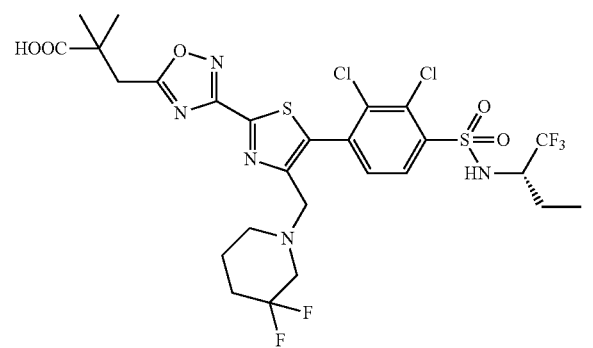 [SMILES: CC[C@H](NS(=O)(=O)c1ccc(-c2sc(-c3noc(CC(C)(C)C(=O)O)n3)nc2CN2CCCC(F)(F)C2)c(Cl)c1Cl)C(F)(F)F]

The title compound was prepared as described for the synthesis of Example 12, using in step a (S)-4-bromo-2,3-dichloro-N-(1,1,1-trifluorobutan-2-yl)benzenesulfonamide (Intermediate 4/3) in place of (S)-4-bromo-3-(difluoromethyl)-2-fluoro-N-(1,1,1-trifluorobutan-2-yl)benzenesulfonamide. ¹H NMR (400 MHz, CDCl₃): δ ppm 8.05 (d, J=8.0 Hz, 1H), 7.61 (d, J=8.0 Hz, 1H), 5.42 (br s, 1H), 3.92-3.86 (m, 1H), 3.68 (s, 2H), 3.28 (s, 2H), 2.60-2.54 (m, 2H), 2.36 (s, 2H), 1.93-1.86 (m, 1H), 1.88-1.75 (m, 5H), 1.35 (s, 6H), 1.09 (t, J=7.2 Hz, 3H). MS (ESI): m/z 720.0 [M+H]⁺.

Example 12/2: 3-(3-(5-(2,3-Dichloro-4-(N—((S)-1,1,1-trifluorobutan-2-yl)sulfamoyl)phenyl)-4-(((S)-4,4-difluoro-2-methylpyrrolidin-1-yl)methyl)thiazol-2-yl)-1,2,4-oxadiazol-5-yl)-2,2-dimethylpropanoic acid

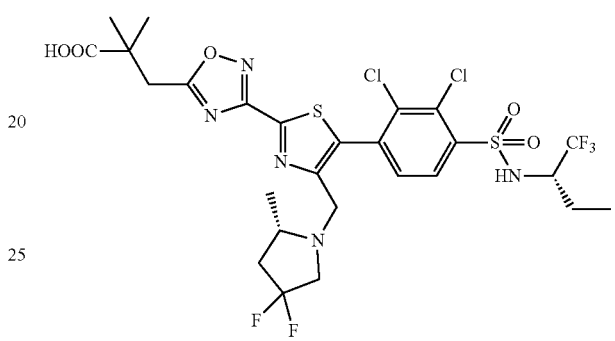

The title compound was prepared as described for the synthesis of Example 12, using in step a (S)-4-bromo-2,3-dichloro-N-(1,1,1-trifluorobutan-2-yl)benzenesulfonamide (Intermediate 4/3) in place of (S)-4-bromo-3-(difluoromethyl)-2-fluoro-N-(1,1,1-trifluorobutan-2-yl)benzenesulfonamide and in step c (S)-4,4-difluoro-2-methylpyrrolidine hydrochloride (Intermediate 16, salt converted to free base with TEA prior to the coupling) in place of 3,3-difluoropiperidine. ¹H NMR (400 MHz, CDCl₃): δ ppm 8.05 (d, J=8.2 Hz, 1H), 7.58 (d, J=8.2 Hz, 1H), 5.44 (br s, 1H), 4.01 (d, J=13.2 Hz, 1H), 3.97-3.89 (m, 1H), 3.47 (d, J=13.2 Hz, 1H), 3.29 (s, 2H), 3.18-3.15 (m, 1H), 2.71-2.60 (m, 2H), 2.28-2.24 (m, 1H), 1.93-1.91 (m, 1H), 1.76-1.62 (m, 2H), 1.38 (s, 6H), 1.12 (t, J=7.2 Hz, 3H), 0.97 (d, J=6.0 Hz, 3H). MS (ESI): m/z 720.1 [M+H]⁺.

Example 12/3: 3-(3-(4-(((S)-4,4-Difluoro-2-methylpyrrolidin-1-yl)methyl)-5-(2-(difluoromethyl)-3-fluoro-4-(N—((S)-1,1,1-trifluorobutan-2-yl)sulfamoyl)phenyl)thiazol-2-yl)-1,2,4-oxadiazol-5-yl)-2,2-dimethylpropanoic acid

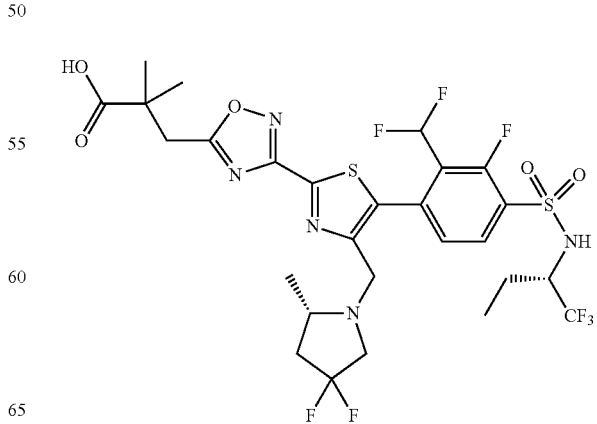

The title compound was prepared as described for the synthesis of Example 12, using in step c (S)-4,4-difluoro-2-methylpyrrolidine hydrochloride (Intermediate 16, salt converted to free base with TEA prior to the coupling) in place of 3,3-difluoropiperidine. $^1$H NMR (400 MHz, CDCl$_3$): δ ppm 8.04 (d, J=7.2 Hz, 1H), 7.38 (d, J=7.6 Hz, 1H), 6.72 (t, J=52.8 Hz, 1H), 3.92 (d, J=13.6 Hz, 1H), 3.43 (d, J=10.8 Hz, 1H), 3.28 (s, 2H), 3.19-3.10 (m, 2H), 2.69-2.62 (m, 2H), 2.29-2.23 (m, 1H), 1.95-1.59 (m, 3H), 1.38 (s, 6H), 1.13 (t, J=7.2 Hz, 3H), 0.90 (d, J=6.0 Hz, 3H). MS (ESI): m/z 720.2 [M+H]$^+$.

Example 12/4: 3-(3-(5-(2-(Difluoromethyl)-3-fluoro-4-(N—((S)-1,1,1-trifluorobutan-2-yl)sulfamoyl)phenyl)-4-(((S)-2-methylpyrrolidin-1-yl)methyl)thiazol-2-yl)-1,2,4-oxadiazol-5-yl)-2,2-dimethylpropanoic acid

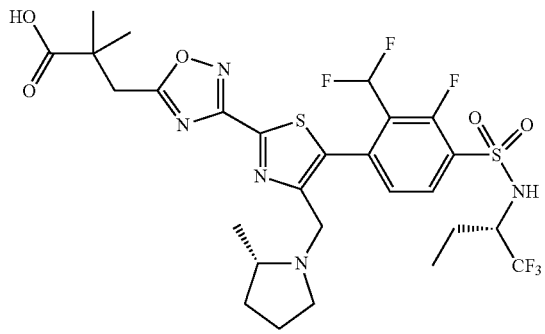 [SMILES: CC[C@H](NS(=O)(=O)c1ccc(-c2sc(-c3noc(CC(C)(C)C(=O)O)n3)nc2CN2CCC[C@@H]2C)c(C(F)F)c1F)C(F)(F)F]

The title compound was prepared as described for the synthesis of Example 12, using in step c (S)-2-methylpyrrolidine in place of 3,3-difluoropiperidine. $^1$H NMR (500 MHz, CDCl$_3$): δ ppm 8.05 (t, J=7.5 Hz, 1H), 7.46 (d, J=8.0 Hz, 1H), 6.73 (t, J=52.5 Hz, 1H), 4.02-3.91 (m, 2H), 3.53 (d, J=13.5 Hz, 1H), 3.25 (s, 2H), 3.16-3.14 (m, 1H), 2.67-2.64 (m, 1H), 2.48-2.44 (m, 1H), 1.92-1.89 (m, 2H), 1.76-1.74 (m, 1H), 1.65-1.62 (m, 2H), 1.47-1.44 (m, 1H), 1.33 (d, J=10.5 Hz, 6H), 1.10 (t, J=7.5 Hz, 3H), 1.01 (d, J=6.5 Hz, 3H). MS (ESI): m/z 684.2 [M+H]$^+$.

Example 12/5: 3-(3-(4-(((S)-3,3-Difluoro-2-methylpyrrolidin-1-yl)methyl)-5-(2-(difluoromethyl)-3-fluoro-4-(N—((S)-1,1,1-trifluorobutan-2-yl)sulfamoyl)phenyl)thiazol-2-yl)-1,2,4-oxadiazol-5-yl)-2,2-dimethylpropanoic acid

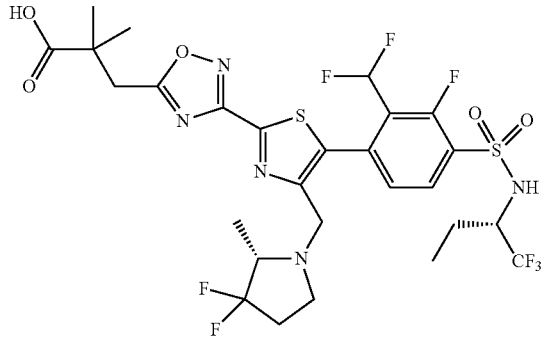 [SMILES: CC[C@H](NS(=O)(=O)c1ccc(-c2sc(-c3noc(CC(C)(C)C(=O)O)n3)nc2CN2CCC(F)(F)[C@@H]2C)c(C(F)F)c1F)C(F)(F)F]

The title compound was prepared as described for the synthesis of Example 12, using in step c (S)-3,3-difluoro-2-methylpyrrolidine (Intermediate 17, salt converted to free base with TEA prior to the coupling) in place of 3,3-difluoropiperidine. $^1$H NMR (500 MHz, CDCl$_3$): δ ppm 8.04 (t, J=7.5 Hz, 1H), 7.37 (d, J=8.0 Hz, 1H), 6.84-6.62 (m, 1H), 3.94-3.84 (m, 2H), 3.43-3.40 (m, 1H), 3.30-3.24 (m, 2H), 2.92-2.91 (m, 1H), 2.54-2.51 (m, 1H), 2.36-2.30 (m, 1H), 2.14-2.09 (m, 2H), 1.94-1.91 (m, 1H), 1.66-1.58 (m, 1H), 1.36 (s, 6H), 1.12 (t, J=7.5 Hz, 3H), 0.91-0.86 (m, 3H). MS (ESI): m/z 720.0 [M+H]$^+$.

Example 12/6: (S)-3-(3-(4-((4,4-Difluoro-2,2-dimethylpyrrolidin-1-yl)methyl)-5-(2-(difluoromethyl)-3-fluoro-4-(N-(1,1,1-trifluorobutan-2-yl)sulfamoyl)phenyl)thiazol-2-yl)-1,2,4-oxadiazol-5-yl)-2,2-dimethylpropanoic acid

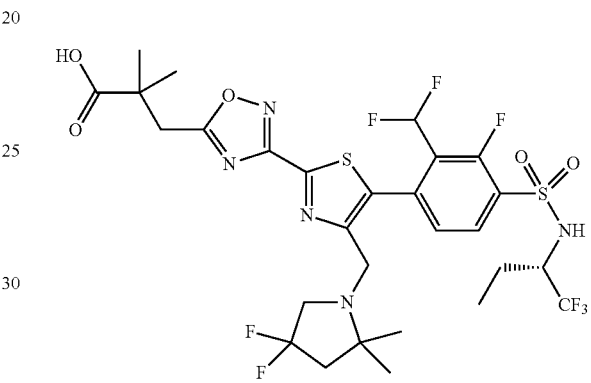

The title compound was prepared as described for the synthesis of Example 12, using in step c 4,4-difluoro-2,2-dimethylpyrrolidine in place of 3,3-difluoropiperidine. $^1$H NMR (500 MHz, CDCl$_3$): δ ppm 8.03 (t, J=7.8 Hz, 1H), 7.36 (d, J=8.0 Hz, 1H), 6.70 (t, J=52.5 Hz, 1H), 3.94-3.91 (m, 1H), 3.62-3.57 (m, 2H), 3.27 (s, 2H), 2.97 (t, J=13.7 Hz, 2H), 2.03-1.90 (m, 3H), 1.65-1.58 (m, 1H), 1.35 (s, 6H), 1.12 (t, J=7.5 Hz, 3H), 0.90 (s, 6H). MS (ESI): m/z 734.0 [M+H]$^+$.

Example 12/7: 3-(3-(5-(2-(Difluoromethyl)-3-fluoro-4-(N—((S)-1,1,1-trifluorobutan-2-yl)sulfamoyl)phenyl)-4-(((R)-2-(fluoromethyl)pyrrolidin-1-yl)methyl)thiazol-2-yl)-1,2,4-oxadiazol-5-yl)-2,2-dimethylpropanoic acid

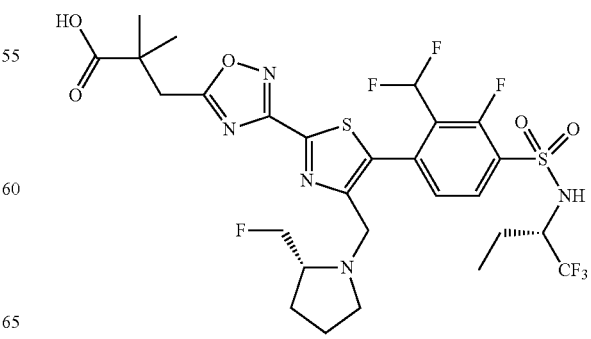

The title compound was prepared as described for the synthesis of Example 12, using in step c (R)-2-(fluoromethyl)pyrrolidine in place of 3,3-difluoropiperidine. $^1$H NMR (500 MHz, CDCl$_3$): δ ppm 8.03 (t, J=7.5 Hz, 1H), 7.39 (d, J=8.0 Hz, 1H), 6.69 (t, J=52.5 Hz, 1H), 5.31 (br s, 1H), 4.19-3.92 (m, 4H), 3.67 (d, J=13.5 Hz, 1H), 3.28 (s, 2H), 2.90-2.83 (m, 2H), 2.39-2.34 (m, 1H), 1.93-1.82 (m, 2H), 1.68-1.63 (m, 3H), 1.48-1.45 (m, 1H), 1.39 (d, J=1.5 Hz, 6H), 1.11 (t, J=7.5 Hz, 3H). MS (ESI): m/z 702.2 [M+H]$^+$.

Example 13: Step a 5-(5-Bromo-4-(cyclohexylmethyl)thiazol-2-yl)-3-methyl-1,2,4-oxadiazole

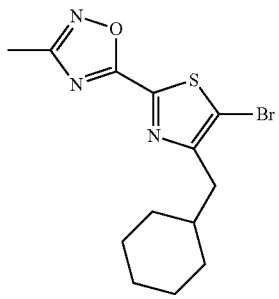 [SMILES: Cc1noc(-c2nc(CC3CCCCC3)c(Br)s2)n1]

To a stirred solution of ethyl 5-bromo-4-(cyclohexylmethyl)thiazole-2-carboxylate (200 mg, 0.602 mmol, prepared as described in WO2013/178362, Example 6, step 3) in toluene (10 mL) was added N-hydroxyacetimidamide (67 mg, 0.90 mmol), and K$_2$CO$_3$ (126 mg, 0.904 mmol), and the solution was refluxed for 24 h. After cooling to rt, the resulting solution was diluted with EtOAc and water. The organic layer was washed with brine, dried over anhydrous Na$_2$SO$_4$, filtered, concentrated to dryness, and purified by FCC on silica gel (EtOAc/PE=1/5) to give the title compound as a colorless solid.

Example 13: N-(tert-Butyl)-4-(4-(cyclohexylmethyl)-2-(3-methyl-1,2,4-oxadiazol-5-yl)thiazol-5-yl)naphthalene-1-sulfonamide

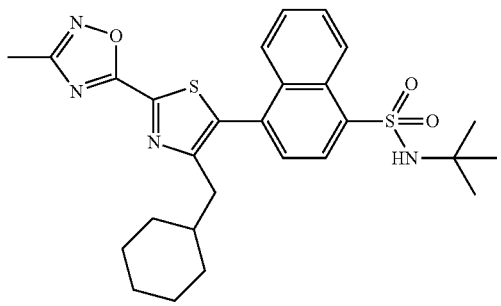 [SMILES: Cc1noc(-c2nc(CC3CCCCC3)c(-c3ccc(S(=O)(=O)NC(C)(C)C)c4ccccc34)s2)n1]

A solution of 5-(5-bromo-4-(cyclohexylmethyl)thiazol-2-yl)-3-methyl-1,2,4-oxadiazole (100 mg, 0.292 mmol, Example 13, step a), N-(tert-butyl)-4-(4,4,5,5-tetramethyl-1,3,2-dioxaborolan-2-yl)naphthalene-1-sulfonamide (142 mg, 0.366 mmol, Intermediate 18), Pd(dppf)Cl$_2$ (24 mg, 29 μmol), and Na$_2$CO$_3$ (2 M in water, 1.6 mL, 3.2 mmol) in DME (5 mL) was purged with nitrogen for 15 min and then heated to reflux overnight. After allowing to cool to rt, the resulting solution was diluted with EtOAc and water. The layers were separated, and the aqueous layer was extracted with EtOAc. The combined organic layers were washed with brine, dried over anhydrous Na$_2$SO$_4$, filtered, concentrated to dryness, and purified by FCC on silica gel (EtOAc/PE=1/1) to give the title compound as a colorless solid. $^1$H NMR (400 MHz, DMSO-d$_6$): δ ppm 8.82 (d, J=8.2 Hz, 1H), 8.29 (d, J=8.2 Hz, 1H), 7.95 (s, 1H), 7.80-7.75 (m, 3H), 7.71-7.67 (m, 1H), 2.48 (s, 3H), 2.43-2.42 (m, 2H), 1.65-1.61 (m, 1H), 1.46-1.44 (m, 5H), 1.09 (s, 9H), 1.04-0.85 (m, 3H), 0.67-0.59 (m, 2H). MS (ESI): m/z 525.2 [M+H]$^+$.

Example 14: Step a (4-(Cyclobutylmethyl)thiazol-2-yl)methanol

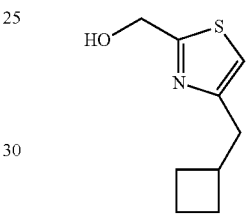

To a solution of ethyl 4-(cyclobutylmethyl)thiazole-2-carboxylate (600 mg, 2.7 mmol, Intermediate 1) in MeOH (10 mL) was slowly added NaBH$_4$ (310 mg, 8.1 mmol) at 0° C., and the mixture was stirred at this temperature for 6 h. Water was then added, and the mixture was extracted with EtOAc three times. The combined organic layers were washed with brine, dried over anhydrous Na$_2$SO$_4$, filtered, and concentrated to dryness to give the title compound as a brown oil.

Example 14: Step b 4-(Cyclobutylmethyl)thiazole-2-carbaldehyde

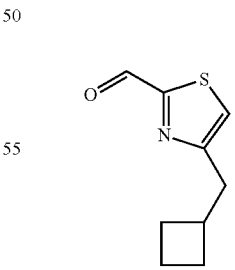

A solution of (4-(cyclobutylmethyl)thiazol-2-yl)methanol (330 mg, 1.8 mmol, Example 14, step a) and IBX (1.0 g, 3.6 mmol) in acetone (10 mL) was heated to reflux overnight. The mixture was allowed to cool, filtered, and the filtrate was concentrated to dryness to give the title compound as a brown oil.

Example 14: Step c

4-(Cyclobutylmethyl)thiazole-2-carbaldehyde oxime

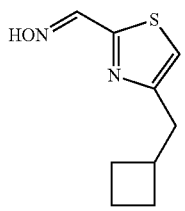

A suspension of 4-(cyclobutylmethyl)thiazole-2-carbaldehyde (280 mg, 1.6 mmol, Example 14, step b), NH$_2$OH.HCl (220 mg, 3.2 mmol), Na$_2$CO$_3$ (340 mg, 3.2 mmol) in EtOH-water (20 mL, 5:1 v/v) was stirred at rt for 1 h. The reaction was concentrated to dryness, and the residue was diluted with water and then extracted with EtOAc. The organic layer was washed with brine, dried over anhydrous Na$_2$SO$_4$, filtered and concentrated to dryness to afford the title compound.

Example 14: Step d

Methyl 3-(3-(4-(cyclobutylmethyl)thiazol-2-yl)isoxazol-5-yl)-2,2-dimethylpropanoate

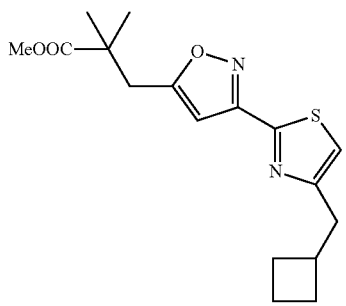 [SMILES: COC(=O)C(C)(C)Cc1cc(-c2nc(CC3CCC3)cs2)no1]

A mixture of 4-(cyclobutylmethyl)thiazole-2-carbaldehyde oxime (250 mg, 1.4 mmol, Example 14, step c) and methyl 2,2-dimethylpent-4-ynoate (190 mg, 1.4 mmol) in DCM (5 mL) was cooled to 0° C. A sodium hypochlorite solution (5% chlorine, 5 mL, 4 mmol) was added dropwise to the solution. The mixture was stirred overnight at rt, and then DCM (20 mL) was added. The layers were separated, and the organic layer was washed sequentially with water, 1 M aqueous HCl, saturated aqueous NaHCO$_3$, and brine, dried over anhydrous MgSO$_4$, filtered and concentrated to dryness. The residue was purified by FCC on silica gel (PE/EtOAc=8:1) to give the title compound as a colorless solid.

Example 14: (S)-3-(3-(4-(Cyclobutylmethyl)-5-(2,3-dichloro-4-(N-(1,1,1-trifluoropropan-2-yl)sulfamoyl)phenyl)thiazol-2-yl)isoxazol-5-yl)-2,2-dimethylpropanoic acid

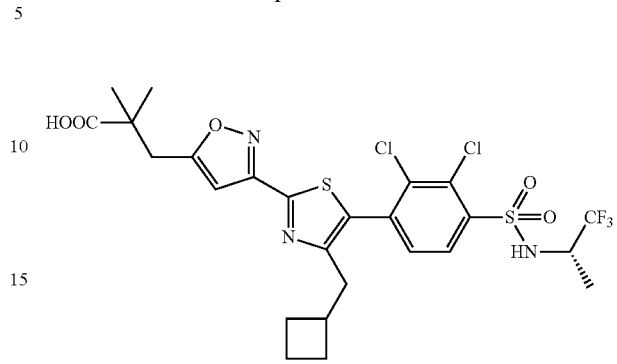

The title compound was prepared as described for the synthesis of Example 3, using in step a methyl 3-(3-(4-(cyclobutylmethyl)thiazol-2-yl)isoxazol-5-yl)-2,2-dimethylpropanoic acid (Example 14, step d) in place of methyl 3-(5-(4-(cyclobutylmethyl)thiazol-2-yl)-1,3,4-oxadiazol-2-yl)-2,2-dimethylpropanoate and (S)-4-bromo-2,3-dichloro-N-(1,1,1-trifluoropropan-2-yl)benzenesulfonamide (Intermediate 4/2) in place of 4-bromo-N-(tert-butyl)-2,3-dichlorobenzenesulfonamide. $^1$H NMR (400 MHz, CD$_3$OD): δ ppm 8.18 (d, J=6.6 Hz, 1H), 7.65 (d, J=6.8 Hz, 1H), 6.77 (s, 1H), 4.13-4.10 (m, 1H), 3.16 (s, 2H), 2.74-2.68 (m, 3H), 2.02-1.98 (m, 2H), 1.83-1.79 (m, 2H), 1.74-1.72 (m, 2H), 1.60-1.56 (m, 3H), 1.37 (d, J=5.6 Hz, 3H), 1.30 (m, 3H). MS (ESI): m/z 640.0 [M+H]$^+$.

Example 15: Step a

4-(Cyclobutylmethyl)thiazol-2-amine

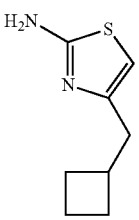
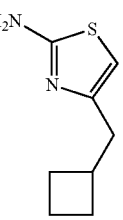

Thiourea (71 mg, 0.93 mmol), 1-bromo-3-cyclobutylpropan-2-one (177 mg, 0.927 mmol, Intermediate 1, step d) in EtOH (3 mL) was stirred at 75° C. overnight. Water was added, and the mixture was extracted with EtOAc three times. The combined organic layers were washed with brine, dried over anhydrous Na$_2$SO$_4$, filtered and concentrated to dryness to give a residue, which was purified by FCC on silica gel (PE/EtOAc=8:1) to afford the title compound.

Example 15: Step b

2-Bromo-4-(cyclobutylmethyl)thiazole

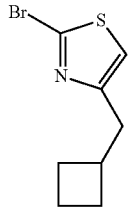

To a solution of 4-(cyclobutylmethyl)thiazol-2-amine (122 mg, 0.726 mmol, Example 15, step a) and isoamyl nitrite (92 mg, 0.79 mmol) in acetonitrile (8 mL) was added CuBr (124 mg, 0.864 mmol). The mixture was stirred at 70° C. for 1 h and then water was added. The mixture was extracted with EtOAc three times and the combined organic layers were washed with brine, dried over anhydrous $Na_2SO_4$, filtered, and concentrated. The residue was purified by FCC on silica gel (PE/EtOAc=20:1) to give the title compound as a brown oil.

Example 15: Step c

Methyl 3-(3-bromophenyl)-2,2-dimethylpropanoate

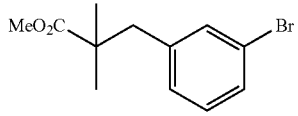

To a solution of methyl isobutyrate (129 mg, 1.26 mmol) in dry THF (10 mL) was added LDA (0.92 mL, 2.5 M solution in THF/n-heptane/ethylbenzene, 2.3 mmol) under Ar at −78° C., and the mixture was stirred at this temperature for 1 h. 1-Bromo-3-(bromomethyl)benzene (286 mg, 1.15 mmol) was added slowly and the solution was stirred at −78° C. for 4 h. The mixture was quenched with aqueous $NH_4Cl$ solution, allowed to warm to rt, and extracted with EtOAc three times. The combined organic layers were washed with brine, dried over anhydrous $Na_2SO_4$, filtered, and concentrated to dryness to give the title compound as a yellow solid.

Example 15: Step d

Methyl 2,2-dimethyl-3-(3-(4,4,5,5-tetramethyl-1,3,2-dioxaborolan-2-yl)phenyl)propanoate

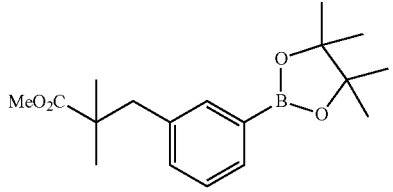 [SMILES: COC(=O)C(C)(C)Cc1cccc(B2OC(C)(C)C(C)(C)O2)c1]

To a solution of methyl 3-(3-bromophenyl)-2,2-dimethylpropanoate (132 mg, 487 μmol, Example 15, step c), bis(pinacolato)diboron (167 mg, 658 μmol) and KOAc (96 mg, 0.98 mmol) in dioxane (4 mL) was added $Pd(dppf)Cl_2$ (15 mg) under Ar. The mixture was stirred at 80° C. overnight. Water was added, and the mixture was extracted with EtOAc three times. The combined organic layers were washed with brine, dried over anhydrous $Na_2SO_4$, filtered, and concentrated to dryness. The yellow residue was purified by FCC on silica gel (PE/EtOAc=20:1) to give the title compound as a colorless solid.

Example 15: Step e

Methyl 3-(3-(4-(cyclobutylmethyl)thiazol-2-yl)phenyl)-2,2-dimethylpropanoate

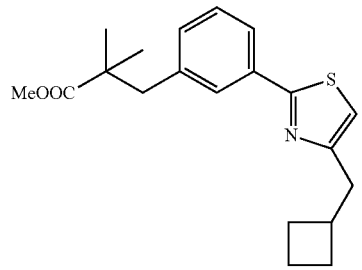 [SMILES: COC(=O)C(C)(C)Cc1cccc(-c2nc(CC3CCC3)cs2)c1]

To a solution of 2-bromo-4-(cyclobutylmethyl)thiazole (56 mg, 0.24 mmol, Example 15, step b), methyl 2,2-dimethyl-3-(3-(4,4,5,5-tetramethyl-1,3,2-dioxaborolan-2-yl)phenyl)propanoate (84 mg, 0.26 mmol, Example 15, step d) and $Na_2CO_3$ (64 mg, 0.60 mmol) in dioxane/water (3 mL, 10:1 v/v) was added $Pd(PPh_3)_4$ (6 mg, 0.0052 mmol) under Ar. The mixture was stirred at 100° C. overnight. The reaction mixture was allowed to cool before water was added, and the resulting mixture was extracted with EtOAc three times. The combined organic layers were washed with brine, dried over anhydrous $Na_2SO_4$ and filtered. The filtrate was concentrated to dryness, and the yellow residue was purified by FCC on silica gel (PE/EtOAc=8:1) to give the title compound as a colorless solid.

Example 15: (S)-3-(3-(4-(Cyclobutylmethyl)-5-(2,3-dichloro-4-(N-(1,1,1-trifluoropropan-2-yl)sulfamoyl)phenyl)thiazol-2-yl)phenyl)-2,2-dimethylpropanoic acid

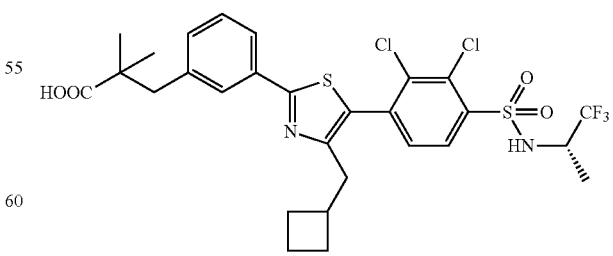

The title compound was prepared as described for the synthesis of Example 3, using in step a methyl 3-(3-(4-(cyclobutylmethyl)thiazol-2-yl)phenyl)-2,2-dimethylpropanoate (Example 15, step e) in place of methyl 3-(5-(4-

(cyclobutylmethyl)thiazol-2-yl)-1,3,4-oxadiazol-2-yl)-2,2-dimethylpropanoate and (S)-4-bromo-2,3-dichloro-N-(1,1,1-trifluoropropan-2-yl)benzenesulfonamide (Intermediate 4/2) in place of 4-bromo-N-(tert-butyl)-2,3-dichlorobenzenesulfonamide. $^1$H NMR (400 MHz, DMSO-d$_6$): δ ppm 12.40 (s, 1H), 9.22 (d, J=9.2 Hz, 1H), 8.09 (d, J=9.2 Hz, 1H), 7.81-7.45 (m, 3H), 7.43 (t, J=7.8 Hz, 1H), 7.30 (d, J=7.8 Hz, 1H), 4.21-4.16 (m, 1H), 2.89 (s, 2H), 2.67-2.62 (m, 3H), 1.97-1.90 (m, 2H), 1.77-1.62 (m, 2H), 1.58-1.51 (m, 2H), 1.26 (d, J=6.8 Hz, 3H), 1.12 (s, 6H). MS (ESI): m/z 649.1 [M+H]$^+$.

Example 16: (S)-3-(6-(4-(Cyclobutylmethyl)-5-(8-(N-(1,1,1-trifluoropropan-2-yl)sulfamoyl)isoquinolin-5-yl)thiazol-2-yl)pyridin-2-yl)-2,2-dimethylpropanoic acid

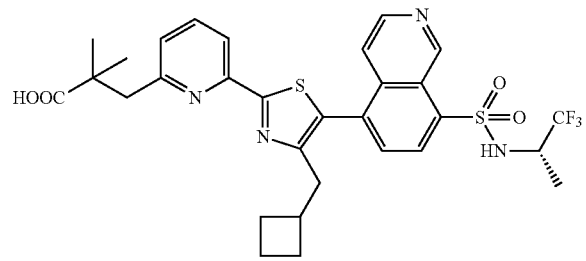 [SMILES: C[C@H](NS(=O)(=O)c1ccc(-c2sc(-c3cccc(CC(C)(C)C(=O)O)n3)nc2CC2CCC2)c2ccncc12)C(F)(F)F]

The title compound was prepared as described for the synthesis of Example 3, using in step a ethyl 3-(6-(4-(cyclobutylmethyl)thiazol-2-yl)pyridin-2-yl)-2,2-dimethylpropanoate (Intermediate 14) in place of methyl 3-(5-(4-(cyclobutylmethyl)thiazol-2-yl)-1,3,4-oxadiazol-2-yl)-2,2-dimethylpropanoate and (5)-5-bromo-N-(1,1,1-trifluoropropan-2-yl)isoquinoline-8-sulfonamide (Intermediate 4/16) in place of 4-bromo-N-(tert-butyl)-2,3-dichlorobenzenesulfonamide. $^1$H NMR (400 MHz, DMSO-d$_6$): δ ppm 10.12 (s, 1H), 9.30 (br s, 1H), 8.72 (d, J=5.6 Hz, 1H), 8.35 (d, J=7.6 Hz, 1H), 8.02-8.00 (m, 2H), 7.91 (t, J=7.6 Hz, 1H), 7.70 (d, J=6.0 Hz, 1H), 7.35 (d, J=8.0 Hz, 1H), 4.18-4.15 (m, 1H), 3.02 (s, 2H), 2.58 (s, 3H), 1.88-1.82 (m, 2H), 1.70-1.53 (m, 2H), 1.44-1.38 (m, 2H), 1.15 (s, 6H), 1.09 (d, J=7.2 Hz, 3H). MS (ESI): m/z 633.3 [M+H]$^+$.

Example 17: (S)-3-(6-(4-(Cyclobutylmethyl)-5-(2,3-dichloro-4-(N-(1,1,1-trifluoropropan-2-yl)sulfamoyl)phenyl)thiazol-2-yl)pyrimidin-4-yl)-2,2-dimethylpropanoic acid

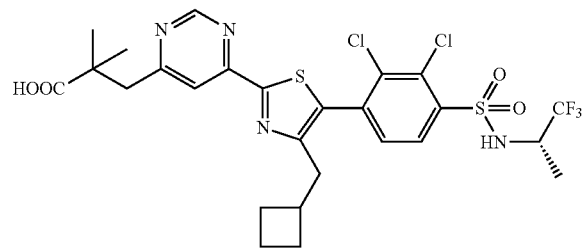 [SMILES: C[C@H](NS(=O)(=O)c1ccc(-c2sc(-c3cc(CC(C)(C)C(=O)O)ncn3)nc2CC2CCC2)c(Cl)c1Cl)C(F)(F)F]

The title compound was prepared as described for the synthesis of Example 3, using in step a ethyl 3-(6-(4-(cyclobutylmethyl)thiazol-2-yl)pyrimidin-4-yl)-2,2-dimethylpropanoate (Intermediate 15) in place of methyl 3-(5-(4-(cyclobutylmethyl)thiazol-2-yl)-1,3,4-oxadiazol-2-yl)-2,2-dimethylpropanoate and (S)-4-bromo-2,3-dichloro-N-(1,1,1-trifluoropropan-2-yl)benzenesulfonamide (Intermediate 4/2) in place of 4-bromo-N-(tert-butyl)-2,3-dichlorobenzenesulfonamide. $^1$H NMR (400 MHz, DMSO-d$_6$): δ ppm 12.34 (s, 1H), 9.22 (d, J=9.2 Hz, 1H), 9.14 (s, 1H), 8.11 (d, J=7.8 Hz, 1H), 7.98 (s, 1H), 7.76 (d, J=7.8 Hz, 1H), 4.22-4.16 (m, 1H), 3.11 (s, 2H), 2.70-2.60 (m, 3H), 1.97-1.90 (m, 2H), 1.75-1.65 (m, 2H), 1.57-1.50 (m, 2H), 1.26 (d, J=6.8 Hz, 3H), 1.19 (s, 6H). MS (ESI): m/z 651.1 [M+H]$^+$.

Example 17/1: (S)-3-(6-(4-(Cyclobutylmethyl)-5-(8-(N-(1,1,1-trifluoropropan-2-yl)sulfamoyl)isoquinolin-5-yl)thiazol-2-yl)pyrimidin-4-yl)-2,2-dimethylpropanoic acid

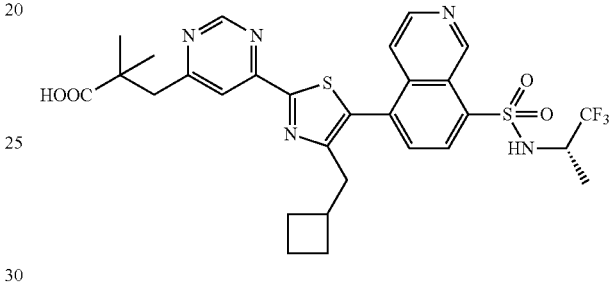

The title compound was prepared as described for the synthesis of Example 3, using in step a ethyl 3-(6-(4-(cyclobutylmethyl)thiazol-2-yl)pyrimidin-4-yl)-2,2-dimethylpropanoate (Intermediate 15) in place of methyl 3-(5-(4-(cyclobutylmethyl)thiazol-2-yl)-1,3,4-oxadiazol-2-yl)-2,2-dimethylpropanoate and (5)-5-bromo-N-(1,1,1-trifluoropropan-2-yl)isoquinoline-8-sulfonamide (Intermediate 4/16) in place of 4-bromo-N-(tert-butyl)-2,3-dichlorobenzenesulfonamide. $^1$H NMR (400 MHz, CDCl$_3$): δ ppm 10.31 (s, 1H), 9.14 (s, 1H), 8.72 (d, J=6.0 Hz, 1H), 8.43 (d, J=7.4 Hz, 1H), 8.08-8.03 (m, 2H), 7.84 (d, J=7.4 Hz, 1H), 7.72 (d, J=6.0 Hz, 1H), 4.04 (s, 1H), 3.22 (s, 2H), 2.68-2.61 (m, 3H), 1.94-1.90 (m, 2H), 1.77-1.61 (m, 2H), 1.47-1.40 (m, 2H), 1.37-1.31 (m, 9H). MS (ESI): m/z 634.1 [M+H]$^+$.

Example 18: (S)-3-(4-(Cyclobutylmethyl)-5-(2,3-dichloro-4-(N-(1,1,1-trifluoropropan-2-yl)sulfamoyl)phenyl)-[2,5'-bithiazol]-2'-yl)-2,2-dimethylpropanoic acid

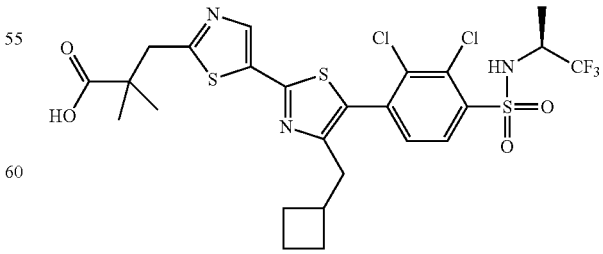

The title compound was prepared as described for the synthesis of Example 15, using in step e ethyl 2,2-dimethyl-3-(5-(4,4,5,5-tetramethyl-1,3,2-dioxaborolan-2-yl)thiazol- 2-yl)propanoate (Intermediate 12) in place of methyl 2,2-dimethyl-3-(3-(4,4,5,5-tetramethyl-1,3,2-dioxaborolan-2-yl)phenyl)propanoate. $^1$H NMR (500 MHz, CDCl$_3$): δ ppm 8.10-8.06 (m, 2H), 7.44 (d, J=8.5 Hz, 1H), 5.40 (d, J=9.5 Hz, 1H), 4.11-4.07 (m, 1H), 3.35 (s, 2H), 2.66-2.60 (m, 3H), 1.98-1.95 (m, 2H), 1.81-1.69 (m, 2H), 1.55-1.51 (m, 2H), 1.42 (d, J=7.0 Hz, 3H), 1.36 (s, 6H). MS (ESI): m/z 656.1 [M+H]$^+$.

The compounds of Example 19-24 can be made according to the procedures described below.

Example 19: (S)-2-(4-(4-((4,4-Difluoro-2-methylpyrrolidin-1-yl)methyl)-2-(5-(2-hydroxypropan-2-yl)-1,3,4-oxadiazol-2-yl)thiazol-5-yl)-3-(difluoromethyl)phenyl)-1,1,1,3,3,3-hexafluoropropan-2-ol

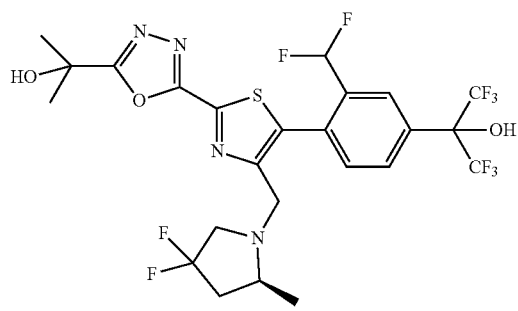 [SMILES: C[C@H]1CC(F)(F)CN1Cc1nc(-c2nnc(C(C)(C)O)o2)sc1-c1ccc(C(O)(C(F)(F)F)C(F)(F)F)cc1C(F)F]

The title compound can be prepared as described in Example 6, using in step a 2-(4-bromo-3-(difluoromethyl)phenyl)-1,1,1,3,3,3-hexafluoropropan-2-ol (Intermediate 11) in place of (S)-4-bromo-2,3-dichloro-N-(1,1,1-trifluorobutan-2-yl)benzenesulfonamide and in step c (S)-4,4-difluoro-2-methylpyrrolidine hydrochloride (Intermediate 16, salt can be converted to the free base with TEA prior to the coupling) in place of 3,3-difluoropiperidine.

Example 20: Step a (S)-4-((4,4-Difluoro-2-methylpyrrolidin-1-yl)methyl)-5-(2-(difluoromethyl)-4-(1,1,1,3,3,3-hexafluoro-2-hydroxypropan-2-yl)phenyl)thiazole-2-carbohydrazide

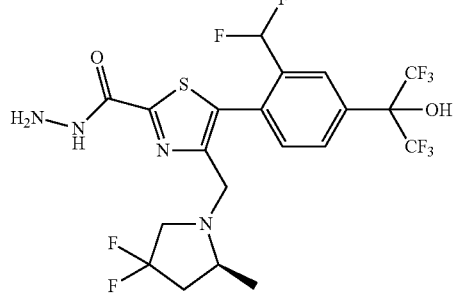

The title compound can be prepared as described in Example 6, steps a-d, using in step a 2-(4-bromo-3-(difluoromethyl)phenyl)-1,1,1,3,3,3-hexafluoropropan-2-ol (Intermediate 11) in place of (S)-4-bromo-2,3-dichloro-N-(1,1,1-trifluorobutan-2-yl)benzenesulfonamide and in step c (S)-4,4-difluoro-2-methylpyrrolidine hydrochloride (Intermediate 16, salt can be converted to the free base with TEA prior to the coupling) in place of 3,3-difluoropiperidine.

Example 20: (S)-3-(5-(4-((4,4-Difluoro-2-methylpyrrolidin-1-yl)methyl)-5-(2-(difluoromethyl)-4-(1,1,1,3,3,3-hexafluoro-2-hydroxypropan-2-yl)phenyl)thiazol-2-yl)-1,3,4-oxadiazol-2-yl)-2,2-dimethylpropanoic acid

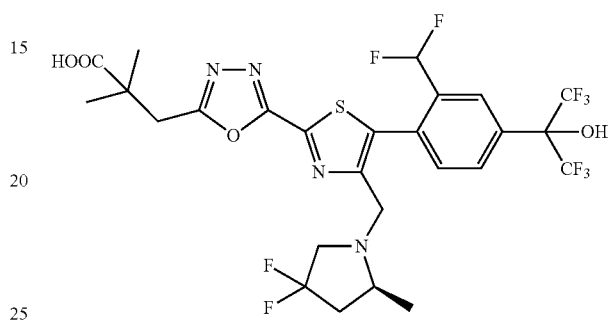

The title compound can be prepared as described in Example 7, using in step a (S)-4-((4,4-difluoro-2-methylpyrrolidin-1-yl)methyl)-5-(2-(difluoromethyl)-4-(1,1,1,3,3,3-hexafluoro-2-hydroxypropan-2-yl)phenyl)thiazole-2-carbohydrazide (Example 20, step a) in place of (S)-2,3-dichloro-4-(4-((3,3-difluoropiperidin-1-yl)methyl)-2-(hydrazine carbonyl)thiazol-5-yl)-N-(1,1,1-trifluorobutan-2-yl)benzenesulfonamide.

Example 21: (S)-3-(3-(4-((4,4-Difluoro-2-methylpyrrolidin-1-yl)methyl)-5-(2-(difluoromethyl)-4-(1,1,3,3,3-hexafluoro-2-hydroxypropan-2-yl)phenyl)thiazol-2-yl)-1,2,4-oxadiazol-5-yl)-2,2-dimethylpropanoic acid

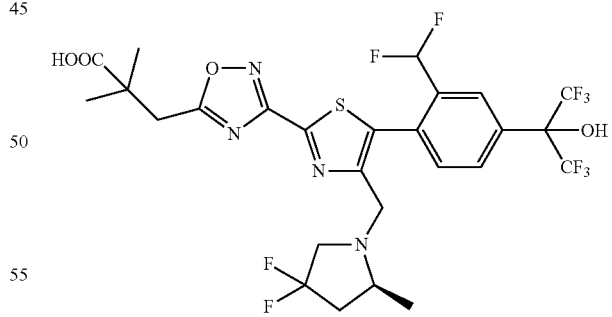

The title compound can be prepared as described in Example 12, using in step a 2-(4-bromo-3-(difluoromethyl)phenyl)-1,1,1,3,3,3-hexafluoropropan-2-ol (Intermediate 11) in place of (S)-4-bromo-3-(difluoromethyl)-2-fluoro-N-(1,1,1-trifluorobutan-2-yl)benzenesulfonamide and in step c (S)-4,4-difluoro-2-methylpyrrolidine hydrochloride (Intermediate 16, salt can be converted to the free base with TEA prior to the coupling) in place of 3,3-difluoropiperidine.

Example 22: Step a

2-(4-Bromo-3-methylphenyl)-1,1,1,3,3,3-hexafluoropropan-2-ol

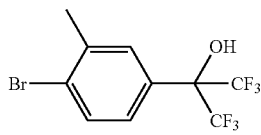

The title compound can be prepared as described in Intermediate 11, using in step b 1-bromo-4-iodo-2-methylbenzene in place of 1-bromo-2-(difluoromethyl)-4-iodobenzene.

Example 22: (S)-2-(4-(4-((4,4-Difluoro-2-methylpyrrolidin-1-yl)methyl)-2-(5-(2-hydroxypropan-2-yl)-1,3,4-oxadiazol-2-yl)thiazol-5-yl)-3-methylphenyl)-1,1,1,3,3,3-hexafluoropropan-2-ol

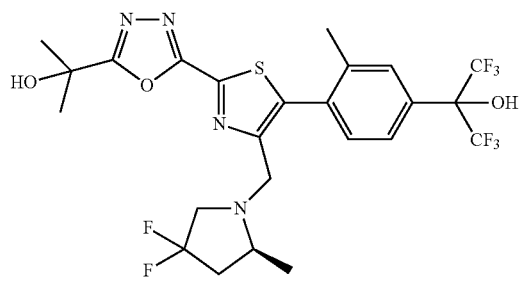 [SMILES: Cc1cc(C(O)(C(F)(F)F)C(F)(F)F)ccc1-c1sc(-c2nnc(C(C)(C)O)o2)nc1CN1CC(F)(F)C[C@@H]1C]

The title compound can be prepared as described in Example 6, using in step a 2-(4-bromo-3-methylphenyl)-1,1,1,3,3,3-hexafluoropropan-2-ol (Example 22, step a) in place of (S)-4-bromo-2,3-dichloro-N-(1,1,1-trifluorobutan-2-yl)benzenesulfonamide and in step c (S)-4,4-difluoro-2-methylpyrrolidine hydrochloride (Intermediate 16, salt can be converted to the free base with TEA prior to the coupling) in place of 3,3-difluoropiperidine.

Example 23: Step a

(S)-4-((4,4-Difluoro-2-methylpyrrolidin-1-yl)methyl)-5-(4-(1,1,1,3,3,3-hexafluoro-2-hydroxypropan-2-yl)-2-methylphenyl)thiazole-2-carbohydrazide

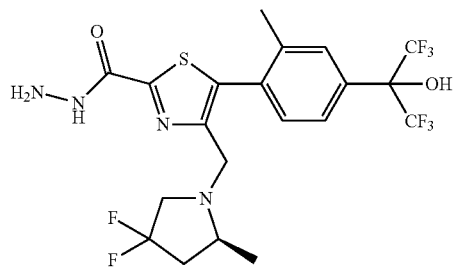 [SMILES: Cc1cc(C(O)(C(F)(F)F)C(F)(F)F)ccc1-c1sc(C(=O)NN)nc1CN1CC(F)(F)C[C@@H]1C]

The title compound can be prepared as described in Example 6, steps a-d, using in step a 2-(4-bromo-3-methylphenyl)-1,1,1,3,3,3-hexafluoropropan-2-ol (Example 22, step a) in place of (S)-4-bromo-2,3-dichloro-N-(1,1,1-trifluorobutan-2-yl)benzenesulfonamide and in step c (S)-4,4-difluoro-2-methylpyrrolidine hydrochloride (Intermediate 16, salt can be converted to the free base with TEA prior to the coupling) in place of 3,3-difluoropiperidine.

Example 23: (S)-3-(5-(4-((4,4-Difluoro-2-methylpyrrolidin-1-yl)methyl)-5-(4-(1,1,1,3,3,3-hexafluoro-2-hydroxypropan-2-yl)-2-methylphenyl)thiazol-2-yl)-1,3,4-oxadiazol-2-yl)-2,2-dimethylpropanoic acid

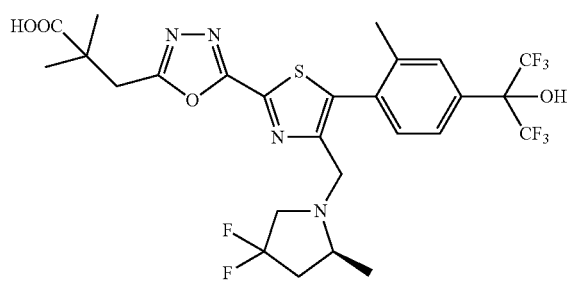 [SMILES: Cc1cc(C(O)(C(F)(F)F)C(F)(F)F)ccc1-c1sc(-c2nnc(CC(C)(C)C(=O)O)o2)nc1CN1CC(F)(F)C[C@@H]1C]

The title compound can be prepared as described in Example 7, using in step a (S)-4-((4,4-difluoro-2-methylpyrrolidin-1-yl)methyl)-5-(4(1,1,1,3,3,3-hexafluoro-2-hydroxypropan-2-yl)-2-methylphenyl)thiazole-2-carbohydrazide (Example 23, step a) in place of (S)-2,3-dichloro-4-(4-((3,3-difluoropiperidin-1-yl)methyl)-2-(hydrazinecarbonyl)thiazol-5-yl)-N-(1,1,1-trifluorobutan-2-yl)benzenesulfonamide.

Example 24: (S)-3-(3-(4-((4,4-Difluoro-2-methylpyrrolidin-1-yl)methyl)-5-(4-(1,1,1,3,3,3-hexafluoro-2-hydroxypropan-2-yl)-2-methylphenyl)thiazol-2-yl)-1,2,4-oxadiazol-5-yl)-2,2-dimethylpropanoic acid

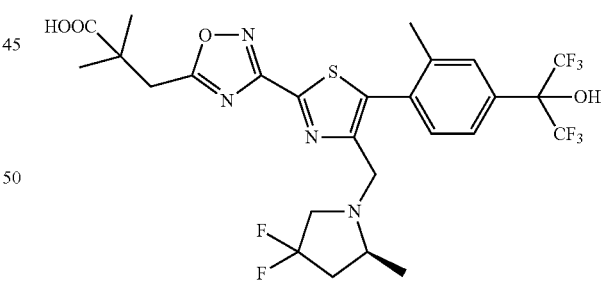

The title compound can be prepared as described in Example 12, using in step a 2-(4-bromo-3-methylphenyl)-1,1,1,3,3,3-hexafluoropropan-2-ol (Example 22, step a) in place of (S)-4-bromo-3-(difluoromethyl)-2-fluoro-N-(1,1,1-trifluorobutan-2-yl)benzenesulfonamide and in step c (5)-4,4-difluoro-2-methylpyrrolidine hydrochloride (Intermediate 16, salt can be converted to the free base with TEA prior to the coupling) in place of 3,3-difluoropiperidine.

In Vitro Biological Data

ThermoFluor® Assay

ThermoFluor® is a fluorescence based assay that estimates ligand binding affinities by measuring the effect of a ligand on protein thermal stability (Pantoliano, M. W., Petrella, E. C., Kwasnoski, J. D., Lobanov, V. S., Myslik, J., Graf, E., Carver, T., Asel, E., Springer, B. A., Lane, P., and Salemme, F. R. (2001) High-density miniaturized thermal shift assays as a general strategy for drug discovery. *J Biomol Screen* 6, 429-40, and Matulis, D., Kranz, J. K., Salemme, F. R., and Todd, M. J. (2005) Thermodynamic stability of carbonic anhydrase: measurements of binding affinity and stoichiometry using ThermoFluor. *Biochemistry* 44, 5258-66). This approach is applicable to a wide variety of systems, and rigorous in theoretical interpretation through quantitation of equilibrium binding constants ($K_D$).

In a ThermoFluor® experiment where protein stability is monitored as the temperature is steadily increased, an equilibrium binding ligand causes the midpoint of an unfolding transition ($T_m$) to occur at a higher temperature. The shift in the melting point described as a $\Delta T_m$ is proportional to the concentration and affinity of the ligand. The compound potency may be compared as a rank order of either $\Delta T_m$ values at a single compound concentration or in terms of $K_D$ values, estimated from concentration response curves.

RORγt ThermoFluor® Assay Construct

For the RORγt construct used in the ThermoFluor® assay, numbering for the nucleotide sequences was based on the reference sequence for human RORγt, transcript variant 2, NCBI Accession: NM_001001523.1 (SEQ ID NO:1). Nucleotides 850-1635 (SEQ ID NO:2) coding for the wild type human RORγt ligand binding domain (RORγt LBD) were cloned into the pHIS1 vector, a modified pET *E. coli* expression vector (Accelagen, San Diego), containing an in-frame N-terminal His-tag and a TurboTEV protease cleavage site (ENLYFQG, SEQ ID NO:3) upstream of the cloned insert sequence. The amino acid sequence for the RORγt construct used in the Thermofluor assay is shown as SEQ ID NO:4.

ThermoFluor® experiments were carried out using instruments owned by Janssen Research and Discovery, L.L.C. through its acquisition of 3-Dimensional Pharmaceuticals, Inc. 1,8-ANS (Invitrogen) was used as a fluorescent dye. Protein and compound solutions are dispensed into black 384-well polypropylene PCR microplates (Abgene) and overlayed with silicone oil (1 µL, Fluka, type DC 200) to prevent evaporation.

Bar-coded assay plates are robotically loaded onto a thermostatically controlled PCR-type thermal block and then heated at a typical ramp-rate of 1° C./min for all experiments. Fluorescence was measured by continuous illumination with UV light (Hamamatsu LC6) supplied via fiber optic and filtered through a band-pass filter (380-400 nm; >6 OD cutoff). Fluorescence emission of the entire 384-well plate was detected by measuring light intensity using a CCD camera (Sensys, Roper Scientific) filtered to detect 500±25 nm, resulting in simultaneous and independent readings of all 384 wells. Images were collected at each temperature, and the sum of the pixel intensity in a given area of the assay plate was recorded versus temperature. Reference wells contained RORγt without compounds, and the assay conditions were as follows:

0.065 mg/mL RORγt
60 µM 1,8-ANS
100 mM Hepes, pH 7.0
10 mM NaCl
2.5 mM GSH
0.002% Tween-20

Project compounds were arranged in a pre-dosed mother plate (Greiner Bio-one) wherein compounds are serially diluted in 100% DMSO by 1:2 from a high concentration of 10 mM over 12 columns within a series (column 12 is a reference well containing DMSO, no compound). The compounds were robotically dispensed directly into assay plates (1×=46 nL) using a Hummingbird capillary liquid handling instrument (Digilab). Following compound dispense, protein and dye in buffer was added to achieve the final assay volume of 3 µL, followed by 1 µL of silicone oil.

The binding affinity was estimated as described previously (Matulis, D., Kranz, J. K., Salemme, F. R., and Todd, M. J. (2005) Thermodynamic stability of carbonic anhydrase: measurements of binding affinity and stoichiometry using ThermoFluor®. *Biochemistry* 44, 5258-66) using the following thermodynamic parameters of protein unfolding:

Reference RORγt $T_m$: 47.8° C.
$\Delta H_{(Tm)}$=115 kcal/mol
$\Delta C_{p(Tm)}$=3 kcal/mol Cell Based Biological Data RORγt (Full-Length Human) Reporter Assay:

Three similar reporter assay protocols, shown below, have been used to test the functional activity of RORγt modulatory compounds on transcriptional activation driven by full-length human RORγt. All three provide similar data and can be used interchangeably.

Conditions A

Cells used in this assay were transiently co-transfected with three different plasmids, one expressing the GAL4-DNA binding domain (DBD)-RORγt fusion protein under control of a CMV promoter (NH2-Gal4-DBD:RORC—COOH in pCMV-BD, Stratagene #211342), and two reporter plasmids—the firefly luciferase reporter under control of a GAL4 promoter (pFR-Luc 2×GAL4) and Renilla luciferase reporter under control of CMV promoter (pRL-CMV, Promega #E2261). The full-length coding sequence was used for human RORγt, i.e., nucleotides 142-1635 of human RORγt, transcript variant 2, NCBI Accession: NM_001001523.1 (SEQ ID NO:1). HEK293T cells were plated at 35000 per well in 96-well plate in medium of MEM with 8.6% FBS. After 18-22 hours incubation, the transfection was carried out by using a PEI solution with 170.5 ng total DNA/well (50 ng pCMV-BD-ROR plus 20 ng of pFR-Luc reporter and 0.5 ng of pRL-CMV reporter plus 100 ng Carrier DNA (Clontech #630440) for each well). 4-6 hours after transfection, cells were treated with compounds for overnight in the medium with final concentration of FBS 1.1% and DMSO 0.1%. After overnight (16 to 20 hours) incubation, media were removed and cells were lysed with 20 µL 1× Passive Lysis Buffer (Promega) for 10-15 minutes. Luminescence was measured using a BMG LUMIstar OPTIMA plate reader, after addition of 75 µL/well firefly luciferase buffer, followed by 75 µL/well Renilla luciferase buffer. To calculate the effect of compounds on RORγt activity, firefly values were normalized against values of DMSO only and values of reference compound at saturating concentration, then further normalized against Renilla signals. IC50s were generated by plotting final Renilla normalized data against compound concentration and percent inhibition was calculated against DMSO control.

Conditions B

Cells used in this assay were transiently co-transfected with three different plasmids, one expressing the GAL4-DNA binding domain (DBD)-RORγt fusion protein under control of a CMV promoter (NH2-Gal4-DBD:RORC—COOH in pCMV-BD, Stratagene #211342), and two reporter plasmids—the firefly luciferase reporter under control of a GAL4 promoter (pFR-Luc 2×GAL4) and Renilla luciferase reporter under control of CMV promoter (pRL-CMV, Promega #E2261). The full-length coding sequence was used for human RORγt, i.e., nucleotides 142-1635 of human RORγt, transcript variant 2, NCBI Accession: NM 001001523.1 (SEQ ID NO:1). HEK293T cells were plated at 35,000 per well in 96-well plate in medium of DMEM with 10% FBS. After 18-22 hours incubation, the transfection was carried out by using a PEI solution with 170.5 ng total DNA/well (50 ng pCMV-BD-ROR plus 20 ng of pFR-Luc reporter and 0.5 ng of pRL-CMV reporter plus 100 ng Carrier DNA (Clontech #630440) for each well). 4-6 hours after transfection, cells were treated with compounds for overnight in the medium with final concentration of FBS 1.3% and DMSO 0.1%. After overnight (16 to 20 hours) incubation, media were removed and cells were lysed with 50 μL Glo Lysis Buffer (Promega) for 10-15 minutes followed by 10 minute incubation with 50 μL Dual Glo reagent (Promega) at room temperature. Firefly luciferase luminescence was measured using a BMG Pherastar plate reader. To each well, 50 μL Stop and Glo reagent was added and incubated for 10 minutes at room temperature. Renilla luminescence was measured using a BMG Pherastar plate reader. To calculate the effect of compounds on RORγt activity, firefly values were normalized against values of DMSO only and values of reference compound at saturating concentration, then further normalized against Renilla signals. IC50s were generated by plotting final Renilla normalized data against compound concentration and percent inhibition was calculated against DMSO control.

Conditions C

Cells used in this assay were transiently co-transfected with three different plasmids, one expressing the GAL4-DNA binding domain (DBD)-RORγt fusion protein under control of a CMV promoter (NH2-Gal4-DBD:RORC—COOH in pCMV-BD, Stratagene #211342), and two reporter plasmids—the firefly luciferase reporter under control of a GAL4 promoter (pFR-Luc 2×GAL4) and Renilla luciferase reporter under control of CMV promoter (pRL-CMV, Promega #E2261). The full-length coding sequence was used for human RORγt, i.e., nucleotides 142-1635 of human RORγt, transcript variant 2, NCBI Accession: NM 001001523.1 (SEQ ID NO:1). HEK293T cells were plated at 8750 cells per well in 384-well plate in medium of DMEM with 10% FBS. After 18-22 hours incubation, the transfection was carried out by using a PEI solution with 42.6 ng total DNA/well (12.5 ng pCMV-BD-ROR plus 5 ng of pFR-Luc reporter and 0.125 ng of pRL-CMV reporter plus 25 ng Carrier DNA (Clontech #630440) for each well). 4-6 hours after transfection, cells were treated with compounds for overnight in the medium with final concentration of FBS 1.3% and DMSO 0.1%. After overnight (16 to 20 hours) incubation, media were removed and cells were lysed with 20 μL Glo Lysis Buffer (Promega) for 10-15 minutes followed by 10 minute incubation with 20 μL Dual Glo reagent (Promega) at room temperature. Firefly luciferase luminescence was measured using a BMG Pherastar plate reader. To each well, 20 μL Stop and Glo reagent was added and incubated for 10 minutes at room temperature. Renilla luminescence was measured using a BMG Pherastar plate reader. To calculate the effect of compounds on RORγt activity, firefly values were normalized against values of DMSO only and values of reference compound at saturating concentration, then further normalized against Renilla signals. IC50s were generated by plotting final Renilla normalized data against compound concentration and percent inhibition was calculated against DMSO control.

Human Th17 Assay

The human Th17 assay tests the effect of RORγt modulatory compounds on IL-17 production by CD4 T cells under conditions which favor Th17 differentiation. Total $CD4^+$ T cells were isolated from the peripheral blood mononuclear cells (PBMC) of healthy donors using a $CD4^+$ T cell isolation kit II, following the manufacturer's instructions (Miltenyi Biotec). Cells were resuspended in a medium of RPMI-1640 supplemented with 10% fetal bovine serum, penicillin, streptomycin, glutamate, and β-mercaptoethanol and were added to 96-well plates at $1.5×10^5$ per 100 μL per well. 50 μL of compound at titrated concentrations in DMSO were added into each well at final DMSO concentration at 0.2%. Cells were incubated for 1 hour, then 50 μL of Th17 cell differentiation medium was added to each well. The final concentrations of antibodies and cytokines (R&D Systems) in differentiation medium were: $3×10^6$/mL anti-CD3/CD28 beads (prepared using human T cell activation/expansion kit, Miltenyi Biotec), 10 μg/mL anti-IL4, 10 μg/mL anti-IFNγ, 10 ng/mL IL1β, 10 ng/mL IL23, 50 ng/mL IL6, 3 ng/mL TGFβ and 20 U/mL IL2. Cells were cultured at 37° C. and 5% $CO_2$ for 3 days. Supernatants were collected and the accumulated IL-17 in culture was measured by using MULTI-SPOT® Cytokine Plate following manufacture's instruction (Meso Scale Discovery). The plate was read using Sector Imager 6000, and IL-17 concentration was extrapolated from the standard curve. The IC50s were determined by GraphPad.

TABLE 1

| Example # | ThermoFluor ® Assay, Kd (μM) | RORγt (FL) Reporter Assay A, IC$_{50}$ (μM) | RORγt (FL) Reporter Assay A, % inhibition @ 6 μM | RORγt (FL) Reporter Assay B or C, IC$_{50}$ (μM) | RORγt (FL) Reporter Assay B or C, % inhibition @ 6 μM | Human Th17 Assay, IC$_{50}$ (μM) |
|---|---|---|---|---|---|---|
| 1 | 0.067 | ND | ND | ND | ND | ND |
| 1/1 | 0.00082 | ND | ND | ND | ND | 0.0078 |
| 2 | 0.012 | ND | ND | ND | ND | 0.037 |
| 3 | 0.0033 | 0.010 | 105* | ND | ND | ND |
| 3/1 | 0.00025 | 0.0034 | 107***** | ND | ND | ND |
| 3/2 | 0.00055 | ND | ND | ND | ND | ND |
| 3/3 | 0.00035 | 0.0052 | 106* | ND | ND | ND |
| 3/4 | 0.000050 | 0.0016 | 103*** | ND | ND | ND |
| 3/5 | 0.0032 | 0.021 | 100* | ND | ND | ND |
| 3/6 | 0.15 | 0.48 | 72* | ND | ND | ND |
| 3/7 | 0.093 | 0.089 | 94* | ND | ND | ND |
| 3/8a | ~0.0030 | 0.015 | 101** | ND | ND | ND |
| 3/8b | 0.14 | 0.17 | 65** | ND | ND | ND |
| 3/9 | 0.00036 | 0.0043 | 105* | ND | ND | ND |
| 3/10 | 0.0054 | 0.037 | 106* | ND | ND | ND |
| 3/11 | 0.0036 | 0.025 | 105* | ND | ND | ND |

TABLE 1-continued

| Example # | ThermoFluor ® Assay, Kd (μM) | RORγt (FL) Reporter Assay A, IC$_{50}$ (μM) | RORγt (FL) Reporter Assay A, % inhibition @ 6 μM | RORγt (FL) Reporter Assay B or C, IC$_{50}$ (μM) | RORγt (FL) Reporter Assay B or C, % inhibition @ 6 μM | Human Th17 Assay, IC$_{50}$ (μM) |
|---|---|---|---|---|---|---|
| 3/12 | 0.0087 | 0.047 | 103* | ND | ND | ND |
| 3/13 | 0.0020 | 0.0090 | 106 | ND | ND | ND |
| 3/14 | 0.022 | 0.061 | 105* | ND | ND | ND |
| 3/15 | 0.00033 | 0.019 | 106* | ND | ND | ND |
| 3/16 | 0.011 | 0.66 | 102 | ND | ND | ND |
| 3/17 | 0.0075 | 0.84 | 102 | ND | ND | 0.75 |
| 3/18 | 0.0054 | 0.015 | 103* | ND | ND | ND |
| 3/19 | 0.0065 | 0.015 | 101* | ND | ND | ND |
| 3/20 | 0.000020 | 0.0030 | 102** | ND | ND | ND |
| 3/21 | 0.00020 | 0.011 | 99**** | ND | ND | ND |
| 3/22 | 0.00033 | 0.094 | 105* | ND | ND | ND |
| 3/23 | 0.000045 | 0.014 | 105* | ND | ND | ND |
| 3/24 | 0.000036 | 0.0080 | 105* | ND | ND | ND |
| 3/25 | 0.000058 | 0.0026 | 105* | ND | ND | ND |
| 3/26 | 0.000025 | 0.0036 | 106** | ND | ND | ND |
| 3/27 | 0.00047 | 0.058 | 107 | ND | ND | ND |
| 3/28 | 0.0033 | 0.50 | 106 | ND | ND | ND |
| 3/29 | 0.000083 | 0.0029 | 102** | ND | ND | ND |
| 3/30 | 0.00028 | 0.0036 | 105* | ND | ND | ND |
| 3/31 | 0.00096 | 0.022 | 108* | ND | ND | ND |
| 3/32 | 0.000044 | 0.0070 | 109 | ND | ND | ND |
| 3/33 | 0.000070 | 0.0080 | 103* | ND | ND | ND |
| 3/34 | 0.018 | 0.12 | 94* | ND | ND | ND |
| 3/35 | 0.0056 | 0.011 | 100* | ND | ND | ND |
| 3/36 | 0.0011 | 0.0046 | 99** | ND | ND | ND |
| 3/37 | 0.0040 | 0.045 | 104* | ND | ND | ND |
| 3/38 | 0.000038 | 0.0032 | 104* | ND | ND | ND |
| 3/39 | 0.00071 | 0.039 | 109 | ND | ND | ND |
| 3/40 | 0.000030 | 0.0080 | 104* | ND | ND | ND |
| 3/41 | 0.000020 | 0.0045 | 104** | ND | ND | ND |
| 3/42 | 0.00012 | 0.0090 | 103* | ND | ND | ND |
| 3/43 | 0.0013 | ND | ND | 0.076 | 103 | ND |
| 4 | 0.0023 | 0.025 | 104 | ND | ND | ND |
| 4/1 | 0.00027 | 0.013 | 109 | 0.011 | 108 | 0.034 |
| 4/2 | 0.000040 | 0.0050 | 98* | ND | ND | ND |
| 5 | 0.0043 | 0.027 | 106* | ND | ND | ND |
| 6 | 0.0012 | 0.0060 | 104** | ND | ND | ND |
| 7 | 0.00032 | 0.021 | 105 | ND | ND | ND |
| 8 | 0.00020 | 0.13 | 108 | ND | ND | 0.082 |
| 8/1 | 0.00012 | 0.089 | 107 | ND | ND | ND |
| 8/2 | 0.0011 | 0.037 | 103* | ND | ND | ND |
| 8/3 | 0.0016 | 0.12 | 79 | ND | ND | 0.093 |
| 9 | 0.014 | 0.016 | 103** | ND | ND | ND |
| 10 | 0.18 | ND | ND | ND | ND | ND |
| 11 | 0.00039 | 0.0036 | 99** | ND | ND | ND |
| 11/1 | 0.00062 | 0.0090 | 99** | ND | ND | ND |
| 11/2 | 0.00012 | 0.0090 | 107* | ND | ND | ND |
| 11/3 | 0.000080 | 0.010 | 106* | ND | ND | ND |
| 11/4 | 0.000060 | 0.0080 | 99****** | ND | ND | ND |
| 11/5 | 0.00021 | 0.016 | 106* | ND | ND | ND |
| 11/6 | 0.00014 | 0.0044 | 105* | ND | ND | ND |
| 11/7 | 0.00027 | 0.0070 | 102* | ND | ND | ND |
| 11/8 | 0.00035 | 0.013 | 105 | ND | ND | ND |
| 11/9 | 0.00015 | 0.0042 | 102** | ND | ND | ND |
| 11/10 | 0.00023 | 0.0032 | 104* | ND | ND | ND |
| 11/11 | 0.000024 | 0.0043 | 106* | ND | ND | ND |
| 12 | 0.00012 | 0.014 | 105 | ND | ND | ND |
| 12/1 | 0.000050 | 0.0033 | 107* | ND | ND | ND |
| 12/2 | 0.000019 | 0.0048 | 107* | ND | ND | ND |
| 12/3 | 0.000063 | 0.014 | 103* | ND | ND | ND |
| 12/4 | 0.0018 | 0.31 | 98 | ND | ND | 0.26 |
| 12/5 | 0.00033 | 0.026 | 107 | ND | ND | ND |
| 12/6 | 0.0016 | 0.029 | 95* | ND | ND | ND |
| 12/7 | 0.00029 | 0.49 | 106 | ND | ND | ND |
| 13 | 0.44 | ND | ND | ND | ND | ND |
| 14 | 0.0027 | 0.0080 | 97** | ND | ND | ND |
| 15 | 0.00062 | 0.0042 | 100** | ND | ND | ND |

TABLE 1-continued

| Example # | ThermoFluor ® Assay, Kd (μM) | RORγt (FL) Reporter Assay A, IC$_{50}$ (μM) | RORγt (FL) Reporter Assay A, % inhibition @ 6 μM | RORγt (FL) Reporter Assay B or C, IC$_{50}$ (μM) | RORγt (FL) Reporter Assay B or C, % inhibition @ 6 μM | Human Th17 Assay, IC$_{50}$ (μM) |
|---|---|---|---|---|---|---|
| 16 | 0.00017 | 0.0049 | 103** | ND | ND | ND |
| 17 | 0.0015 | 0.015 | 103* | ND | ND | ND |
| 17/1 | 0.023 | 0.19 | 100* | ND | ND | ND |
| 18 | 0.00046 | 0.011 | 108* | ND | ND | ND |

All data shown in Table 1 is either the value of one data point or the average of more than one data point.
ND: value not determined.
*% inhibition is shown at 2 μM compound concentration,
**% inhibition is shown at 0.67 μM compound concentration,
***% inhibition is shown at 0.5 μM compound concentration,
****% inhibition is shown at 0.22 μM compound concentration,
*****% inhibition is shown at 0.19 μM compound concentration,
******% inhibition is shown at 0.17 μM compound concentration.

All data shown in Table 1 is either the value of one data point or the average of more than one data point.

ND: value not determined. *% inhibition is shown at 2 μM compound concentration, % inhibition is shown at 0.67 μM compound concentration, *% inhibition is shown at 0.5 μM compound concentration, **% inhibition is shown at 0.22 μM compound concentration, *% inhibition is shown at 0.19 μM compound concentration, ****% inhibition is shown at 0.17 μM compound concentration.

While the foregoing specification teaches the principles of the present invention, with examples provided for the purpose of illustration, it will be understood that the practice of the invention encompasses all of the usual variations, adaptations and/or modifications as come within the scope of the following claims and their equivalents.

All documents cited herein are incorporated by reference.

We claim:
1. A compound of Formula I:

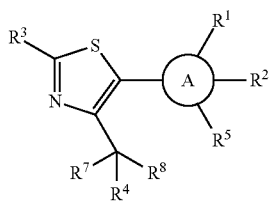

Formula I wherein:

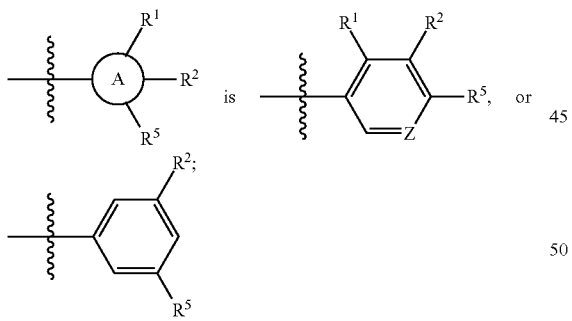

is

Z is N, or CH;
$R^1$ is H, Cl, $OCF_3$, $C_{(1-3)}$alkyl, —CN, F, $OC_{(1-3)}$alkyl, $OCHF_2$, Br, I, or cyclopropyl; wherein said $C_{(1-3)}$alkyl is optionally substituted with up to five fluorine atoms;
$R^2$ is H, F, Cl, —CN, $OCH_3$, $OCHF_2$, $OCF_3$, cyclopropyl, or $C_{(1-4)}$alkyl; wherein said $C_{(1-4)}$alkyl is optionally substituted with up to five fluorine atoms, and said cyclopropyl is optionally substituted with OH, $CH_3$, $CF_3$, —CN, and up to five fluorine atoms; or $R^1$ and $R^2$ may be taken together with their attached ring A to form a fused ring system selected from the group consisting of naphthalenyl, isoquinolinyl, tetrahydronaphthalenyl, and quinolinyl, wherein said naphthalenyl, isoquinoli-nyl, tetrahydronaphthalenyl, and quinolinyl are optionally substituted with F, $CHF_2$, $CH_2F$, $CF_3$, or $CH_3$; provided that $R^2$ may not be H if $R^f$ is H;
$R^3$ is oxadiazolyl, thiazolyl, thiadiazolyl, isoxadiazolyl, isoxazolyl, phenyl, oxazolyl, triazolyl, tetrazolyl, 1,2,4-oxadiazol-5(4H)-on-3-yl, pyridyl, pyrimidyl, pyridazyl, pyrazyl, imidazolyl, or pyrrolyl; wherein said oxadiazolyl, thiazolyl, thiadiazolyl, isoxadiazolyl, isoxazolyl, phenyl, oxazolyl, triazolyl, pyridyl, pyrimidyl, pyridazyl, pyrazyl, imidazolyl, or pyrrolyl is optionally substituted with $R^6$;
$R^6$ is

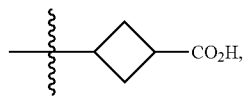

$C_{(1-4)}$alkyl, $C(O)NH_2$, or —CN; wherein said $C_{(1-4)}$alkyl is optionally substituted with up to six fluorine atoms, $CO_2H$, OH, or CN;
$R^4$ is $C_{(3-6)}$cycloalkyl, isopropyl, $C(CH_3)_2OCH_3$, $OC_{(1-4)}$alkyl, fluorophenyl, difluorophenyl, pyridyl, $CH_2SO_2CH_3$, or $NA^1A^2$, wherein said $C_{(3-6)}$cycloalkyl is optionally substituted with $OCH_3$, two fluoro groups or two methyl groups;
$A^1$ is H, or $C_{(1-3)}$alkyl; wherein said $C_{(1-3)}$alkyl is optionally substituted with up to five fluorine atoms, Cl, —CN, $OCH_3$, $OCHF_2$, or $OCF_3$;
$A^2$ is $C_{(1-4)}$alkyl, $C_{(0-2)}$alkyl-$C_{(3-6)}$cycloalkyl, $CH_2$—$C_6H_4$—$C(O)NH_2$, —$C_6H_4$—F, or $CH_2$—CCH; wherein said $C_{(1-4)}$alkyl, and said $C_{(0-2)}$alkyl-$C_{(3-6)}$cycloalkyl are optionally substituted with up to three fluorine atoms, Cl, —CN, $OCH_3$, $OCHF_2$, or $OCF_3$;
or $A^1$ and $A^2$ may be taken together with their attached nitrogen to form a ring selected from the group consisting of:

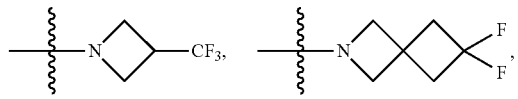

191

-continued

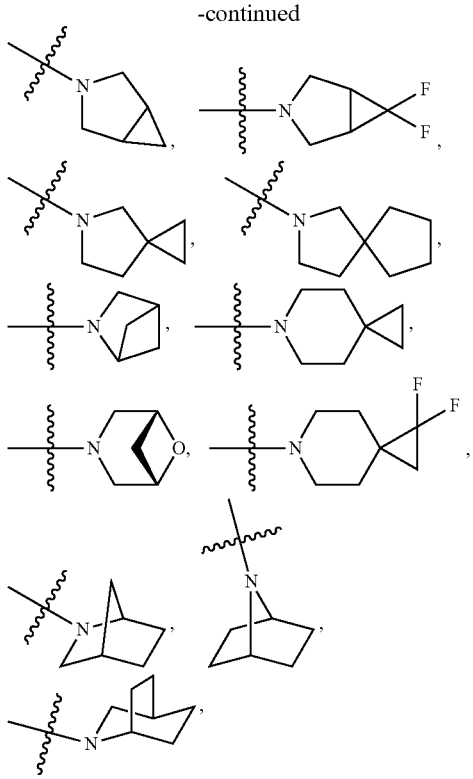

thiomorpholinyl, piperidinyl, pyrrolidinyl, piperazinyl, and morpholinyl; wherein said piperidinyl, pyrrolidinyl, piperazinyl, and morpholinyl are optionally substituted with $CF_3$, $CH_2F$, $CH_2CH_2F$, $C_{(1-2)}$alkyl, —CN, OH, $CH_2OH$, F, Cl, $OCH_3$, $OCHF_2$, or $OCF_3$, and up to three additional substituents selected from the group consisting of $CH_3$, and F;

$R^5$ is $SO_2NA^3A^4$, $C_{(1-6)}$alkyl,

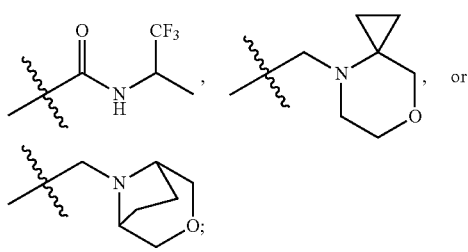

wherein said $C_{(1-6)}$alkyl is optionally substituted with OH, Cl, —CN, $OCH_3$, $OCHF_2$, $OCF_3$, or $NA^3A^4$; and up to six fluorine atoms;

$A^3$ is H, or $C_{(1-4)}$alkyl; wherein said $C_{(1-4)}$alkyl is optionally substituted with OH, Cl, —CN, $OCH_3$, $OCHF_2$, or $OCF_3$; and up to six fluorine atoms;

$A^4$ is $C_{(1-6)}$alkyl, $C_{(3-6)}$cycloalkyl, oxetanyl, or tetrahydrofuranyl; wherein said $C_{(1-6)}$alkyl is optionally substituted with cyclopropyl, morpholinyl, OH, $OCH_3$, or $C(O)NH_2$, and additionally substituted with up to three fluorine atoms; and wherein said $C_{(3-6)}$cycloalkyl, oxetanyl, and tetrahydrofuranyl are optionally substituted with $CF_3$, $CH_3$, —CN, or $C(O)NH_2$;

or $A^3$ and $A^4$ can be taken together with their attached nitrogen to form a ring selected from the group

192 consisting of azetidinyl, piperidinyl, morpholinyl, piperazinyl, and pyrrolidinyl wherein said azetidinyl, piperidinyl, morpholinyl, and piperazinyl are optionally substituted with up to four groups selected from the group consisting of $CF_3$, OH, and $CH_3$; and further optionally substituted with up to six fluorine atoms;

$R^7$ is H, F, OH, or $OCH_3$;

$R^8$ is H;

and pharmaceutically acceptable salts thereof.

2. The compound of claim 1, wherein:

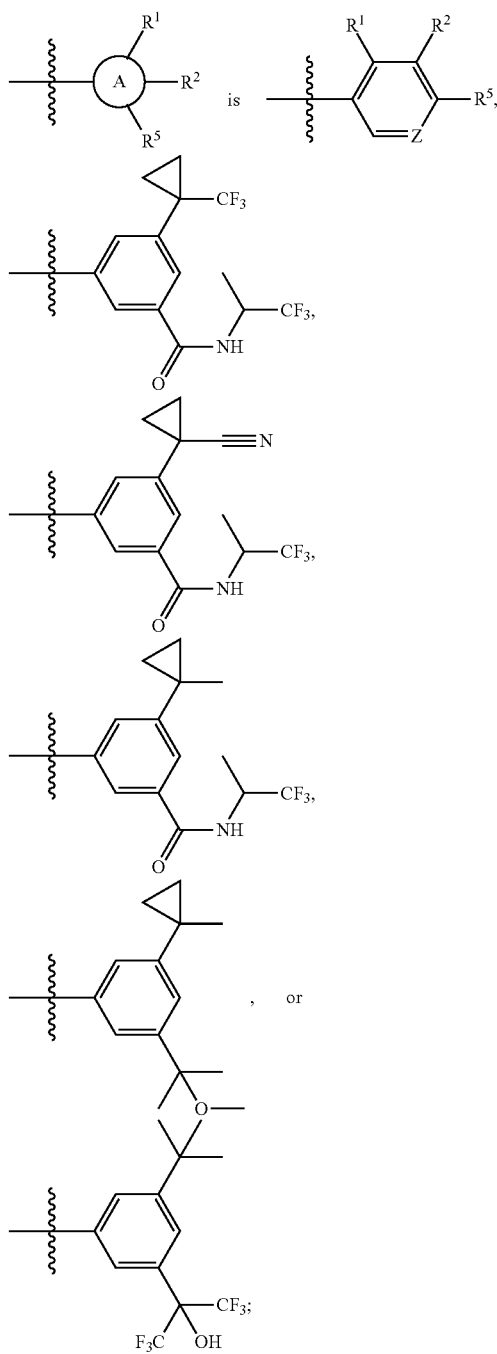

$R^1$ is H, Cl, OCF$_3$, C$_{(1-3)}$alkyl, —CN, F, OC$_{(1-3)}$alkyl, OCHF$_2$, or cyclopropyl, wherein said C$_{(1-2)}$alkyl is optionally substituted with up to five fluorine atoms;

$R^2$ is CHF$_2$, CF$_3$, H, F, Cl, —CN,

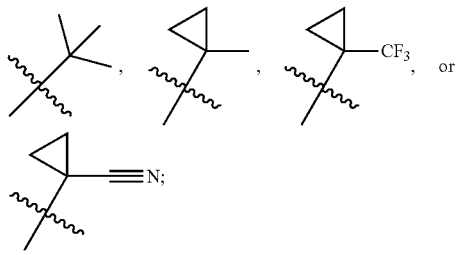

or $R^1$ and $R^2$ may be taken together with their attached ring A to form a fused ring system selected from the group consisting of naphthalenyl, isoquinolinyl, tetrahydronaphthalenyl, and quinolinyl, wherein said naphthalenyl, isoquinolinyl, tetrahydronaphthalenyl, and quinolinyl are optionally substituted with F, CHF$_2$, CH$_2$F, CF$_3$, or CH$_3$; provided that $R^2$ may not be H if $R^1$ is H;

$R^3$ is oxadiazolyl, thiazolyl, thiadiazolyl, isoxadiazolyl, isoxazolyl, phenyl, oxazolyl, triazolyl, tetrazolyl, 1,2,4-oxadiazol-5(4H)-on-3-yl, pyridyl, pyrimidyl, pyridazyl, or pyrazyl; wherein said oxadiazolyl, thiazolyl, thiadiazolyl, isoxadiazolyl, isoxazolyl, phenyl, oxazolyl, triazolyl, pyridyl, pyrimidyl, pyridazyl, or pyrazyl is optionally substituted with $R^6$;

$R^6$ is

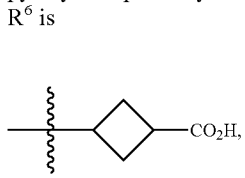

C$_{(1-2)}$alkyl, CH$_2$C(CH$_3$)$_2$CO$_2$H, C$_{(0-1)}$alkylC(CH$_3$)$_2$OH, CH$_2$C(CH$_3$)$_2$CN, C(O)NH$_2$, or —CN; wherein said C$_{(1-2)}$alkyl is optionally substituted with up to five fluorine atoms;

$R^4$ is C$_{(3-6)}$cycloalkyl, isopropyl, C(CH$_3$)$_2$OCH$_3$, OC$_{(1-4)}$alkyl, fluorophenyl, difluorophenyl, pyridyl, CH$_2$SO$_2$CH$_3$, or NA$^1$A$^2$, wherein said C$_{(3-6)}$cycloalkyl is optionally substituted with OCH$_3$, two fluoro groups or two methyl groups;

$A^1$ is H, or C$_{(1-3)}$alkyl; wherein said C$_{(1-3)}$alkyl is optionally substituted with up to five fluorine atoms;

$A^2$ is C$_{(1-4)}$alkyl, C$_{(0-2)}$alkyl-C$_{(3-6)}$cycloalkyl, CH$_2$—C$_6$H$_4$—C(O)NH$_2$, —C$_6$H$_4$—F, CH$_2$—CCH, or CH$_2$CH$_2$—CN; wherein said C$_{(1-4)}$alkyl, and said C$_{(0-2)}$alkyl-C$_{(3-6)}$cycloalkyl are optionally substituted with up to three fluorine atoms;

or $A^1$ and $A^2$ may be taken together with their attached nitrogen to form a ring selected from the group consisting of:

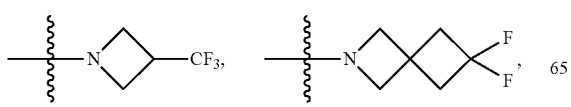

-continued

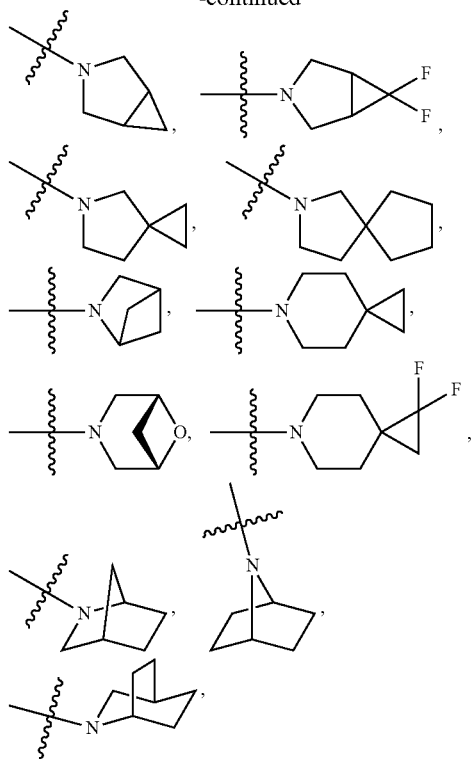

thiomorpholinyl, piperidinyl, pyrrolidinyl, piperazinyl, and morpholinyl; wherein said piperidinyl, pyrrolidinyl, piperazinyl, and morpholinyl are optionally substituted with CF$_3$, CH$_2$F, CH$_2$CH$_2$F, C$_{(1-2)}$alkyl, —CN, OH, CH$_2$OH, or F, and up to three additional substituents selected from the group consisting of CH$_3$, and F;

$R^5$ is SO$_2$NA$^3$A$^4$, C$_{(1-6)}$alkyl,

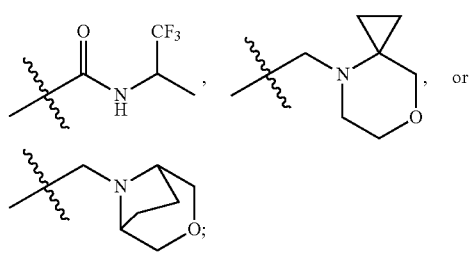

wherein said C$_{(1-6)}$alkyl is optionally substituted with OH, OCH$_3$, or, NA$^3$A$^4$, and up to six fluorine atoms;

$A^3$ is H, or C$_{(1-4)}$alkyl;

$A^4$ is C$_{(1-6)}$alkyl, cyclopropyl, cyclobutyl, oxetanyl, or tetrahydrofuranyl; wherein said C$_{(1-6)}$alkyl is optionally substituted with cyclopropyl, morpholinyl, OH, OCH$_3$, or C(O)NH$_2$, and additionally substituted with up to three fluorine atoms; and wherein said cyclopropyl cyclobutyl, oxetanyl, and tetrahydrofuranyl are optionally substituted with CF$_3$, CH$_3$, —CN, or C(O)NH$_2$;

or $A^3$ and $A^4$ can be taken together with their attached nitrogen to form a ring selected from the group consisting of aztetidinyl, piperidinyl, morpholinyl, piperazinyl, and pyrrolidinyl wherein said aztetidinyl, piperidinyl, morpholinyl, and piperazinyl are optionally substituted with up to two groups selected from the group consisting of $CF_3$, OH, and $CH_3$; and further optionally substituted with up to three fluorine atoms;

and pharmaceutically acceptable salts thereof.

3. The compound of claim 2, wherein:

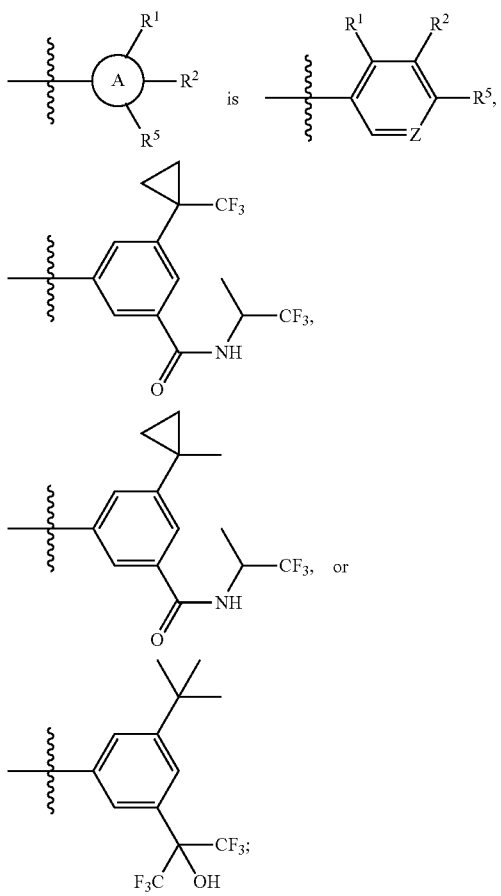

$R^1$ is H, Cl, $OCF_3$, $CF_3$, $CHF_2$, $C_{(1-3)}$alkyl, —CN, F, $OC_{(1-3)}$alkyl, or $OCHF_2$;

$R^2$ is $CHF_2$, $CF_3$, H, F, Cl,

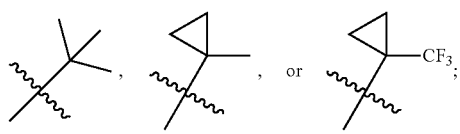

or $R^1$ and $R^2$ may be taken together with their attached ring A to form a fused ring system selected from the group consisting of naphthalenyl, isoquinolinyl, and tetrahydronaphthalenyl; provided that $R^2$ may not be H if $R^1$ is H;

$R^3$ is oxadiazolyl, thiazolyl, thiadiazolyl, isoxadiazolyl, isoxazolyl, phenyl, oxazolyl, triazolyl, tetrazolyl, 1,2,4-oxadiazol-5(4H)-on-3-yl, pyridyl, or pyrimidyl, wherein said oxadiazolyl, thiazolyl, thiadiazolyl, isoxadiazolyl, isoxazolyl, phenyl, oxazolyl, triazolyl, pyridyl or pyrimidyl is optionally substituted with $R^6$;

$R^6$ is

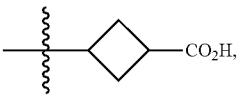 [SMILES: *C1CC(C(=O)O)C1]

$CH_3$, $CH_2C(CH_3)_2CO_2H$, $C_{(0-1)}$alkyl$C(CH_3)_2OH$, $CH_2C(CH_3)_2CN$, or $C(O)NH_2$;

$R^4$ is $C_{(3-6)}$cycloalkyl, isopropyl, $C(CH_3)_2OCH_3$, $OCH(CH_3)_2$, $OC(CH_3)_3$, fluorophenyl, difluorophenyl, or $NA^1A^2$, wherein said $C_{(3-6)}$cycloalkyl is optionally substituted with $OCH_3$, two fluoro groups or two methyl groups;

$A^1$ is H, $C_{(1-3)}$alkyl, or $CH_2CH_2F$;

$A^2$ is $C_{(2-4)}$alkyl, $CH_2$-cyclopentyl, $CH_2CH_2$-cyclopropyl, $C_{(3-4)}$cycloalkyl,

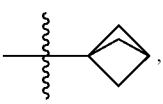

$CH_2$—$C_6H_4$—$C(O)NH_2$, —$C_6H_4$—F, $CH_2$—CCH, or $CH_2CH_2$—CN; wherein said $C_{(3-4)}$cycloalkyl is optionally substituted with one fluorine atom and said $C_{(2-4)}$alkyl is optionally substituted with up to three fluorine atoms;

or $A^1$ and $A^2$ may be taken together with their attached nitrogen to form a ring selected from the group consisting of:

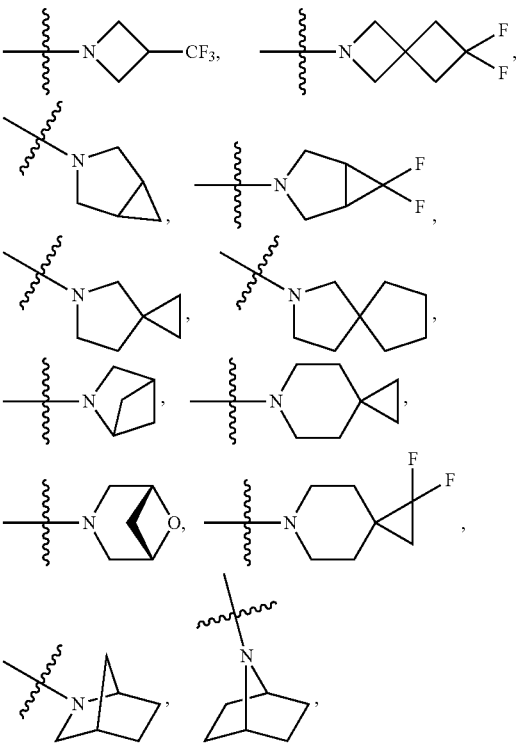

-continued

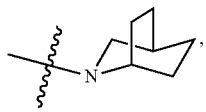

thiomorpholinyl, piperidinyl, pyrrolidinyl, and morpholinyl; wherein said piperidinyl, and pyrrolidinyl are optionally substituted with $CF_3$, $CH_2F$, $CH_2CH_2F$, $C_{(1-2)}$alkyl, —CN, OH, or $CH_2OH$, and up to three additional substituents selected from the group consisting of $CH_3$, and F;

$R^5$ is $SO_2NA^3A^4$, $C(CF_3)_2OH$,

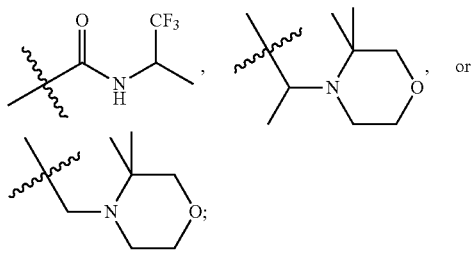

$A^3$ is H, $CH_3CH_2$, or $C(CH_3)_3$;
$A^4$ is $C_{(1-6)}$alkyl,

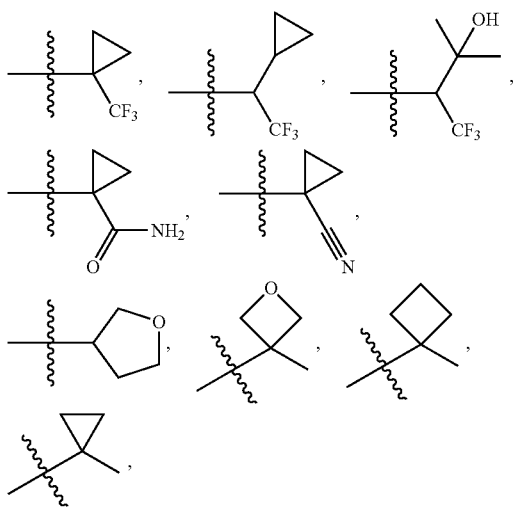

$C(CH_3)_2CH_2OCH_3$, $C(CH_3)_2CH_2OH$, $C(CH_3)_2CH_2$-morpholinyl, $C(CH_3)_2CH_2CH_2OH$, $C(CH_3)_2CH_2C(O)NH_2$, or $CH_2C(CH_3)_2OH$; wherein said $C_{(1-6)}$alkyl is optionally substituted with up to three fluorine atoms;

or $A^3$ and $A^4$ can be taken together with their attached nitrogen to form a ring selected from the group consisting of

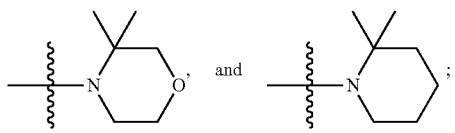

and pharmaceutically acceptable salts thereof.

4. The compound of claim 3, wherein:
$R^1$ is H, Cl, $OCF_3$, $CF_3$, $CHF_2$, or F;
$R^2$ is $CHF_2$, $CF_3$, H, F, Cl,

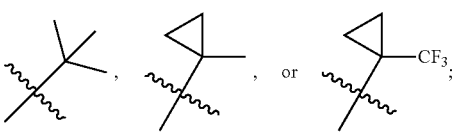

or $R^1$ and $R^2$ may be taken together with their attached ring A to form a fused ring system selected from the group consisting of naphthalenyl, and isoquinolinyl; provided that $R^2$ may not be H if $R^1$ is H;

$R^3$ is

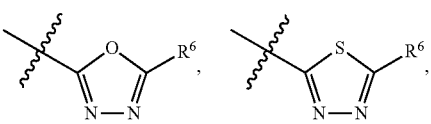

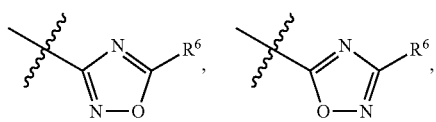

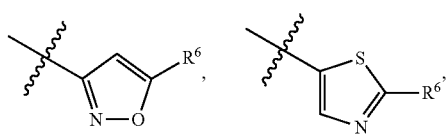

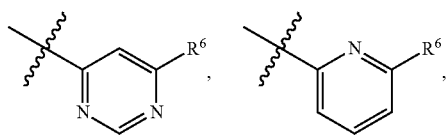

or phenyl, wherein said phenyl is optionally substituted with $R^6$;

$R^6$ is

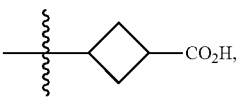 [SMILES: *C1CC(C(=O)O)C1]

$CH_3$, $CH_2C(CH_3)_2CO_2H$, or $C(CH_3)_2OH$;

$R^4$ is $C_{(4-6)}$cycloalkyl, isopropyl, $C(CH_3)_2OCH_3$, $OCH(CH_3)_2$, difluoropiperidinyl, fluoropiperidinyl, fluorophenyl, or $NA^1A^2$, wherein said $C_{(4-6)}$cycloalkyl is optionally substituted with $OCH_3$, two fluoro groups or two methyl groups; and wherein $A^1$ and $A^2$ are taken together with their attached nitrogen to form a pyrrolidinyl ring, wherein said pyrrolidinyl ring is optionally substituted with CH₃, CH₂F, and up to three additional substituents selected from the group consisting of CH₃, and F;
R⁵ is SO₂NA³A⁴, C(CF₃)₂OH,
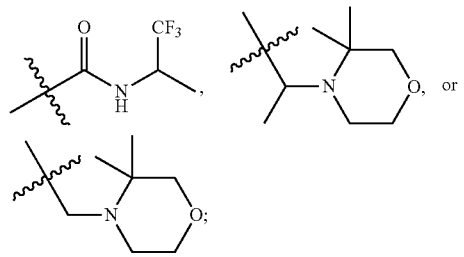
A³ is H;
A⁴ is
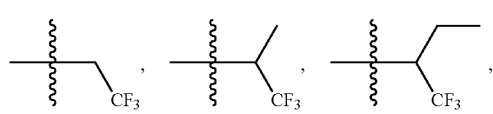
or C(CH₃)₃;
and pharmaceutically acceptable salts thereof.
5. The compound of claim 4 selected from the group consisting of:
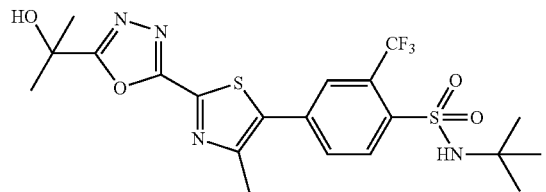
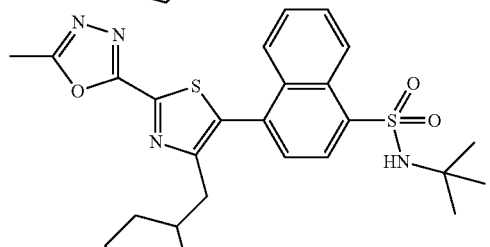
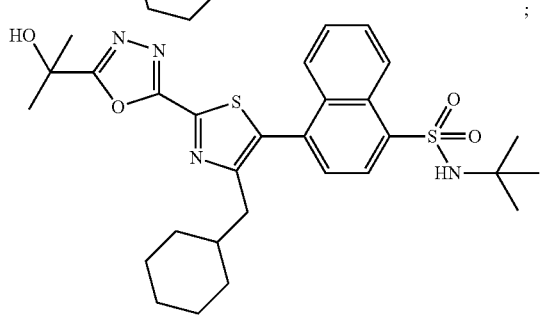
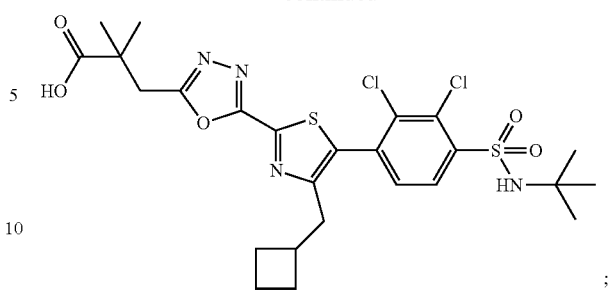
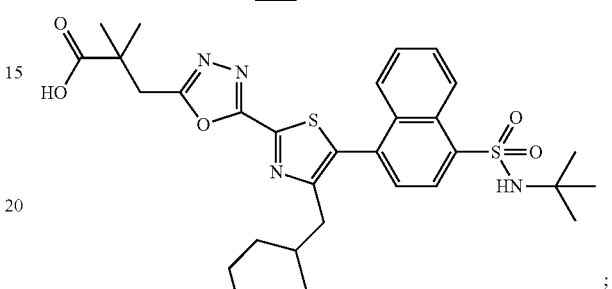
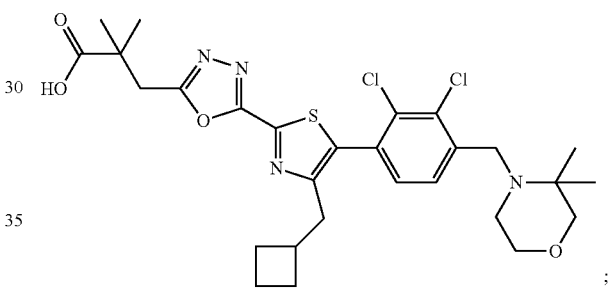
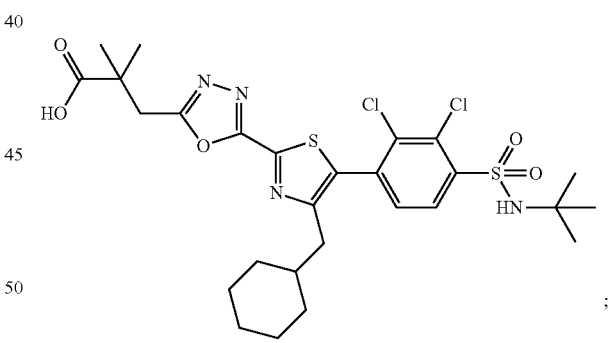
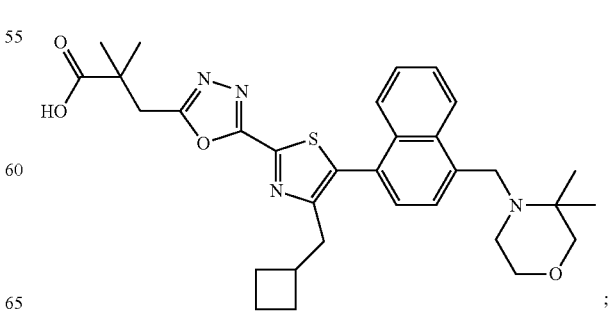

| 201 | 202 |
|---|---|
| -continued | -continued |
| 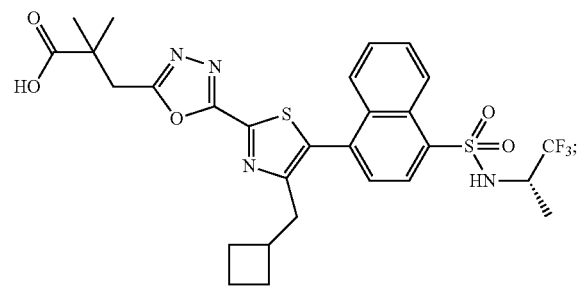 | 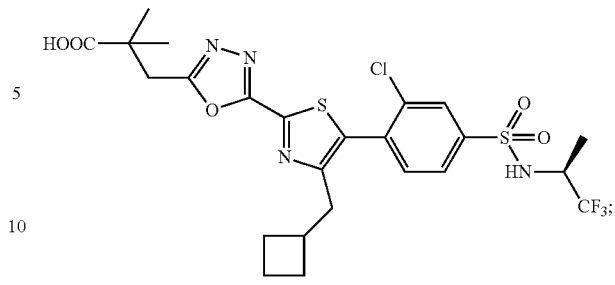 |
| 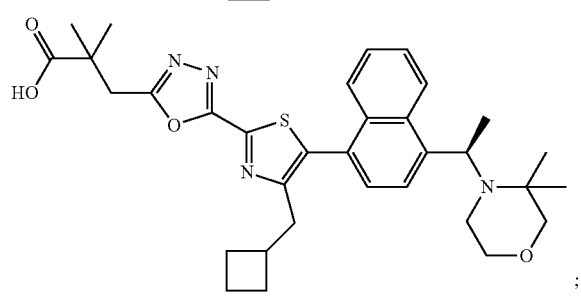 | 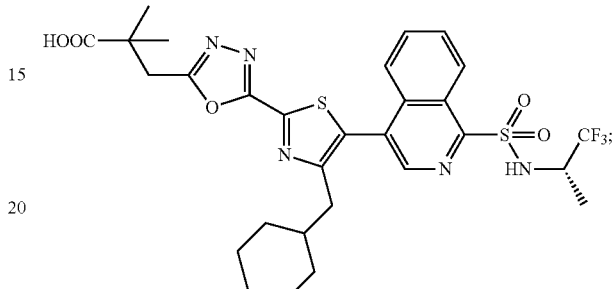 |
| 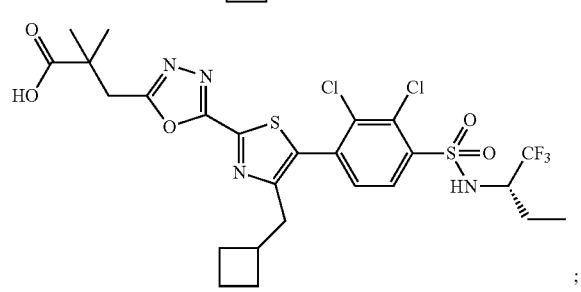 | 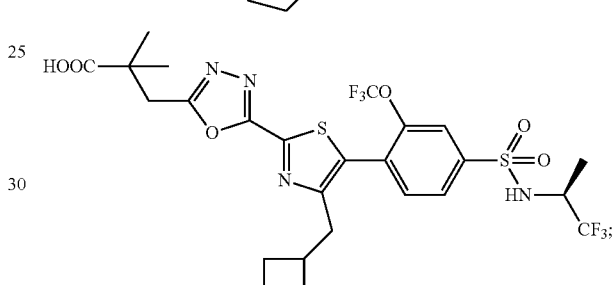 |
| 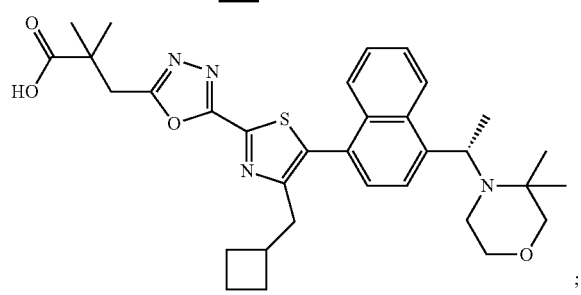 | 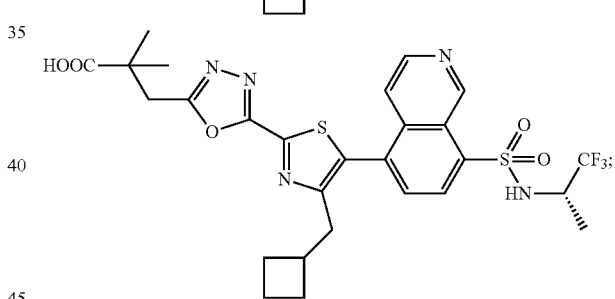 |
| 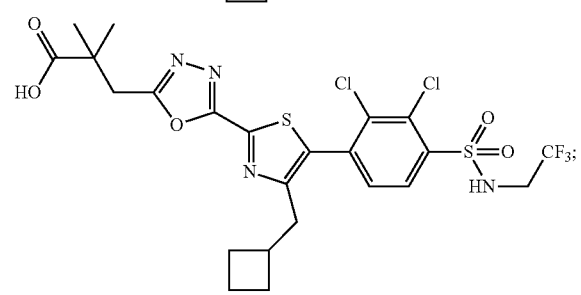 | 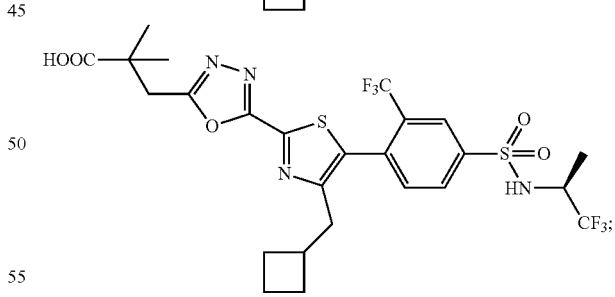 |
| 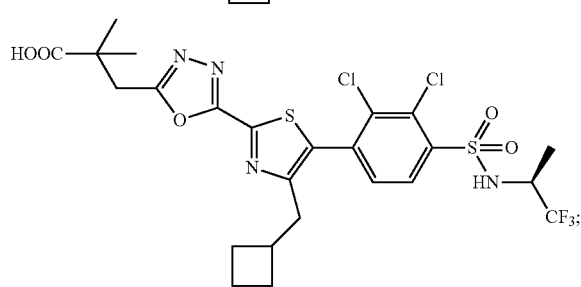 | 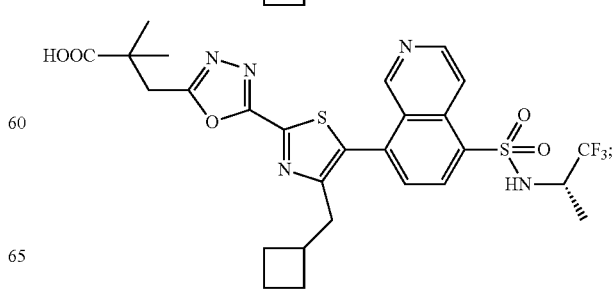 |

203
-continued
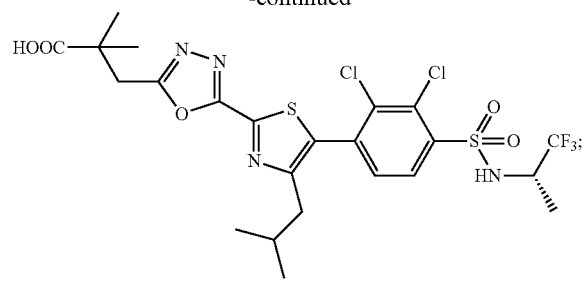
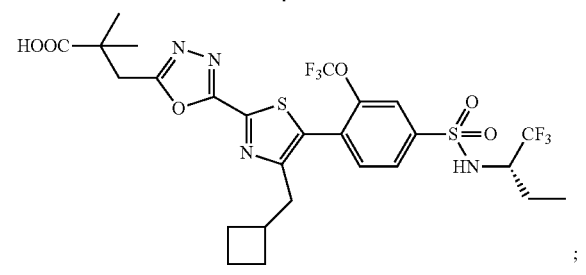
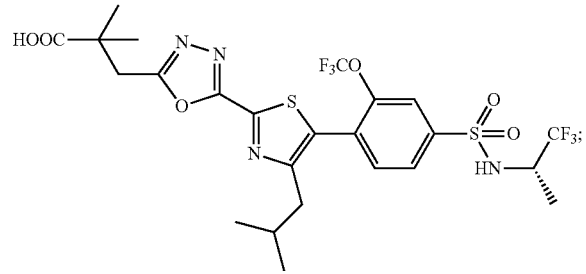
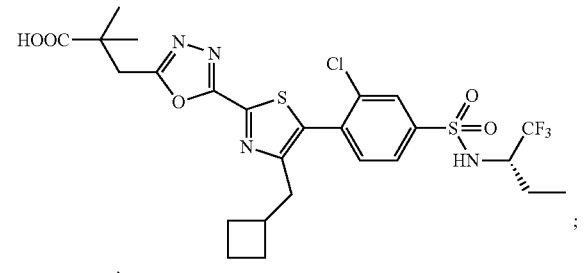
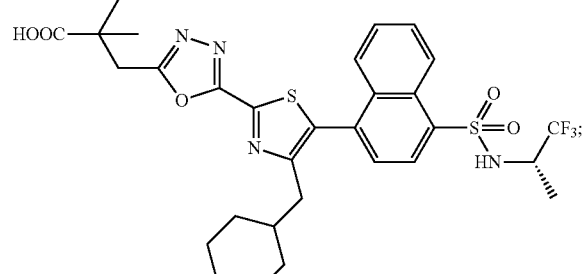
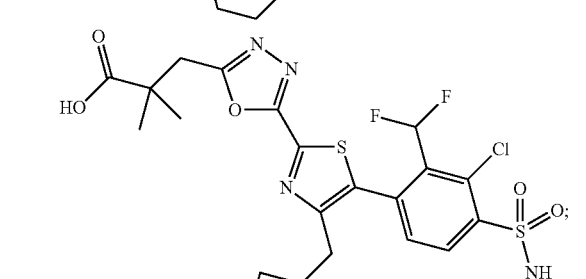
204
-continued
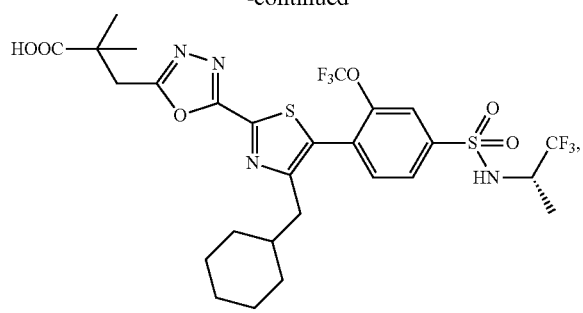
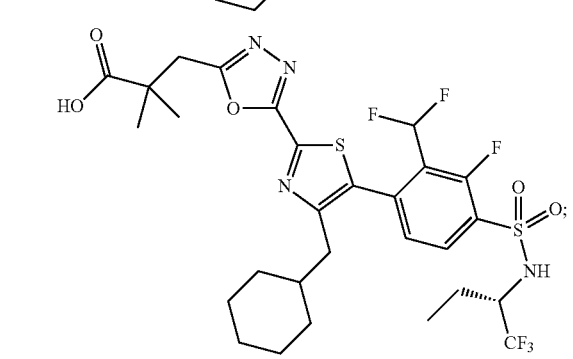
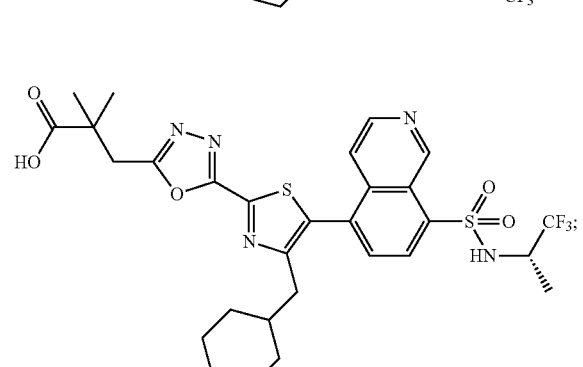
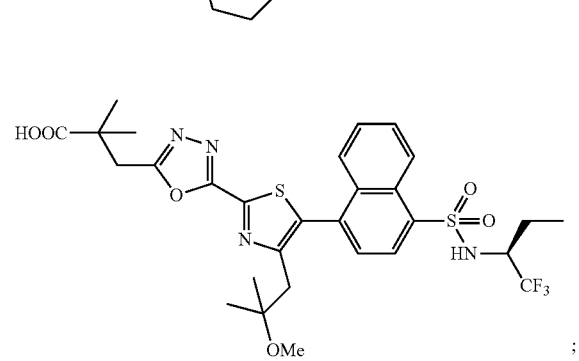
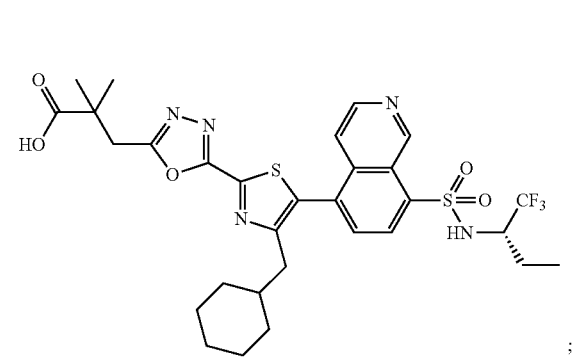

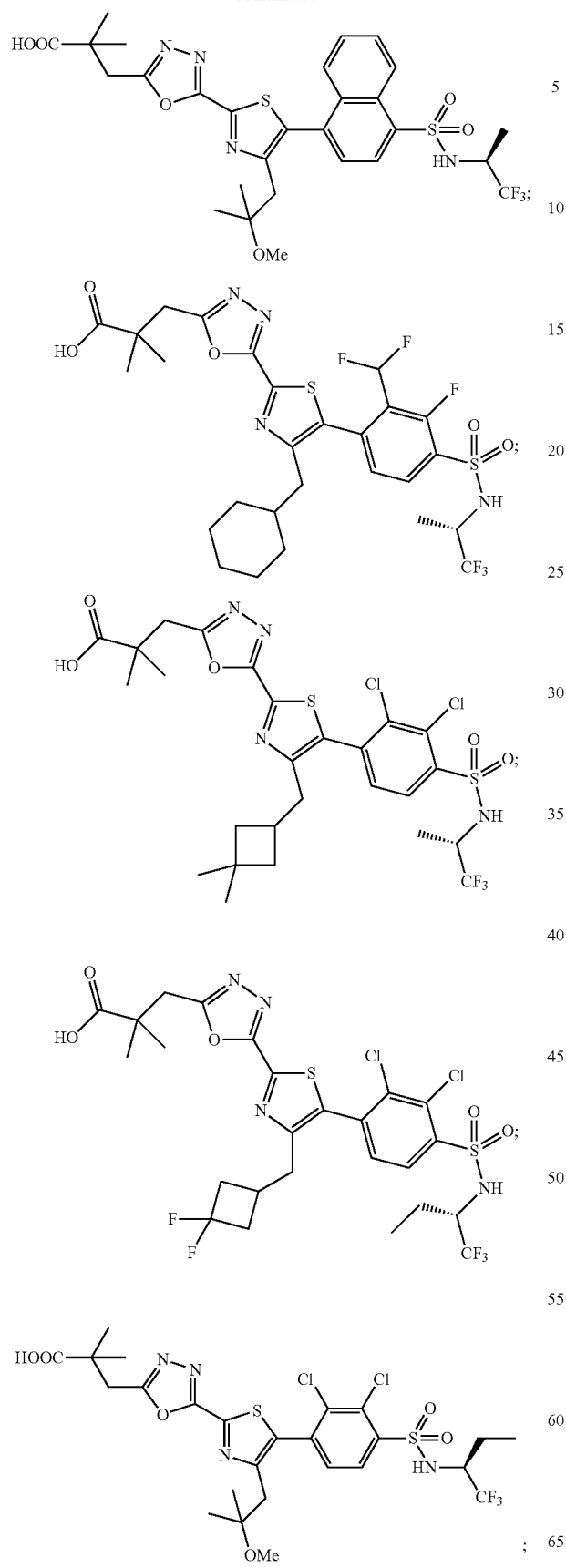
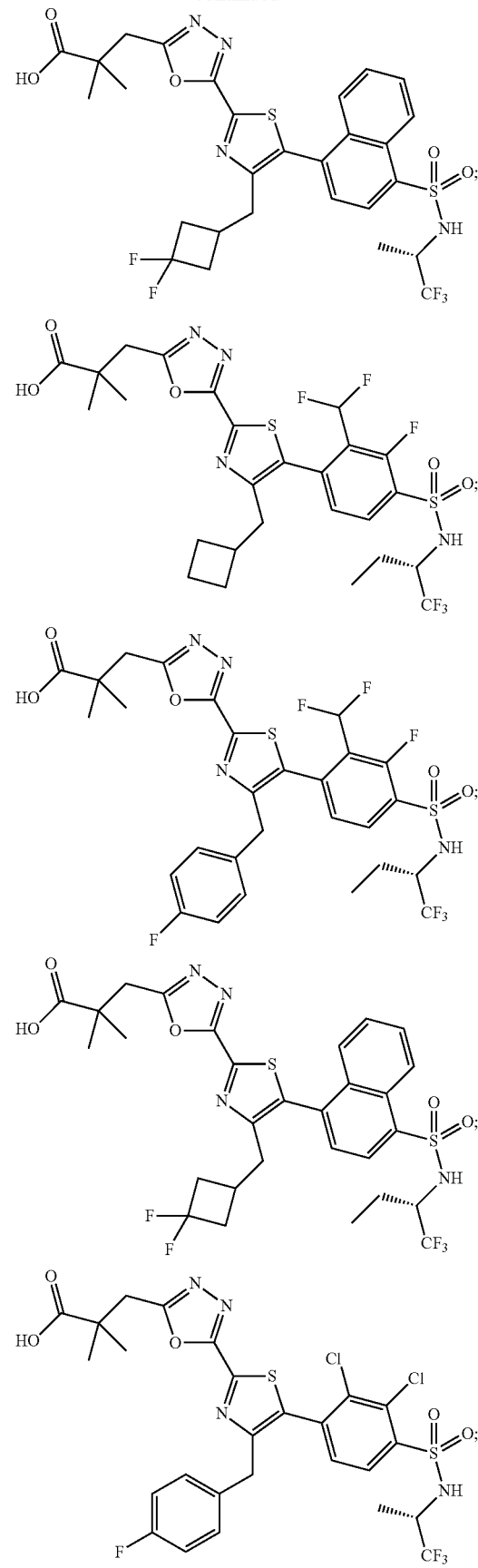

207
-continued
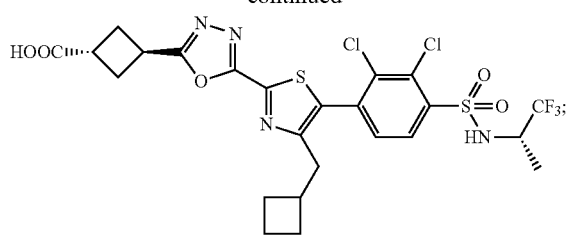
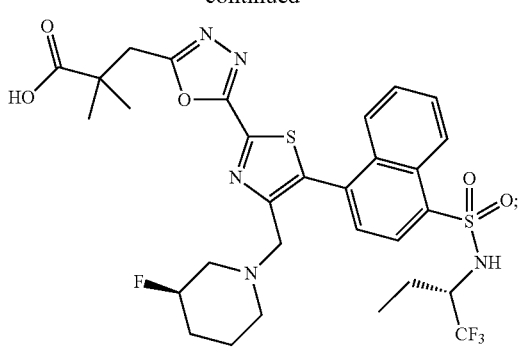
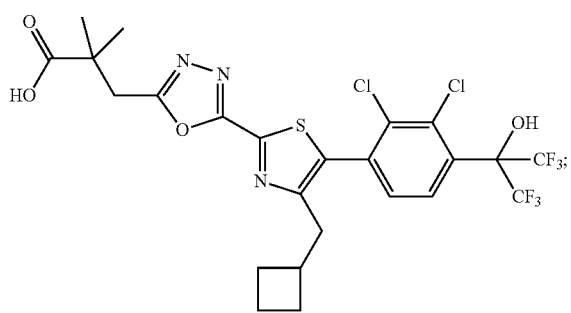
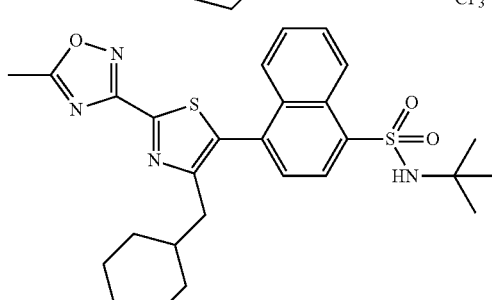
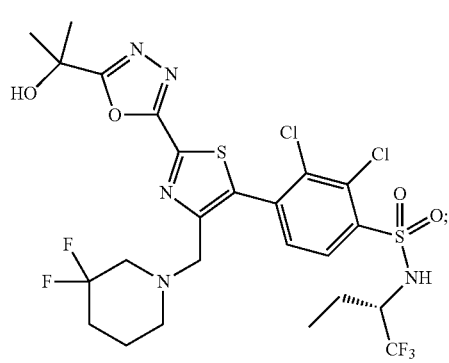
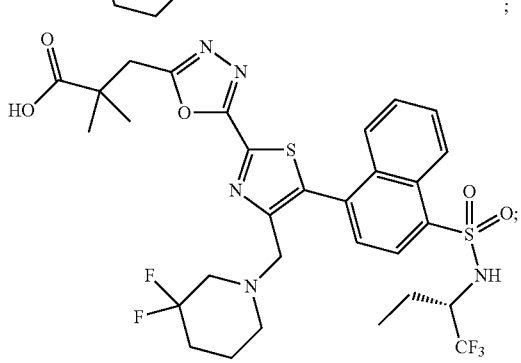
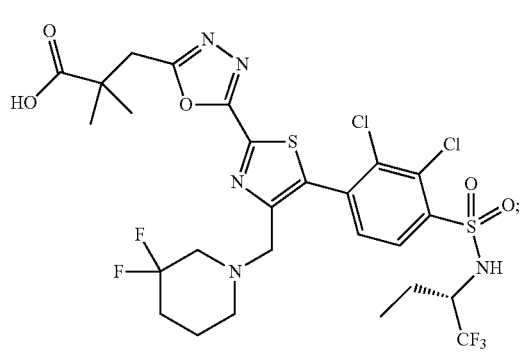
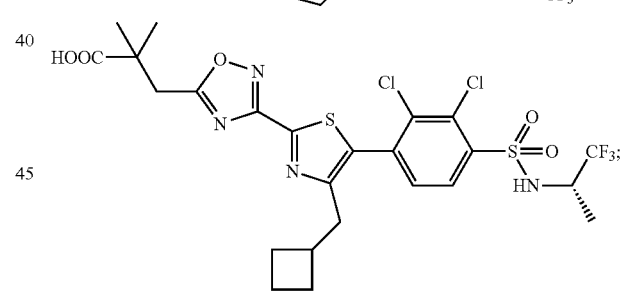
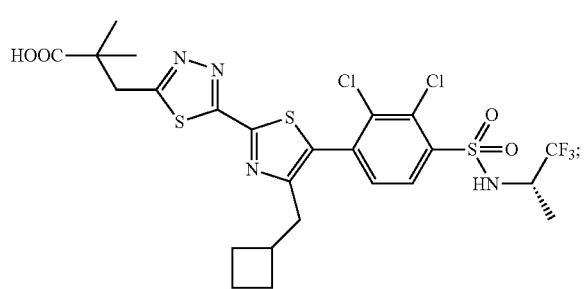
208
-continued
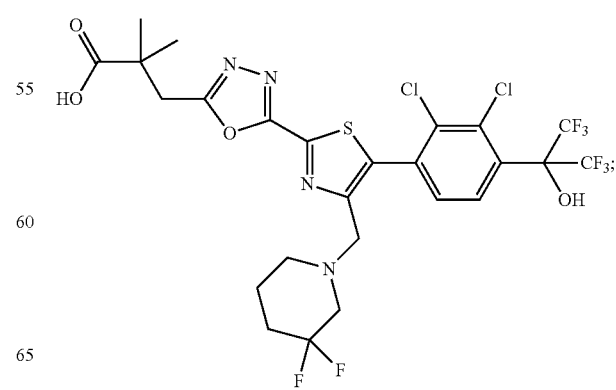

209
-continued
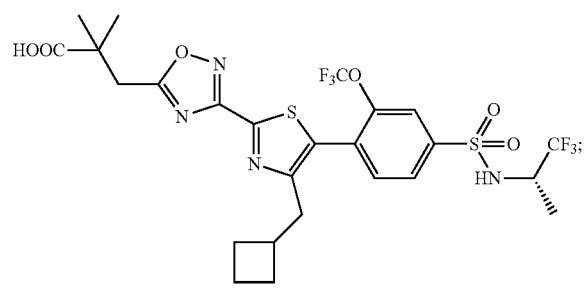
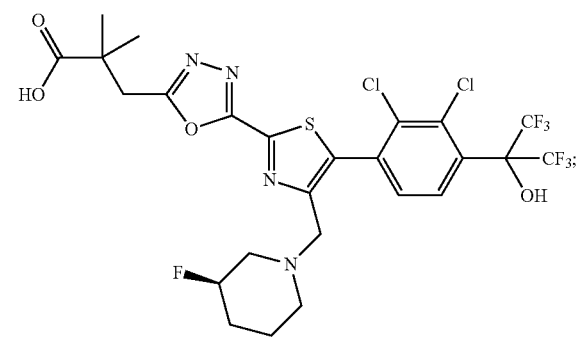
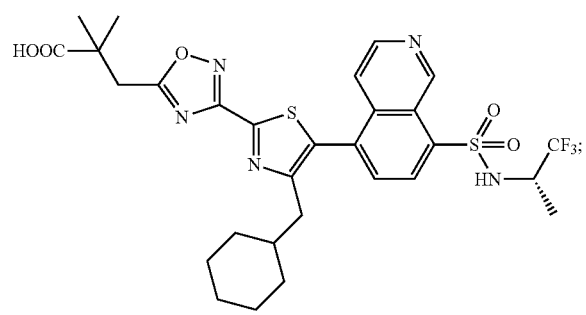
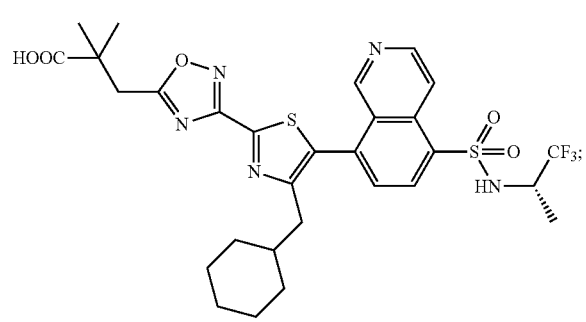
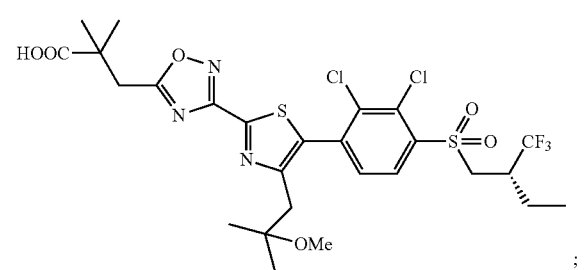
210
-continued
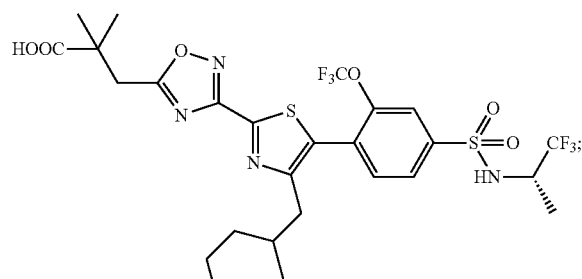
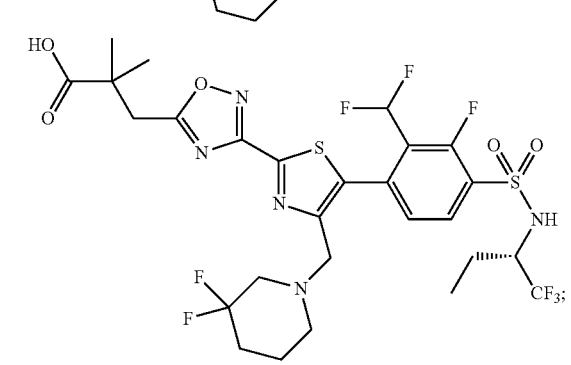
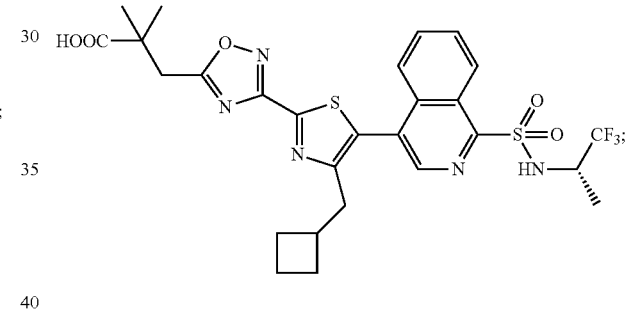
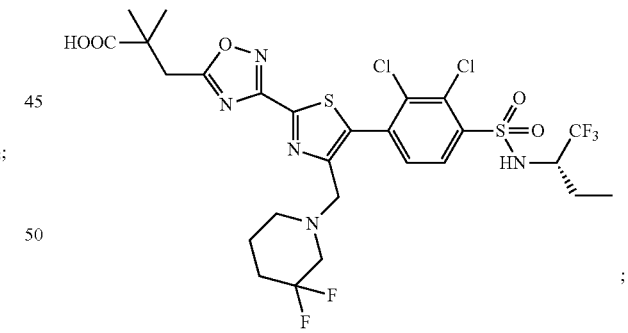
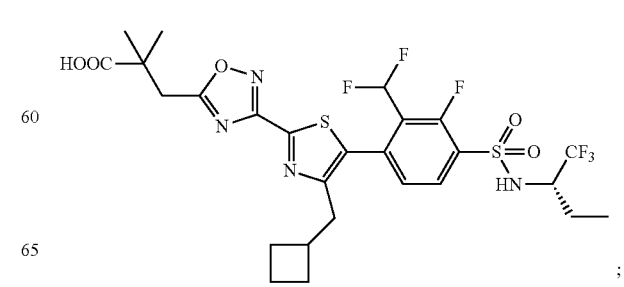

211
-continued
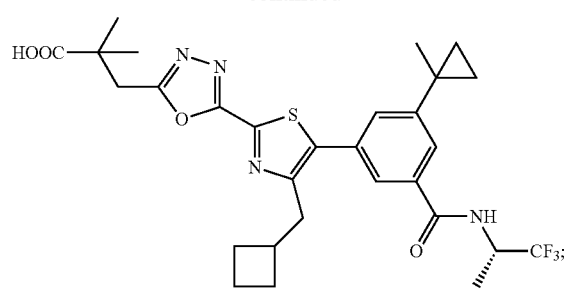
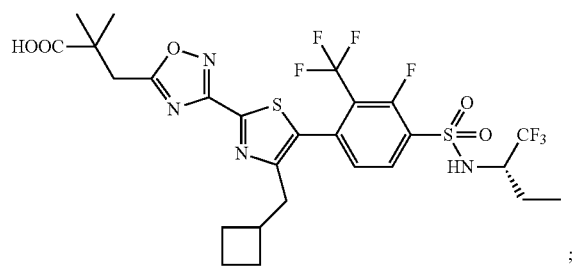
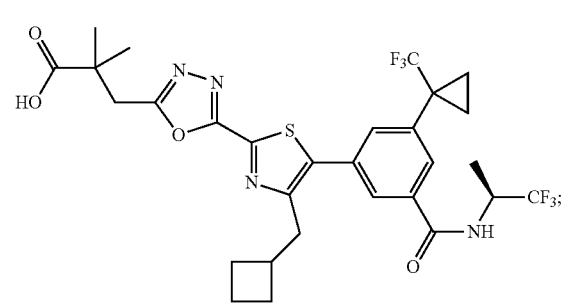
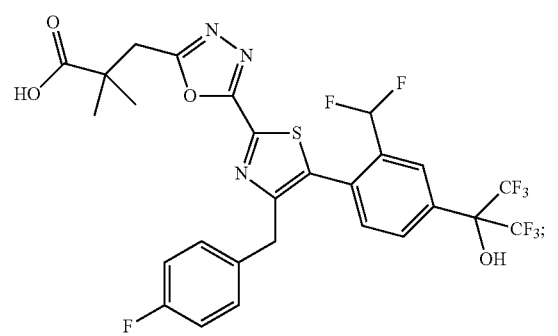
212
-continued
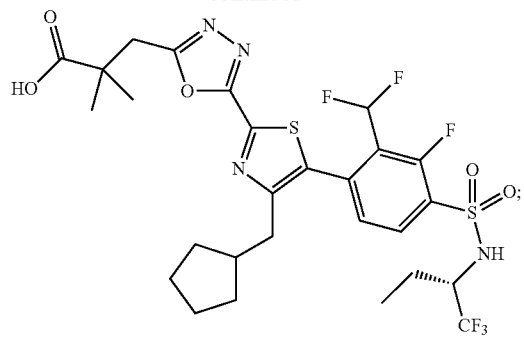
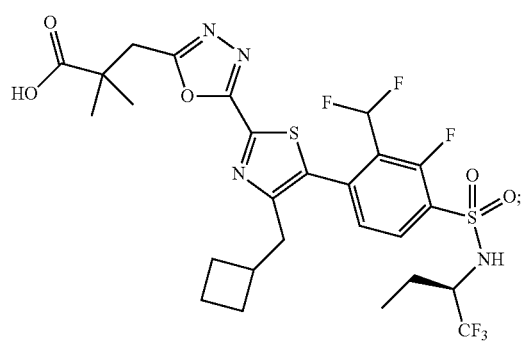
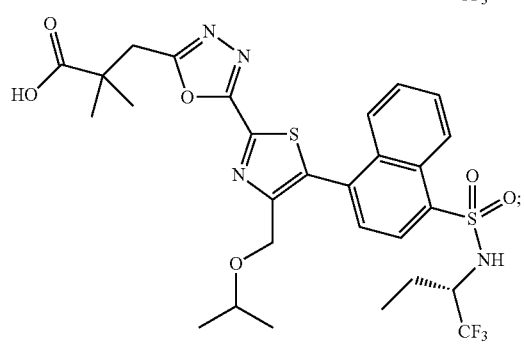
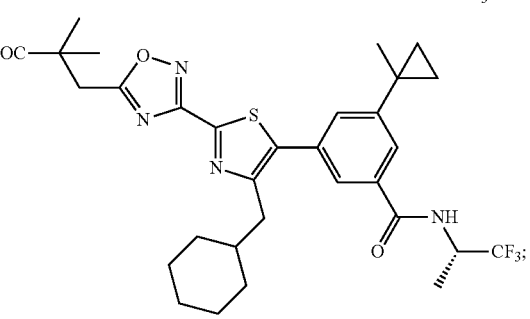
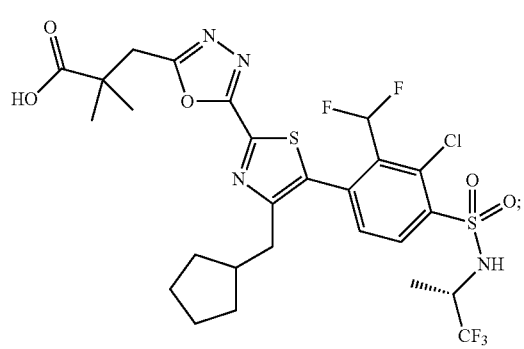

213
-continued
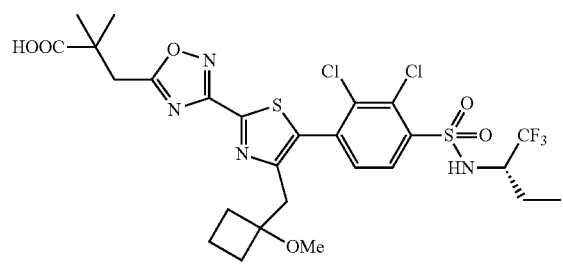
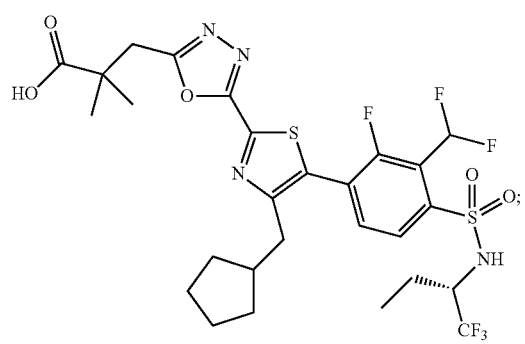
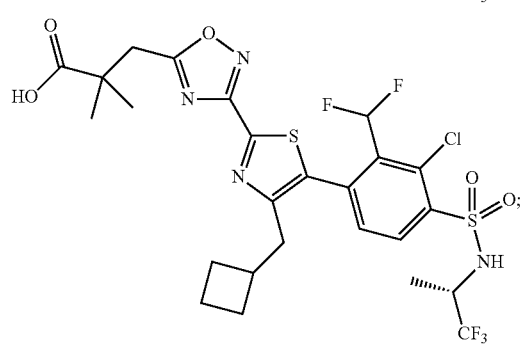
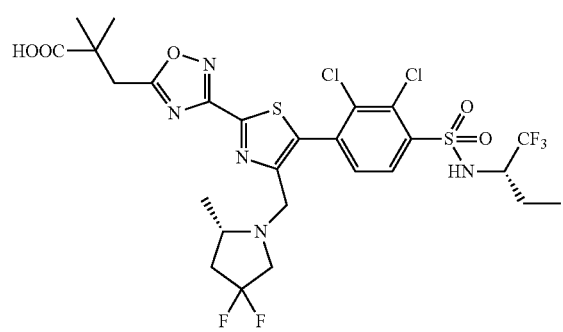
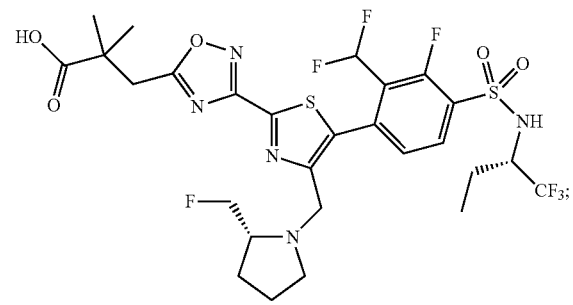
214
-continued
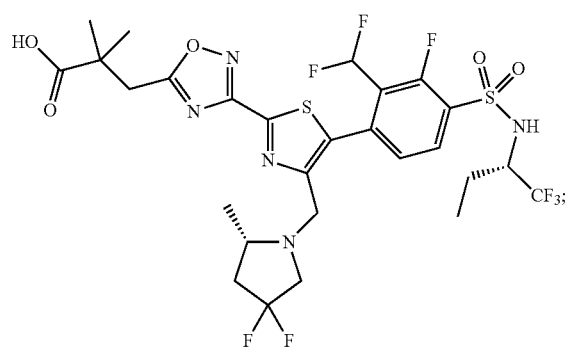
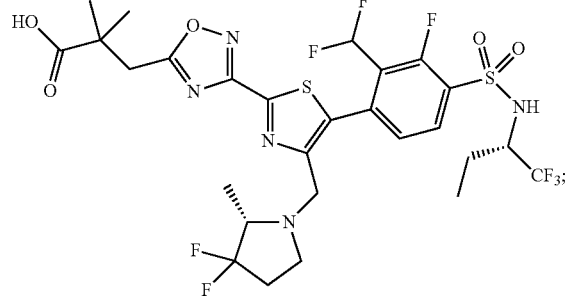

-continued
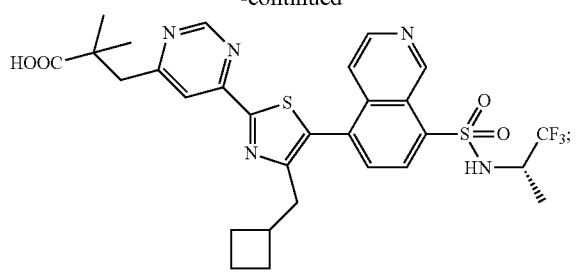
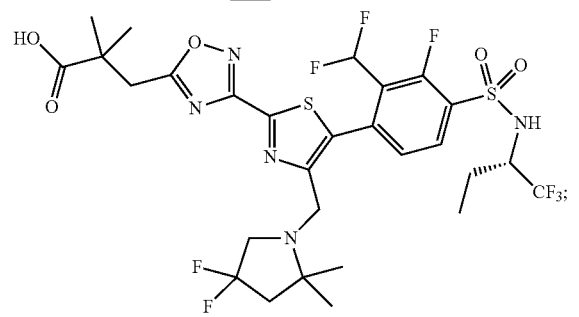
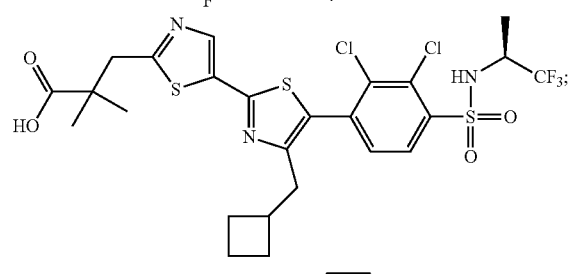
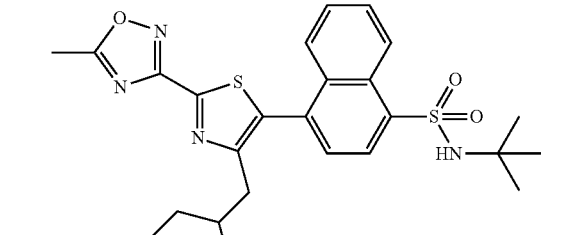
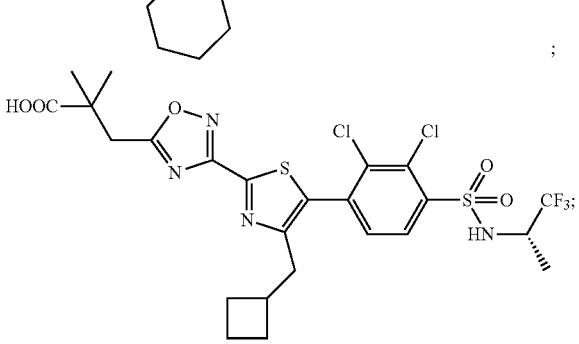
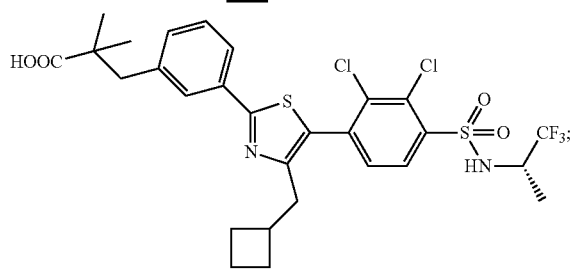
and pharmaceutically acceptable salts thereof.
6. The compound of claim 3 selected from the group consisting of:
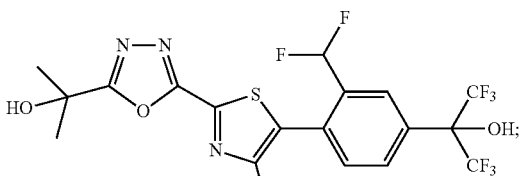
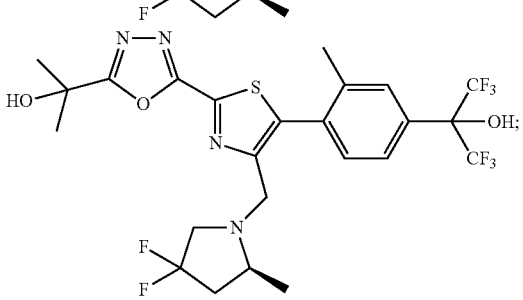
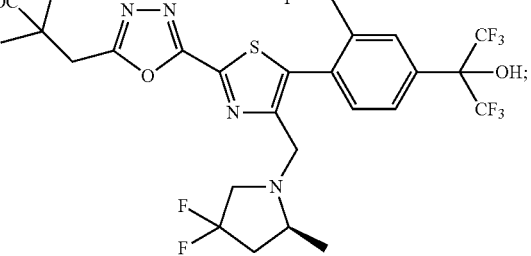
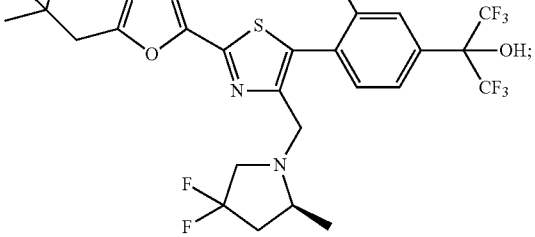
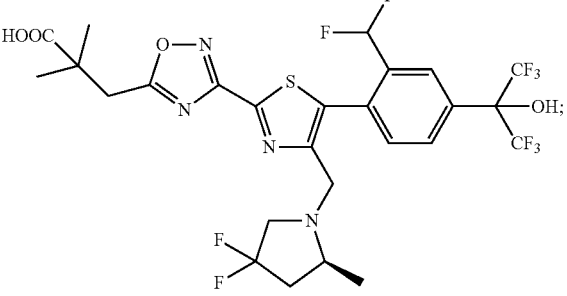

-continued
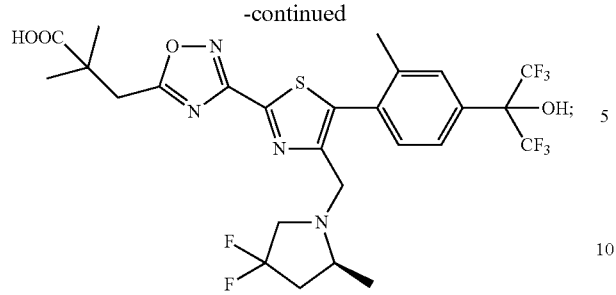
and pharmaceutically acceptable salts thereof.
7. A pharmaceutical composition, comprising a compound of claim 1 and a pharmaceutically acceptable carrier.
8. A pharmaceutical composition made by mixing a compound of claim 1 and a pharmaceutically acceptable carrier.
* * * * *

SEQUENCE LISTING

```
<160> NUMBER OF SEQ ID NOS: 4

<210> SEQ ID NO 1
<211> LENGTH: 3054
<212> TYPE: DNA
<213> ORGANISM: Homo sapiens

<400> SEQUENCE: 1
agagagctag gtgcagagct tcaggctgag gcgctgctga gagggcctcg ccccgcctct      60
gccgccagct gcaccccact cctggaccac cccctgctga gaaggacagg gagccaaggc     120
cggcagagcc aaggctcagt catgagaaca caaattgaag tgatcccttg caaaatctgt    180
ggggacaagt cgtctgggat ccactacggg gttatcacct gtgaggggtg caagggcttc     240
ttccgccgga gccagcgctg taacgcggcc tactcctgca cccgtcagca gaactgcccc     300
atcgaccgca ccagccgaaa ccgatgccag cactgccgcc tgcagaaatg cctggcgctg     360
ggcatgtccc gagatgctgt caagttcggc cgcatgtcca agaagcagag ggacagcctg     420
catgcagaag tgcagaaaca gctgcagcag cggcaacagc agcaacagga accagtggtc     480
aagacccctc cagcagggc ccaaggagca gatacccctca cctacacctt ggggctccca    540
gacgggcagc tgcccctggg ctcctcgcct gacctgcctg aggcttctgc ctgtccccct     600
ggcctcctga aagcctcagg ctctgggccc tcatattcca caacttggc caaggcaggg     660 ctcaatgggg cctcatgcca ccttgaatac agccctgagc ggggcaaggc tgagggcaga     720
gagagcttct atagcacagg cagccagctg acccctgacc gatgtggact tcgtttttgag   780 gaacacaggc atcctgggct tggggaactg ggacagggcc cagacagcta cggcagcccc     840
agtttccgca gcacaccgga ggcacccctat gcctccctga cagagataga gcacctggtg    900
cagagcgtct gcaagtccta cagggagaca tgccagctgc ggctggagga cctgctgcgg     960
```

| | |
|---|---|
| cagcgctcca acatcttctc ccgggaggaa gtgactggct accagaggaa gtccatgtgg | 1020 |
| gagatgtggg aacggtgtgc ccaccacctc accgaggcca ttcagtacgt ggtggagttc | 1080 |
| gccaagaggc tctcaggctt tatggagctc tgccagaatg accagattgt gcttctcaaa | 1140 |
| gcaggagcaa tggaagtggt gctggttagg atgtgccggg cctacaatgc tgacaaccgc | 1200 |
| acggtctttt ttgaaggcaa atacggtggc atggagctgt tccgagcctt gggctgcagc | 1260 |
| gagctcatca gctccatctt tgacttctcc cactccctaa gtgccttgca cttttccgag | 1320 |
| gatgagattg ccctctacac agcccttgtt ctcatcaatg cccatcggcc agggctccaa | 1380 |
| gagaaaagga agtagaaca gctgcagtac aatctggagc tggcctttca tcatcatctc | 1440 |
| tgcaagactc atcgccaaag catcctggca aagctgccac ccaaggggaa gcttcggagc | 1500 |
| ctgtgtagcc agcatgtgga aaggctgcag atcttccagc acctccaccc catcgtggtc | 1560 |
| caagccgctt tccctccact ctacaaggag ctcttcagca ctgaaaccga gtcacctgtg | 1620 |
| gggctgtcca agtgacctgg aagagggact ccttgcctct ccctatggcc tgctggccca | 1680 |
| cctccctgga ccccgttcca ccctcaccct tttcctttcc catgaaccct ggagggtggt | 1740 |
| ccccaccagc tctttggaag tgagcagatg ctgcggctgg cttttctgtca gcaggccggc | 1800 |
| ctggcagtgg gacaatcgcc agagggtggg gctggcagaa caccatctcc agcctcagct | 1860 |
| ttgacctgtc tcatttccca tattccttca cacccagctt ctggaaggca tggggtggct | 1920 |
| gggatttaag gacttctggg ggaccaagac atcctcaaga aaacaggggc atccagggct | 1980 |
| ccctggatga atagaatgca attcattcag aagctcagaa gctaagaata gccctttgaa | 2040 |
| atacctcatt gcatttccct ttgggcttcg gcttggggag atggatcaag ctcagagact | 2100 |
| ggcagtgaga gcccagaagg acctgtataa aatgaatctg gagctttaca ttttctgcct | 2160 |
| ctgccttcct cccagctcag caaggaagta tttgggcacc ctacccttta cctggggtct | 2220 |
| aaccaaaaat ggatgggatg aggatgagag gctggagata attgttttat gggatttggg | 2280 |
| tgtgggacta gggtacaatg aaggccaaga gcatctcaga catagagtta aaactcaaac | 2340 |
| ctcttatgtg cactttaaag atagacttta ggggctggca caaatctgat cagagacaca | 2400 |
| tatccataca caggtgaaac acatacagac tcaacagcaa tcatgcagtt ccagagacac | 2460 |
| atgaacctga cacaatctct cttatccttg aggccacagc ttggaggagc ctagaggcct | 2520 |
| caggggaaag tcccaatcct gagggaccct cccaaacatt tccatggtgc tccagtccac | 2580 |
| tgatcttggg tctggggtga tccaaatacc accccagctc cagctgtctt ctaccactag | 2640 |
| aagacccaag agaagcagaa gtcgctcgca ctggtcagtc ggaaggcaag atcagatcct | 2700 |
| ggaggacttt cctggcctgc ccgccagccc tgctcttgtt gtggagaagg aagcagatgt | 2760 |
| gatcacatca ccccgtcatt gggcaccgct gactccagca tggaggacac cagggagcag | 2820 |
| ggcctgggcc tgtttcccca gctgtgatct tgcccagaac ctctcttggc ttcataaaca | 2880 |
| gctgtgaacc ctcccctgag ggattaacag caatgatggg cagtcgtgga gttgggggg | 2940 |
| ttggggggtgg gattgtgtcc tctaagggga cgggttcatc tgagtaaaca taaaccccaa | 3000 |
| cttgtgccat tctttataaa atgatttta aggcaaaaaa aaaaaaaaaa aaaa | 3054 |

<210> SEQ ID NO 2
<211> LENGTH: 786
<212> TYPE: DNA
<213> ORGANISM: Homo sapiens

<400> SEQUENCE: 2

| | |
|---|---|
| agcacaccgg aggcacccta tgcctccctg acagagatag agcacctggt gcagagcgtc | 60 |

-continued

```
tgcaagtcct acagggagac atgccagctg cggctggagg acctgctgcg gcagcgctcc    120
aacatcttct cccgggagga agtgactggc taccagagga agtccatgtg ggagatgtgg    180
gaacggtgtg cccaccacct caccgaggcc attcagtacg tggtggagtt cgccaagagg    240
ctctcaggct ttatggagct ctgccagaat gaccagattg tgcttctcaa agcaggagca    300
atggaagtgg tgctggttag gatgtgccgg gcctacaatg ctgacaaccg cacggtcttt    360
tttgaaggca aatacggtgg catggagctg ttccgagcct tgggctgcag cgagctcatc    420
agctccatct ttgacttctc ccactcccta agtgccttgc acttttccga ggatgagatt    480
gccctctaca cagcccttgt tctcatcaat gcccatcggc cagggctcca agagaaaagg    540
aaagtagaac agctgcagta caatctggag ctggcctttc atcatcatct ctgcaagact    600
catcgccaaa gcatcctggc aaagctgcca cccaagggga agcttcggag cctgtgtagc    660
cagcatgtgg aaaggctgca gatcttccag cacctccacc ccatcgtggt ccaagccgct    720
ttccctccac tctacaagga gctcttcagc actgaaaccg agtcacctgt ggggctgtcc    780
aagtga                                                                786
```

<210> SEQ ID NO 3
<211> LENGTH: 7
<212> TYPE: PRT
<213> ORGANISM: Artificial Sequence
<220> FEATURE:
<223> OTHER INFORMATION: TurboTEV protease cleavage site

<400> SEQUENCE: 3

Glu Asn Leu Tyr Phe Gln Gly
1               5

<210> SEQ ID NO 4
<211> LENGTH: 283
<212> TYPE: PRT
<213> ORGANISM: Artificial Sequence
<220> FEATURE:
<223> OTHER INFORMATION: Construct used in the Thermofluor assay

<400> SEQUENCE: 4

Met Ala His His His His His His Ala Gly Gly Ala Glu Asn Leu Tyr
1               5                   10                  15

Phe Gln Gly Ala Met Asp Ser Thr Pro Glu Ala Pro Tyr Ala Ser Leu
            20                  25                  30

Thr Glu Ile Glu His Leu Val Gln Ser Val Cys Lys Ser Tyr Arg Glu
        35                  40                  45

Thr Cys Gln Leu Arg Leu Glu Asp Leu Leu Arg Gln Arg Ser Asn Ile
    50                  55                  60

Phe Ser Arg Glu Glu Val Thr Gly Tyr Gln Arg Lys Ser Met Trp Glu
65                  70                  75                  80

Met Trp Glu Arg Cys Ala His His Leu Thr Glu Ala Ile Gln Tyr Val
                85                  90                  95

Val Glu Phe Ala Lys Arg Leu Ser Gly Phe Met Glu Leu Cys Gln Asn
            100                 105                 110

Asp Gln Ile Val Leu Leu Lys Ala Gly Ala Met Glu Val Val Leu Val
        115                 120                 125

Arg Met Cys Arg Ala Tyr Asn Ala Asp Asn Arg Thr Val Phe Phe Glu
    130                 135                 140

Gly Lys Tyr Gly Gly Met Glu Leu Phe Arg Ala Leu Gly Cys Ser Glu
145                 150                 155                 160

```
Leu Ile Ser Ser Ile Phe Asp Phe Ser His Ser Leu Ser Ala Leu His
            165                 170                 175
Phe Ser Glu Asp Glu Ile Ala Leu Tyr Thr Ala Leu Val Leu Ile Asn
            180                 185                 190
Ala His Arg Pro Gly Leu Gln Glu Lys Arg Lys Val Glu Gln Leu Gln
        195                 200                 205
Tyr Asn Leu Glu Leu Ala Phe His His His Leu Cys Lys Thr His Arg
    210                 215                 220
Gln Ser Ile Leu Ala Lys Leu Pro Pro Lys Gly Lys Leu Arg Ser Leu
225                 230                 235                 240
Cys Ser Gln His Val Glu Arg Leu Gln Ile Phe Gln His Leu His Pro
            245                 250                 255
Ile Val Val Gln Ala Ala Phe Pro Pro Leu Tyr Lys Glu Leu Phe Ser
            260                 265                 270
Thr Glu Thr Glu Ser Pro Val Gly Leu Ser Lys
            275                 280
```